(12) United States Patent
Kelley et al.

(10) Patent No.: US 9,089,605 B2
(45) Date of Patent: Jul. 28, 2015

(54) QUINONE DERIVATIVES, PHARMACEUTICAL COMPOSITIONS, AND USES THEREOF

(75) Inventors: Mark R. Kelley, Zionsville, IN (US); Richard F. Borch, Lafayette, IN (US); Rodney L. Nyland, II, Baltimore, MD (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 239 days.

(21) Appl. No.: 12/679,828

(22) PCT Filed: Sep. 22, 2008

(86) PCT No.: PCT/US2008/077213
§ 371 (c)(1),
(2), (4) Date: Aug. 5, 2010

(87) PCT Pub. No.: WO2009/042544
PCT Pub. Date: Apr. 2, 2009

(65) Prior Publication Data
US 2010/0297113 A1    Nov. 25, 2010

Related U.S. Application Data

(60) Provisional application No. 60/975,396, filed on Sep. 26, 2007, provisional application No. 60/989,566, filed on Nov. 21, 2007.

(51) Int. Cl.
| | | |
|---|---|---|
| C07D 233/02 | (2006.01) |
| A61K 31/196 | (2006.01) |
| A61K 45/06 | (2006.01) |
| A61K 31/122 | (2006.01) |
| A61K 31/13 | (2006.01) |
| A61K 31/195 | (2006.01) |
| A61K 31/203 | (2006.01) |
| A61K 31/282 | (2006.01) |
| A61K 31/454 | (2006.01) |

(52) U.S. Cl.
CPC ............. *A61K 45/06* (2013.01); *A61K 31/122* (2013.01); *A61K 31/13* (2013.01); *A61K 31/195* (2013.01); *A61K 31/203* (2013.01); *A61K 31/282* (2013.01); *A61K 31/454* (2013.01)

(58) Field of Classification Search
CPC .......................... C07D 233/02; A61K 31/196
See application file for complete search history.

(56) References Cited

U.S. PATENT DOCUMENTS

| | | | | |
|---|---|---|---|---|
| 3,438,998 | A | * | 4/1969 | Sproston, Jr. ................. 435/125 |
| 5,385,942 | A | * | 1/1995 | Abe et al. ....................... 514/568 |
| 5,849,793 | A | | 12/1998 | Pan et al. |
| 2003/0229004 | A1 | | 12/2003 | Zarling et al. |

OTHER PUBLICATIONS

Armstrong et al. The Structure of Lambertellin. J.Chem.Soc., 1965, 5927-5930.*

(Continued)

*Primary Examiner* — Anna Pagonakis
(74) *Attorney, Agent, or Firm* — Barnes & Thornburg LLP

(57) ABSTRACT

This application describes quinone derivatives which target the redox site of Ape1/Ref1. Also included in the invention are pharmaceutical formulations containing the derivatives and therapeutic uses of the derivatives.

2 Claims, 45 Drawing Sheets

(56) References Cited

OTHER PUBLICATIONS

Univar Canada. Excipients/Processing Aids. Version Mar. 1, 2005. 4 pages. Electronic Resource. [http://www.univarcanada.com/pdfdoc/pharmaceutical/Excipients.pdf].*
Cunha et al. Synthesis of novel napthoquinone-spermidine conjugates and their effects on DNA-topoisomerase II and II-alpha. J. Braz. Chem. Soc. vol. 17, No. 3, 439-442, 2006.*
Barbosa et al. New 1,2,3,4-tetrahydro-1-aza-anthraquinones and 2-aminoalkyl compounds from norlapachol with molluscicidal activity. Bioorganic & Medicinal Chemistry, 13, 2005, 6464-6469.*
Boudalis et al. Synthesis, spectroscopic, structural and electrochemical studies of carboxyl substituted 1,4-naphthoquinones. Inorganic Chimica Acta, 2008, 361: 1681-1688.*
Commandeur et al. Study of radiacl decarboxylation toward functionalization of naphthoquinones. Eur. J. Org. Chem. 2007, 3045-3052.*
Yamada et al. Cleavage at 5-methylcytosine in DNA by photosensitized oxidation with 2-methyl-1,4-naphthoquinone tethered oligodeoxynucleotides. Bioorganic & Medicinal Chemistry Letters, 2005, 15: 665-668.*
Mital et al. Synthesis and biological evaluation of substituted naphthoquinone derivatives as potent antimyobacterial agents. (ARKIVOC, 2008, 16: 176-192).*
Williams et al. Foye's Principles of Medicinal Chemistry, 5th edition, pp. 59-61, 2002.*
PCT International Search Report for PCT/US2008/077213 completed by the EP Searching Authority on Feb. 9, 2009.
PCT International Search Report for PCT/US2008/077210 completed by the EP Searching Authority on Dec. 19, 2008.
Fishel Melissa L et al: "The DNA base excision repair protein Apel/Ref-1 as a therapeutic and chemopreventive target." Molecular Aspects of Medicine Jun.-Aug. 2007, vol. 28, No. 3-4, Jun. 2007, pp. 375395, XP002508296 ISSN: 0098-2997.
Luo Meihua et al: "Inhibition of the human apurinic/apyrimidinic endonuclease DNA base excision repair enzyme/redox factor (APEI/Ref-1) using small molecule redox and repair inhibitors: Therapeutic implications" Proceedings of the Annual Meeting of the American Association for Cancer Research, New York, NY, vol. 45, Mar. 1, 2004 pp. 703704, XP001537017 ISSN: 0197-016X.
Database WPI Section Ch, Week 1995 1996, Thomson Scientific, London, GB; AN 1996-017132 XP002508298 Goto Masaki et al.: "NfkB transcription factor inhibitor" & JP 07 291859 A (Eisai Co Ltd) Nov. 7, 1995.
Fayette J et al: "Use of angiogenesis inhibitors in tumour treatment" European Journal of Cancer, Pergamon Press, Oxford, GB, vol. 41, No. 8, May 1, 2005, pp. 1109-1116, XP004906861 ISSN: 09598049.
Alka Mital et al.: "Syntheis of novel 2-substituted 1,4-napthoquinones using Heck reaction in "green" reaction media" Arkivoc Journal, vol. 11, No. ISSN: 1424-6376, 2006, pp. 99-106, xp008101612 Gainsville, FL, US.
Jiang Yanlin et al: "Implications of apurinic/apyrimidinic endonuclease in reactive oxygen signaling response after cisplatin treatment of dorsal root ganglion neurons" Cancer Research / American Association for Cancer Research, Philadelphia, PA. : AACR, vol. 68, No. 15, Aug. 1, 2008, pp. 6425-6434, XP008099535, ISSN: 1538-7445 p. 6427.
Reed April M et al: "Potentiation of melphalan-induced cytotoxicity through targeting of the base excision repair pathway in multiple myeloma" Blood, American Society of Hematology, US, vol. 110, No. 11,Part 2, Nov. 1, 2007, p. 273B, XP008099536 ISSN: 0006-4971, p. 237B.
Bondinell, William E., et al. "Synthesis of 2-methyl-3-vinyl-1, 4-naphthoquinones." *The Journal of Organic Chemistry* 33.12 (1968): 4351-4362.

* cited by examiner

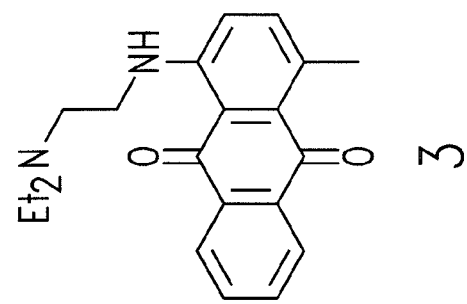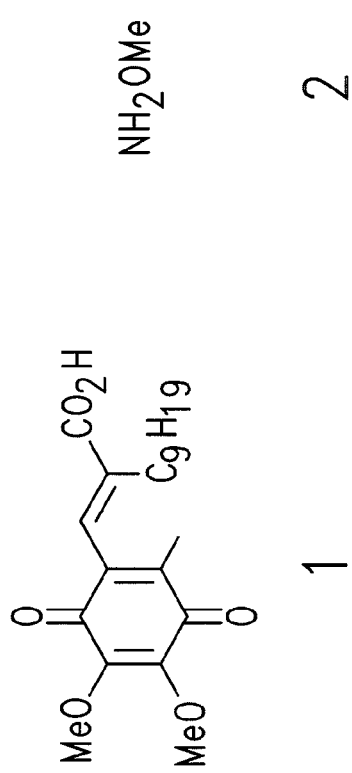
Fig. 6

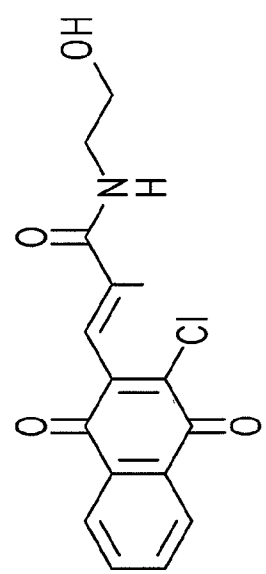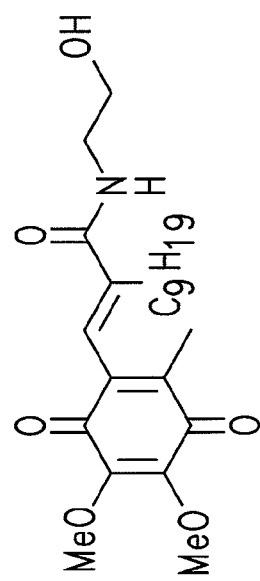
Fig. 8

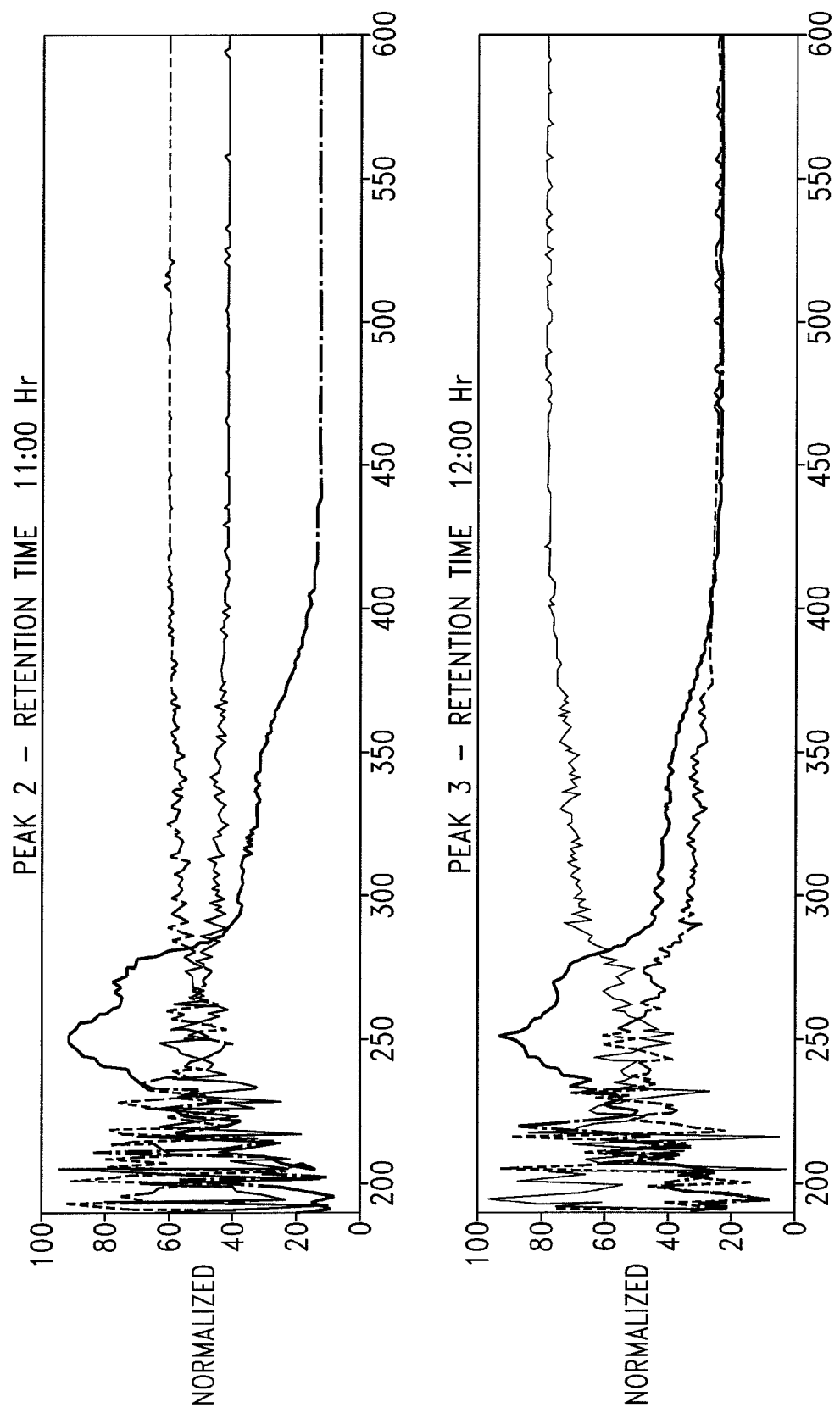

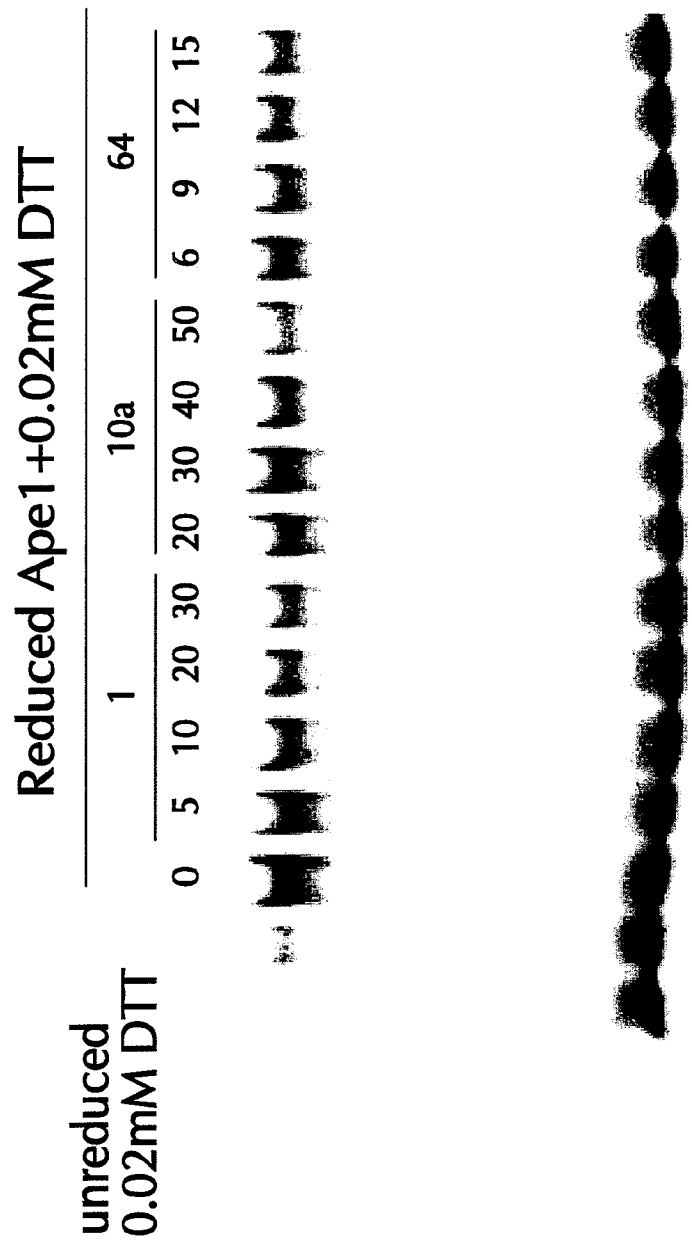
Figure 10: EMSA data for E3330 (1) and derivatives 10a (unsubstituted double bond) and 64 (methoxyethyl substituted double bond).

Figure 11: EMSA data for E3330 (1) and derivatives 10e (nbutyl substituted olefin)

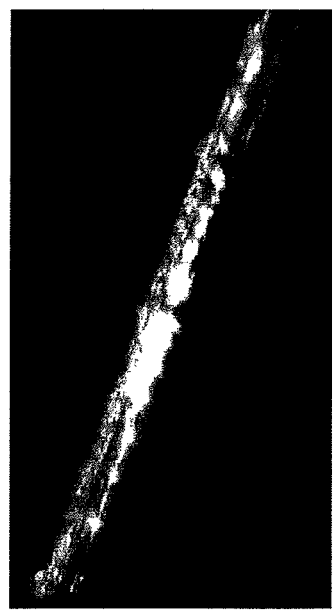
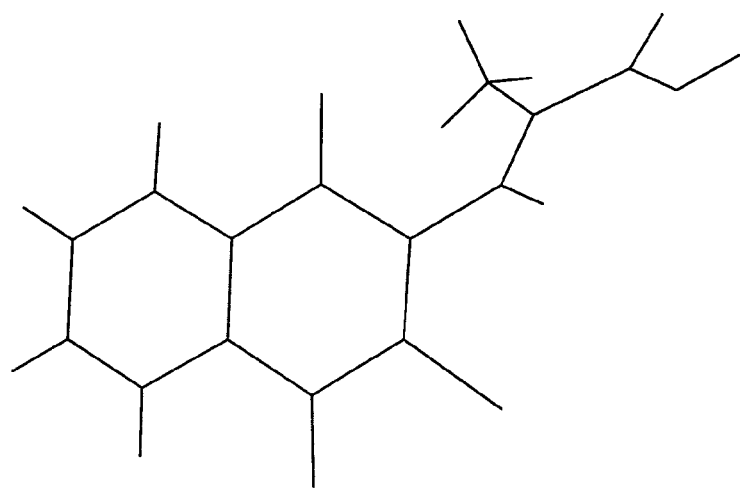
Figure 12: A. Crystal of inhibitor 43a used for X-ray diffraction study. B. Structure generated from data collected from X-ray diffraction studies on 43a.
Fig. 12

Figure 13: Structure derived from X-ray diffraction study shows both the relationship between quinone and unsaturated acid planes as well as tran-diene like unsaturated acid conformation.

QUINONE DERIVATIVES, PHARMACEUTICAL COMPOSITIONS, AND USES THEREOF

This application is a U.S. national counterpart application of international application serial No. PCT/US2008/077213 filed Sep. 22, 2008, which claims priority to U.S. Provisional Patent Application No. 60/975,396 filed Sep. 26, 2007 and to U.S. Provisional Patent Application No. 60/989,566 filed Nov. 21, 2007. The entire disclosures of PCT/US2008/077213, U.S. Ser. No. 60/975,396 and U.S. Ser. No. 60/989,566 are hereby incorporated by reference.

FIELD OF INVENTION

The present invention relates generally to the fields of molecular biology, biochemistry, and pathology. More specifically, in certain aspects, the invention relates to quinone derivatives useful as Ape1/Ref-1 redox inhibitors.

BACKGROUND

Apurinic/apyrimidic endonuclease (Ape1), also known as redox effector factor (Ref-1) (hereinafter Ape1/Ref-1 or Ape1) is an enzyme with a dual role. In addition to its DNA base excision repair (BER) activity, Ape1/Ref-1 also functions as a redox effector maintaining transcription factors in an active reduced state. All X-ray structures currently available for Ape1 depict the base excision repair (BER) site, and little structural information is known about the redox site. Cysteine 65 is the critical residue for redox function, unfortunately it is not solvent accessible in any structure.

Ape1/Ref-1 has been shown to stimulate the DNA binding activity of several transcription factors such as HIF-1α, NFκβ, AP-1 and p53, and others known and unknown, which are related to tumor survival and progression (Evans et al., *Mutat Res* 2000, 461, 83). Ape1/Ref-1 expression has been shown to be altered in a variety of cancers including breast, cervical, germ cell tumors, adult and pediatric gliomas, osteosarcomas, rhabdomyosarcomas, non-small cell lung cancer, and multiple myeloma (Puglisi et al., *Oncol Rep* 2002, 9, 11; Thomson et al., *Am J Pediatr Hematol Oncol* 2001, 23, 234; Roberston et al., *Cancer Res* 2001, 61, 2220; Puglisi et al., *Anticancer Res* 2001, 21, 4041; Koukourakis et al., *Int J Radiat Oncol Biol Phys* 2001, 50, 27; Kakolyris et al., *Br J Cancer* 1998, 77, 1169; Bobola et al., *Clin Cancer Res* 2001, 7, 3510). High Ape1/Ref-1 expression has also been associated with a poor outcome for chemoradiotherapy, poor complete response rate, shorter local relapse-free interval, poorer survival, and high angiogenesis (Koukourakis et al., *Int J Radiat Oncol Biol Phys* 2001, 50, 27; Kakolyris et al., *Br J Cancer* 1998, 77, 1169; Bobola et al., *Clin Cancer Res* 2001, 7, 3510).

Angiogenesis is an important component of cancer growth and metastasis. The formation of new blood vessels at the site of a cancerous tumor provides a source of nutrients for accelerated tumor growth and expansion as well as a path for tumor cells to enter the bloodstream and spread to other parts of the body. Thus, effective inhibition of angiogenesis is a useful mechanism to slow or prevent the growth and spread of cancer. An increase in Ape1/Ref-1 activity has been associated with angiogenesis. Vascular endothelial growth factor (VEGF) is an important signaling protein involved in both vasculogenesis and angiogenesis. Ape1/Ref-1 is a component of the hypoxia-inducible transcriptional complex formed on the vascular endothelial growth factor (VEGF) gene's hypoxic response element (Ziel et al., *Faseb J* 2004, 18, 986).

In addition to cancer, altered angiogenesis contributes to pathological conditions related to, among others, cardiovascular disease, chronic inflammatory disease, rheumatoid arthritis, diabetic retinopathy, degenerative maculopathy, retrolental fibroplasias, idiopathic pulmonary fibrosis, acute adult respiratory distress syndrome, asthma, endometriosis, psoriasis, keloids, and systemic sclerosis.

Inhibition of angiogenesis is a desirable clinical outcome for the amelioration or prevention of diseases involving altered angiogenesis.

Given the role the redox site looks to play in pathologies, it is desirable to design and synthesize compounds which preferably selectively inhibit the redox pathway.

SUMMARY OF INVENTION

This application describes quinone derivatives which target the redox site of Ape1/Ref1. Also included in the invention are pharmaceutical formulations containing the derivative and therapeutic uses of the derivatives.

BRIEF DESCRIPTION OF THE DRAWINGS

FIG. 6: Inhibitors of the Ape1 protein.

FIG. 7: Proposed mechanism for intramolecular esterification during nitric acid oxidation of (Z)-44a.

FIG. 8: Simple amide derivatives.

FIG. 10: EMSA data for E3330 (1) and derivatives 10a (unsubstituted double bond) and 64 (methoxyethyl substituted double bond).

FIG. 12: A. Crystal of inhibitor 43a used for X-ray diffraction study. B. Structure generated from data collected from X-ray diffraction studies on 43a.

DETAILED DESCRIPTION

Figure 1A:
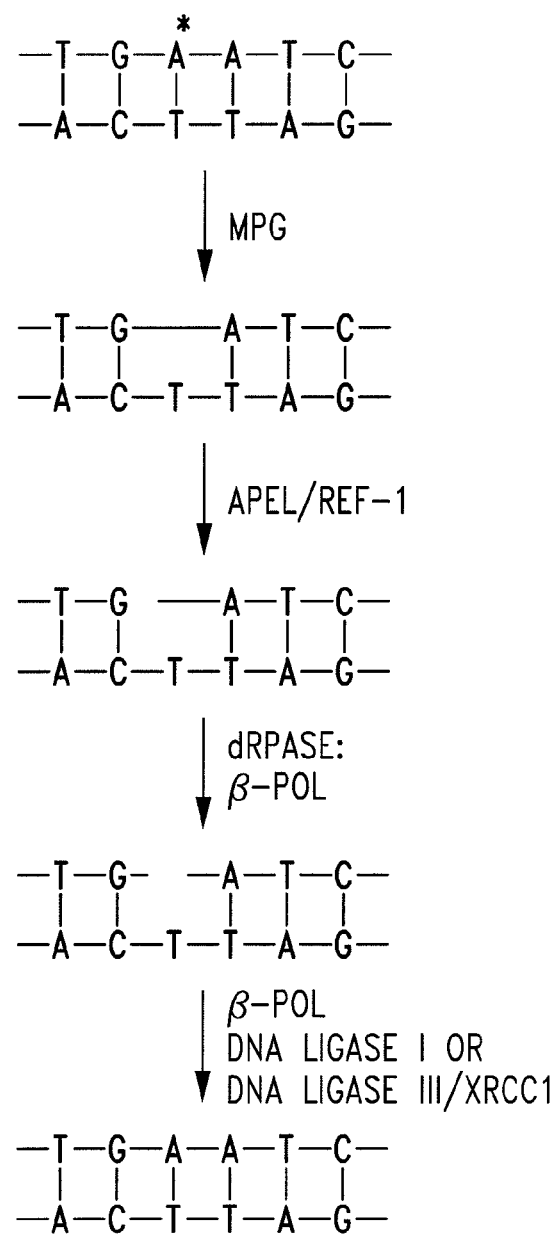
FIG. 1: Pathways of BER following either simple or complex glycosylase activity
Figure 1B:
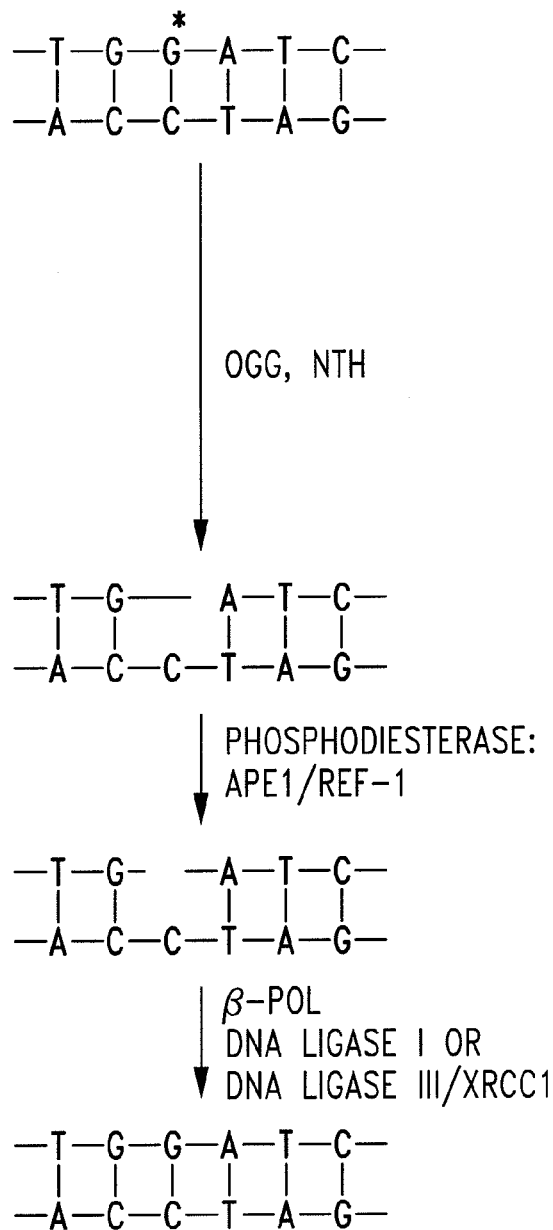

The most important regulatory processes for the genome are sustaining the fidelity and integrity of DNA, as well as appropriately expressing the genes contained therein. More than 130 genes are directly involved in maintaining fidelity within DNA, and potentially more than 2000 transcription factors regulate the expression of genes.[1] Human apurinic endonuclease-1/redox-enhancing factor-1 (Ape1/Ref1) functions in two capacities. The first function plays an integral role in the base excision repair (BER) pathway. BER is extremely important in regulating DNA fidelity as well as repairing DNA damage from exogenic and endogenic sources, such as alkylating agents and reactive oxygen species (ROS) respectively.[2] The BER pathway proceeds via the removal of a purine or pyrimidine base by either a simple or complex glycosylase, resulting in the formation of an apurinic site (AP site). (FIG. 1) AP sites form on the order of $10^4$ times per cell per day through spontaneous glycosidic bond hydrolyses alone, and when combined with bases damaged by alkylating agents, ROS, genotoxins, etc., the barrage of genetic damage is monumental.[3] Abasic sites pose detrimental consequences for the cell including single and double strand breaks, mutations, and ultimately apoptosis.[2] Ape1 is able to counter this genetic onslaught by being the only endonuclease capable of nicking the phosphate backbone 5' to the AP site in the case of a simple glycosylase, or excising a 3'-deoxyribose phosphate (dRP) in the case of a complex glycosylase (FIG. 1A and FIG. 1B, respectively).[2]

Figure 1C:
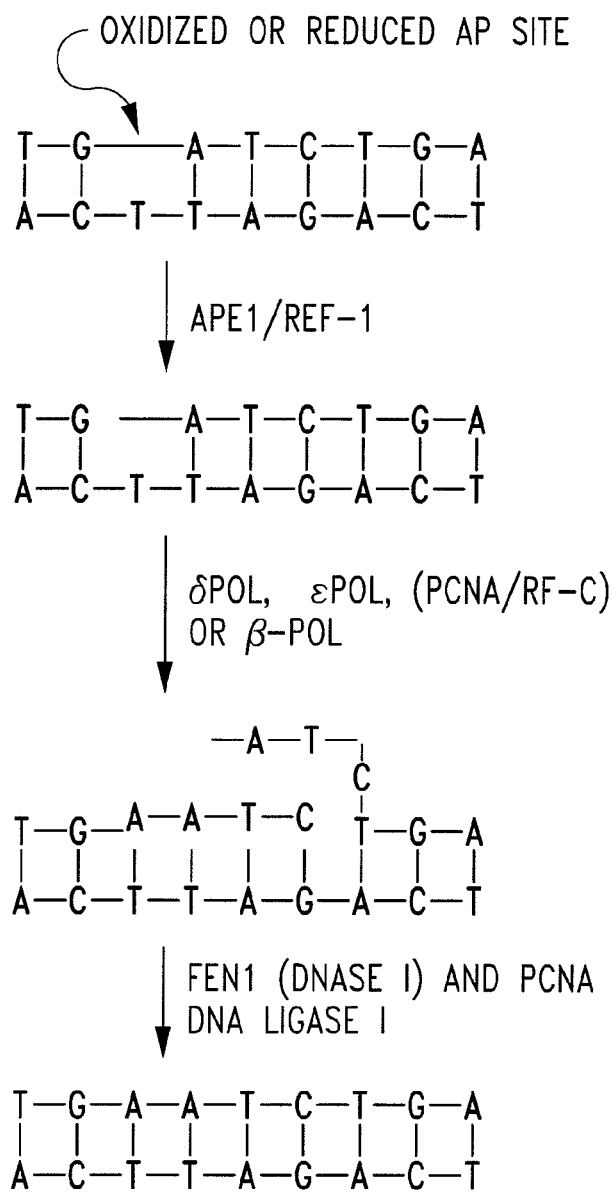

FIG. 1: Pathways of BER following either simple or complex glycosylase activity. A. Following base removal by a simple glycosylase (MPG) the phosphate backbone is still intact bearing an apurinic site. Ape1 acts as the 5' to 3' endonuclease, cleaving the backbone 5' to the abasic site, leaving a 5' phosphate and a 3' hydroxyl. β-polymerase then acts as the phosphodiesterase, removing the abasic site. B. Base removal by a complex glycosylase (OGG, NTH) results in an abasic site flanked by a 3' nick bearing a phosphate attached to the 3' hydroxyl. Ape1 then performs 3' to 5' exonuclease activity to remove the abasic site, preparing for base replacement by β-polymerase. C. Infrequently the sugar at the abasic site can become either reduced or oxidized, and Ape1 is then responsible for nicking 5' to the abasic site. Long Patch BER then takes place where multiple nucleotides are joined 5' to the AP site and then ligated to the damaged strand.[2]

The portion of genetic information that ultimately becomes transcribed into mRNA for processing into proteins needs to be regulated as tightly as the fidelity of the DNA. The second function of Ape1 controls the oxidation state of a multitude of transcription factors responsible for cell cycle progression, cell proliferation, and apoptosis, including activator protein-1 (AP1), hypoxia-inducible factor-1α (HIF-1α), and nuclear factor-κB (NFκB).[2,4] These transcription factors all contain cysteine residues that bind a specific promoter region in a DNA, and after a cycle of transcription activation these factors become oxidized. It is hypothesized that cysteine 65 of Ape1 performs the reduction of oxidized transcription factors.[5] The significance of C65 is supported by both the loss of redox activity in the C65A mutant, as well as gain of function in the corresponding zebrafish model where a critical cysteine residue is introduced in the T58C mutant (FIG. 2)[6] Conflicting data also exist that suggest C65 is not necessary for redox function. (FIG. 3)[7] Even though a majority of research seems to support a role for C65 in the redox regulation of transcription factors, a redox mechanism is not readily apparent because cysteine 65 is buried within the protein and therefore not solvent accessible (FIG. 5A).

Figure 2:
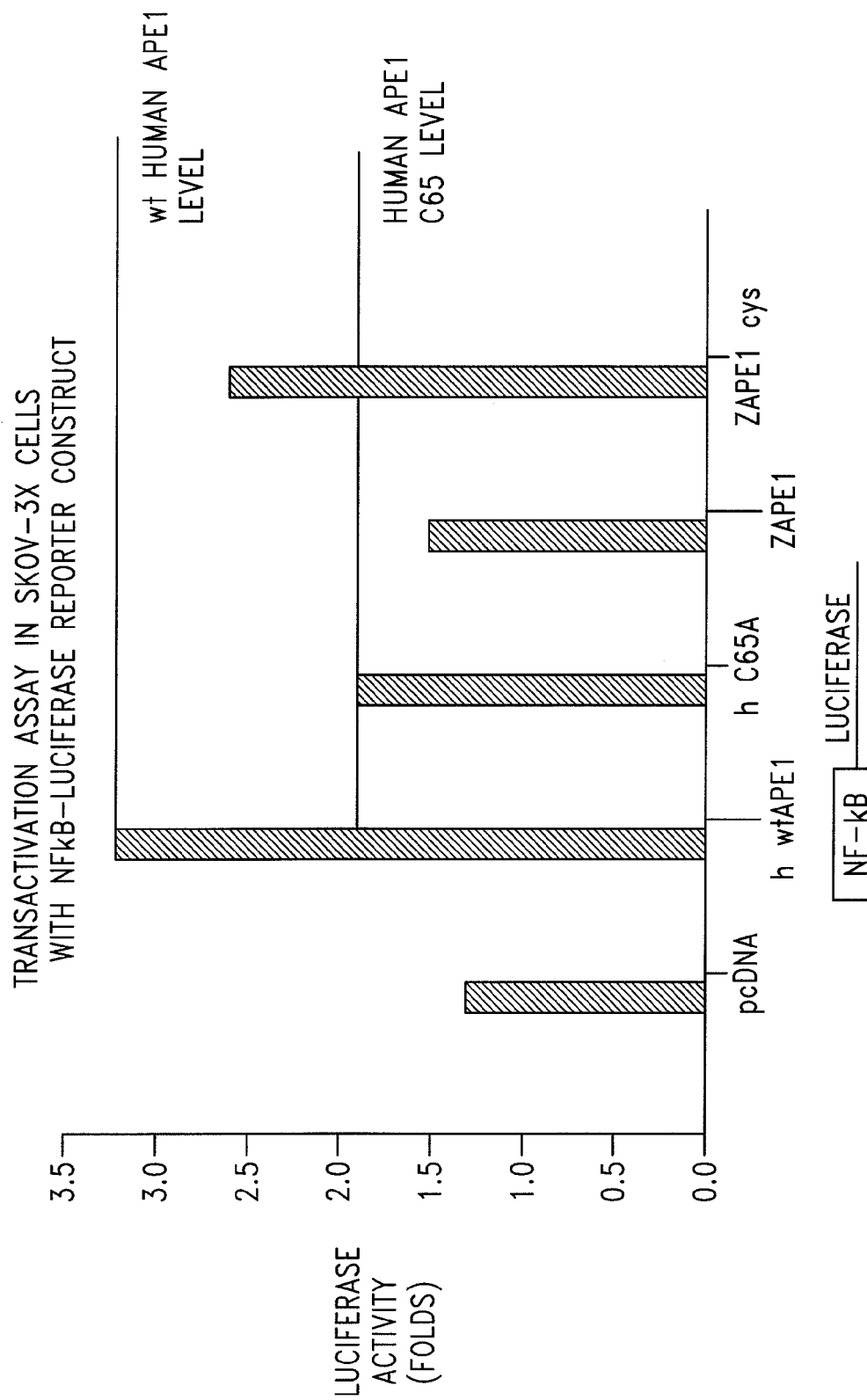
FIG. 2: Point mutation T58C to introduce derivativeous cysteine into zebrafish Ape1.

FIG. 2: Point mutation T58C to introduce derivativeous cysteine into zebrafish Ape1 affects redox abilities in the zebrafish model as measured by luciferase assay.[6]

Figure 3:
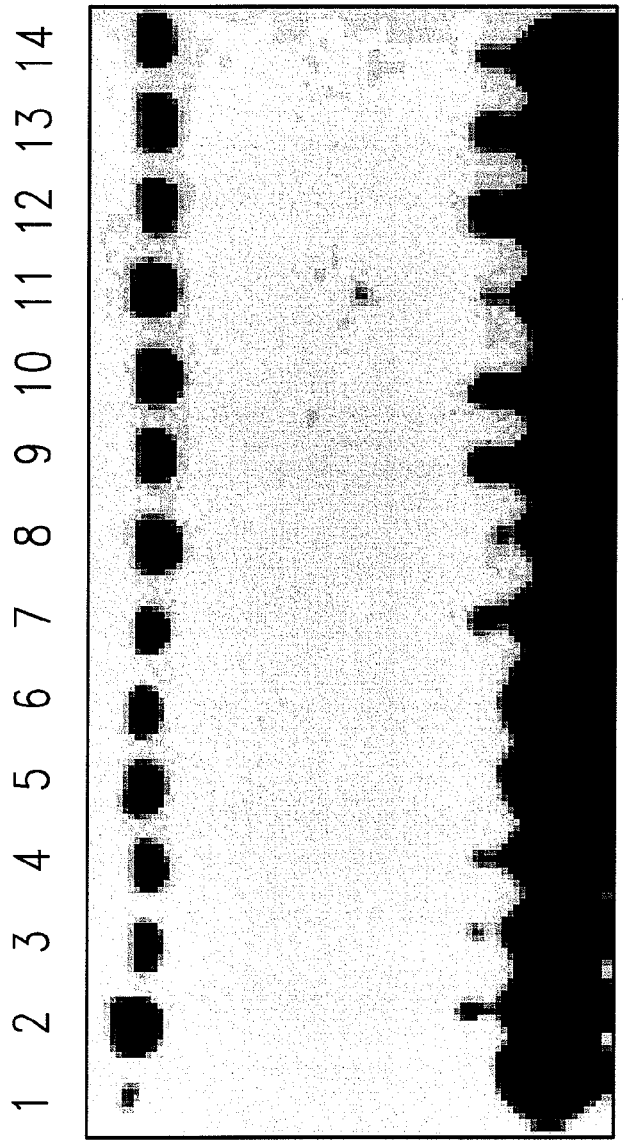
FIG. 3: EMSA data for wildtype Ape1 (C65) and C65A/C65A mutants.

FIG. 3: EMSA data for wildtype Ape1 (C65) and C65A/C65A mutants. The C64A point mutation does not affect redox function in human Ape1 suggesting this cysteine is not necessary for redox regulation of transcription factors. Lanes: 1) dilution buffer alone; 2) 10 mM DTT; 3 to 5) 10, 25, and 50 ng of wild-type lung extract, respectively; 6 to 8) 10, 25, and 50 ng of C64A/C64A lung extract, respectively; 9 to 11) 10, 25, and 50 ng of wild-type heart extract, respectively; 12 to 14) 10, 25, and 50 ng of C65A/C64A heart extract, respectively. C64 in murine Ape1 corresponds to C65 in human Ape1. The arrow indicates free DNA probe.[7]

Figure 4:
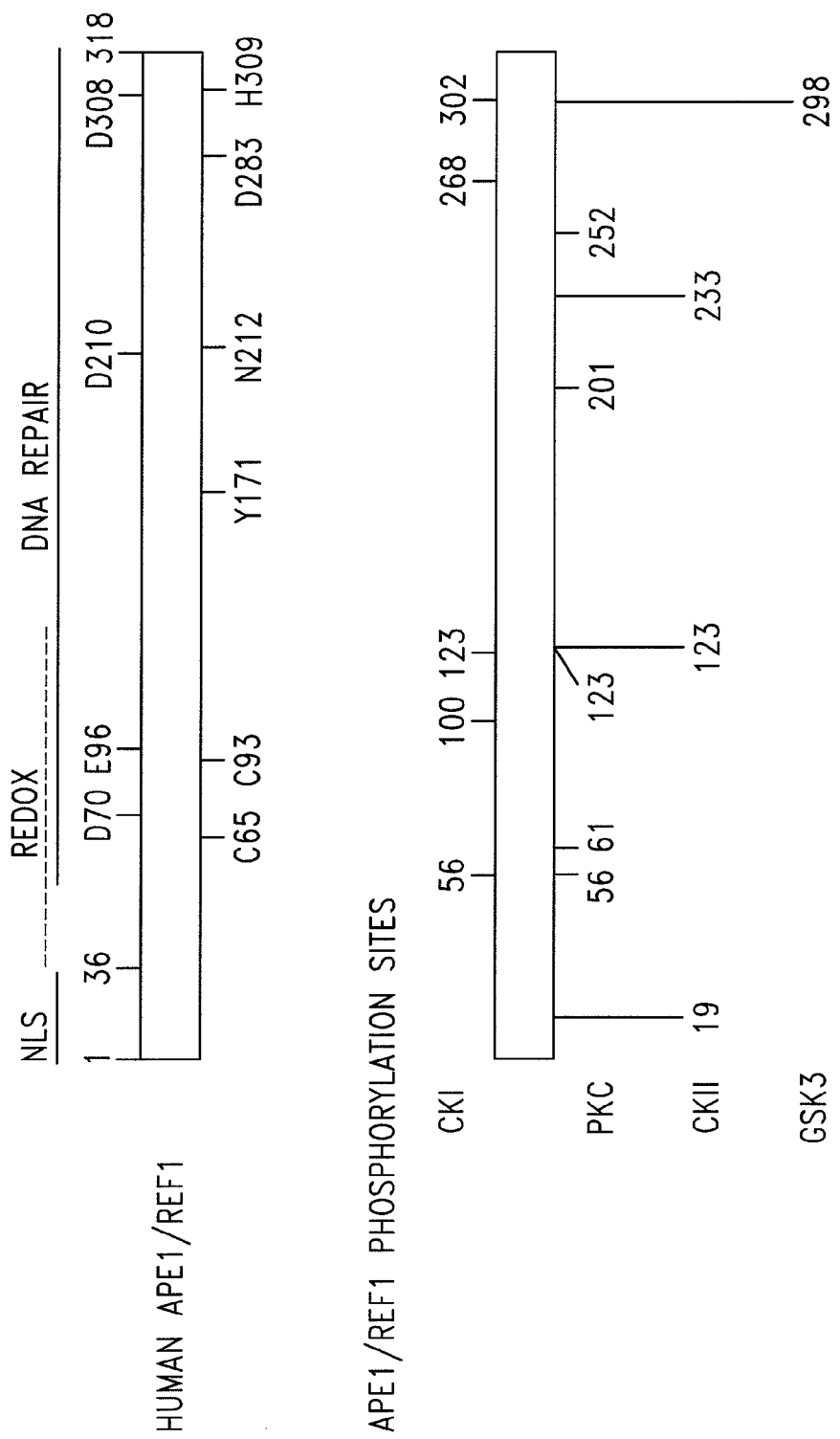
FIG. 4: Distribution of redox and repair domains (top) as well as the nuclear localization sequence in Ape1.

The BER and redox functions of Ape1 were discovered separately which led to the belief that they existed in two different proteins; this codiscovery is responsible for the Ape1/Ref1 dual name. Only years after the identification of both functions was it determined that they belonged to two slightly-overlapping domains of the same protein (FIG. 4).[8] Distribution of redox and repair domains (top) as well as the nuclear localization sequence in Ape1. Phosphorylation sites (bottom) located throughout the Ape1 sequence.[2]

Figure 5B:
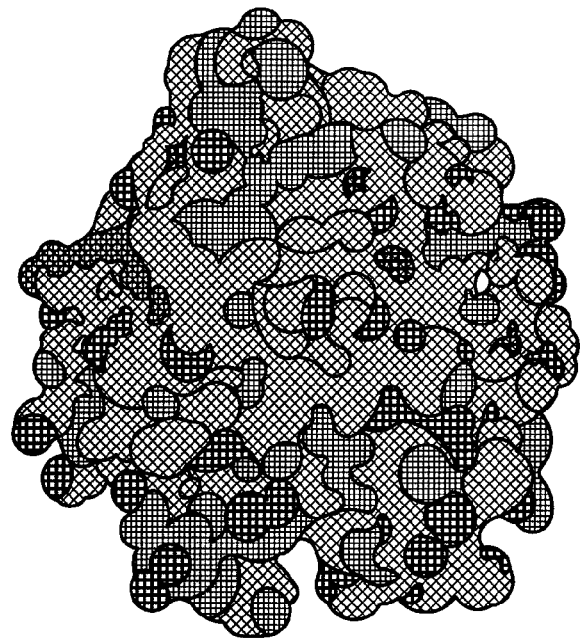
FIG. 5: A. Surface rendering of the 1DEW pdb crystal for Ape1.[9] Cysteine 65 is indicated by the arrow. B. Representation of the BER active site on the same pdb structure.
Figure 5A:
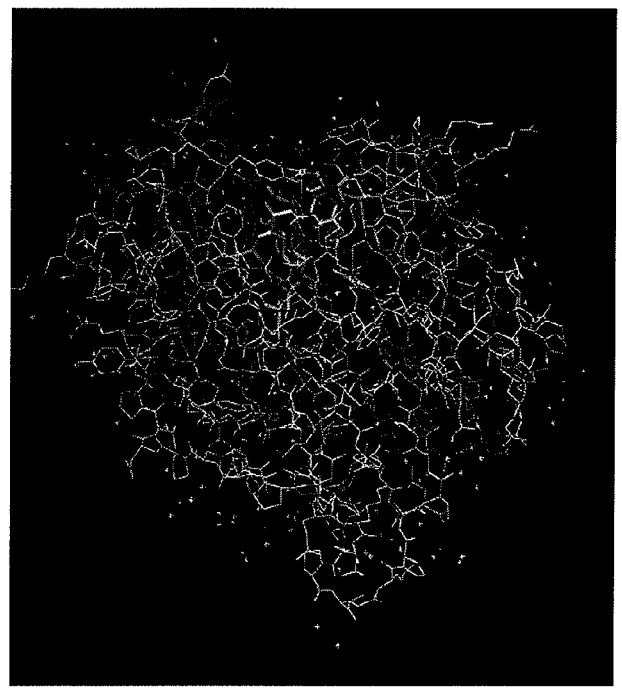

FIG. 5: A. Surface rendering of the 1DEW pdb crystal for Ape1.[9] Cysteine 65 is indicated by the arrow. B. Representation of the BER active site on the same pdb structure.

Ape1 has been found upregulated in small-cell lung, head and neck, prostate, cervical, germ cell, colon, and ovarian cancers.[2] AP sites caused by DNA damaging agents are efficiently repaired by Ape1, thus overexpression of Ape1 in cancer confers resistance to drugs that modify DNA. The redox function of overexpressed Ape1 also aids the tumor cell, where the unregulated redox-cycling of transcription factors enables the cancer cell to bypass fundamental cell-cycle checkpoints. Ape1 becomes an attractive target for drug design because of these two inherently important functions, but the salient questions that arise are which function should be inhibited and how?

Structurally there is significant information regarding the repair site, with a crystal structure of the protein bound to an abasic site on a short segment of double stranded DNA.[9] There is still very little known about the structure of the redox site. As previously mentioned the apparent redox cysteine is buried in all known crystal structures, and a redox active conformation may exist that has yet to be captured by crystallography. This leads to a great deal of ambiguity for a rational drug design approach, and thus inhibitor design requires a structure activity relationship (SAR) approach to determine preferences of the active site.

Presently there are only a few compounds shown to inhibit Ape1. Lucanthone, a natural product discovered and synthesized in the early 1950's, appears to act through an intercalative mechanism to inhibit the repair function of Ape1.[10] (Compound 3, FIG. 6) Methoxyamine also acts to inhibit the BER function; methoxyamine condenses with the aldehyde present in the hemiacetal of the abasic sugar, and Ape1 can no longer recognize the AP site for repair.[11] (Compound 2, FIG. 6) Both of these compounds act in an indirect way to inhibit the BER function of Ape1, but to date nothing has been shown to interact directly with the BER site on the Ape1 protein. Affinity chromatography and western blotting with radiolabeled drug were used to show E3330 (Compound 1, FIG. 6) was specific for only Ape1 from a crude cell lysate.[12]

The redox function of Ape1/Ref-1 was found to be selectively inhibited by 3-[(5-(2,3-dimethoxy-6-methyl-1,4-benzoquinoyl)]-2-nonyl-2-proprionic acid, below (hereinafter "E3330", also referred to as "RN3-3").

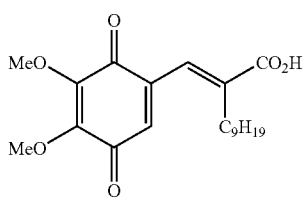

Further information on E33300 may be found in Abe et al., U.S. Pat. No. 5,210,239, fully incorporated herein by reference. Further, it has been determined with E3330 that selective inhibition of the redox function of Ape1/Ref-1 results in the inhibition of altered angiogenesis and cancer.

Based on the findings related to E3330, an effort was made to synthesize a range of quinone derivatives (benzoquinones and naphthoquinones) to determine their effect on the redox active site of Ape1. Another desire was to conjugate the derivatives to biotin in order to provide molecular tools for determining specificity and dissociation constants ($K_D$).

As the quinone E3330 has been shown to selectively inhibit the redox site of Ape1, this provided a starting point for further synthetic efforts. Without structural information regarding the redox active site on Ape1 the project began with a SAR approach, first examining the structure of E3330 to determine what aspects were important, and later applying this knowledge to the quinone derivatives.

The Emmons condensation of 6-methyl-2,3,4,5-tetramethoxybenzaldehyde (Compound 7, Scheme 1) was performed with a variety of alkylated phosphonoacetates. To make E3330 more druggable the n-nonyl sidechain needed to be truncated significantly, but it was equally important to ensure that reducing the size of the chain did not have less desirable affects on activity. The nonyl sidechain was replaced with n-butyl, n-propyl, ethyl, and methyl substituents, as well as an unsubstituted derivative. A methoxyethyl sidechain was also included to compare to the aliphatic sidechains. In order to modify the methyl substituent of the ring the des-methyl aldehyde (Compound 19, Scheme 1) was synthesized. The 2-chloro derivative was chosen because it presented a facile synthesis and would further develop knowledge regarding electronics of the benzoquinone ring. The chlorine substituent would be isosteric to the methyl group of E3330, while electronically different. Observations from the benzoquinone series would then be utilized to generate a series of naphthoquinone inhibitors.

Naphthoquinone inhibitors with a variety of substituents in the 3 position were synthesized, while maintaining a group of sidechains. Methyl substitution was first examined to correlate to the E3330 series. The halogenated derivatives (bromo, chloro, fluoro) were next synthesized to examine the effects of electronegative substituents replacing the ring methyl group. Then methoxy and methylthio derivatives were tested to observe the affect of including substituents that are electronegative, but significantly larger than the parent methyl compound.

Also, the epoxidation and reduction of the double bond, as well as synthesis of the Z isomer, were employed. The carboxylate functional group was modified by preparation of the methyl ester and hydroxyethylamide. These final derivatives shed light upon the importance regarding the entire unsaturated acid moiety of the naphthoquinone derivatives.

E3330 Derivatives

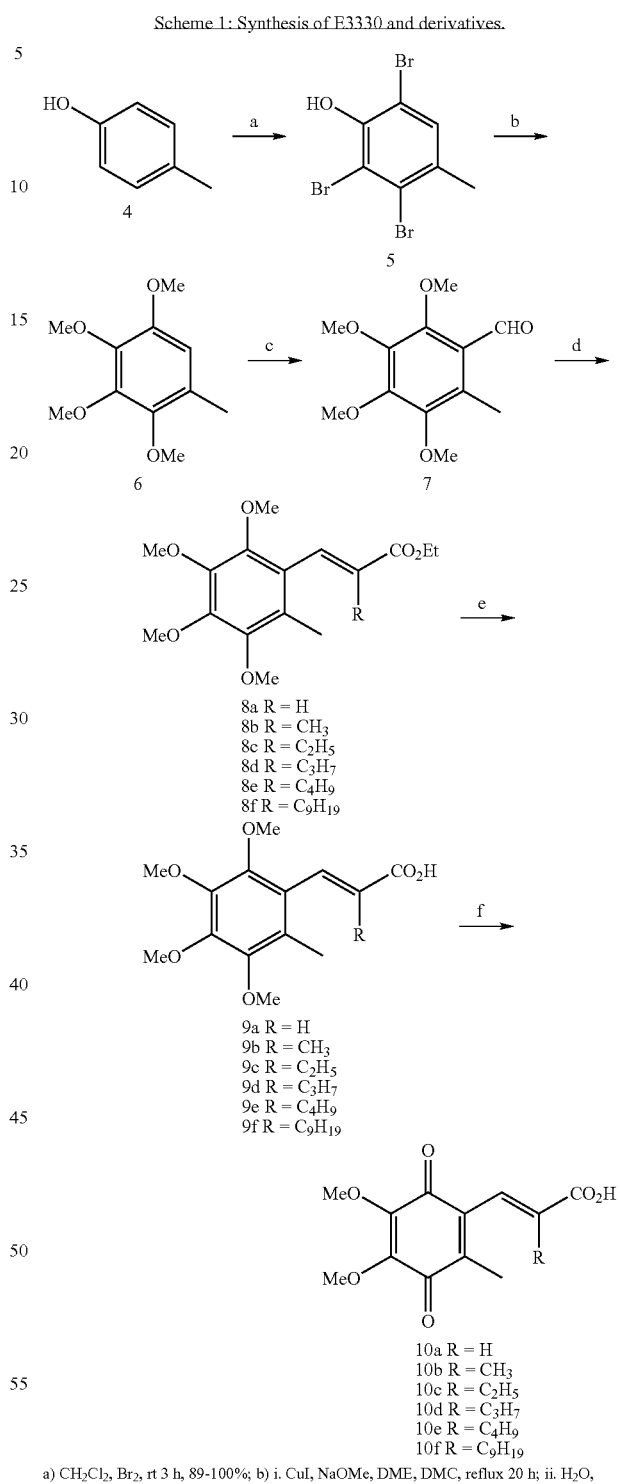

Scheme 1: Synthesis of E3330 and derivatives.

a) $CH_2Cl_2$, $Br_2$, rt 3 h, 89-100%; b) i. CuI, NaOMe, DME, DMC, reflux 20 h; ii. $H_2O$, $Me_2SO_4$, 4 h, 40-65%; c) $TiCl_4$, $CHCl_2OCH_3$, $CH_2Cl_2$, 0° C. to rt 4 h, 89%; d) NaH, $(EtO)_2P(O)CHRCO_2Et$, THF, rt 12 h, 42-88%; e) KOH, EtOH, reflux 30 min, 78-100%; f) $HNO_3$, AcOH, EtOAc, rt 4 h, 31-59%

First, E3330 was synthesized. The synthesis of E3330 (1) was performed based on a 1993 Japanese patent as shown in Scheme 1.[13] The first step of the synthesis requires the tribromination of 4-methylphenol (4) which proceeds rapidly at room temperature.[13,14] The reactions result in approximately a 90% yield of a white crystalline solid that can be readily separated from 2,6-dibromo-4-methylphenol via recrystallization from hexane.

The second step in the synthesis of E3330 is the most problematic, where the Ullmann-type methanolysis of 2,3,6-tribromo-4-methylphenol (5) results in multiple reduction byproducts that are not disclosed in the literature.[13,14] The optimized Ullmann conditions in our hands result in a mixture of 4-methyl-2,3,6-trimethoxyphenol (11, 75-85%), 2,6-dimethoxy-4-methylphenol (12, 10-15%), and 2,5-dimethoxy-4-methylphenol (13, 5-10%). (Scheme 2) The resulting phenols are alkylated to generate 2,3,4,5-tetramethoxytoluene (6) and the two trimethoxytoluenes (14 and 15). The isolated yield is considerably lower than the observed conversion by NMR, and removal of the two reaction sideproducts is necessary because both lead to E3330 derivatives missing crucial methoxy substituents.

Scheme 2: Observed reduction products during the Ullmann reaction of 4-methyl-2,3,6-tribromophenol.

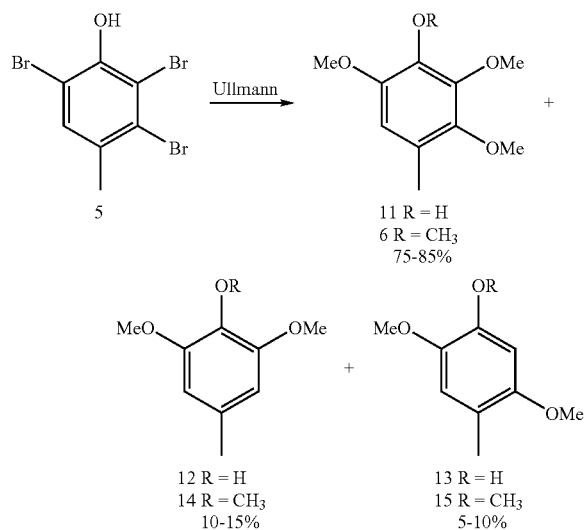

The Ullmann reaction can be quenched and worked up after the copper-mediated methanolysis of the aryl bromide to yield phenol 11, or subsequent in situ alkylation with methyl sulfate results in tetramethoxytoluene 6. The first option results in a decreased yield most likely resultant of the problematic workup with the Cu salts. The latter results in sideproduct 15 that is difficult to separate, and 14 with which separation is impossible. The first route provides a 50-60% yield of 6 following tedious chromatography. The second route results in 85% conversion by NMR and a mixture contaminated with 10% of 14.[13,14]

Formylation of 2,3,4,5-tetramethoxytoluene (6) to generate aldehyde 7 has been reported and proceeds in high yield.[15] The subsequent Emmons reactions with various alkylated phosphonoacetate reagents result in exclusive E-olefin formation at room temperature with 6-methyl-2,3,4,5-tetramethoxybenzaldehyde (8a-f; R=H, $CH_3$, $C_2H_5$, $C_3H_7$, $C_4H_9$, and $C_9H_{19}$). The hydrogen derivative (10a) represents complete removal of the sidechain, and the methyl derivative (10b) provides the shortest sidechain possible.

Hydrolysis of the ester is readily performed with KOH in EtOH and results in quantitative yield of the corresponding acid. Ring oxidation is the final transformation to quinone (10a-e, R=H, $CH_3$, $C_2H_5$, $C_3H_7$, $C_4H_9$; and 1, R=$C_9H_{19}$), where reported yields are below 50%.[13,16] Ceric ammonium nitrate (CAN) oxidation results in comparable yield to the published nitric acid oxidation reaction; however, the resulting product from the nitric acid oxidation is much purer.[13,16] Recrystallization is readily possible with the crude nitric acid oxidation product, whereas the CAN product typically needs chromatographic purification prior to recrystallization.

Scheme 3: Alternative synthesis of 6 enabling ring-modified derivatives.

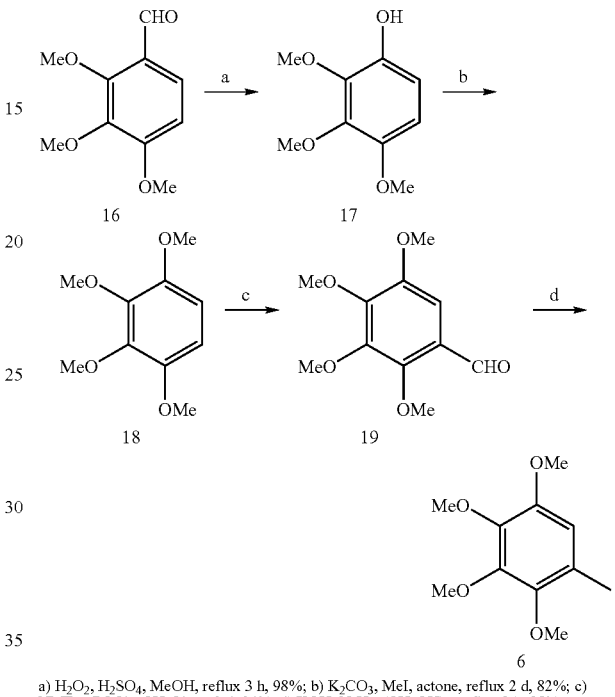

a) $H_2O_2$, $H_2SO_4$, MeOH, reflux 3 h, 98%; b) $K_2CO_3$, MeI, actone, reflux 2 d, 82%; c) NMFA, $POCl_3$, $CH_2Cl_2$, rt 2 d, 94%; d) KOH, $N_2H_4$, $(CH_2OH)_2$, reflux 8 h, 85%

An alternative method for generating tetramethoxytoluene 6 in a cleaner and slightly longer route is shown above in Scheme 3. In order to circumvent the problems associated with the Ullmann reaction a new method for incorporating the four methoxy substituents was devised that utilizes the cleavage of trimethoxybenzaldehyde to the corresponding phenol and then O-alkylation to tetramethoxybenzene. At this stage formylation followed by Wolffe-Kishner reduction provides toluene 6 in higher yield than direct alkylation of benzene 18. Another notable aspect of this synthesis is that it leads to a 2-unsubstituted benzaldehyde (19) ready for incorporation of 2-position substituents that is not accessible in the literature synthesis.

Bayer-Villiger oxidation of trimethoxybenzaldehyde (16) followed by in situ hydrolysis of the formate provides quantitative formation of trimethoxyphenol (17). Phenol 17 can then be alkylated in 85% yield to generate 1,2,3,4-tetramethoxybenzene (18).[17,18] The first transformation is sufficiently clean to avoid further purification of 17, and tetramethoxybenzene is readily recrystallized.[17] Formylation of tetramethoxybenzene proceeds in quantitative yield, and a Wolffe-Kishner reduction is then performed on the resulting benzaldehyde 19 to generate tetramethoxytoluene in greater than 90% yield.[19-21] This is another clean transformation not requiring further purification. The remaining transformations beginning with compound 6 are already described in the original E3330 synthesis and do not need further elaboration. (Scheme 1) This modified synthesis of 6 implements more facile steps to generate E3330 and takes the literature procedure of 7 steps with an overall yield of 15% to an 8 step synthesis with an overall yield of 24%.

2-Chloro E3330

Scheme 4: Ring modified derivatives synthesized from precursor 19.

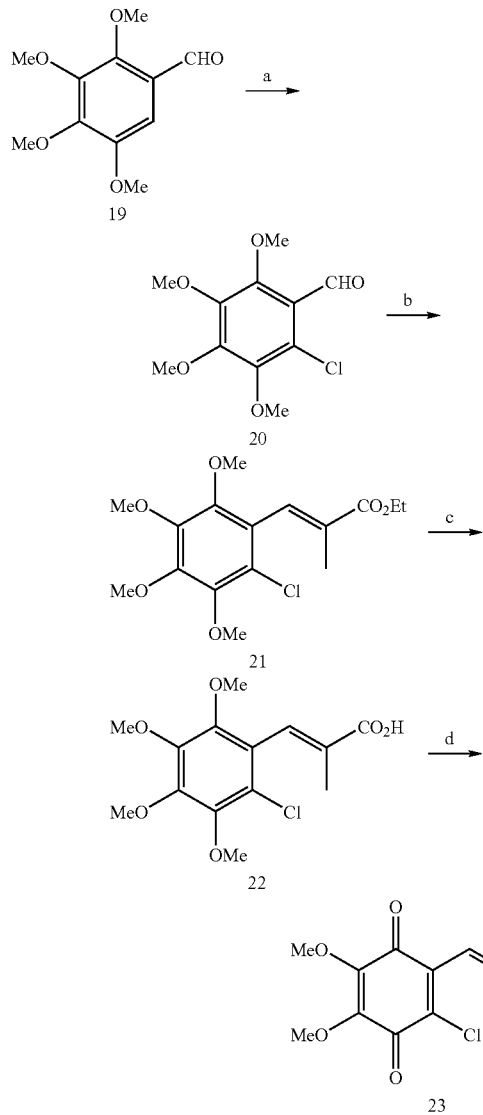

a) $SO_2Cl_2$, $CH_2Cl_2$, rt 15 min, 97%; b) NaH, $(EtO)_2P(O)CHCH_3CO_2Et$, toluene, reflux 8 h, 49%; c) KOH, EtOH, reflux 30 min, 95%; d) CAN, $H_2O:CH_3CN$ 1:1, rt 3 h, 22%

The modified synthesis of E3330 also enables ring substitution not possible with the literature method. A chlorine substituent at the 2-position of E3330 would affect the electronics of the ring while maintaining an isosteric substitution to the ring methyl. To generate the 2-chloro derivative of E3330 (23), aldehyde 19 was chlorinated using $SO_2Cl_2$ at room temperature, which proceeds in excellent yield. Unlike the 3-methyl derivatives, the 3-chloro derivative 20 suffered from reduced E selectivity during the Emmons reaction, where up to 15% of the Z product is observed at room temperature. E and Z isomers were easily distinguished by the chemical shift of the vinyl proton. The E isomer vinyl proton appears downfield of the Z isomer by as much as 0.5 ppm in some derivatives. Emmons condensation of 20 in refluxing toluene provides 100% E product, which can then be saponified in KOH/EtOH. (scheme 4) The final oxidation to 23 was initially attempted with nitric acid and no starting material or product was recovered. This suggested the nitric acid conditions were too harsh for either the tetramethoxybenzene or the quinone product. CAN was then evaluated and found to be a sufficiently mild oxidant to perform the transformation without destroying the product or starting material. Thus 23 was finally synthesized from 22 in 40% yield via oxidation with CAN.

3-Unsubstituted Naphthoquinones

Scheme 5: Literature based synthesis of alcohol 26 and subsequent transformations to supply 3-unsubstituted naphthoquinones 30a,b.

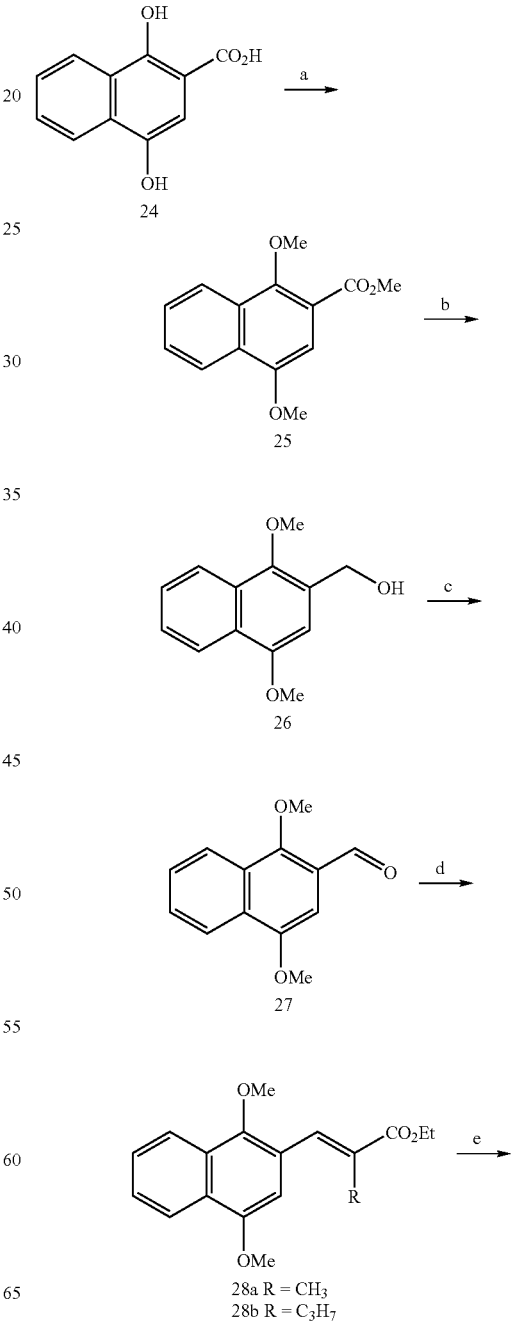

28a R = $CH_3$
28b R = $C_3H_7$

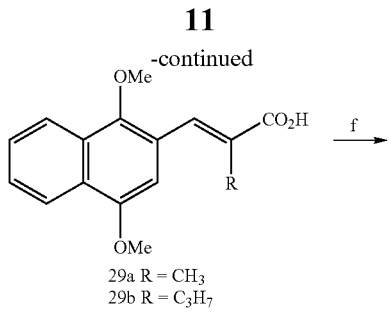

29a R = CH₃
29b R = C₃H₇

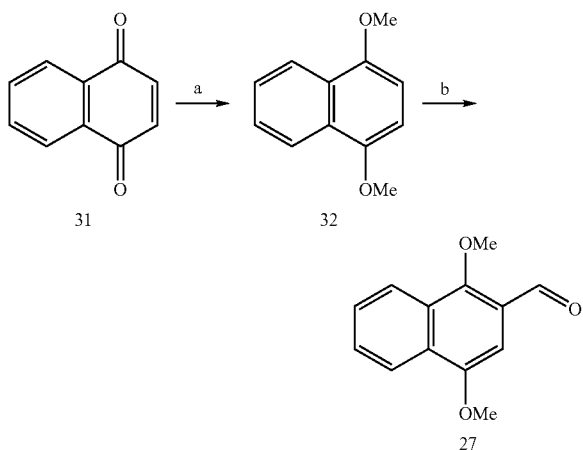

30a R = CH₃
30b R = C₃H₇ a) K₂CO₃, MeI, acetone, reflux 12 h, 96%; b) LiAlH₄, THF, rt 8 h, 97%; c) PCC, CH₂Cl₂, rt 8 h, 85%; d) NaH, (EtO)₂P(O)CHRCO₂Et, toluene, reflux 8 h, 59-73%; e) KOH, EtOH, reflux 30 min, 83-99%; f) HNO₃, AcOH, EtOAc, rt 4 h, 37-58%

Efforts were then directed toward synthesis of naphthoquinone derivatives. The simplest series included no substituent at the 3-position; without a sterically hindering substituent these compounds would help to expose the potential for Michael addition reactions on the quinone.

Initially, the synthesis of aldehyde 27 was performed using a route that had been previously used in the Borch group to generate alcohol 26.[22] (Scheme 5) This route was also used to generate 3-methyl derivatives where alcohol 26 was alkylated using nBuLi/MeI; unfortunately, this alkylation resulted in 70-80% yields where the starting material and product were difficult to separate. This led to the investigation of other means to generate 1,4-dimethoxy-2-naphthylaldehyde (27) and 1,4-dimethoxy-3-methyl-2-naphthylaldehyde (34). The reductive alkylation of 1,4-naphthoquinone leads to 1,4-dimethoxynaphthalene 32 in quantitative yield.[23] (Scheme 6) Formylation of 32 using TiCl₄/CHCl₂OCH₃ provides aldehyde 27.[24]

Scheme 6: Synthesis of aldehyde 27.

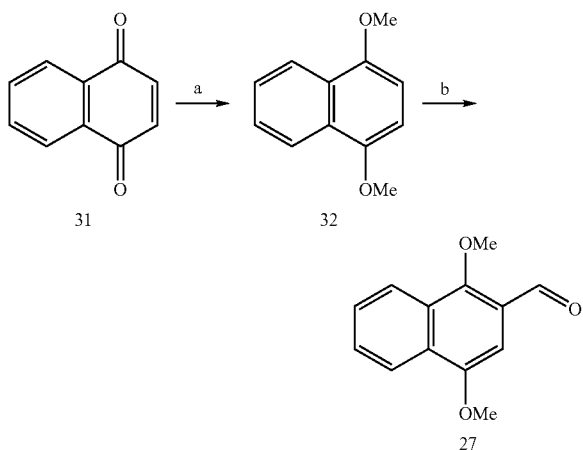

a) i. Pd/C, H₂, THF, rt 4 h, ii. NaH, Me₂SO₄, rt 2 h, 99%; b) NMFA, POCl₃, rt 24 h, 83%

Aldehyde 27 was then utilized in the Emmons reaction with either ethyl 2-phosphonopropionate or ethyl 2-phosphonopentanoate to generate esters 28a and 28b, respectively. The Emmons condensation with aldehyde 27 preceded at room temperature to produce nearly 100% E product. Saponification and oxidation of the resulting derivatives proceeded without incident. (Scheme 5) The final oxidation of the 3-unsubstituted naphthalenes resulted in 70% yield.

3-Methyl Naphthoquinones

Scheme 7: Efficient synthesis of 3-Methyl naphthoquinone derivatives.

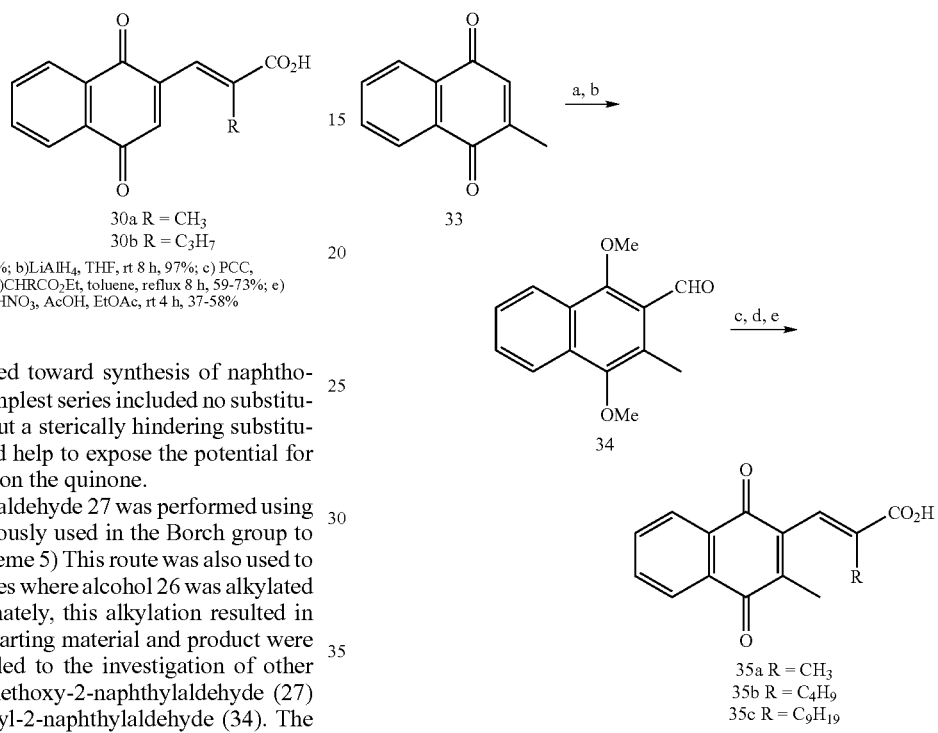

35a R = CH₃
35b R = C₄H₉
35c R = C₉H₁₉ a) i. Pd/C, H₂, THF, rt 4 h, ii. NaH, Me₂SO₄, rt 2 h, 99%; b) DMF, POCl₃, rt 24 h, 69%; c) NaH, (EtO)₂P(O)CHRCO₂Et, toluene, reflux 8 h, 34-65%; d) KOH, EtOH, reflux 30 min, 83-100%; e) HNO₃, AcOH, EtOAc, rt 4 h, 36-65%

The 3-methyl derivatives were then prepared Synthesis of the 3-methyl series began with the reductive alkylation of naphthoquinone 33 followed by formylation to generate aldehyde 34.[23,24] (Scheme 7) The Emmons reaction with aldehyde 34 resulted in approximately 85% E product when carried out in THF at room temperature and essentially 100% E in refluxing toluene. Separation of E and Z isomers by chromatography was difficult; typically the Z isomer could not be isolated in pure form. Ester hydrolysis using KOH/EtOH proceeded rapidly at 80° C., and the oxidation was performed with nitric acid in ethyl acetate.

3-Bromo Naphthoquinones

Scheme 8: Initial synthetic strategy for incorporating the 3-bromo substitution in naphthoquinone derivatives.

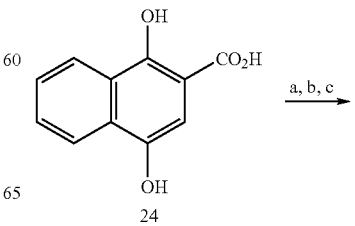

24

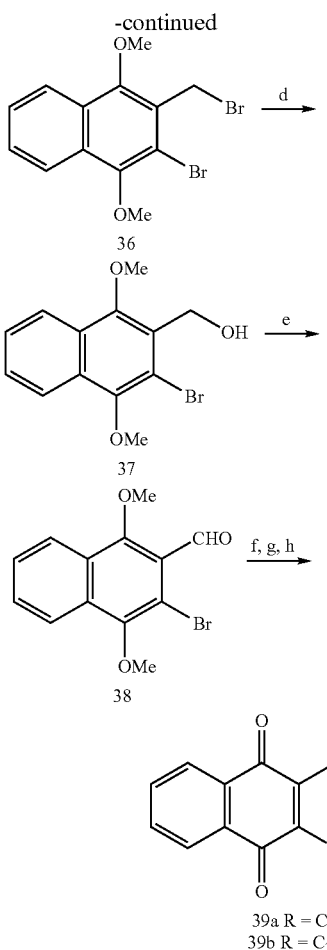

36

37

38

39a R = CH$_3$
39b R = C$_3$H$_7$ a) K$_2$CO$_3$, MeI, acetone, reflux 12 h, 96%; b) LiAlH$_4$, THF, rt 8 h, 97%; c) i. HBr, CH$_2$Cl$_2$; ii. Br$_2$, CH$_2$Cl$_2$, 56%; d) CaCO$_3$, H$_2$O:Glyme 1:1, reflux 12 h, 100%; e) PCC, CH$_2$Cl$_2$, rt 8 h, 88%; f) NaH, (EtO)$_2$P(O)CHRCO$_2$Et, toluene, reflux 8 h, 41-47%; g) KOH, EtOH, reflux 30 min, 47-100%; h) Ag(II)O, HNO$_3$, AcOH, EtOAc, rt 30 min, 46%

Substituents at the 3-position were prepared. Bromine and chlorine substitution were the first derivatives explored, and later fluorine with the greatest electronegativity was prepared.

The 3-bromo derivatives were initially prepared by a lengthy synthesis. (Scheme 8) Problems were encountered with the bromination of aldehyde 27 using bromine, where oxidation to the carboxylic acid was observed as a side reaction. In order to avoid this problem, bromination of alcohol 26 (Scheme 5) was attempted, and it was discovered that regardless of conditions, in situ generated HBr displaced the alcohol to generate dibromide 36. (Scheme 8) The 3-bromo alcohol 37 could be easily regenerated from 36 in quantitative yield using CaCO$_3$/glyme.[25] Oxidation of the alcohol provided aldehyde 38 in reasonable yield. Subsequently it was determined that the best route was to brominate 1,4-dimethoxy-2-naphthaldehyde (27), accepting the loss of product due to oxidation.

As an Emmons substrate the 3-bromo aldehyde 38 produced a significant amount of Z-olefin product; even in boiling toluene 15% Z isomer was observed. This led to low yields of purified E product due to typical difficulties separating the E and Z isomers. After hydrolysis, oxidation to the quinone was first attempted using HNO$_3$/EtOAc/AcOH, but only starting material was recovered. By adding Ag(II)O to the nitric acid conditions complete conversion to the quinone was observed by TLC and NMR.[16,22] (Scheme 8) The resulting quinones were obtained in 70% yield.

3-Chloro Naphthoquinones

Scheme 9: Synthesis of 3-chloro naphthoquinones from common precursor 27.

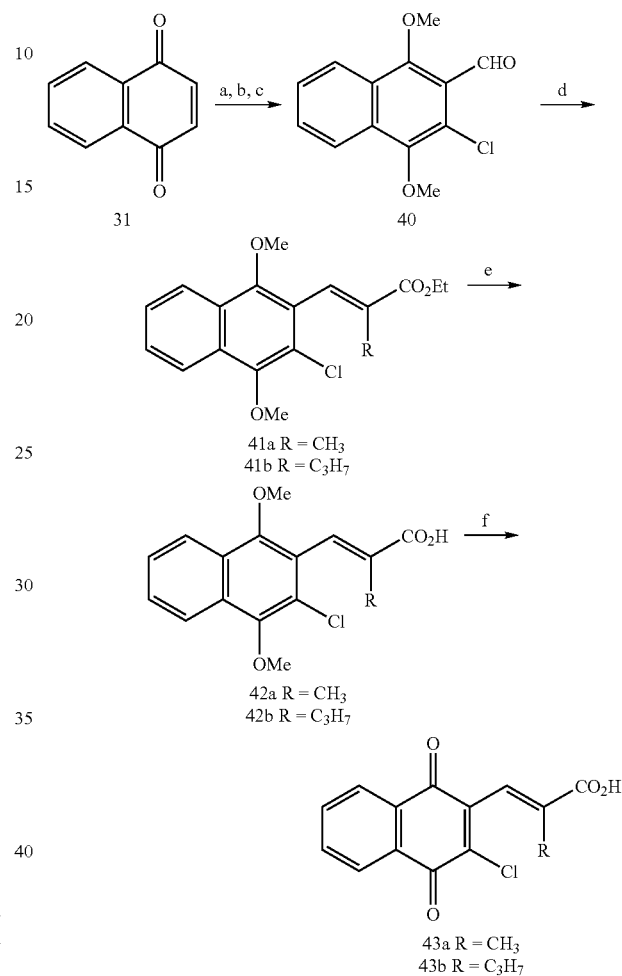

31

40

41a R = CH$_3$
41b R = C$_3$H$_7$

42a R = CH$_3$
42b R = C$_3$H$_7$

43a R = CH$_3$
43b R = C$_3$H$_7$ a) i. Pd/C, H$_2$, THF, rt 4 h, ii. NaH, Me$_2$SO$_4$, rt 2 h, 99%; b) NMFA, POCl$_3$, rt 24 h, 83%; c) SO$_2$Cl$_2$, CH$_2$Cl$_2$, rt 2 d, 66%; d) NaH, (EtO)$_2$P(O)CHRCO$_2$Et, toluene, reflux 8 h, 27-54%; e) KOH, EtOH, reflux 30 min, 98-100%; f) Ag(II), HNO$_3$, AcOH, EtOAc, rt 30 min, 16-33%; OR f) Ag(II)O, 6M HNO$_3$, dioxane, rt 2 min, 67%

Synthesis of the 3-chloronaphthoquinone series was undertaken starting with aldehyde 27. SO$_2$Cl$_2$ proved to be a much milder reagent than the brominating reagents, thus no problems were encountered converting 27 to chloroaldehyde 40. (Scheme 9) As an alternative approach, attempts were made to formylate 2-chloro- and 2-bromo-1,4-dimethoxynaphthalene. However, it seems the electron withdrawing nature of the halogens was too great to allow formylation of these substrates.

Aldehyde 40 was used as the substrate for the Emmons reaction, generating esters 41a,b in 75% yield. The Emmons reaction with aldehyde 40 resulted in low E-selectivity, approximately 15% Z isomer was produced in boiling toluene. (Scheme 9) Hydrolysis and final ring oxidation utilized the same conditions as the 3-bromo derivatives and proceeded well to give quinones 43a,b.

The possibility of separating E and Z isomers after final oxidation was to be explored, so a mixture of E and Z Emmons products (E-41a and Z-41a) was saponified and oxidized under typical conditions. ((Scheme 9, Scheme 10)

Scheme 10: Unexpected transformation of Z-isomer Emmons products upon oxidation of hydrolyzed Z-42b.

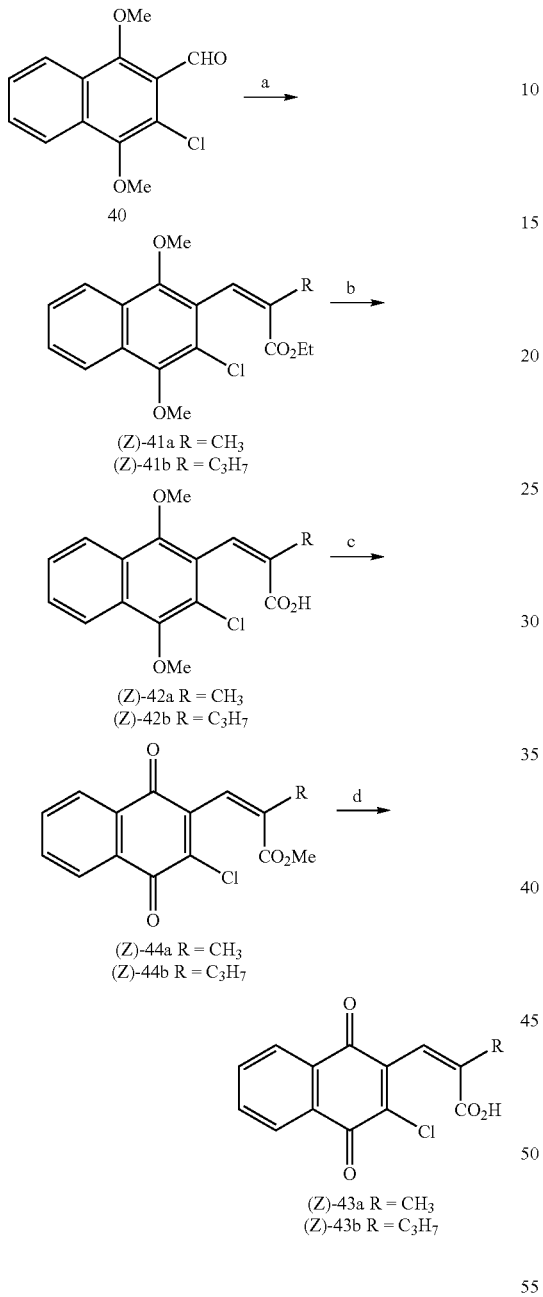

a) NaH, (EtO)$_2$P(O)CHRCO$_2$Et, toluene, reflux 8 h, 5-10%; b) KOH, EtOH, reflux 30 min, 99%; c) Ag(II)O, HNO$_3$, AcOH, EtOAc, rt 30 min, 14%; d) 2M HCl, EtOH, reflux 1 h, 49%

The resulting mixture of E and Z products was chromatographed, and two products were readily separated and analyzed by MS and NMR. The slow eluting band was identified as pure E isomer 43a. The less polar compound appeared to be the Z isomer although an additional 3-proton peak at 3.06 ppm was observed. NMR and MS analysis ultimately confirmed that the product was the methyl ester Z-44a.

Figure 7:
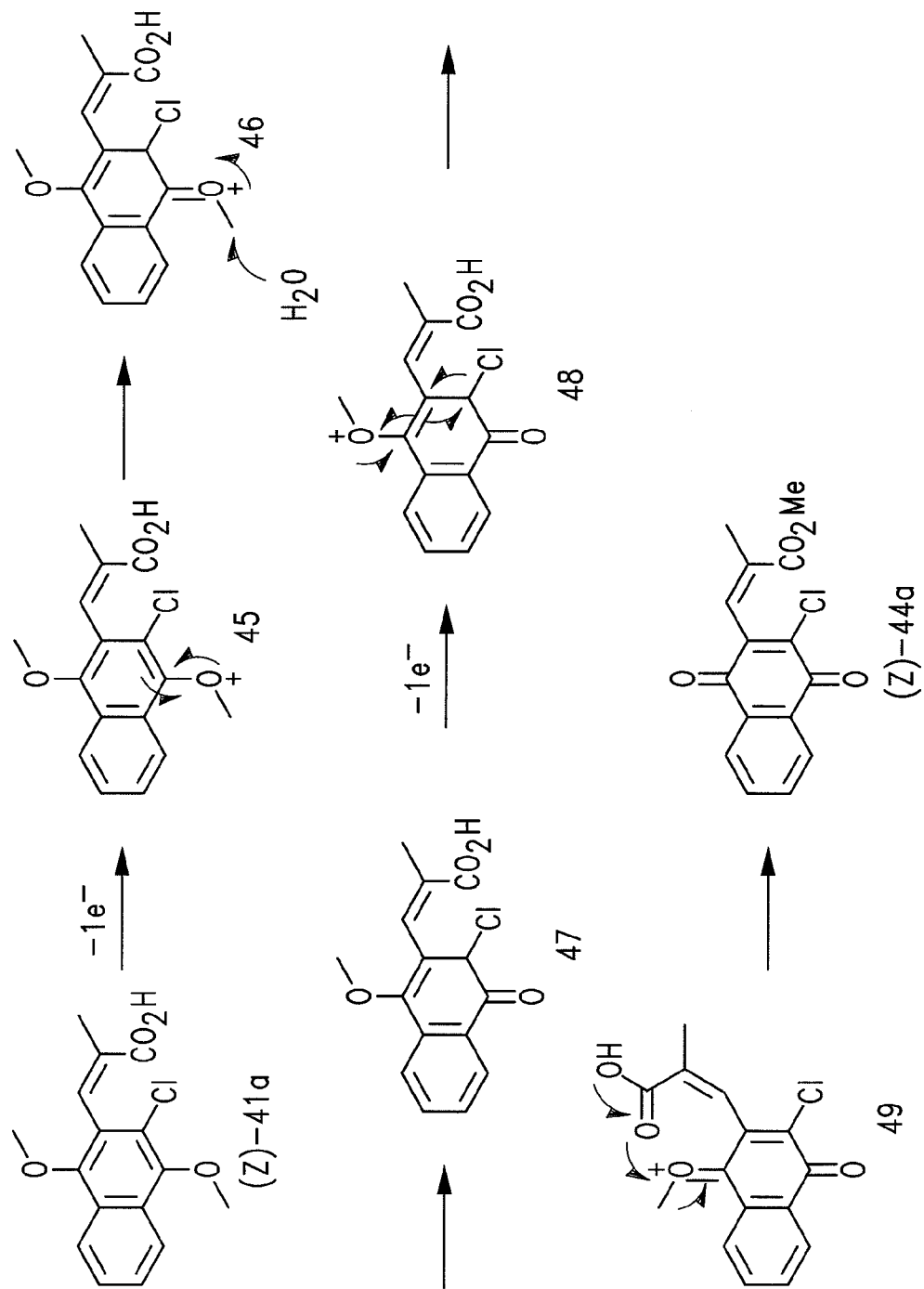

Figure 7: Proposed mechanism for intramolecular esterification during nitric acid oxidation of (Z)-44a.

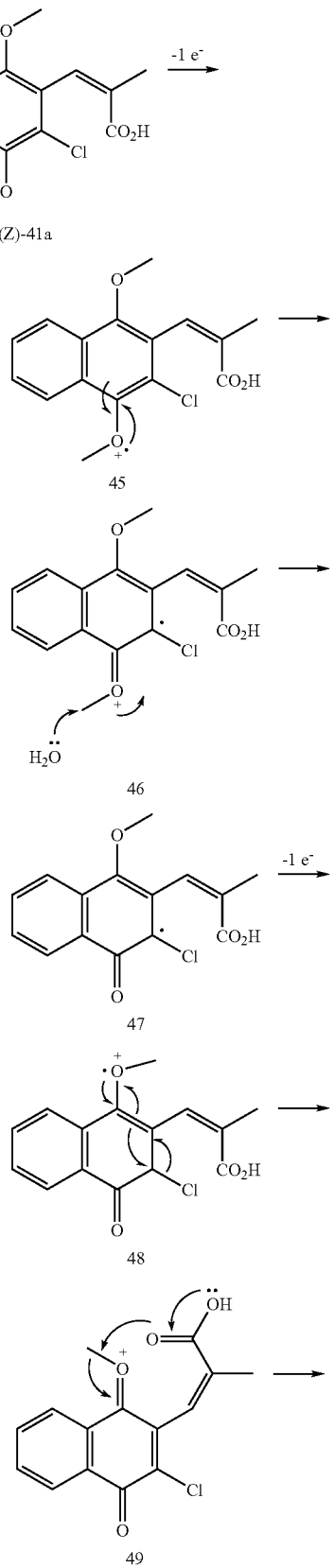

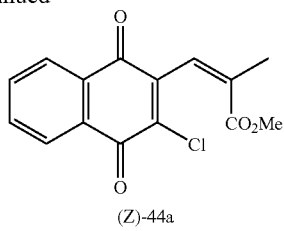

(Z)-44a

After examining the potential rotamers of the Z isomer it became apparent that during oxidation, the carboxylic acid of the Z isomer would be able to attack the methyl group of the oxonium intermediate 49, performing an intramolecular esterification. (FIG. 7) This was further verified by hydrolysis of the ester (Z-44a) in HCl/EtOH; KOH/EtOH was attempted but destroyed the starting material. Therefore it was postulated that separation of E and Z ester isomers is not necessary after the Emmons reaction, because the Z methyl ester and E carboxylic acid are readily separable after final oxidation. The only series that did not appear to undergo this intramolecular esterification was the 3-unsubstituted derivatives, suggesting substitution at the 3 position favors the rotamer that can undergo cyclization.

3-Fluoro Naphthoquinones

Scheme 11: Initial synthetic strategy for preparing 3-fluoro naphthylaldehyde 51.

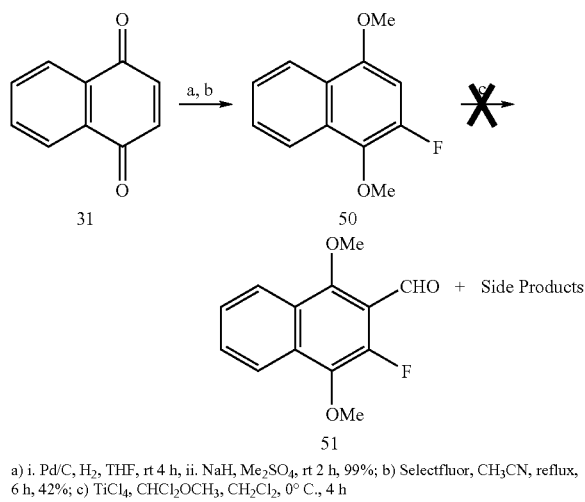

a) i. Pd/C, H$_2$, THF, rt 4 h, ii. NaH, Me$_2$SO$_4$, rt 2 h, 99%; b) Selectfluor, CH$_3$CN, reflux, 6 h, 42%; c) TiCl$_4$, CHCl$_2$OCH$_3$, CH$_2$Cl$_2$, 0° C., 4 h Aromatic fluorinations can be difficult transformations to execute; fortunately, advances in fluoride cation chemistry have enabled the synthesis of compounds that were previously inaccessible. Based on reactivity, the approach outlined in Scheme 11 was considered to generate aldehyde 51, because the aromatic ring of 1,4-dimethoxynaphthalene (Compound 32, Scheme 6) would be more electron rich than that of aldehyde 27. Fluorination of both 1,4-dimethoxynaphthalene to prepare 50, and 1,4-dimethoxy-2-naphthaldehyde to produce 51 proceeded well in refluxing acetonitrile, although the reaction with aldehyde 27 produced side products that resulted in lower yields. Formylation of 50 was then attempted using TiCl$_4$ and CHCl$_2$OCH$_3$ in CH$_2$Cl$_2$, and surprisingly the starting material was completely consumed within 4 hours. It was expected that with the electron withdrawing fluorine adjacent to the formylation site this transformation would be difficult; however, TLC of the reaction mixture showed one component that had the same R$_f$ as previously synthesized aldehyde 51. Upon examination of the reaction product by NMR it was determined that the formylated compound was not simply aldehyde 51, but a mixture of four regioisomers. $^{19}$F NMR gave the most compelling analysis of the reaction mixture, for there were three sets of doublets corresponding to fluorine atoms adjacent to an aromatic proton, and one singlet corresponding to the 3-fluoro product 51 obtained through fluorination of unsubstituted aldehyde 27. The doublets possessed the same coupling constants observed in 1,4-dimethoxy-2-fluoronaphthalene, and it was obvious that the strategy outlined in Scheme 11 was not going to work.

Scheme 12: Revised synthesis of 3-fluoro aldehyde 51 and subsequent transformation to generate 3-fluoro naphthoquinone 52.

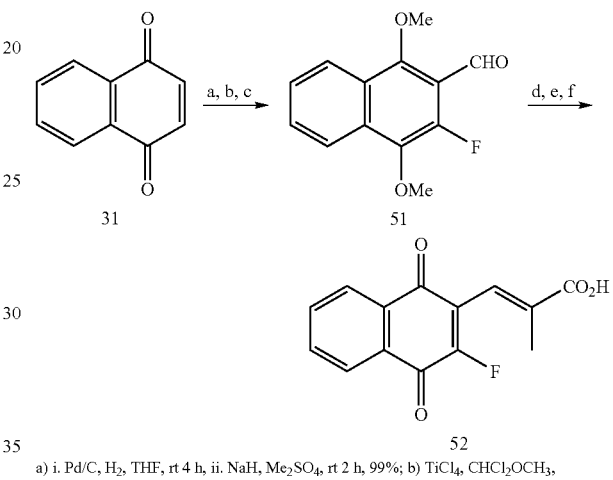

a) i. Pd/C, H$_2$, THF, rt 4 h, ii. NaH, Me$_2$SO$_4$, rt 2 h, 99%; b) TiCl$_4$, CHCl$_2$OCH$_3$, CH$_2$Cl$_2$, 0° C., 4 h, 93%; c) Selectfluor, CH$_3$CN, reflux 2 h, 45%; d) NaH, (EtO)$_2$P(O)CHCH$_3$CO$_2$Et, toluene, reflux 8 h, 77%; e) KOH, EtOH, reflux 30 min, 83%; f) Ag(II)O, HNO$_3$, AcOH, EtOAc, rt 4 h, 23%

Fortunately, aldehyde 51 had previously been synthesized via fluorination of aldehyde 27, so the Emmons reaction was then carried out using 51. (Scheme 12) Aldehyde 51 possessed similar E:Z selectivity to the other 3-halo aldehydes, where the crude reaction mixture was approximately 5:1 E:Z. Small amounts of pure Emmons isomers were collected for spectral analysis. The majority of the product was collected as a mixture of the two isomers, and the mixture was used in the subsequent saponification and oxidation. As expected the Z isomer was completely converted to the methyl ester during the final oxidation reaction, allowing rapid separation from the E acid final product. The Z methyl ester was then hydrolyzed with 2 M HCl in THF to generate the Z product.

3-Methoxy Naphthoquinones

Scheme 13: Synthetic strategy for preparing 3-methoxynaphthoquinone 55.

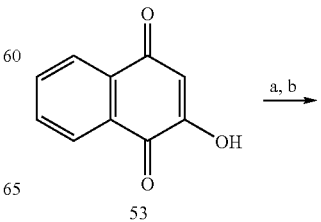

53

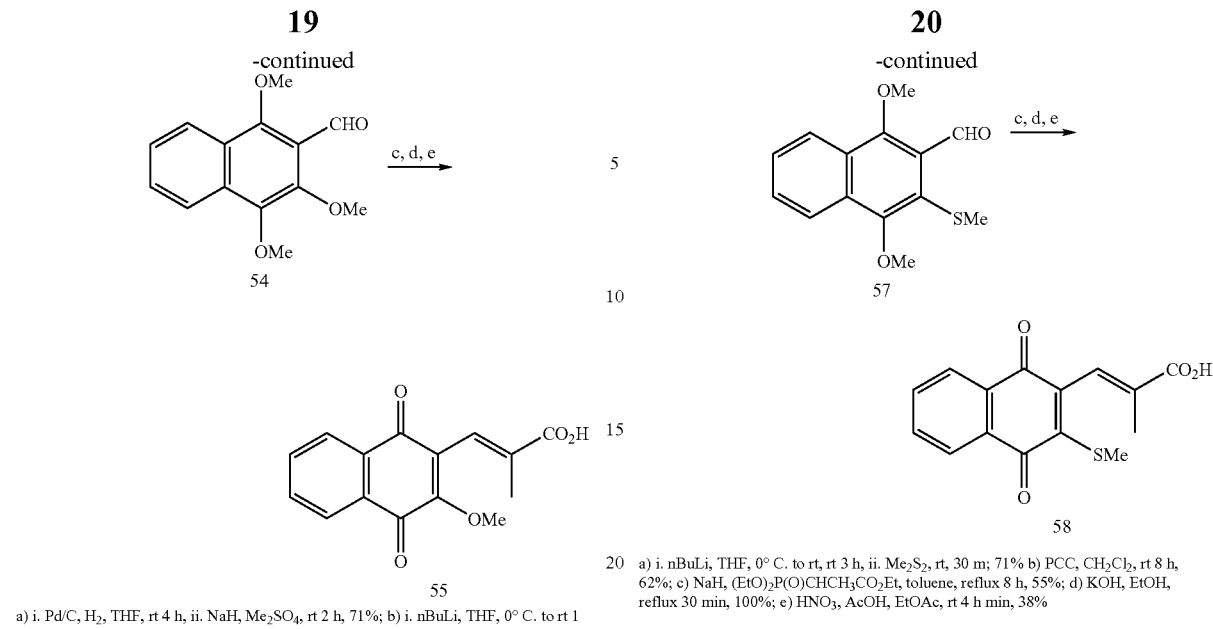

a) i. Pd/C, H₂, THF, rt 4 h, ii. NaH, Me₂SO₄, rt 2 h, 71%; b) i. nBuLi, THF, 0° C. to rt 1 h, ii. DMF, rt 20 min, 89%; c) NaH, (EtO)₂P(O)CHCH₃CO₂Et, toluene, reflux 8 h, 27%; d) KOH, EtOH, reflux 30 min, 100%; e) HNO₃, AcOH, EtOAc, rt 4 h, 27%

Electronegative atoms have already been substituted at the 3-position of the naphthoquinone derivatives; however, all of the substituents were halogens that are relatively isosteric to the methyl group. Methoxy and methylthio substituents were later explored that would retain an electronegative character but possess greater steric bulk The synthesis of 3-methoxy substituted naphthoquinone derivative 55 is outlined in Scheme 3. The Emmons reaction with aldehyde 54 as a substrate resulted in the lowest E selectivity of any substrate encountered; nearly 50% Z is observed in boiling toluene. Separation of the resulting E and Z esters proved difficult and only small quantities of purified E isomer were collected. The final saponification and oxidation were carried out without problems.

3-Methylthio Naphthoquinones

Scheme 14: Literature based synthesis of methylthio alcohol 56 and subsequent transformations to produce methylthio naphthoquinone 58.

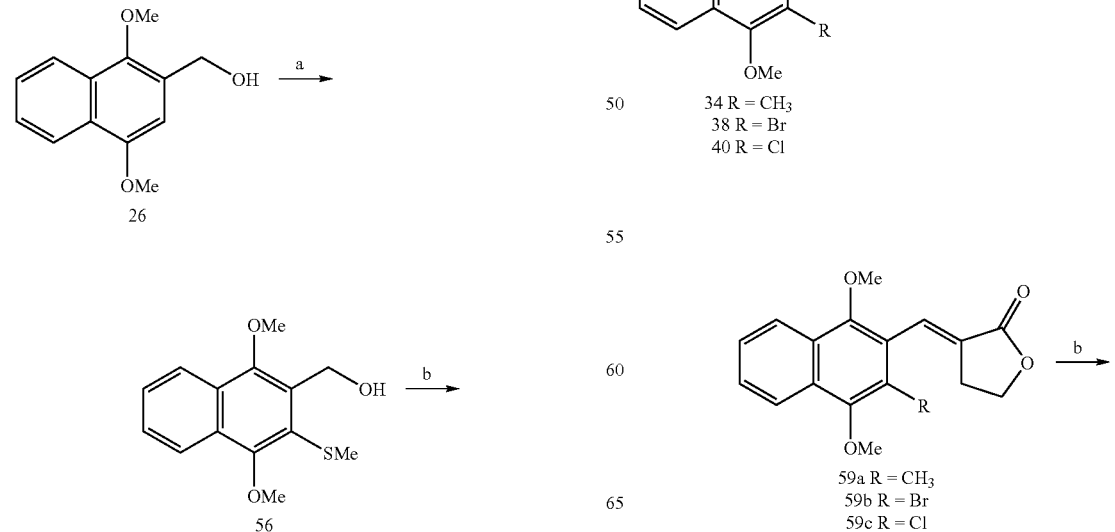

a) i. nBuLi, THF, 0° C. to rt, rt 3 h, ii. Me₂S₂, rt, 30 m; 71% b) PCC, CH₂Cl₂, rt 8 h, 62%; c) NaH, (EtO)₂P(O)CHCH₃CO₂Et, toluene, reflux 8 h, 55%; d) KOH, EtOH, reflux 30 min, 100%; e) HNO₃, AcOH, EtOAc, rt 4 h min, 38%

To generate the 3-methylthio naphthoquinone derivatives, alcohol 26 was deprotonated using nBuLi and allowed to react with methyldisulfide.[22] (Scheme 14) A reproducible 80% yield was observed in the formation of 56. The Emmons reaction proceeded with low E selectivity; approximately 30% Z isomer was observed by NMR. Interestingly, of all the naphthoquinones synthesized, the 3-unsubstituted derivatives had the highest E selectivity when the Emmons reaction was run at room temperature. This is most likely due to the steric influence the unsaturated acid moiety experiences from the bulkier 3-position substituents. The purified E isomer was saponified and oxidized to generate 58 as a red solid.

Ether Side Chain Quinones

Scheme 15: Synthetic strategy for incorporating an ether sidechain into the benzoquinone and naphthoquinone series.

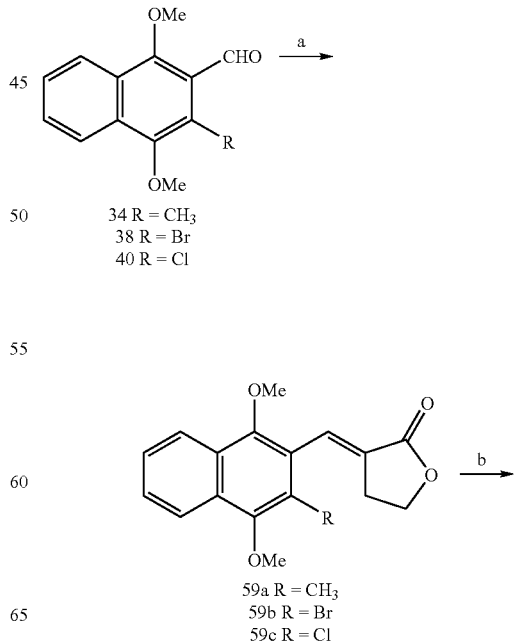

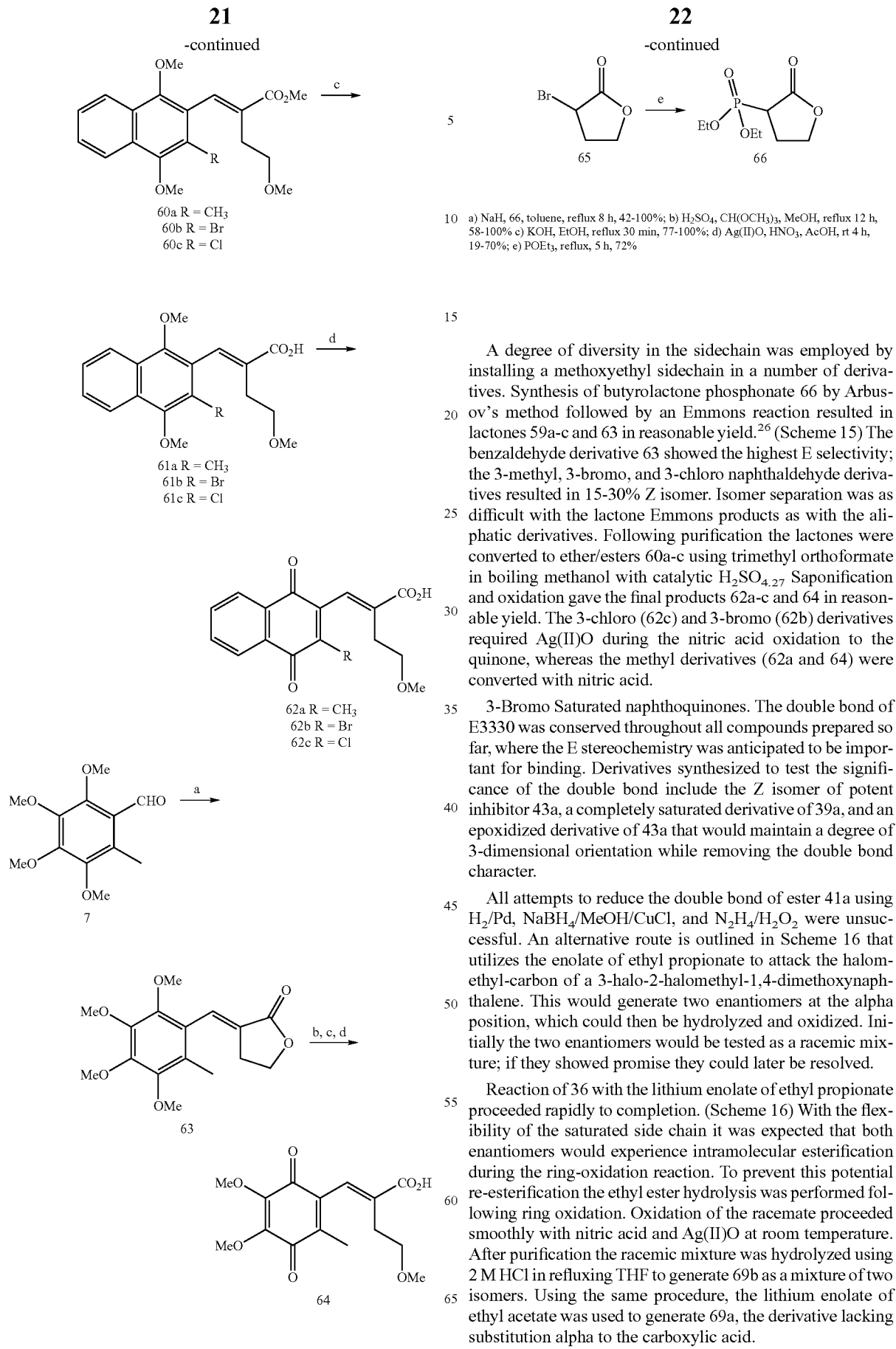

a) NaH, 66, toluene, reflux 8 h, 42-100%; b) H$_2$SO$_4$, CH(OCH$_3$)$_3$, MeOH, reflux 12 h, 58-100% c) KOH, EtOH, reflux 30 min, 77-100%; d) Ag(II)O, HNO$_3$, AcOH, rt 4 h, 19-70%; e) POEt$_3$, reflux, 5 h, 72%

A degree of diversity in the sidechain was employed by installing a methoxyethyl sidechain in a number of derivatives. Synthesis of butyrolactone phosphonate 66 by Arbusov's method followed by an Emmons reaction resulted in lactones 59a-c and 63 in reasonable yield.[26] (Scheme 15) The benzaldehyde derivative 63 showed the highest E selectivity; the 3-methyl, 3-bromo, and 3-chloro naphthaldehyde derivatives resulted in 15-30% Z isomer. Isomer separation was as difficult with the lactone Emmons products as with the aliphatic derivatives. Following purification the lactones were converted to ether/esters 60a-c using trimethyl orthoformate in boiling methanol with catalytic H$_2$SO$_{4.27}$ Saponification and oxidation gave the final products 62a-c and 64 in reasonable yield. The 3-chloro (62c) and 3-bromo (62b) derivatives required Ag(II)O during the nitric acid oxidation to the quinone, whereas the methyl derivatives (62a and 64) were converted with nitric acid.

3-Bromo Saturated naphthoquinones. The double bond of E3330 was conserved throughout all compounds prepared so far, where the E stereochemistry was anticipated to be important for binding. Derivatives synthesized to test the significance of the double bond include the Z isomer of potent inhibitor 43a, a completely saturated derivative of 39a, and an epoxidized derivative of 43a that would maintain a degree of 3-dimensional orientation while removing the double bond character.

All attempts to reduce the double bond of ester 41a using H$_2$/Pd, NaBH$_4$/MeOH/CuCl, and N$_2$H$_4$/H$_2$O$_2$ were unsuccessful. An alternative route is outlined in Scheme 16 that utilizes the enolate of ethyl propionate to attack the halomethyl-carbon of a 3-halo-2-halomethyl-1,4-dimethoxynaphthalene. This would generate two enantiomers at the alpha position, which could then be hydrolyzed and oxidized. Initially the two enantiomers would be tested as a racemic mixture; if they showed promise they could later be resolved.

Reaction of 36 with the lithium enolate of ethyl propionate proceeded rapidly to completion. (Scheme 16) With the flexibility of the saturated side chain it was expected that both enantiomers would experience intramolecular esterification during the ring-oxidation reaction. To prevent this potential re-esterification the ethyl ester hydrolysis was performed following ring oxidation. Oxidation of the racemate proceeded smoothly with nitric acid and Ag(II)O at room temperature. After purification the racemic mixture was hydrolyzed using 2 M HCl in refluxing THF to generate 69b as a mixture of two isomers. Using the same procedure, the lithium enolate of ethyl acetate was used to generate 69a, the derivative lacking substitution alpha to the carboxylic acid.

Scheme 16: Syntheses of saturated 3-bromo naphthoquinones 69a and b.

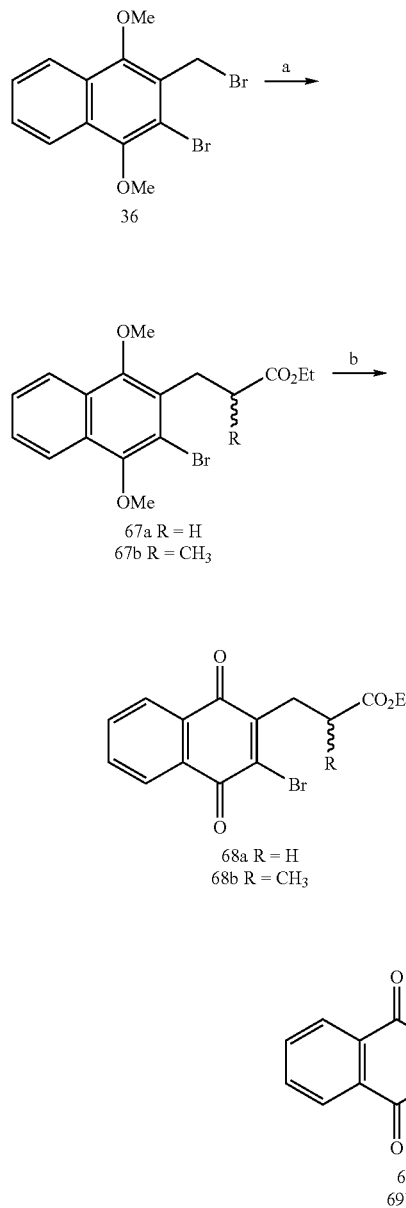

a) Li(SiMe$_3$)$_2$N, RCH$_2$CO$_2$Et, THF, -78° C. to rt 4 h, 86-100%; b) Ag(II)O, HNO$_3$, AcOH, EtOAc, rt 4 h, 27-41%; c) HCl, EtOH, reflux; 63-78%

Scheme 17: Darzens condensation to generate epoxide derivatives of 41a results in four diastereomers.

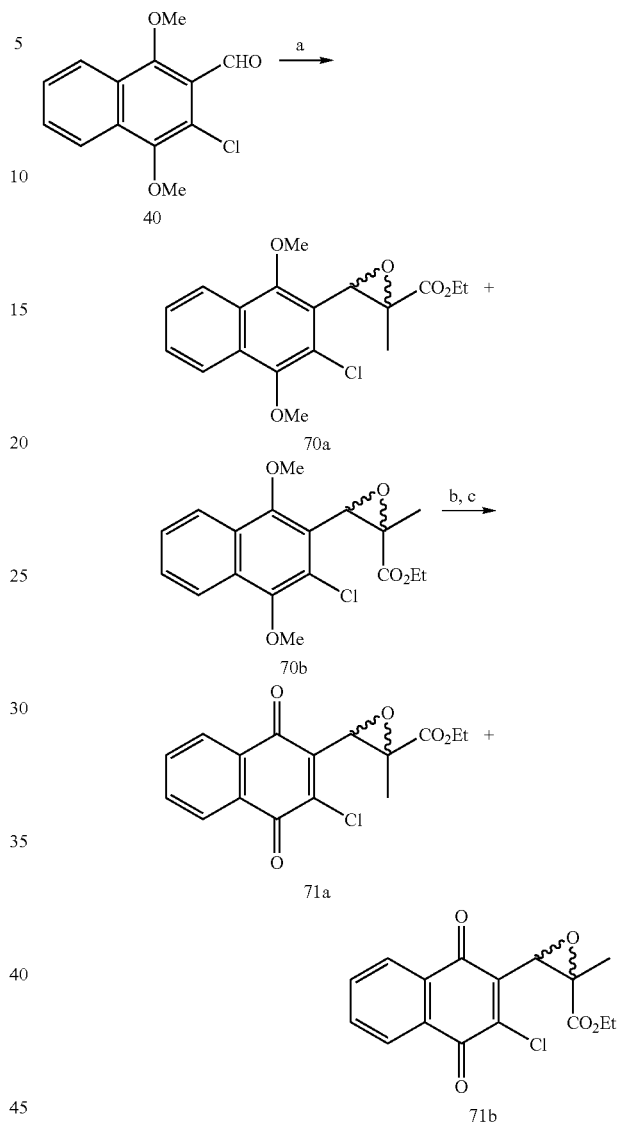

a) Li(SiMe$_3$)$_2$N, CH$_3$CHBrCO$_2$Et, THF, -78° C. to rt 4 h, 97%; b) KOH, EtOH, reflux, 1 h, 100%; c) Ag(II)O, HNO$_3$, AcOH, EtOAc, rt 3 h, 20%

The Darzens reaction was carried out on 40, and the diastereomeric mixture was hydrolyzed and oxidized. Efforts would then be directed to separating the individual isomers.

Amide and Biotin Derivatives. Derivatives with high redox inhibitory activities were selected for derivatization of the carboxylate to generate the corresponding amides. Amides were desired to enable modification of the parent compounds without affecting the naphthalene core which is expected to be of great significance to binding. Derivatives with an amide functional group would provide a site for increasing hydrophilicity or tethering to other organic molecules. Derivatives tethered to biotin through an amide linkage would act as molecular tools in various experiments including affinity chromatography and surface plasmon resonance (SPR). The former experiment would enable the isolation of proteins that interact with the derivative, while the latter would provide dissociation constant (K$_D$) data for specific proteins. Simple hydroxyethylamides were first synthesized to determine the effects of modifying the carboxylate group.

3-Chloro Epoxide naphthoquinones. Initially, the most promising route to forming epoxides 70a,b appeared to be performing a Prelezhof reaction on ester 41a. Unfortunately, t-BuOOH, mCPBA, and H$_2$O$_2$ all failed to generate the epoxide. An alternative strategy was to condense the 3-chloroaldehyde 40 with the lithium enolate of ethyl 2-bromopropionate in a Darzens reaction to generate the epoxide.[28] (Compounds 71a and b, Scheme 17) Although this was an established route of epoxide formation, the Darzens reaction had the potential for generating four diastereomers, whereas the direct epoxidation of 41a would only produce two enantiomers.

Model Chemistry. Derivatives bearing an amide function needed to be tested for activity prior to developing complex biotin-conjugated species. Hydroxyethylamide derivatives of 1 and 43a were to be synthesized to ensure that derivatization of the carboxylic acid did not negatively affect redox inhibition. (72 and 73, respectively; FIG. 8) In addition to synthesizing model amides, model chemistry was also required to optimize the transformation of precious intermediates to biotinylated compounds.

The most direct approach to amides 72 and 73 begins with amidation of the corresponding dimethoxyarenes followed by oxidation to the quinone. The first step was optimized using trans o-methoxycinnamic acid and ethanolamine. Scheme 18) N,N'-Dicyclohexylcarbodiimide (DCC) was determined to give higher yields than 1-[3-(Dimethylamino)propyl]-3-ethylcarbodiimide (EDC/EDCI), where complete conversion was observed with the former and roughly 50% conversion with the latter. Finally the stoichiometry of the reagents was examined; two equivalents of DCC with 1 equivalent of amine provided complete conversion to the corresponding amide.

Scheme 18: Model chemistry for optimal Steglich conditions

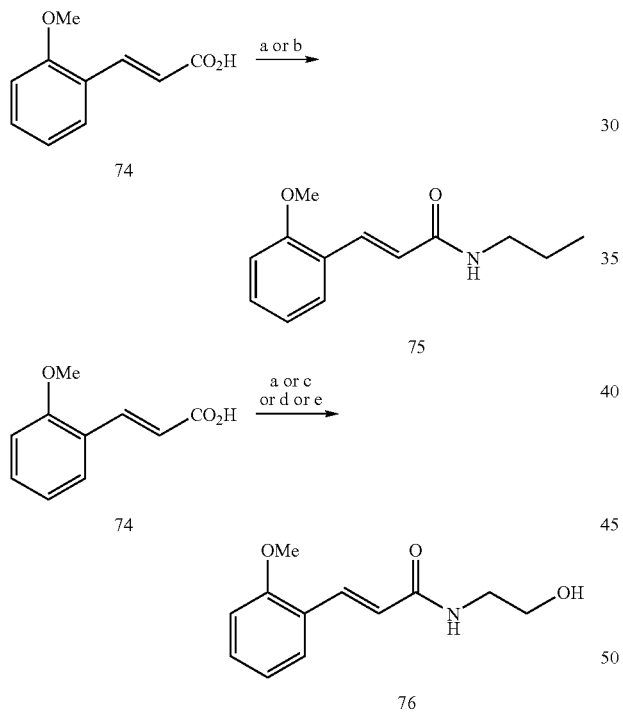

a) Acid, HOBt 0.1 eq, EDCl 1 eq, DMF:CH$_2$Cl$_2$ 1:2, rt 40 min, then amine 1.5 eq rt, stir 18 h rt.
b) Acid, HOBt 0.1 eq, DCC 1 eq, DMF:CH$_2$Cl$_2$ 1:2, rt 40 min, then amine 1.5 eq rt, stir 18 h rt.
c) Acid, HOBt 0.1 eq, DCC 2 eq, DMF:CH$_2$Cl$_2$ 1:1, stir rt 80 min, then amine 1 eq, stir 18 h rt.
d) Acid, HOBt 0.1 eq, DCC 1 eq, DMF:CH$_2$Cl$_2$ 1:1, stir rt 80 min, then amine 2 eq, stir 18 h rt.
e) Acid, HOBt 0.1 eq, DCC 2 eq, DMF:CH$_2$Cl$_2$ 1:1, stir rt 80 min, then amine 2 eq, stir 18 h rt.

The second transformation modeled was the ring oxidation of dimethoxynaphthalenes 41a and 77 using ceric ammonium nitrate (CAN) in acetonitrile/water. (Scheme 19) CAN-mediated oxidations result in reaction mixtures requiring more extensive purification than when using nitric acid. Unfortunately, the sulfide moiety in biotin is not stable to nitric acid and would likely oxidize to the sulfoxide or sulfone. Only one reference has shown oxidation of a biotinylated substrate using CAN at 0° C. for 20 minutes without oxidation of biotin.[29] However, the reported HPLC data suggests oxidation to the sulfone and sulfoxides took place. Thus the oxidation reaction of dimethoxyarenes needed to be studied to determine the minimum equivalents of CAN and time required to perform the oxidation. Both substrates 41a and 77 were converted to the corresponding naphthoquinones using 6 equivalents of CAN at 0° C. in less than 20 minutes.

Scheme 19: Model oxidation chemistry using CAN.

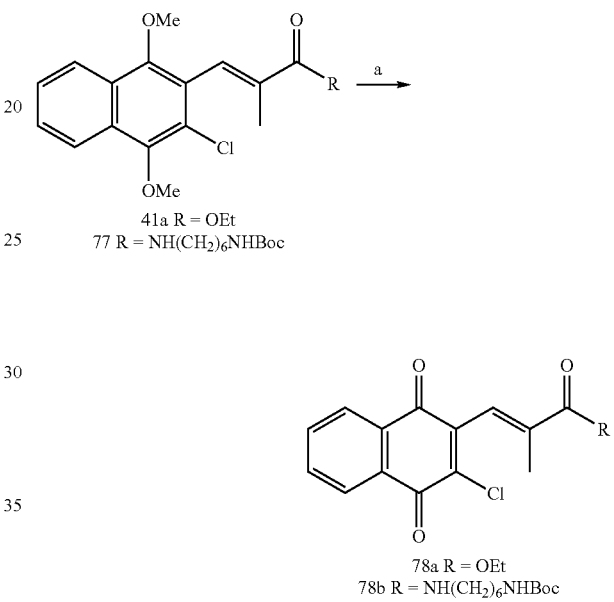

a) CAN 6 eq, MeCN:H$_2$O 1:1, 0° C., 20 min

Scheme 20: Synthesis of amide 73.

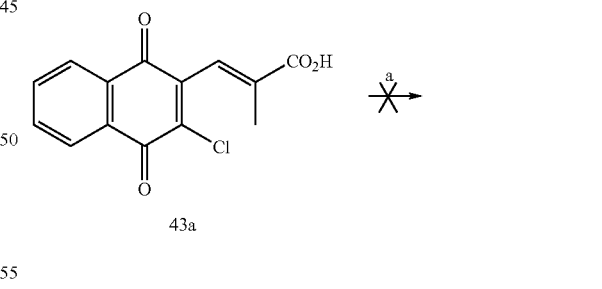

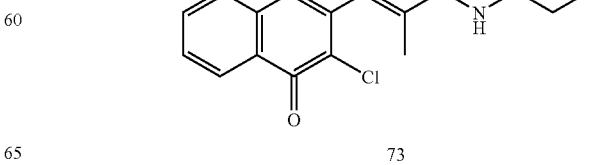

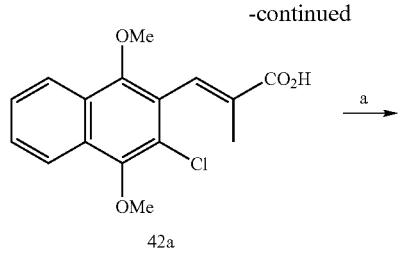

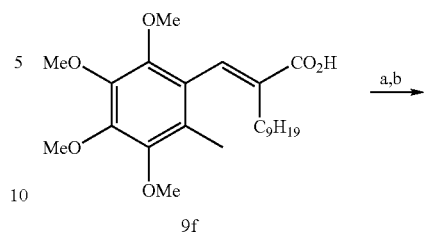

Scheme 21: Synthesis of model amide 72.

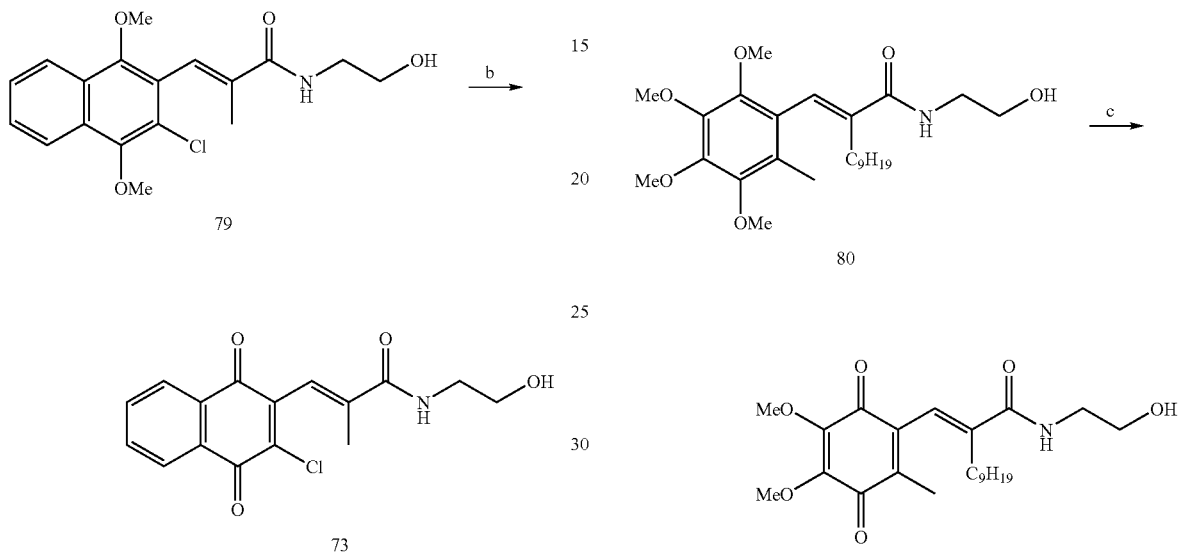

a) i. HOBt 0.1 eq, DCC 2.0 eq, DMF: CH₂Cl₂ 1:1, rt 1.5 h
ii. Ethanolamine 1.5 eq., rt 12 h, 83% b) Ag(II)O, HNO₃, AcOH, EtOAc, rt 30 min, 60% a) i. HOBt 0.1 eq, DCC 2.0 eq, DMF: CH₂Cl₂ 1:1, rt 1.5 h; b) Ethanolamine 1.5 eq., rt 12 h, 81%; c) Ag(II)O, HNO₃, AcOH, EtOAc, rt 30 min, 45%

With the model chemistry completed the synthesis of amides 72 and 73 could begin. Quinone 43a was initially used as a substrate for amidation to prepare quinone 73; however, no conditions were found to efficiently perform the transformation. (Scheme 20) The alternative strategy was to perform the oxidation after coupling dimethoxynaphthalene 42a to ethanolamine. Carboxylic acid 42a was completely consumed under optimized Steglich conditions, and the resulting product was oxidized with nitric acid. The simple amides lacked the biotin group that necessitated the use of a mild oxidant, enabling the use of nitric acid to readily perform the oxidations. Quinone 72 was synthesized in the same manner as 73. (Scheme 21)

Amido-quinones 72 and 73 were comparable in activity to the original carboxylic acids, and therefore the amide was determined to be a practical method for conjugating the molecules to biotin, or for imparting further modifications to improve the water solubility and target selectivity of the drugs.

Biotinylated derivative amidation reactions. Two strategies were available for conjugating dimethoxyarenes 42a and 9f to biotin through an aliphatic linker. The first strategy was to couple the dimethoxyarene acids to N-Boc-1,6-diaminohexane and then couple the deprotected linker to biotin. (Scheme 22) The second strategy was to generate biotinylating reagent 85 and couple this directly to the dimethoxyarene unsaturated carboxylic acids. (Scheme 23) The second strategy proved the shortest and biotinylating reagent 85 was readily synthesized.

Scheme 22: Amidation route utilizing iterative coupling strategy.

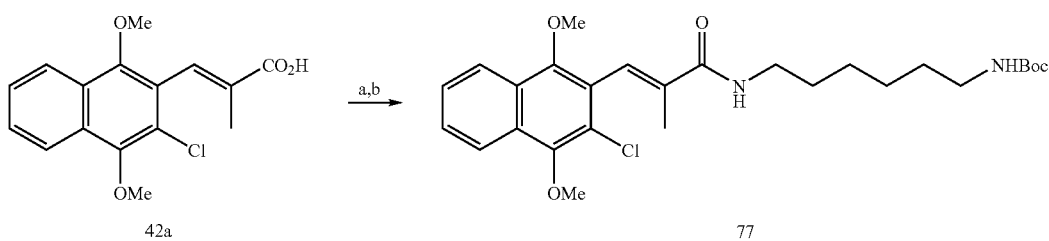

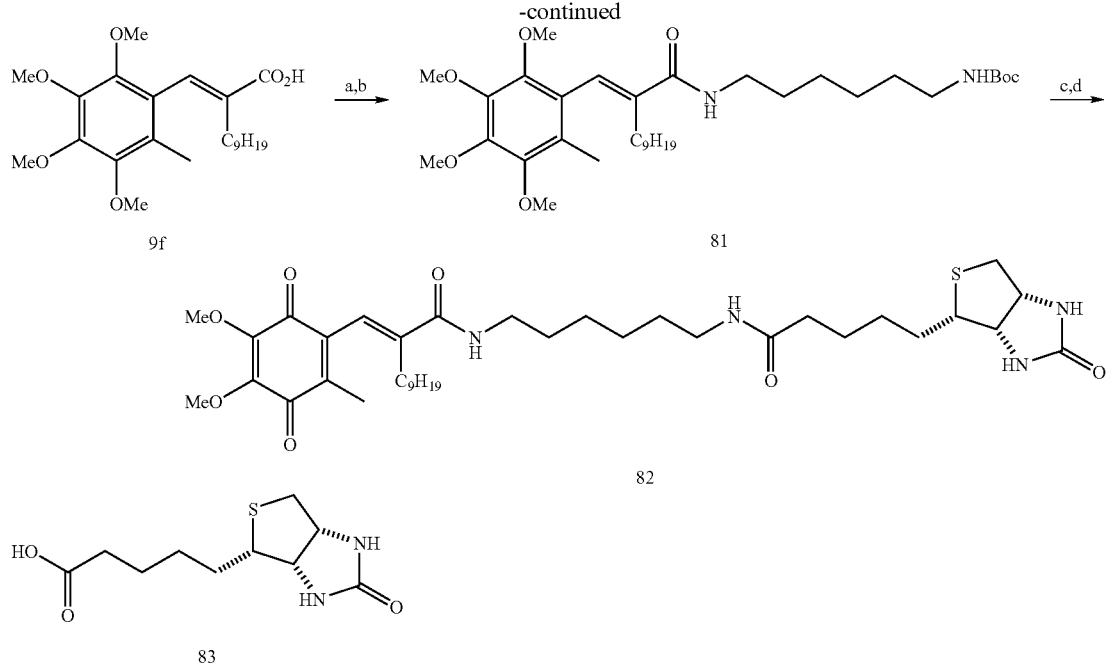

a) HOBt 0.1 eq, DCC 2.0 eq, DMF:CH₂Cl₂ 1:1, rt 1.5 h; b) N-Boc-1,6-diaminohexane 1.5 eq., rt 12 h, 78-100%; c) 20% TFA/CH₂Cl₂, rt 20 m, 100%; d) HOBt 0.1 eq, DCC 2.0 eq, DMF, rt 1 h; d) 82, Et₃N, rt 12 h, 90%

Even though the second route was ultimately utilized in the synthesis of the biotinylated reagents, the first route provided insight into unexpected problems with the DCC coupling reaction. Optimized Steglich conditions were applied to both dimethoxyarenes 9f and 42a with N-Boc-1,6-diaminohexane as the amine component. The reaction began with pure E1,4-dimethoxyarene reagents; however, purification resulted in two components in a ratio of approximately 1:1. The two compounds were identified as E and Z isomers of the coupled products through HMQC and nOe NMR experiments. DCC conditions were resulting in isomerization of the E double bond and had to be replaced to retain isomeric purity. The substrate used for model chemistry lacked a substituent on the double bond alpha to the carbonyl; thus it is likely the cis and trans isomers were sufficiently different in energy to prevent isomerization. Acid 42a was later converted to the corresponding amide using either methyl chloroformate, oxalyl chloride, or PyBOP without double bond isomerization. (Scheme 23)

Scheme 23: Synthetic pathway to amides using biotinylating reagent

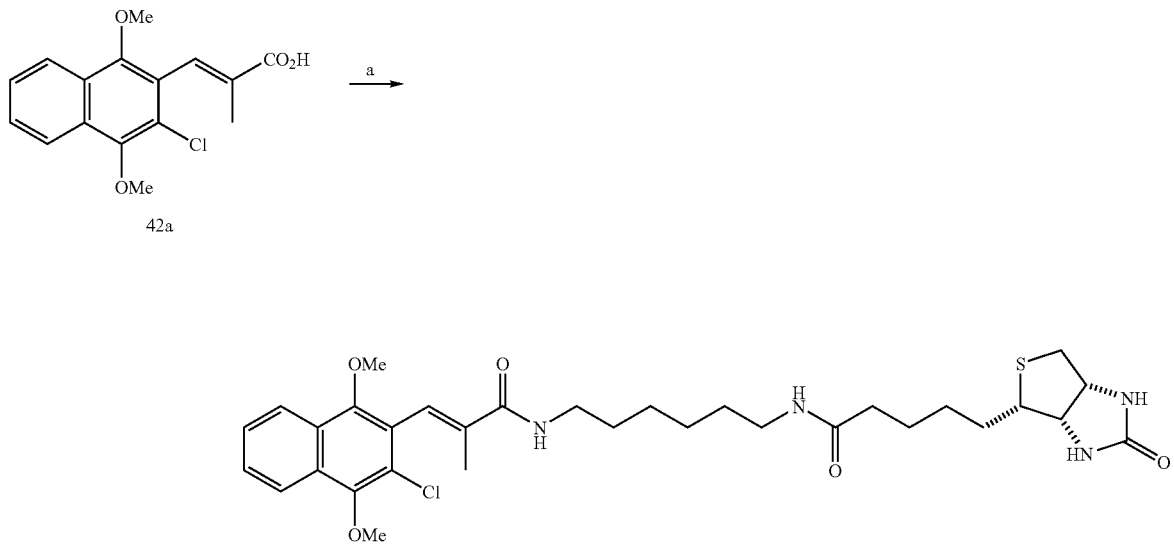

31

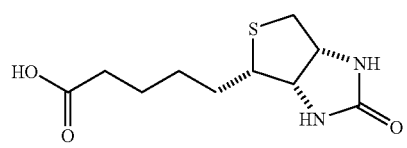

83

-continued

32

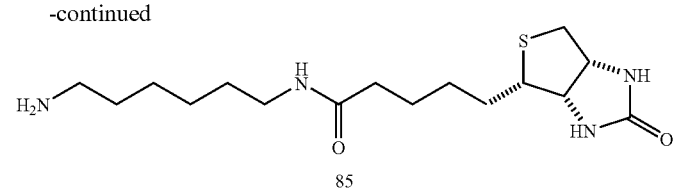

85 a) ClCO₂Me, Et₃N, 85, 1.5 eq., rt 12 h, 99%; b) I. PyBOP, Et₃N, DMF, rt 30 min; ii. N-Boc-1,6-diaminohexane, 69%; d) 20% TFA/CH₂Cl₂, rt 20 min, 100%

Biotinylated dimethoxyarene oxidation. Avidin attached to the surface of SPR chips provides a pseudocovalent interaction with biotin enabling the chip to be coated with drug molecules. The sulfide of biotin is highly reactive toward oxidizing reagents, which can oxidize the sulfide to the corresponding sulfoxides (R and S) or further to the sulfone. Biotinylated 84 was initially oxidized using the minimum conditions previously determined for derivativeous amide 77; however, the reaction required an hour at room temperature to see complete disappearance of methoxy groups in the $^1$H NMR spectrum. (Scheme 24) The methylene protons and methide carbon adjacent to the sulfur of biotin were expected to be the most diagnostic of sulfide oxidation. Unfortunately, both regions were obscured by resonances from the aminohexane linker.

An alternative strategy was to monitor the CAN oxidation using HPLC. The ratio of UV absorbance at 300 and 245 nm was determined for compounds containing either a dimethoxynaphthalene or naphthoquinone moiety, where the ratio was approximately 0.16 for the former and 0.25 for the latter. A CAN-mediated oxidation of 84 was then monitored by HPLC, where the reaction was stirred at 0° C. and with 18 equivalents of CAN. The first HPLC trace was taken after 5 minutes reaction, and no starting material was present. Interestingly, NMR spectra taken after 30 minutes showed substantial methoxy peaks. This indicates that the sulfide oxidation is taking place rapidly at 0° C., because a new dimethoxynaphthalene species began to appear in less than 5 min.

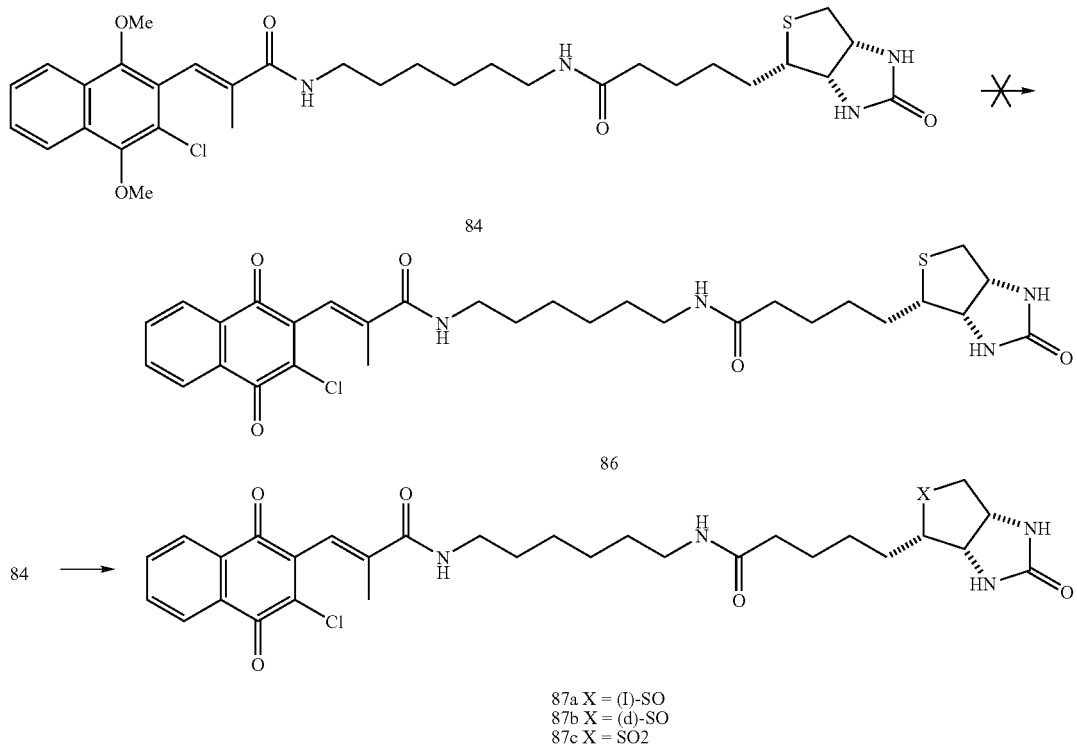

Fortunately, both sulfoxides (R and S) and the sulfone of biotin bind avidin with 30-40% of the affinity of the parent sulfide.[30] With this information, coupled to the discovery that the dimethoxynaphthalene moiety could not be oxidized without oxidation of the sulfide of biotin, it was determined that the reaction should be allowed to proceed until only quinone-sulfone 87c was observed by HPLC. (Scheme 24) It was hypothesized that if no dimethoxynaphthalene is present in the sample, a mixture of the four biotinylated quinones (86 and 87a-c) should all bind in a pseudocovalent manner to the avidin-coated chip. CAN transformed 84 to 87c; however, separation of the quinone from CAN was difficult.

Column purification of 87c was only possible with MeOH/CH$_2$Cl$_2$ conditions, and these conditions also eluted CAN. More than 15 equivalents of CAN were required to complete the transformation to 87c, thus removing CAN through chromatography or precipitation was not efficient. Reverse-phase HPLC purification was an alternative, but would be slow for milligram scale preparation.

Biotin sulfone derivatives. An alternative strategy was then devised that would generate only the biotinsulfone quinones. (Scheme 25) The sulfonobiotinylating reagent 90 was synthesized via oxidation of biotin followed by coupling to N-Boc-1,6-diaminohexane and deprotection of the terminal amine. Biotinsulfone and the corresponding Boc protected 6-aminohexylamide are insoluble in most organic solvents, making subsequent transformations very difficult. The solubility profiles did lend to purification, where the oxidation of biotin precipitates the sulfone from the acetic acid solution, and the coupling reaction precipitates the product from the DMF solution. Both products are collected and washed to give pure product in excellent yield. Unfortunately, the insolubility of the biotinylating reagent makes coupling to the dimethoxynaphthalene difficult. Desthiobiotin is another molecular tool available for conjugation where the biotin sulfide is removed. The cyclic urea of desthiobiotin only sacrifices a 20-fold loss in activity from the femptomolar binding affinity of biotin ($10^{-15}$ M).

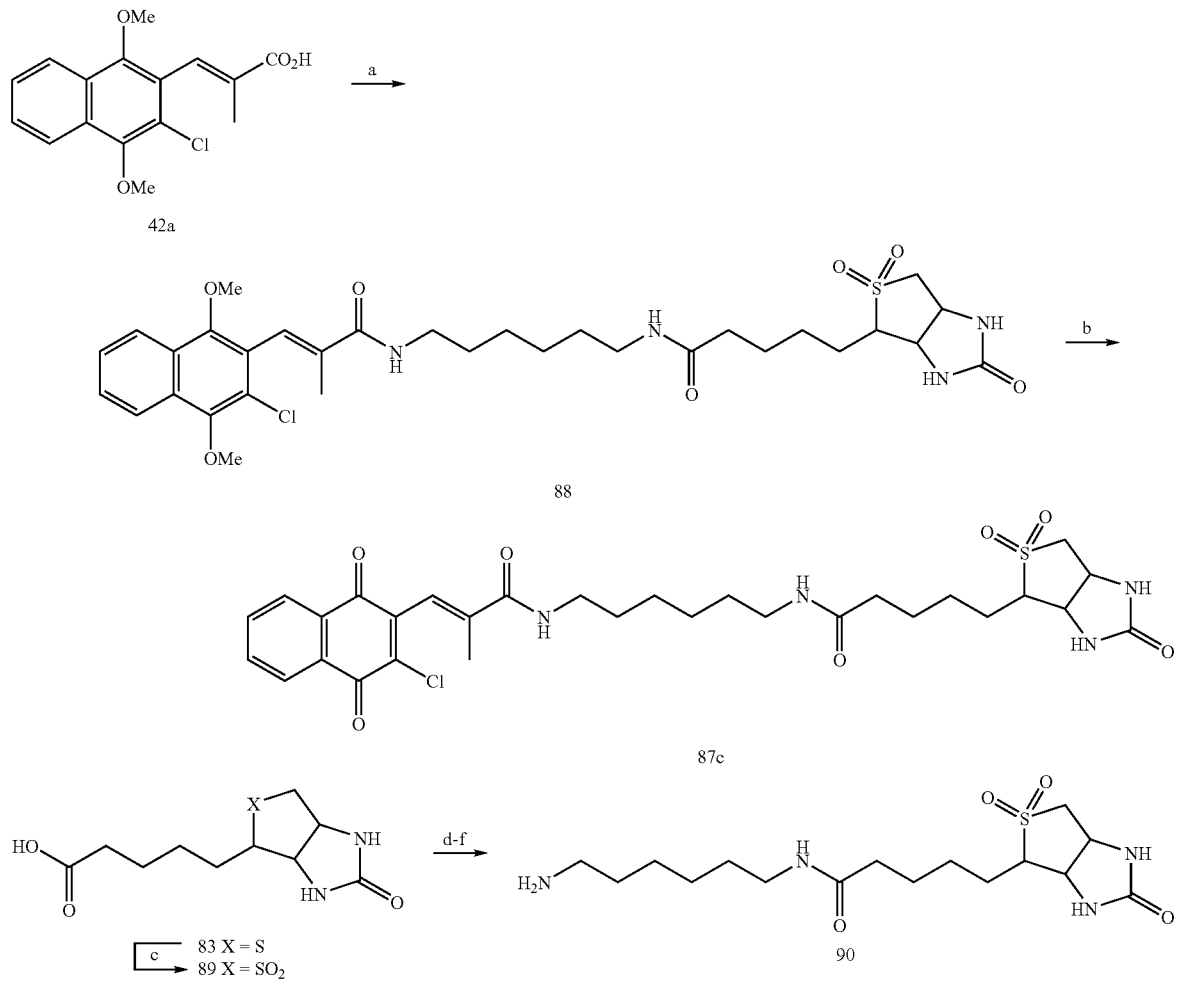

Desthiobiotin derivatives. Desthiobiotin (93) is an derivative of biotin that lacks the sulfide heterocycle. The biotin sulfoxides and sulfone bind avidin approximately 3-fold weaker than biotin; comparatively desthiobiotin binds avidin approximately 20-fold weaker than biotin.[31,32] Biotin binds avidin with a dissociation constant in the femptomolar range ($10^{-15}$ M); a loss of between one and two orders of magnitude by using desthiobiotin will still provide pseudocovalent adhesion of the drug molecule to the SPR chip.

The synthesis of desthiobiotinylated 43a proceeded without problems following the previously devised chemistries. (Scheme 26) Desthiobiotin reagent 94 was synthesized using PyBOP coupling with N-Boc-1,6-diaminohexane in 65-70% yield following recrystallization. Dimethoxynaphthalene 42a was then coupled to 94 using PyBOP, and the product was then oxidized using 5 equivalents of CAN at room temperature. Desthiobiotin derivative 92 was synthesized in milligram quantities and purified by flash chromatography for characterization.

and this transformation resulted in a substantially cleaner oxidation product than CAN. (FIG. 9B) Although the silver (II) oxidation was cleaner than the CAN oxidation, the resulting reaction mixture still required HPLC purification. An alternative silver (II) oxidation procedure was then employed that used dilute nitric acid in 1,4-dioxane to generate a soluble silver nitrate salt.[33] This transformation was complete in less

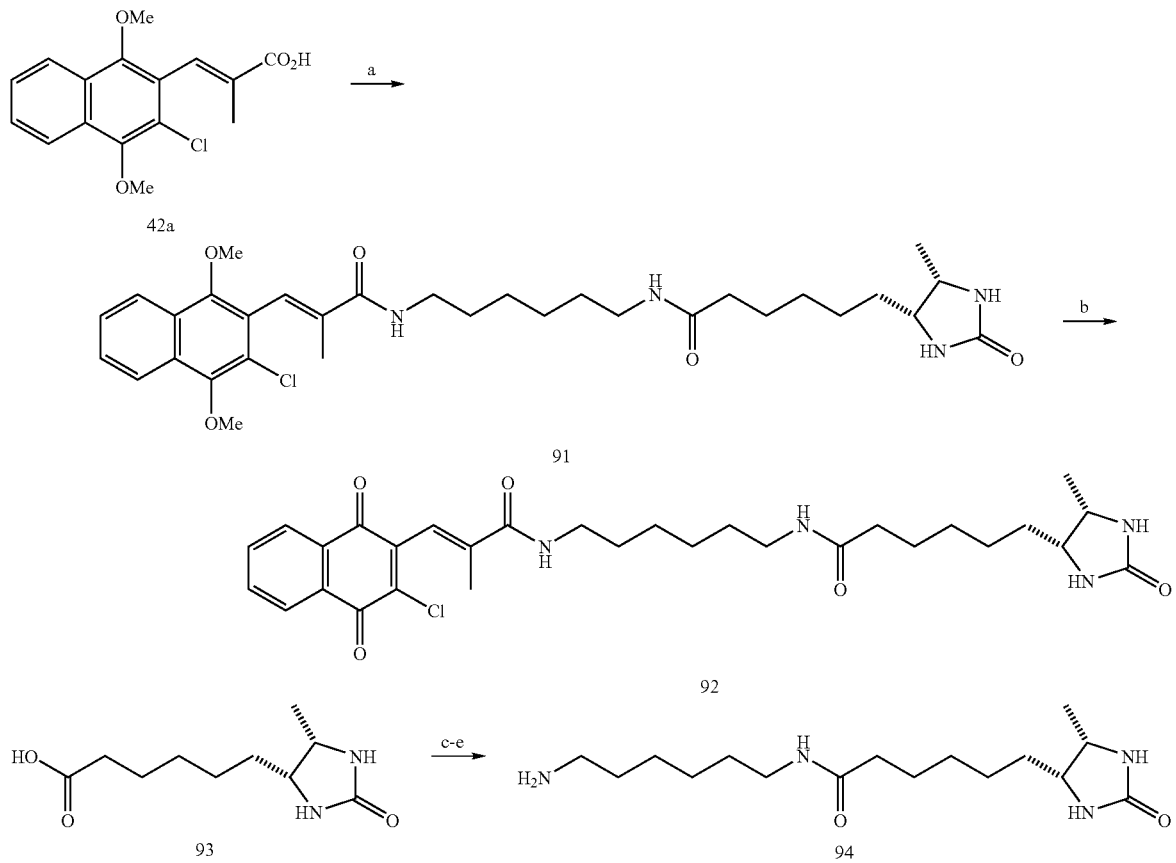

Scheme 26: Synthesis of desthiobiotinylated 43a.

a) ClCO$_2$Me, Et$_3$N, 94 1.5 eq., rt 12 h, 68%; b) Ag(II)O, 6M HNO$_3$, dioxane, rt 2-5 min, 70%; c) 93, PyBOP, Et$_3$N, DMF; d) N-Boc-1,6-diaminohexane, rt 4 h, 73%; e) 20% TFA/CH$_2$Cl$_2$, rt 20 min, 100%

Figure 9A:
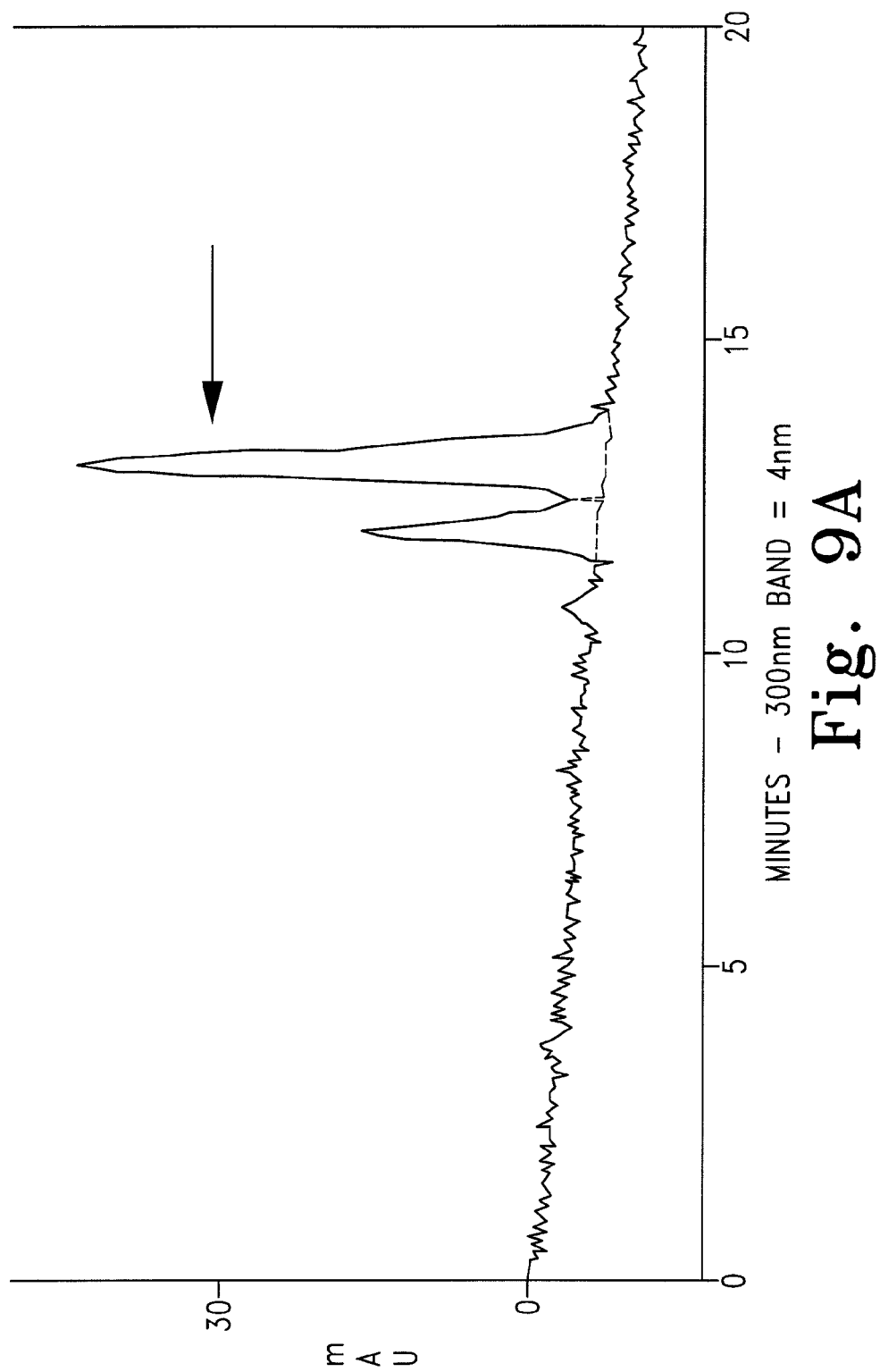
FIG. 9: HPLC spectra of oxidation and coupling reactions to synthesize quinone 92.
Figure 9B:
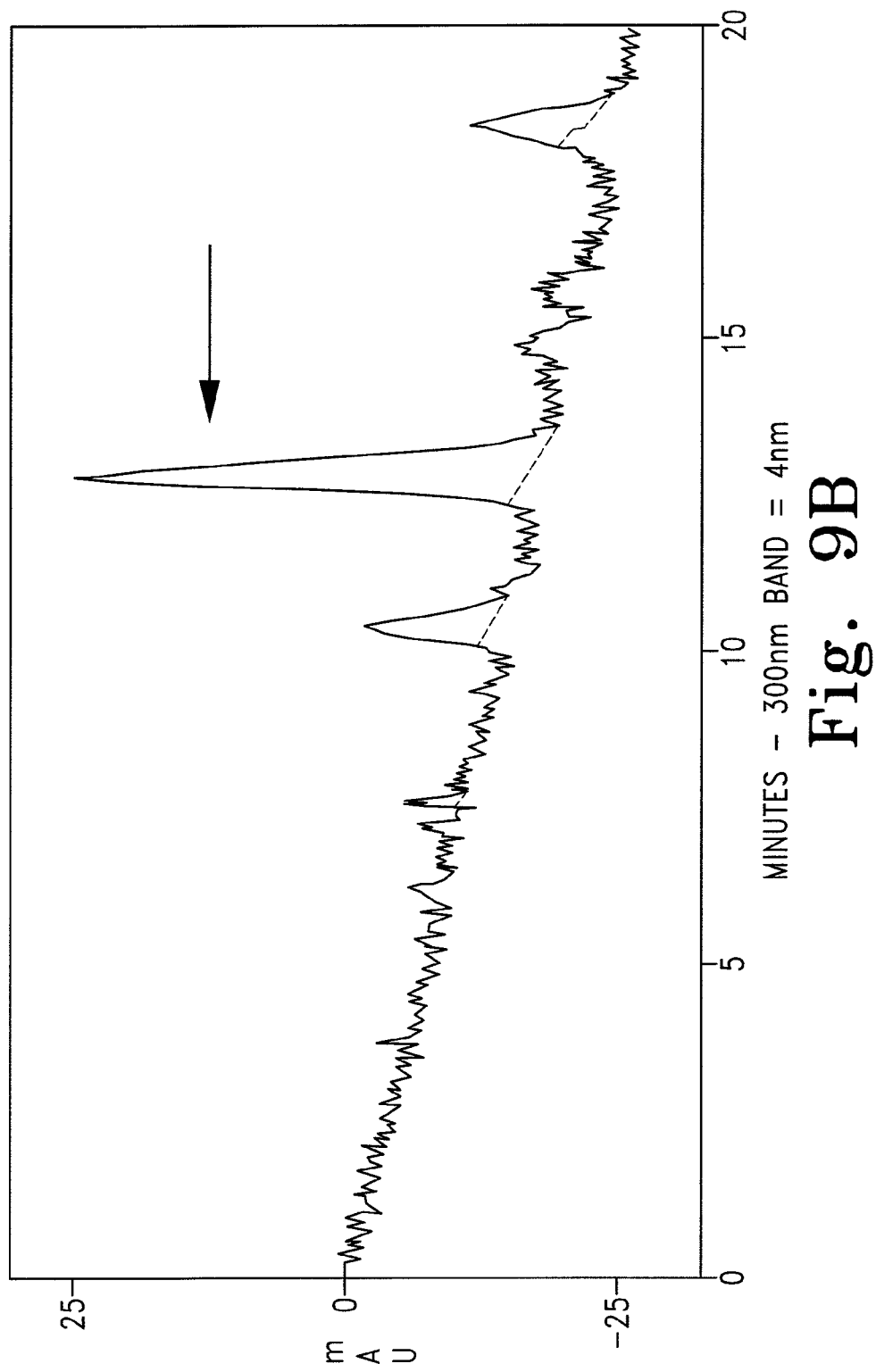
Figure 9C:
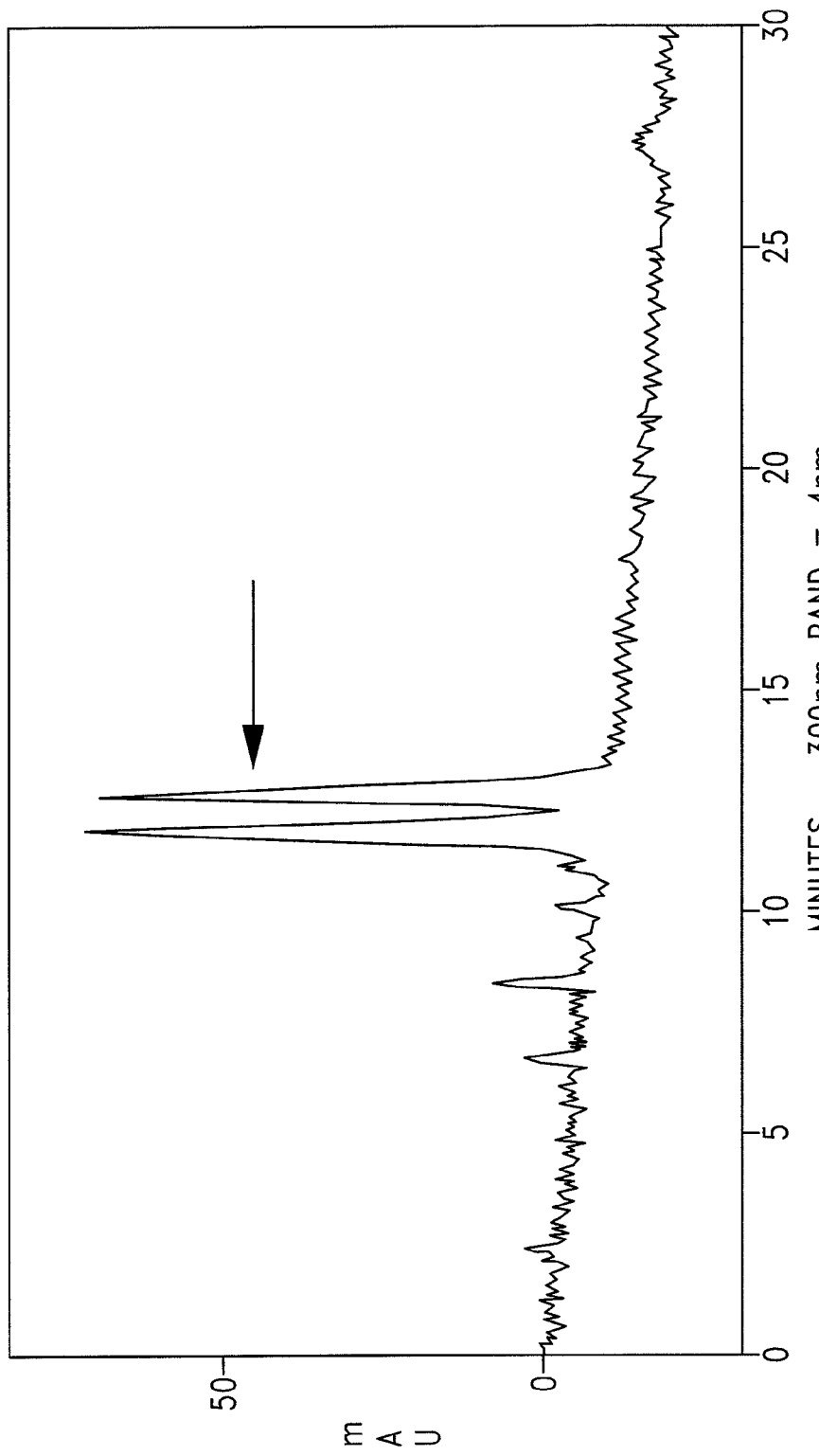
Figure 9E:
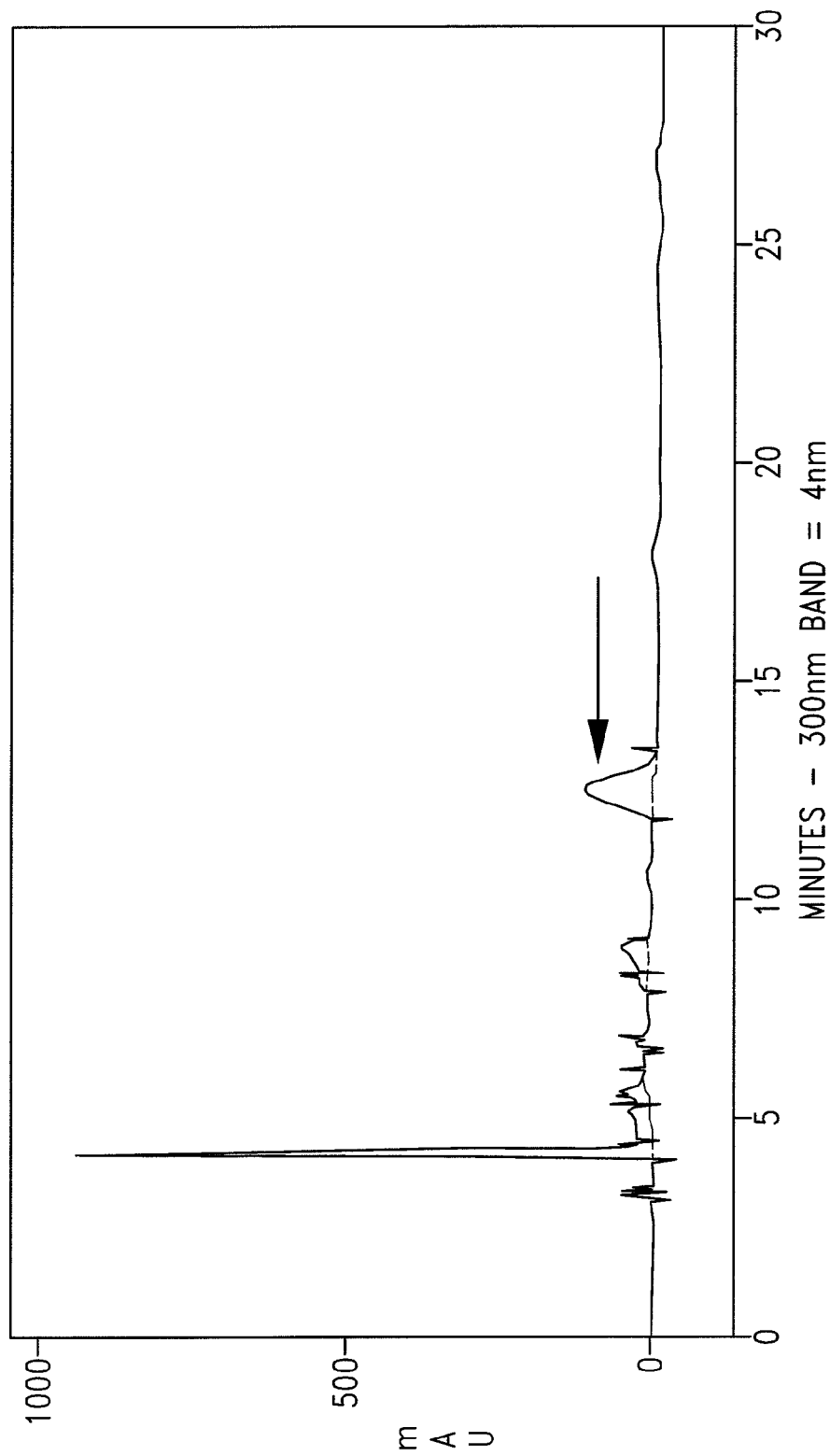
Figure 9F:
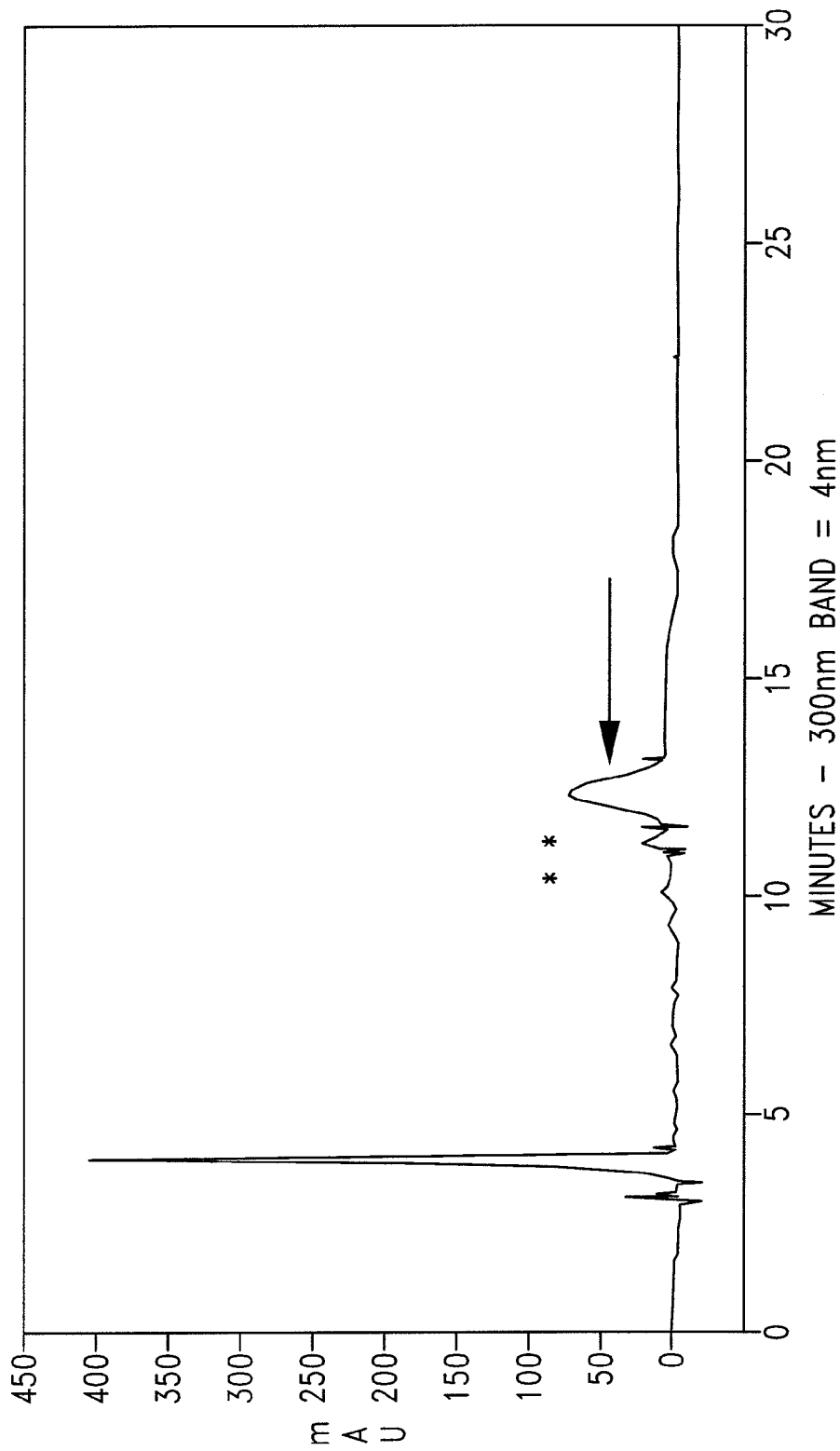
Figure 9G:
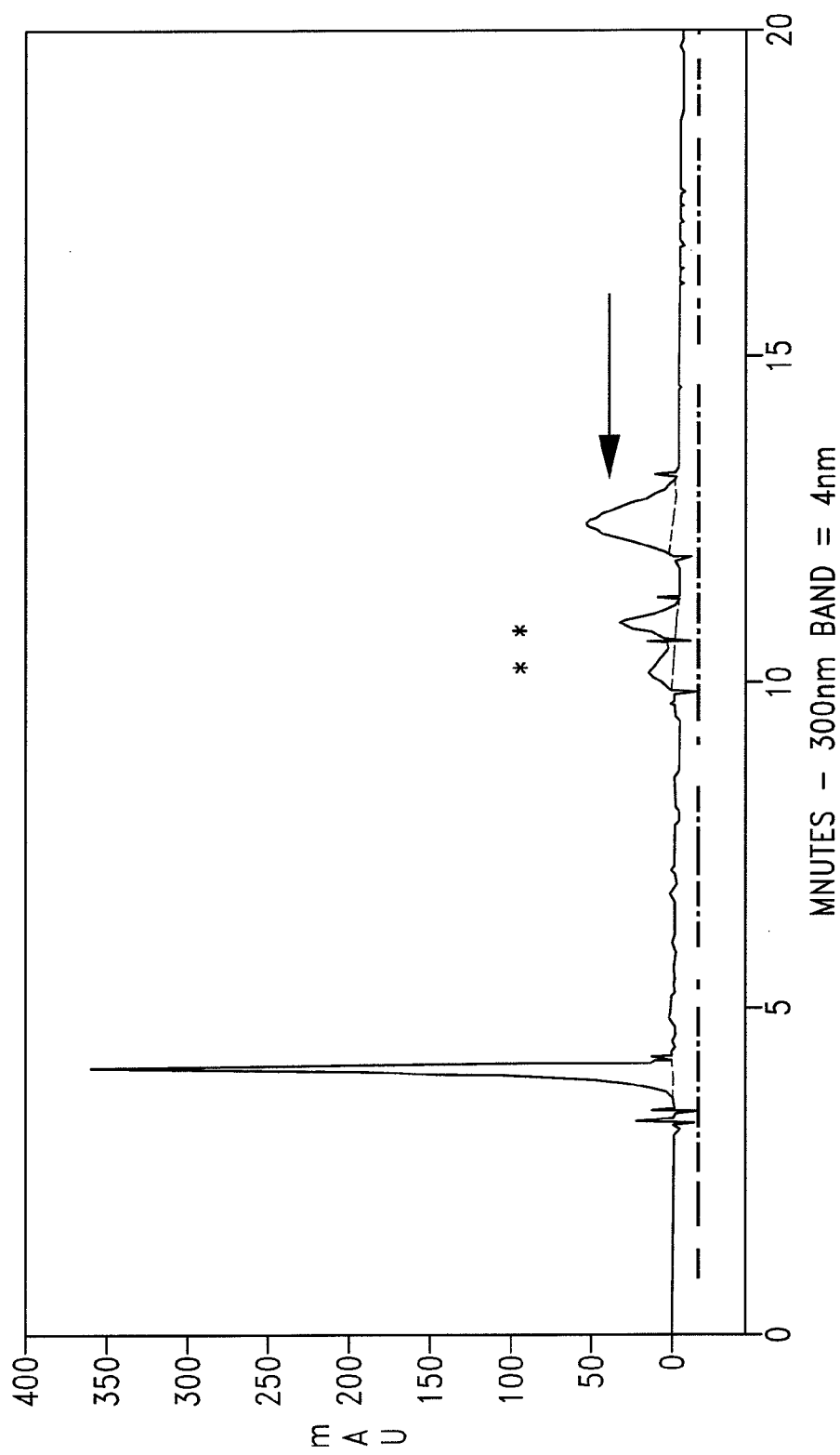

Samples of purified 92 from oxidation reactions were used with HPLC to monitor the coupling of quinone 43a to generate 92 via a non-oxidative route. Both oxalyl chloride and PyBOP conditions resulted in the formation of the activated carboxyl; however, PyBOP conditions resulted in only traces of product and oxalyl chloride resulted in no product formation. Desthiobiotin 92 is inseparable from dimethoxynaphthalene precursor 91 by liquid chromatography, where only 1:19 to 1:9 MeOH:CH$_2$Cl$_2$ is capable of moving the compound on TLC. Furthermore, the CAN-mediated oxidation was not a clean reaction, and HPLC purification would be required. The HPLC trace of a crude CAN-mediated oxidation is shown in FIG. 9A.

Authentic 92 had been synthesized and characterized through the CAN oxidation reaction, and all that remained was to optimize the synthesis to get the cleanest product directly from the final transformation. Nitric acid and Ag(II)O were applied to the oxidation of 91 following the method previously used to oxidize all 3-halo dimethoxynaphthalenes, than 3 minutes at room temperature with 5-7 equivalents of Ag(II)O and resulted in an extremely clean product.

FIG. 9: HPLC spectra of oxidation and coupling reactions to synthesize quinone 92. A. The crude reaction mixture of a 1 hour CAN-mediated oxidation using 6 equivalents of oxidant. B. Standard nitric acid/argentic oxide oxidation of dimethoxynaphthalene 91. C. New nitric acid/argentic oxide conditions utilizing soluble silver nitrate in dioxane for the oxidation of 91. D. UV spectra of product (92) faster eluting component from Ag(II)O oxidation in dioxane. E. Crude reaction mixture of PyBOP coupling quinone 43a to desthiobiotinylating reagent 94. F. Flash chromatography purification of PyBOP coupling reaction from FIG. 9E. G. Sample from FIG. 9F after storage in MeCN for 8 days at −20° C. All samples were run at 40:60 acetonitrile:water on a C8 analytical column, spectra collected at 300 nm. The retention time for the product is 12.6 min and the peak is indicated by an arrow. Decomposition products are indicated by an asterix.

All of the sideproducts observed in the CAN and original silver (II) oxidations were absent from the reaction in dioxane, although there were now two peaks with identical UV spectra and similar retention times. (FIG. 9C) The only product observed in both $^1$H and $^{13}$C NMR of the crude reaction mixture corresponded to that of previously synthesized quinone 92. This led to the hypothesis that the new species observed at 11.6 minutes was likely a silver complex with either the olefin or the quinone bonds of 92. Washing the sample with dilute HCl and brine reduced the quantity of the 11.6 minute peak, consistent with the hypothesis that this is a complex between the product observed at 12.6 minutes and silver (I).

Concurrently, a coupling reaction between quinone 43a and amine 94 was being explored via HPLC. The methods were oxalyl chloride and PyBOP coupling, where the activation step of both reactions was confirmed by either gas evolution (oxalyl chloride) or $^{31}$P NMR (PyBOP). HPLC analysis showed no product in the oxalyl chloride reaction and minimal product in the PyBOP coupling. (FIG. 9D/E) The reacting quinone is easily separated from the desthiobiotinylated quinone, thus optimizing this reaction would lead to a product that could be purified by flash chromatography.

Allowing the reaction to activate with PyBOP and triethylamine for too long (2 h) resulted in the initial gold solution turning deep red, which has previously been an indication that the quinone has decomposed in the presence of a nucleophile. When the resulting red solution was then treated with amine 94 only traces of coupled product were observed by HPLC. The activation step was then shortened to 10 minutes followed by a 30 minute treatment with amine 94 and a homogeneous yellow solution was maintained throughout the reaction with a yield of greater than 60%. As predicted, the coupling reaction to synthesize 92 provided a reaction mixture that was easily purified by flash chromatography. However, the reaction between a quinone and an amine has been very difficult to control, frequently resulting in a dark green or red solution following base addition during the activation step. Thus the coupling route to 92 is advantageous in that product can be easily separated from other quinone or desthiobiotin containing species, but unfavorable in the respect that the reaction can take a catastrophic turn for presently unapparent reasons.

Without structural data for Ape1, it was hypothesized that collecting sufficient biological data from a wide range of inhibitors would drive a qualitative structure activity relationship (QSAR) assessment. Thus, a crystal structure of the 3-chloro derivative 43a was sought to provide a solid foundation for QSAR studies.

FIG. 12: A. Crystal of inhibitor 43a used for X-ray diffraction study. B. Structure generated from data collected from X-ray diffraction studies on 43a.

Figure 13:
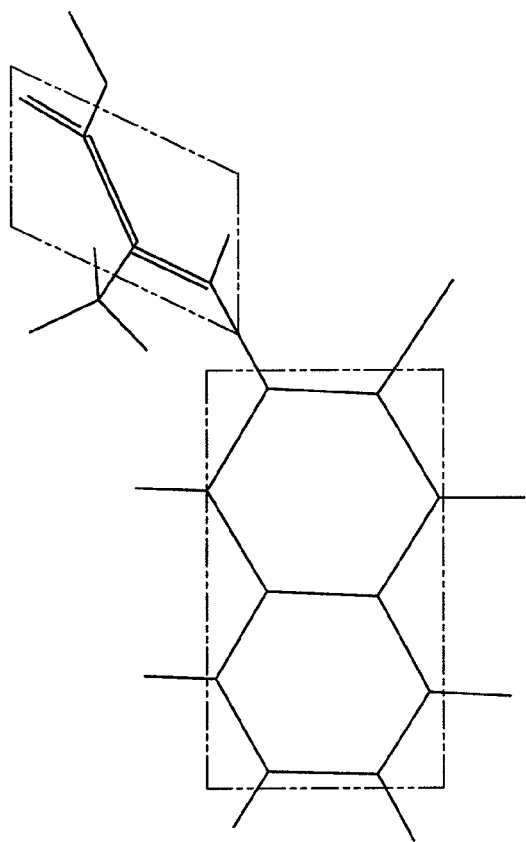
FIG. 13: Structure derived from X-ray diffraction study.

Crystals of inhibitor 43a (FIG. 12A) were grown using vapor diffusion, and the data collected was used to generate the structure in FIG. 12B. From this crystal structure a conformation of the inhibitor was derived. The unsaturated acid moiety of the crystal structure possesses an anticipated trans-diene configuration, and the quinone ring is slightly contorted into a boat conformation. The exocyclic double bond and the ring reside nearly 30° from parallel, which is most likely due to sterics of the 3-chloro substituent. (FIG. 13) Structure derived from X-ray diffraction study shows both the relationship between quinone and unsaturated acid planes as well as trans-diene like unsaturated acid conformation.

When mixtures of E and Z isomers were produced, from either the Emmons reaction or later from isomerizations encountered in the Steglich reaction, definitive assignments of E and Z needed to be given to the compounds isolated. The $^1$H NMR chemical shift of the vinyl proton is significantly different for E and Z isomers, where the E vinyl proton appears further downfield by as much as 0.7 ppm. However, a more convincing analysis was sought to further prove the identity of the isomers. A concrete foundation was given to this developing evidence by the X-ray crystal structure determined for 43a. The observable E double bond geometry in the crystal structure is unquestionable, and the preceding E and Z isomers could be identified in the unsaturated acid series of the naphthalene compounds by tracing the lineage of E-43a backwards. As expected the E isomers had the downfield vinyl protons, and the upfield shifts corresponded to the Z isomers.

For the naphthalene unsaturated acids comparing the vinyl proton shifts was sufficient for later compound identification. However, when isomers were encountered with the Steglich conditions, the vinyl protons in the amide products were appearing further upfield than expected. The relative shifts of the vinyl protons, as well as the expected geometrical effects on shifts of other protons including the amide and alpha protons, all correlated to the expected assignment of E and Z isomers. To ensure our assignments were correct with these new unsaturated amides, 2D and nOe NMR were taken to identify the beta carbon in the former and observe enhancements of the vinyl proton in the latter.

Figure 14A:
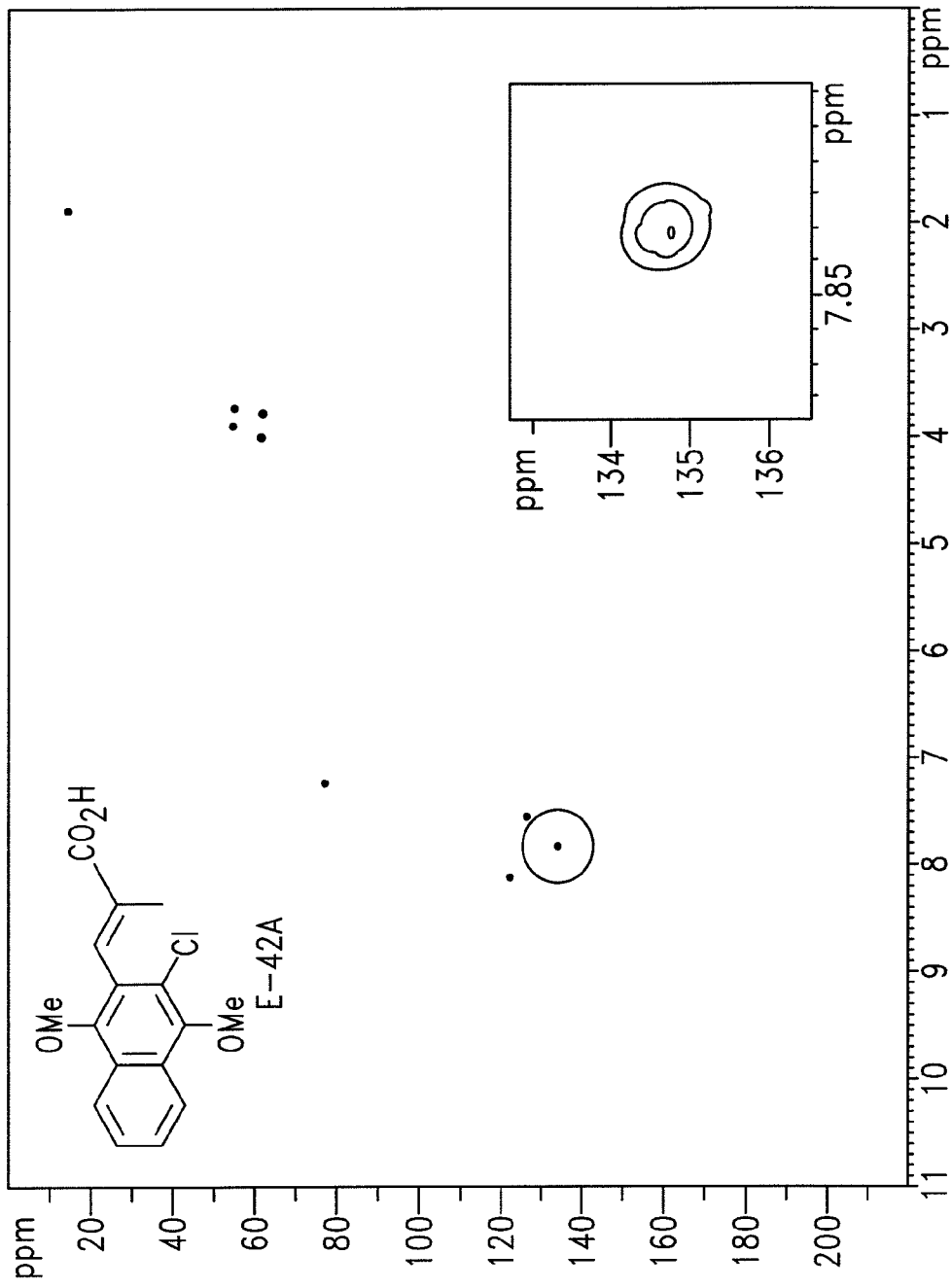
FIG. 14: HMQC spectra of A. E-42a; B. Z-42a; C. 9f; and D. 79.
Figure 14B:
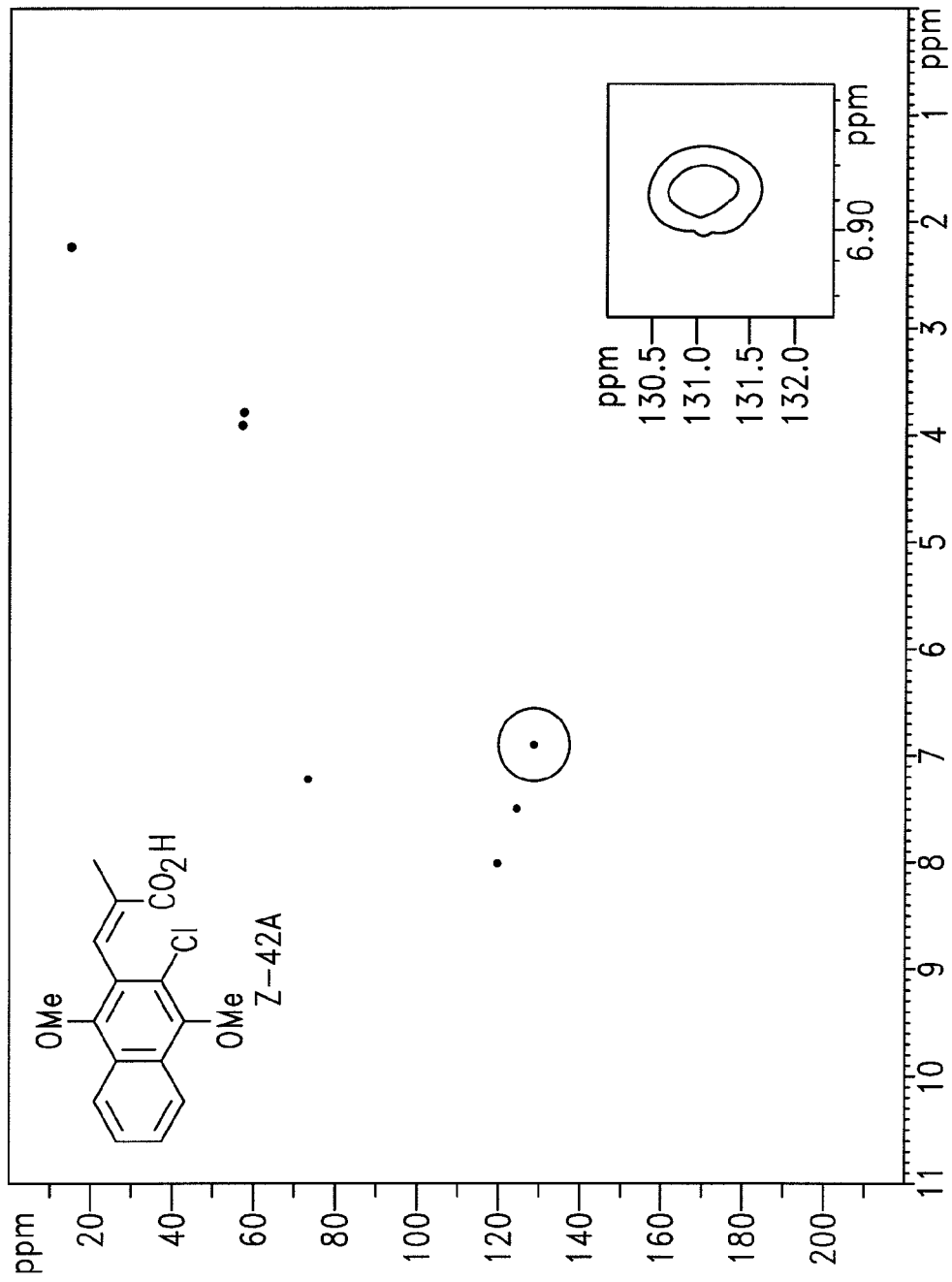
Figure 14C:
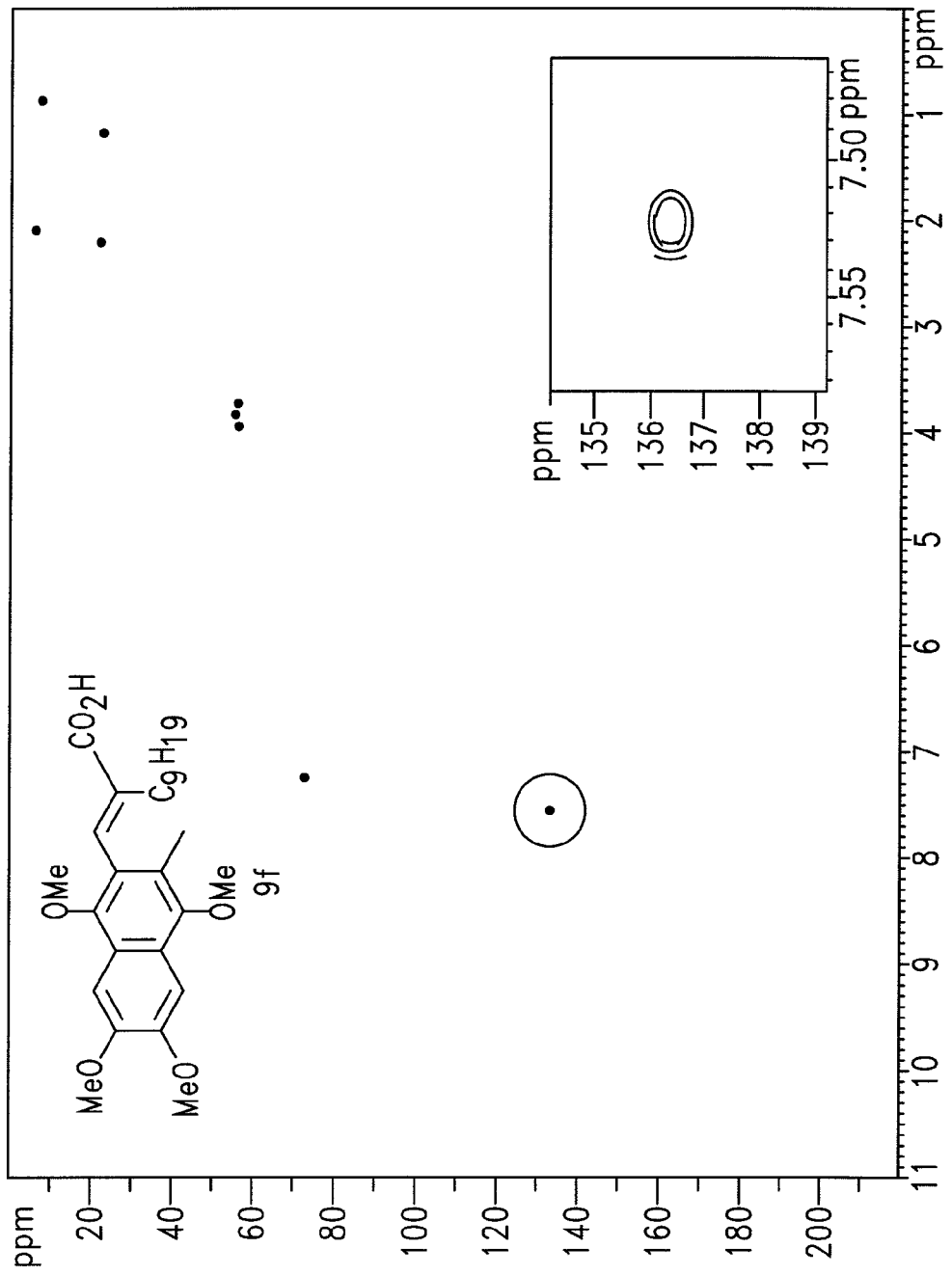
Figure 14D:
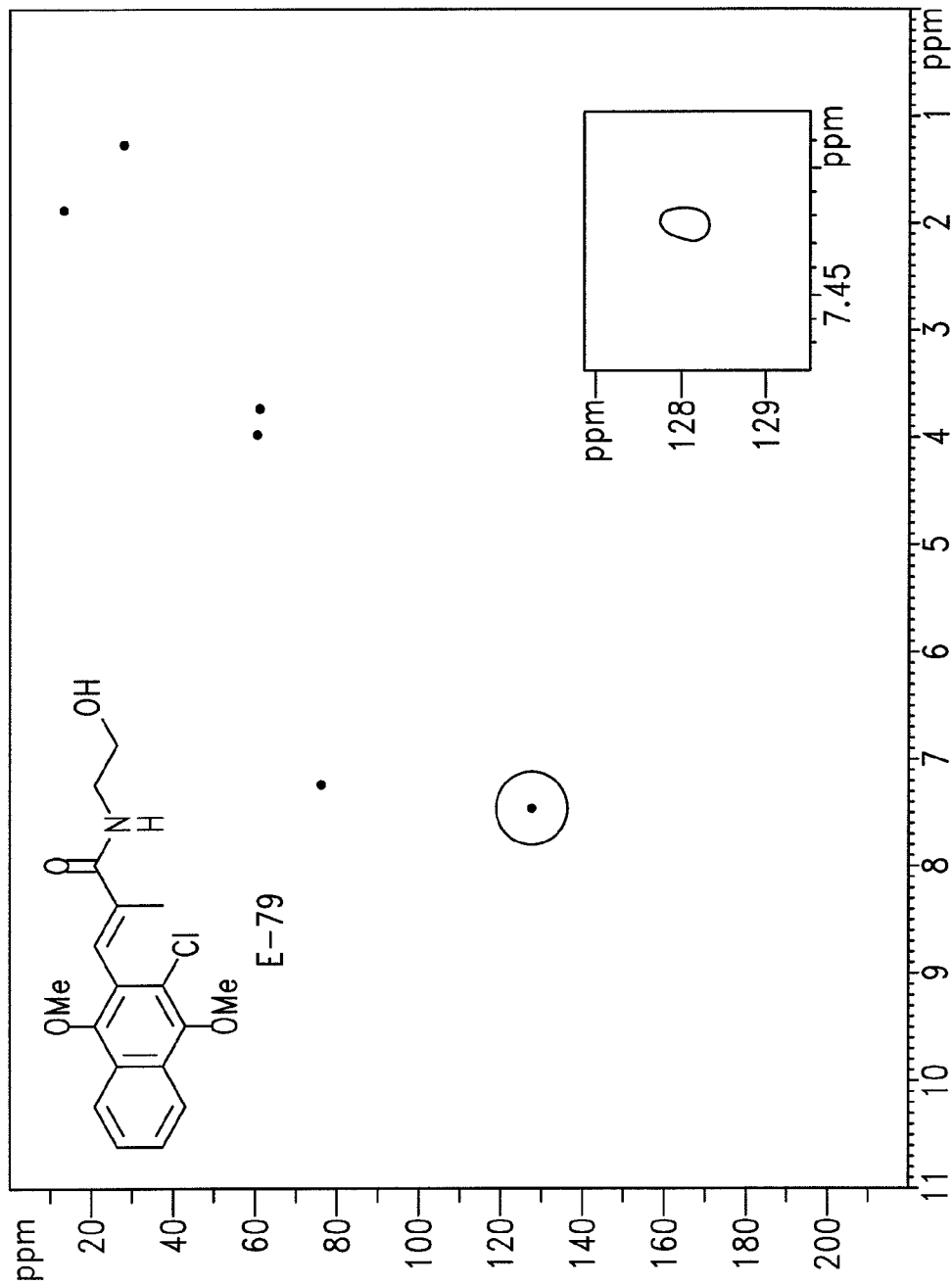
Figure 15A:
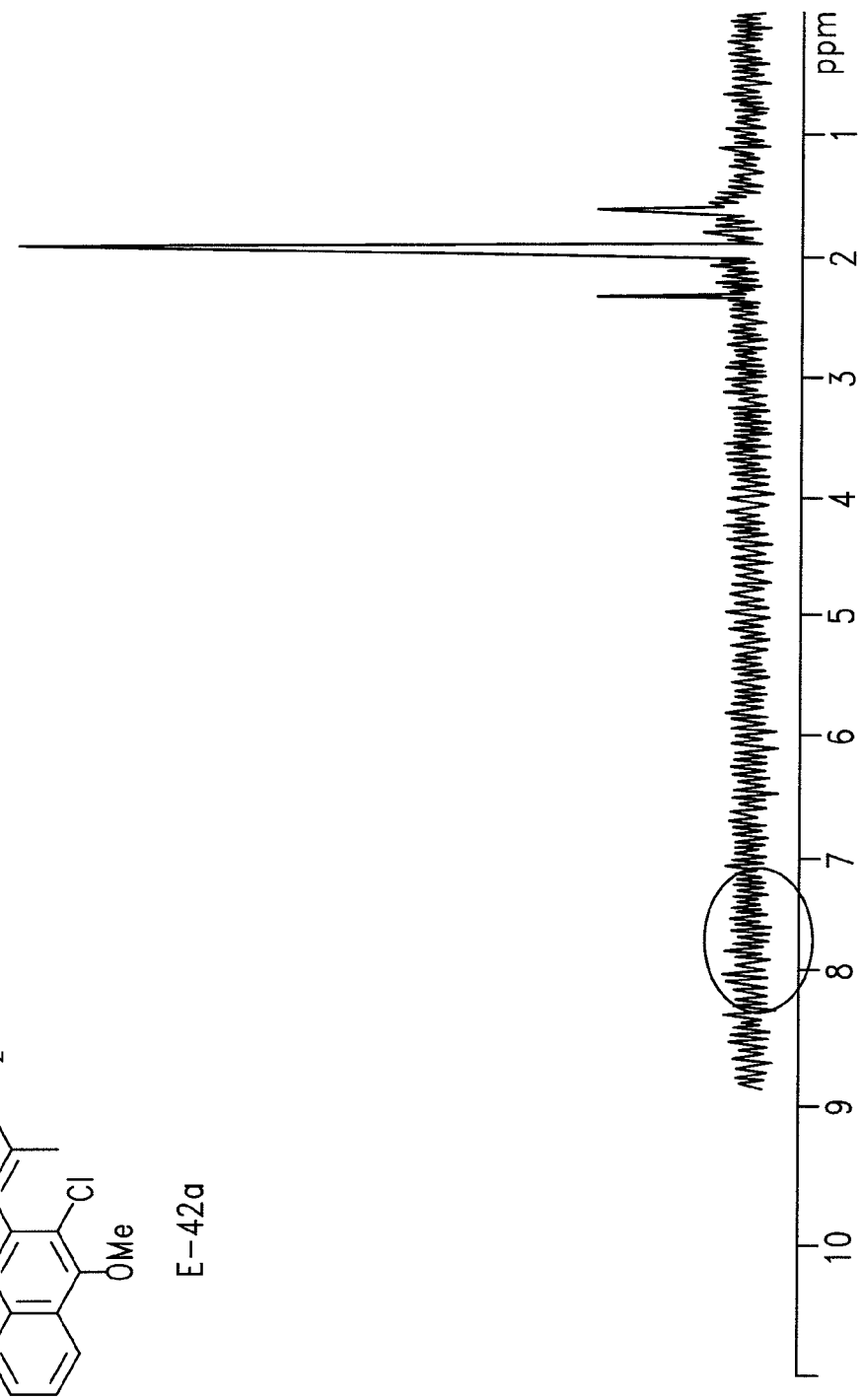
FIG. 15: nOe spectra of A. E-42a; B. Z-42a; C. 9f; and D. 79.
Figure 15B:
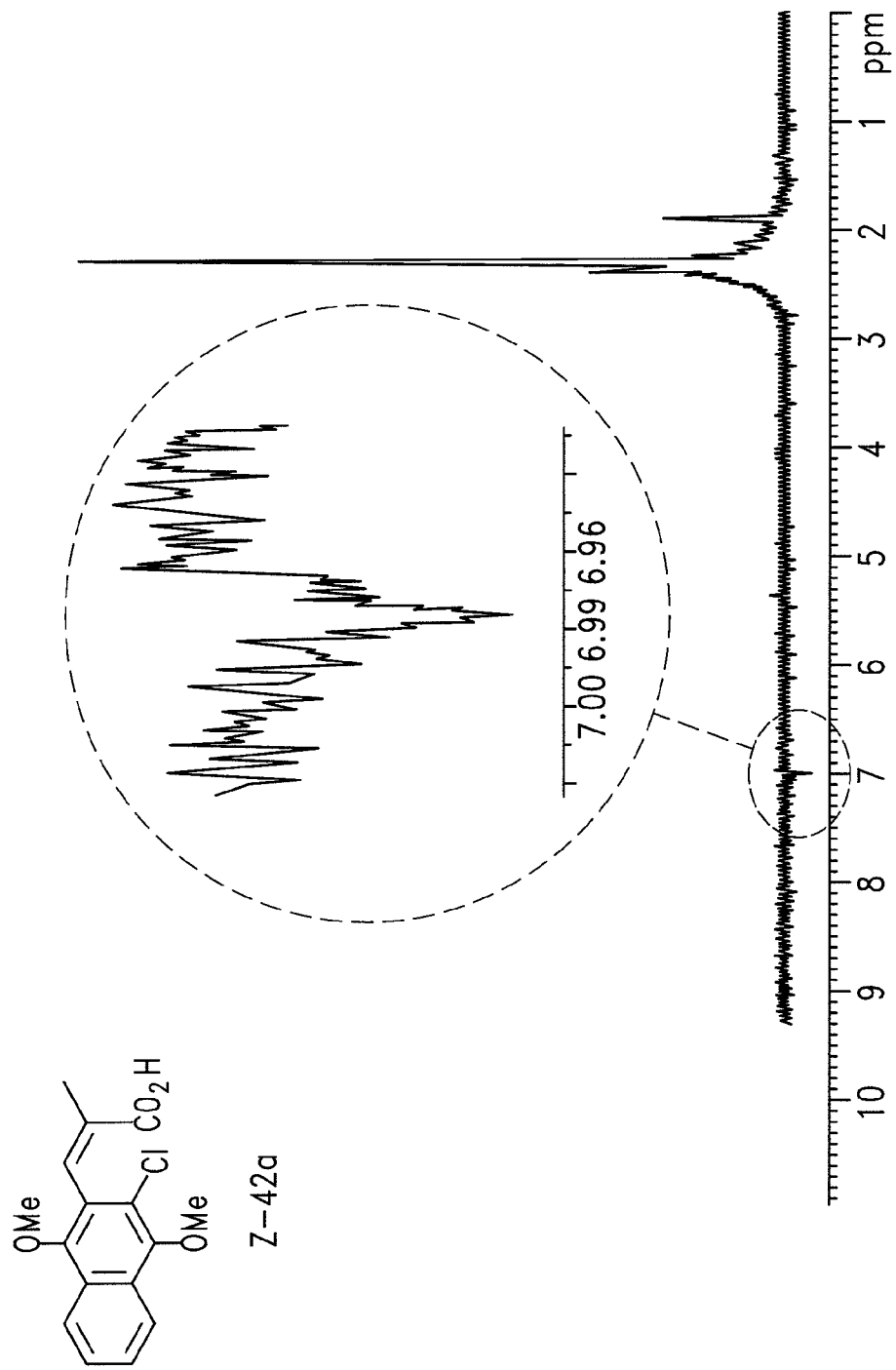
Figure 15C:
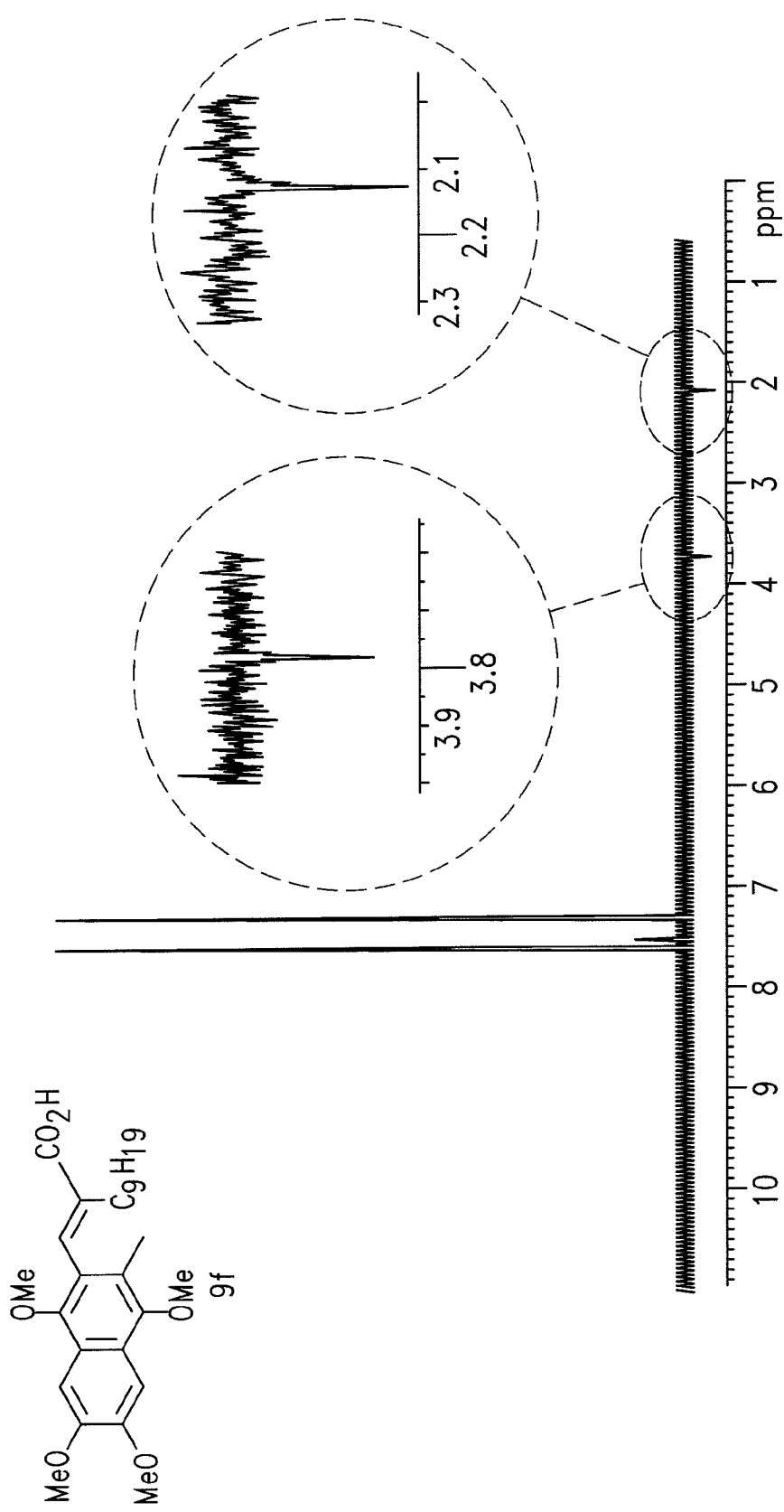
Figure 15D:
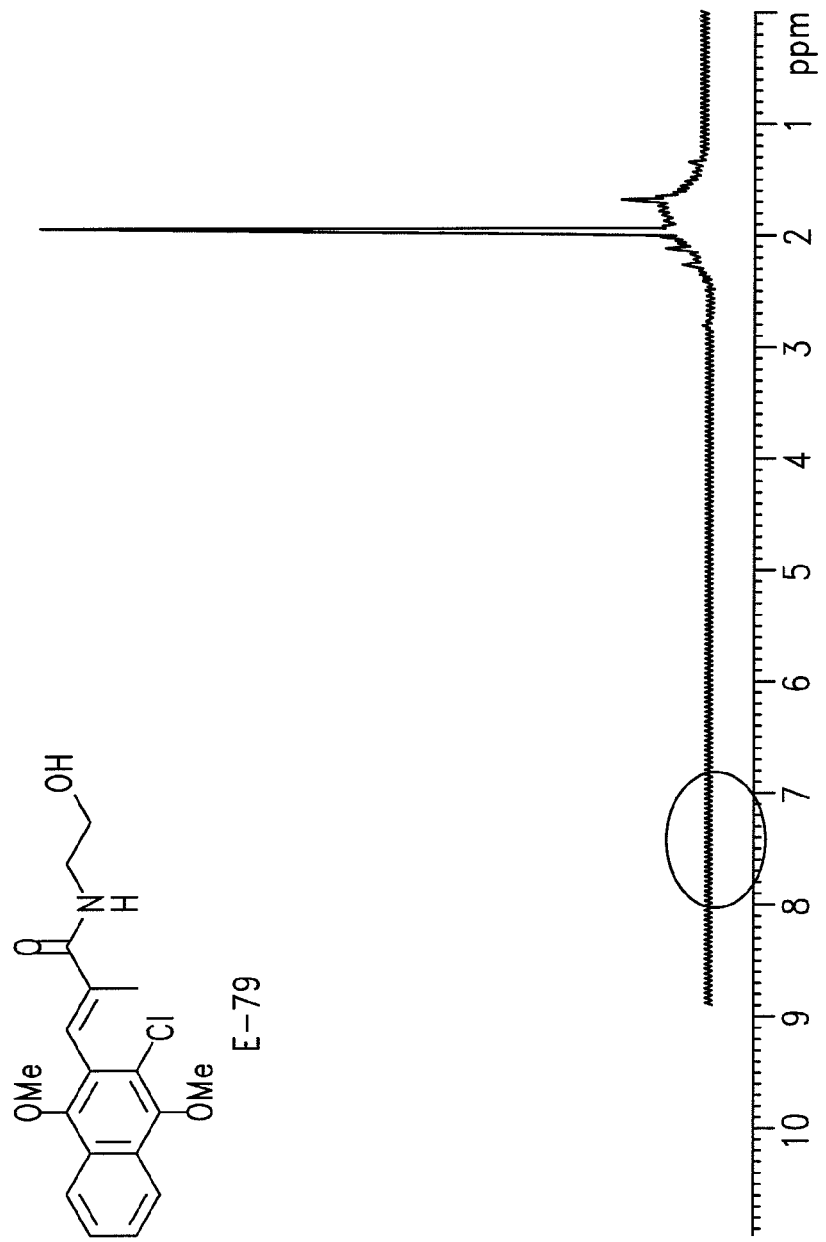
Figure 16A:
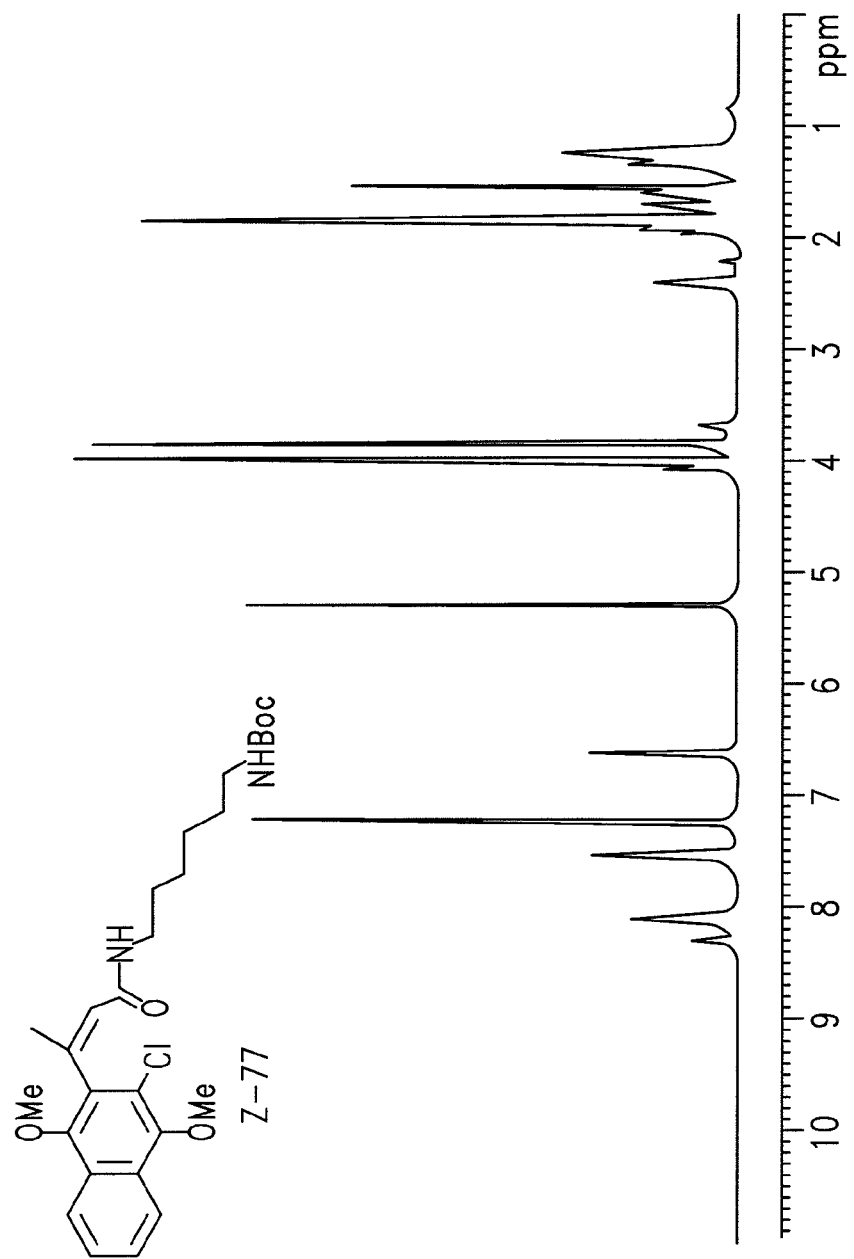
FIG. 16: Analysis of Z and E isomers (Z)-77 and (E)-77, respectively, by direct comparison of $^1$H NMR spectra (A/B), HMQC spectra (C/D), nOe enhancement from irradiation of allylic protons (E/F), and nOe enhancement from irradiation of vinyl protons (G/H). A/B.
Figure 16B:
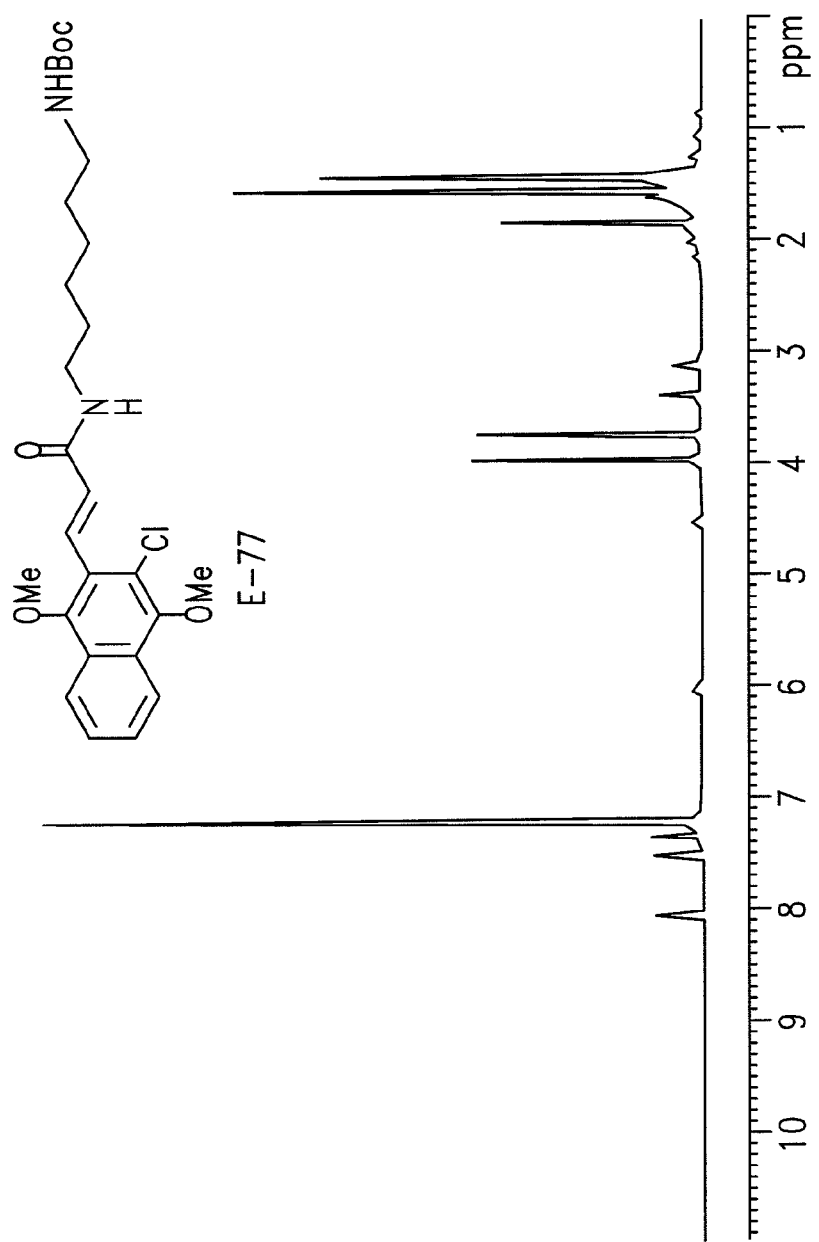
Figure 16C:
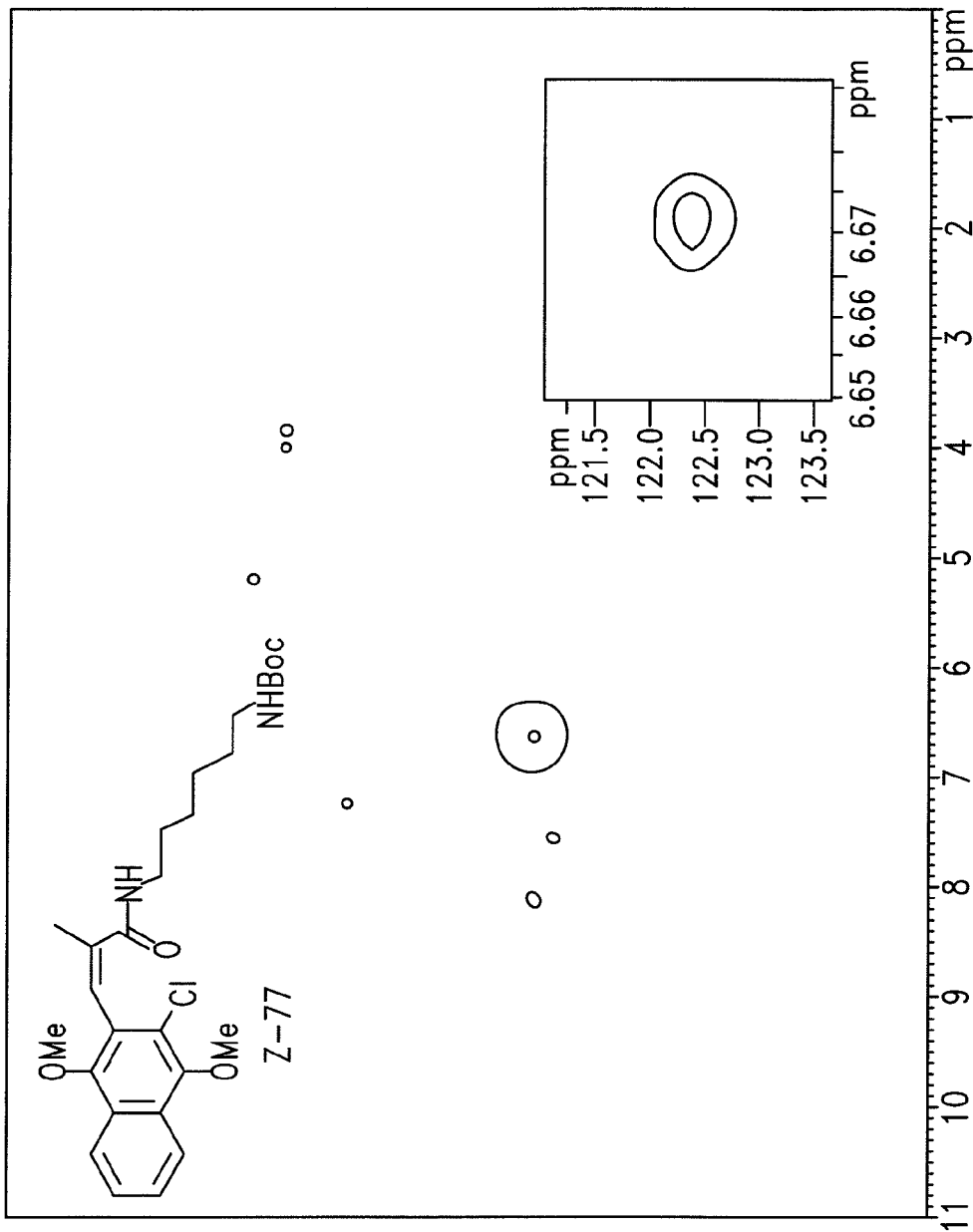
Figure 16D:
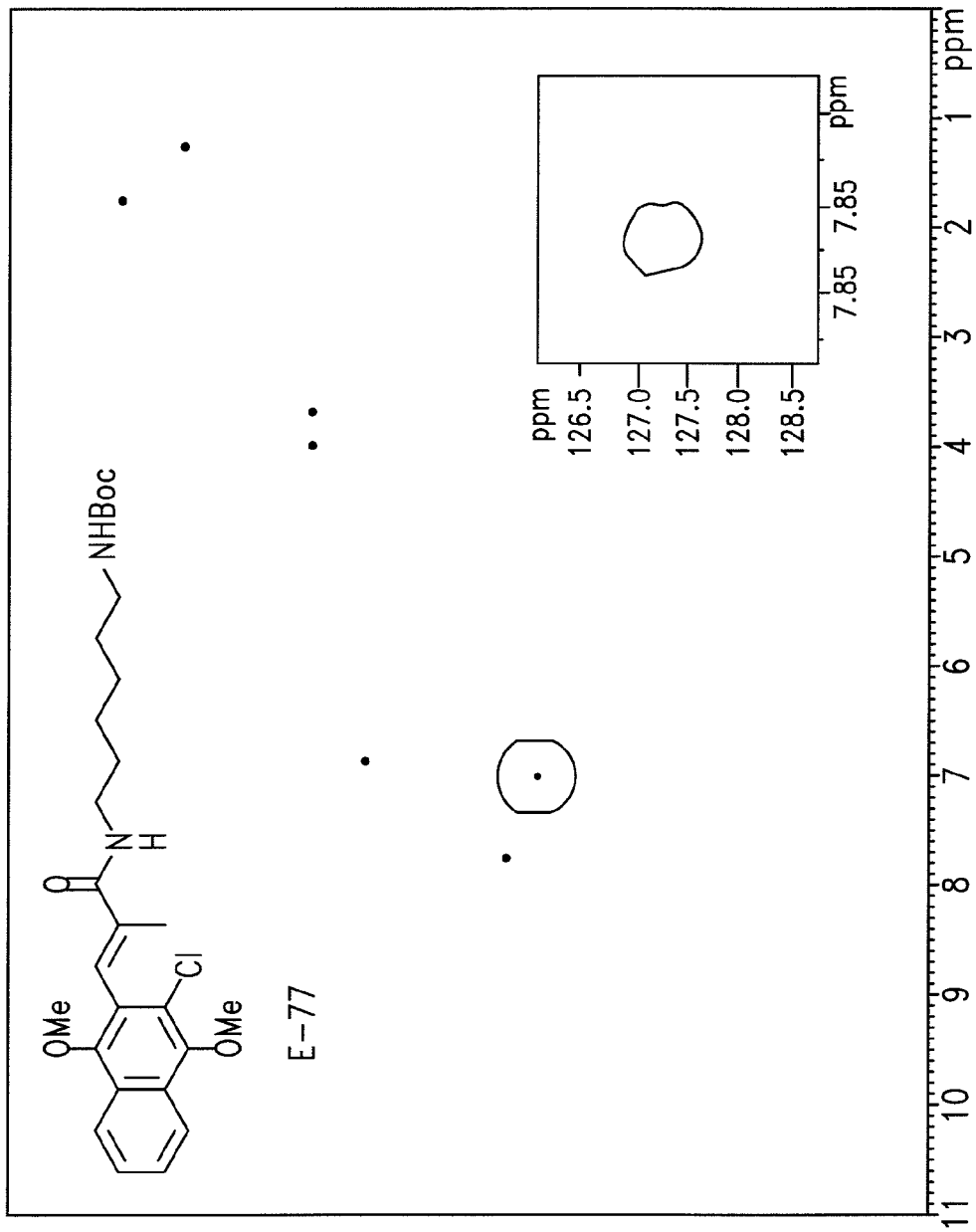
Figure 16E:
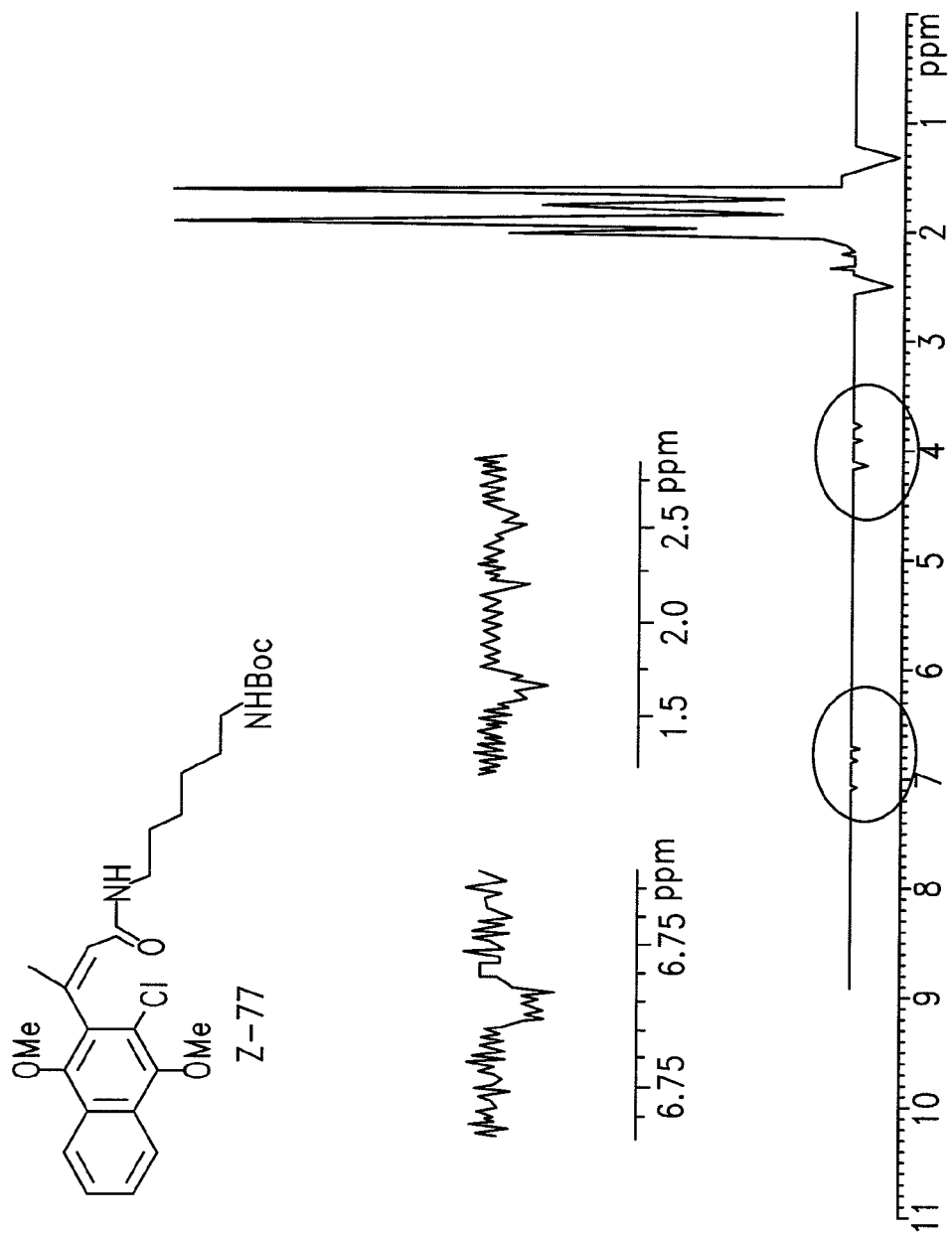
Figure 16F:
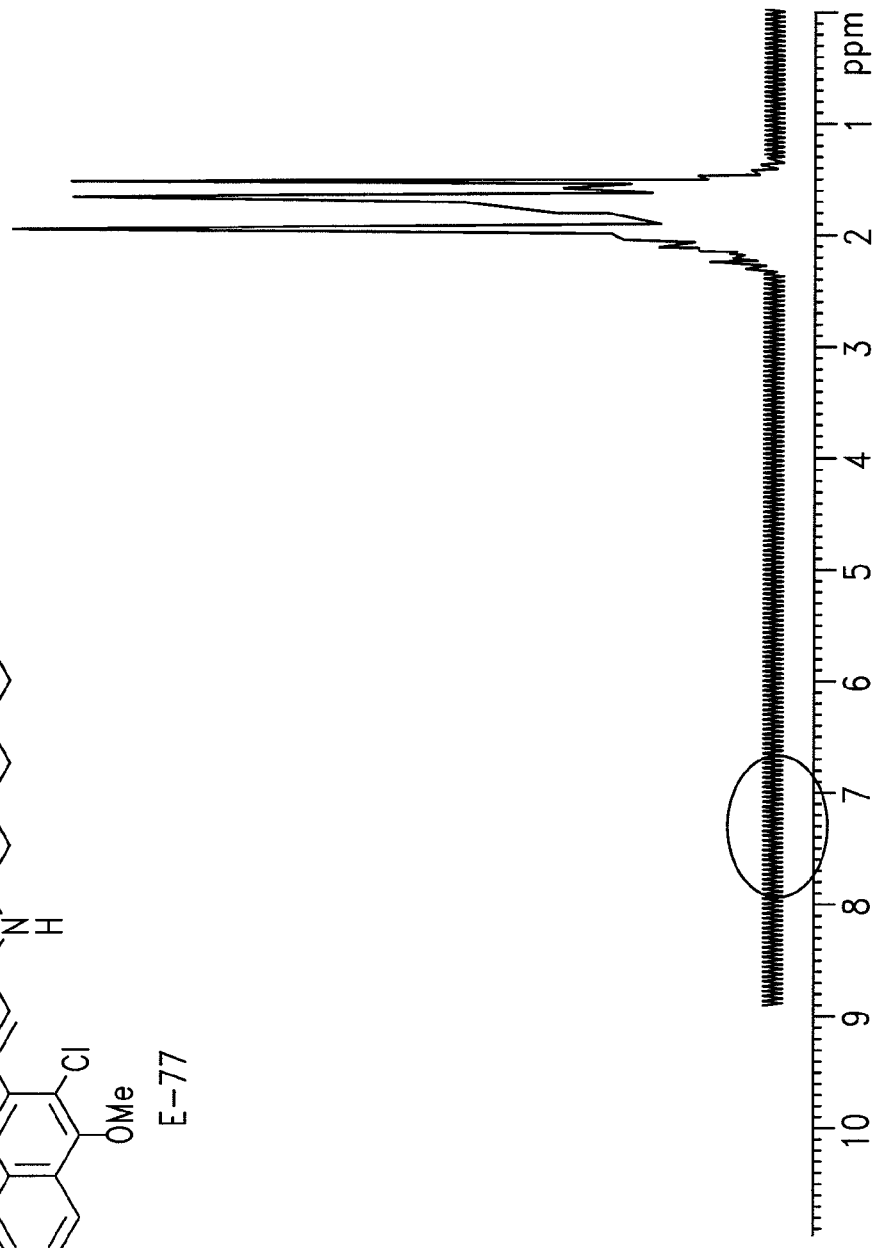
Figure 16G:
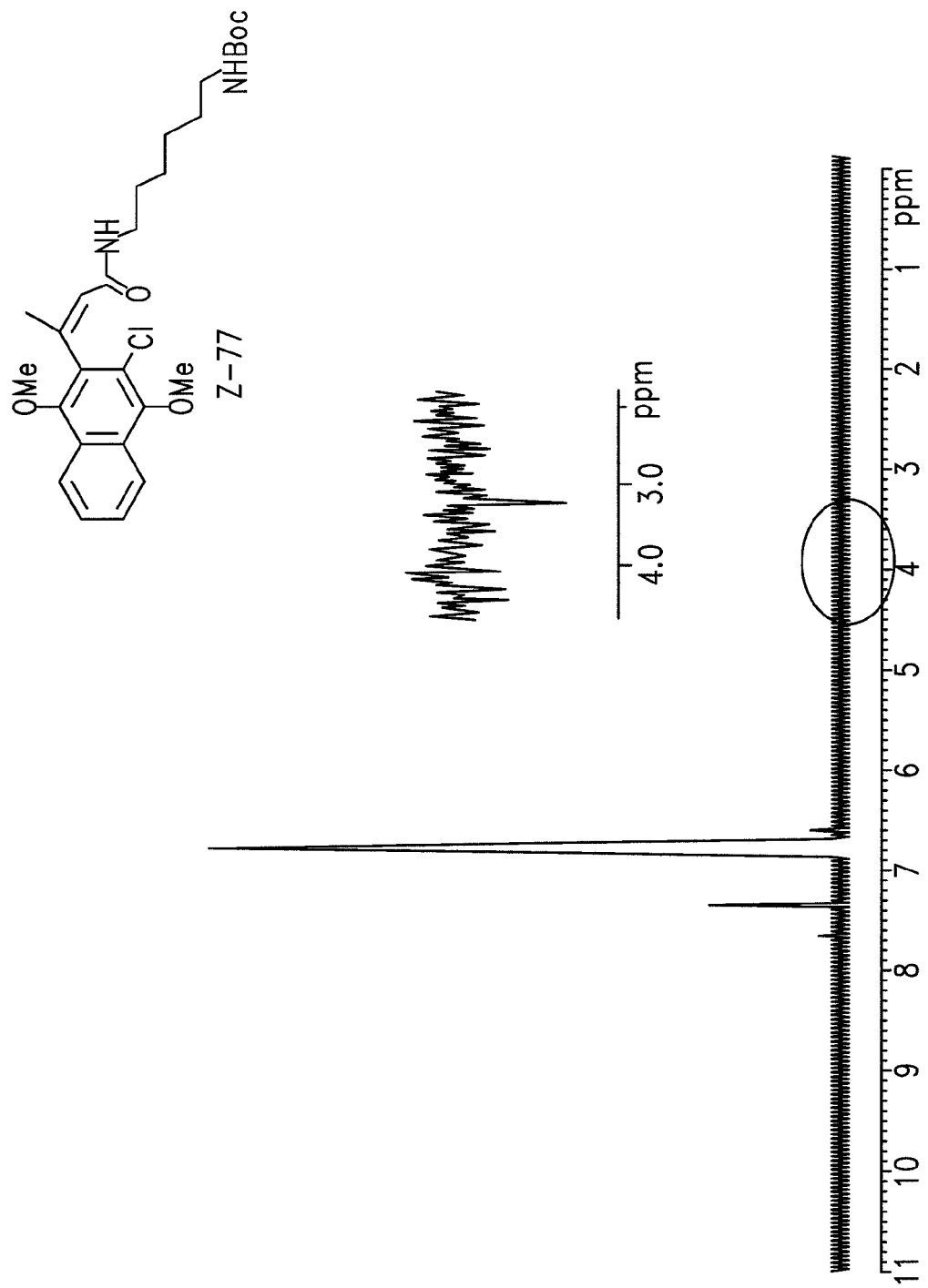
Figure 16H:
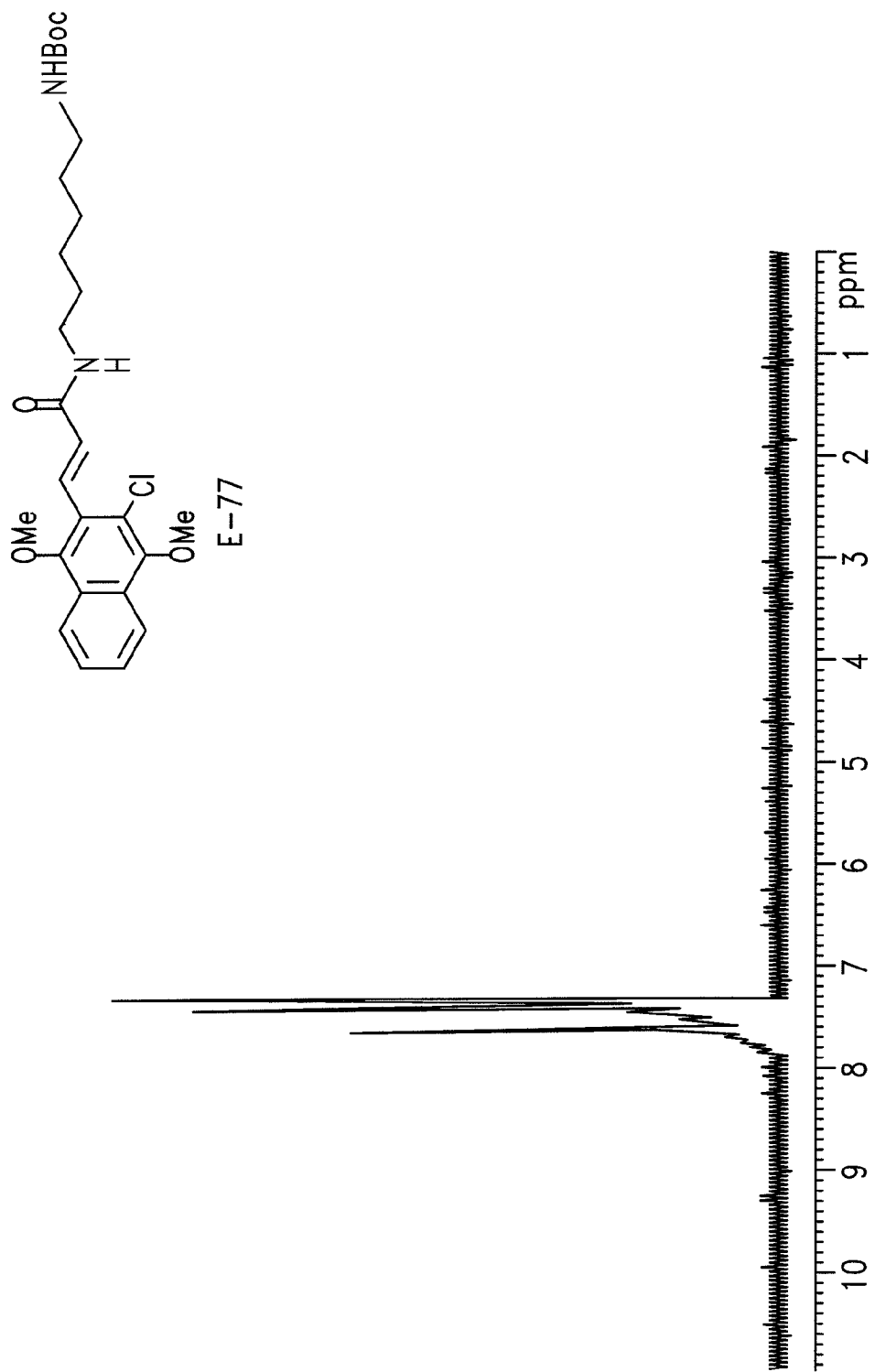
Figure 17A:
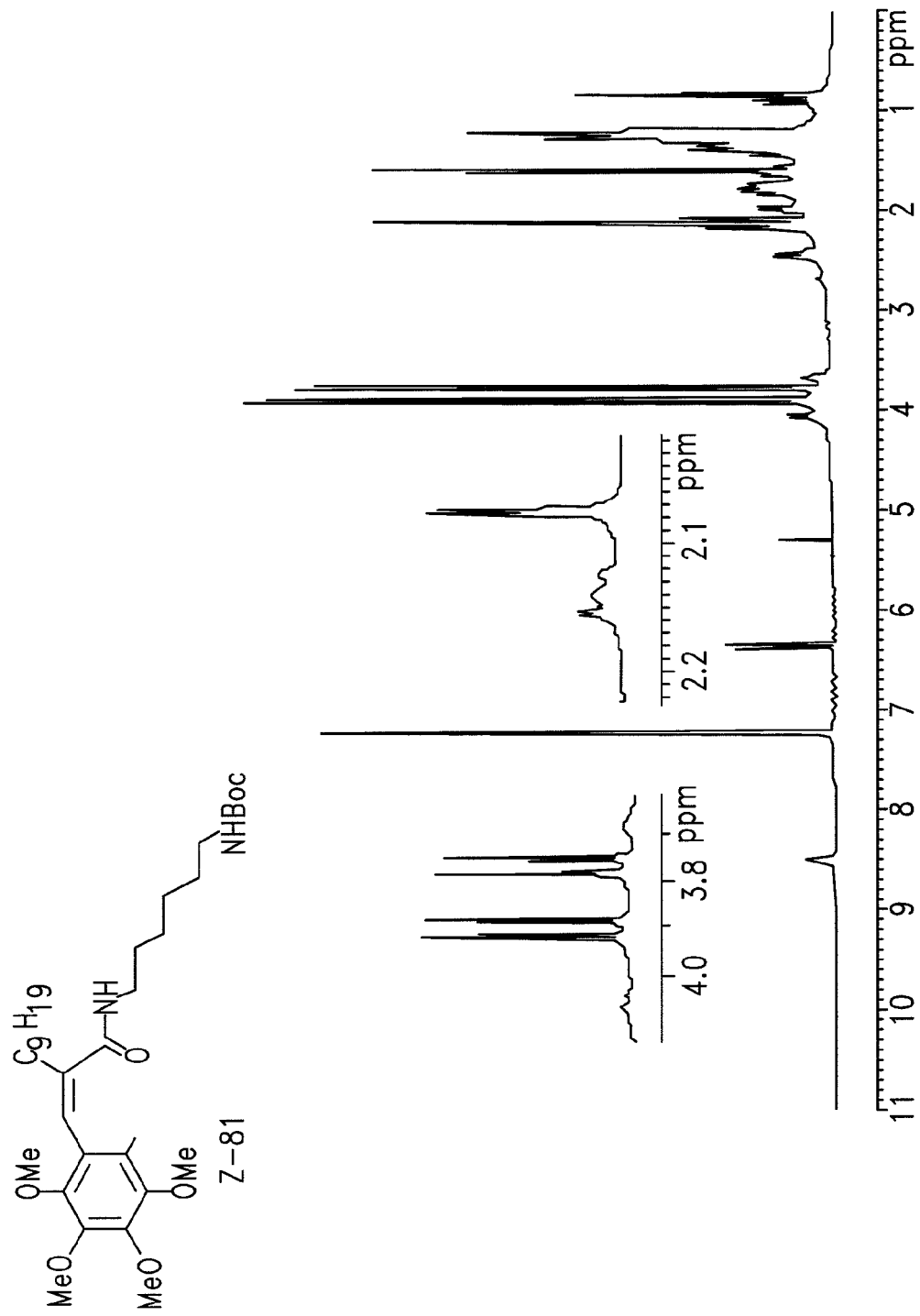
FIG. 17: Direct comparison of Z and E isomers (Z)-81 and (E)-81, respectively, by their corresponding $^1$H NMR spectra (A/B), HMQC spectra (C/D), and nOe enhancement from irradiation of vinyl protons (E/F).
Figure 17B:
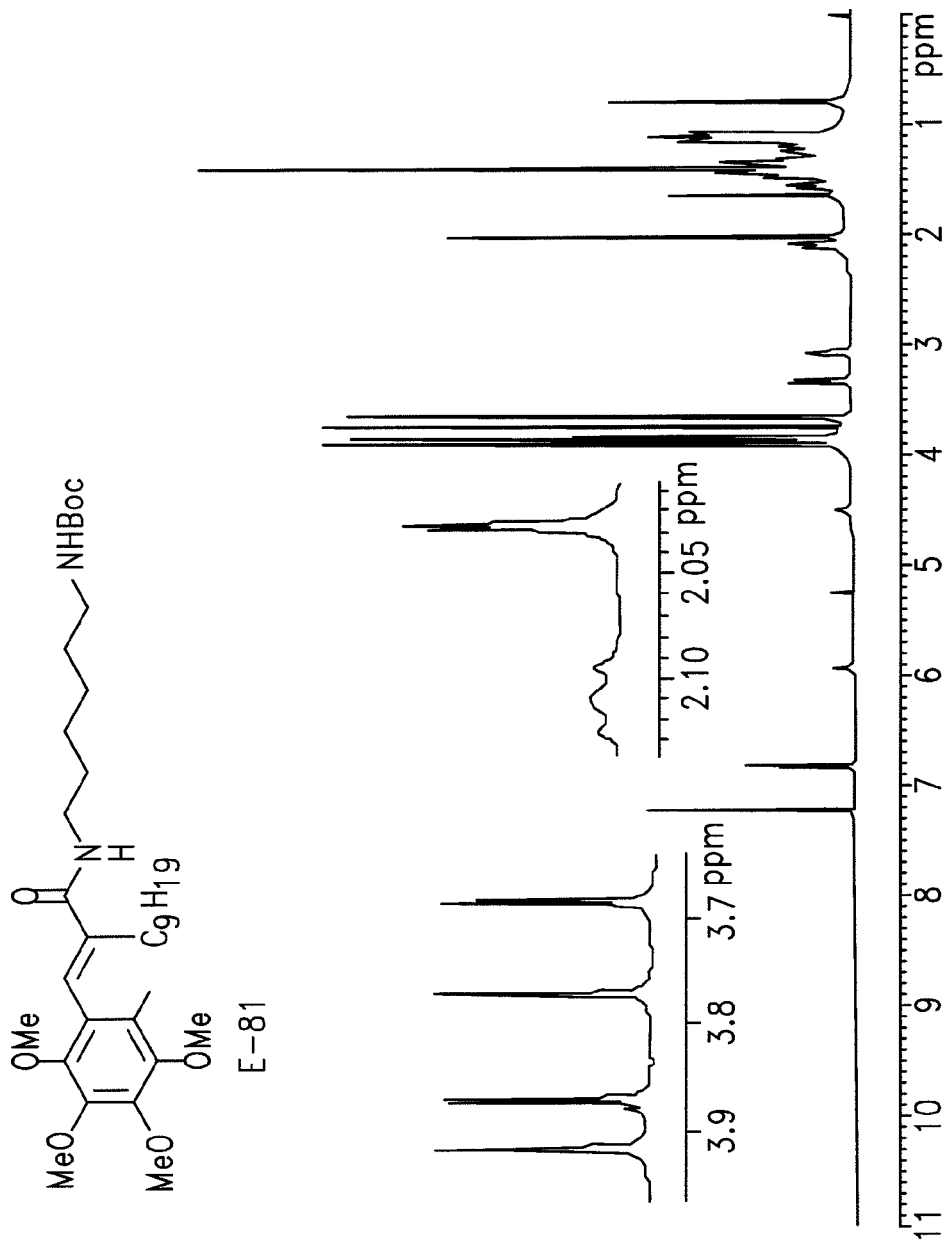
Figure 17C:
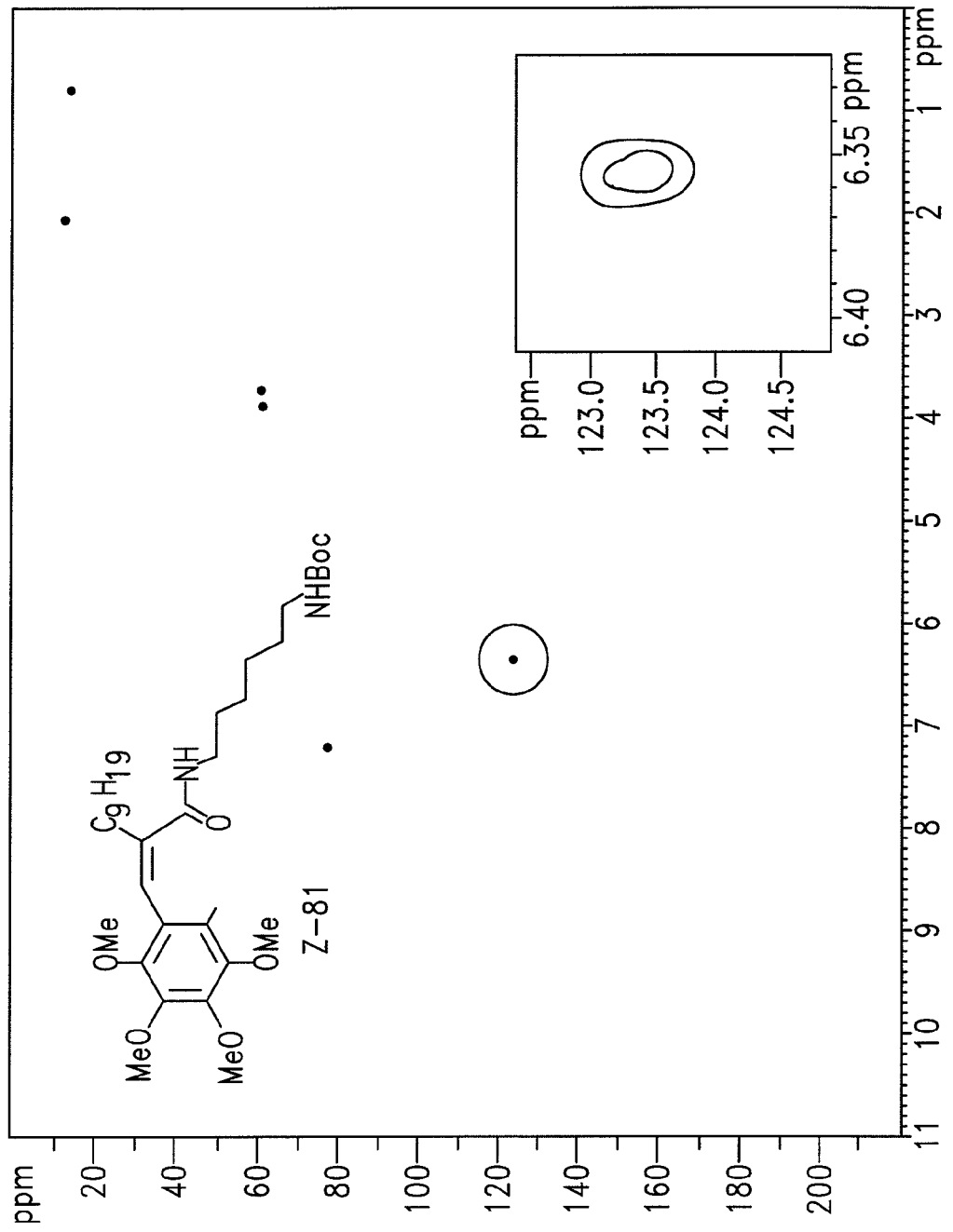
Figure 17D:
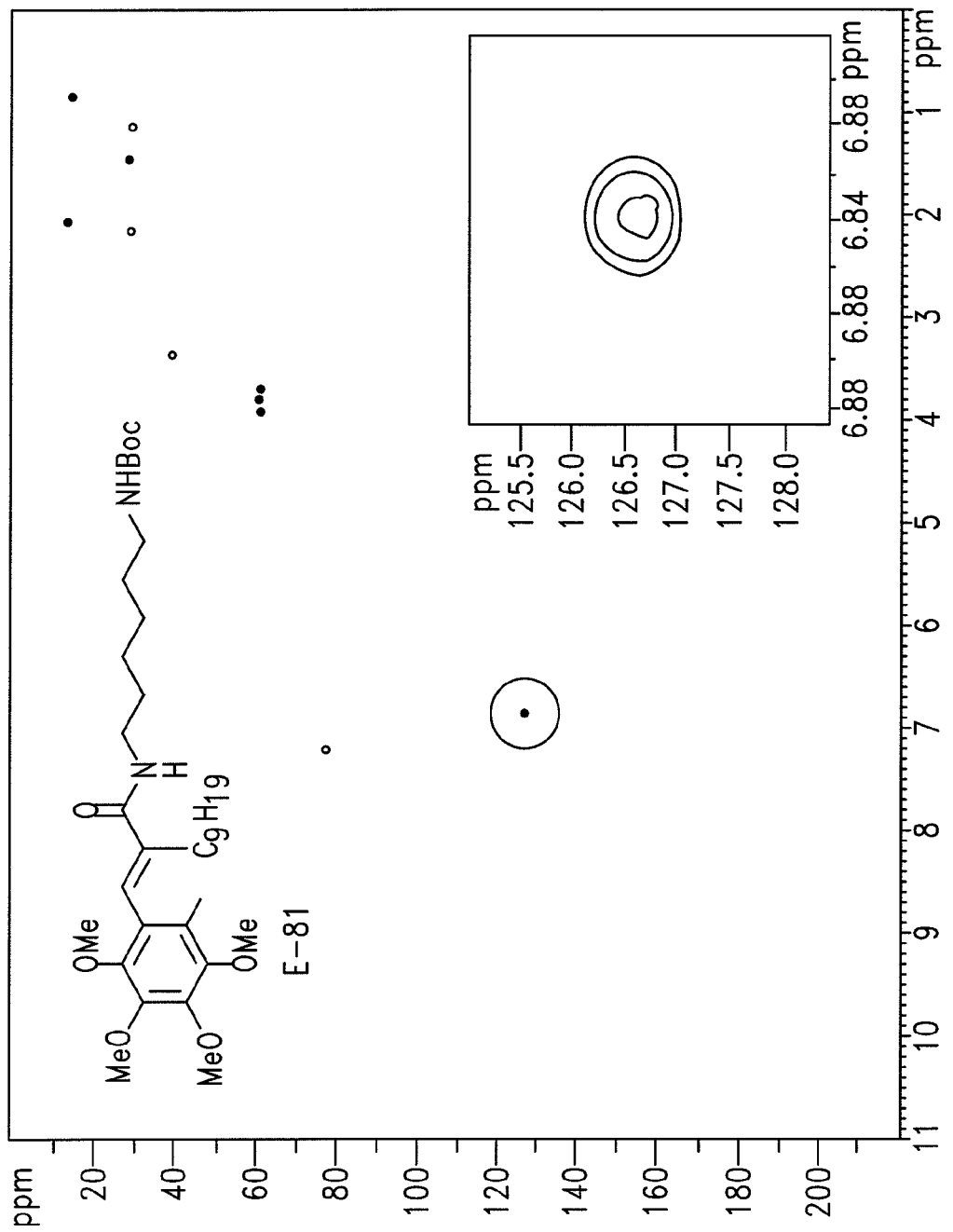
Figure 17E:
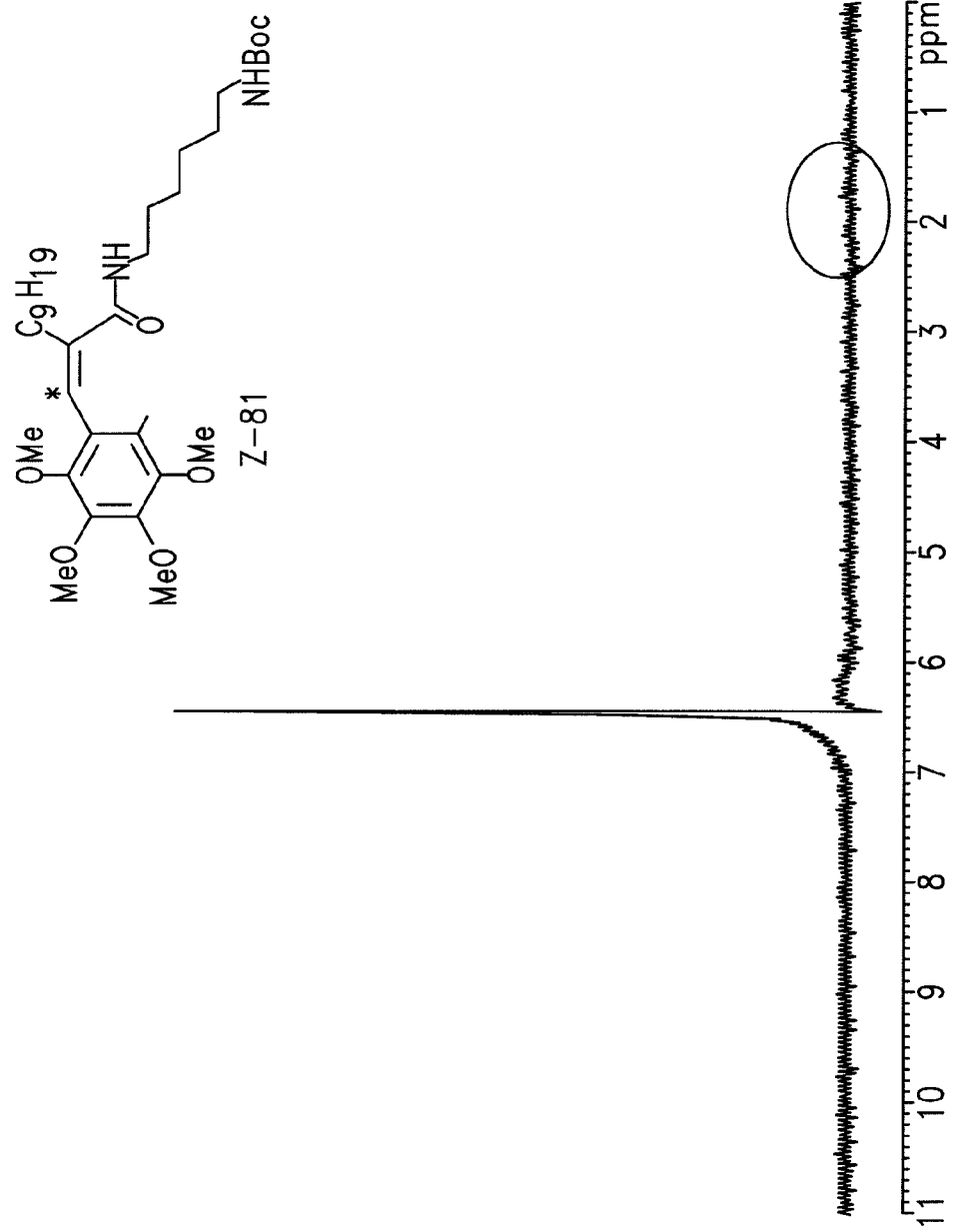
Figure 17F:
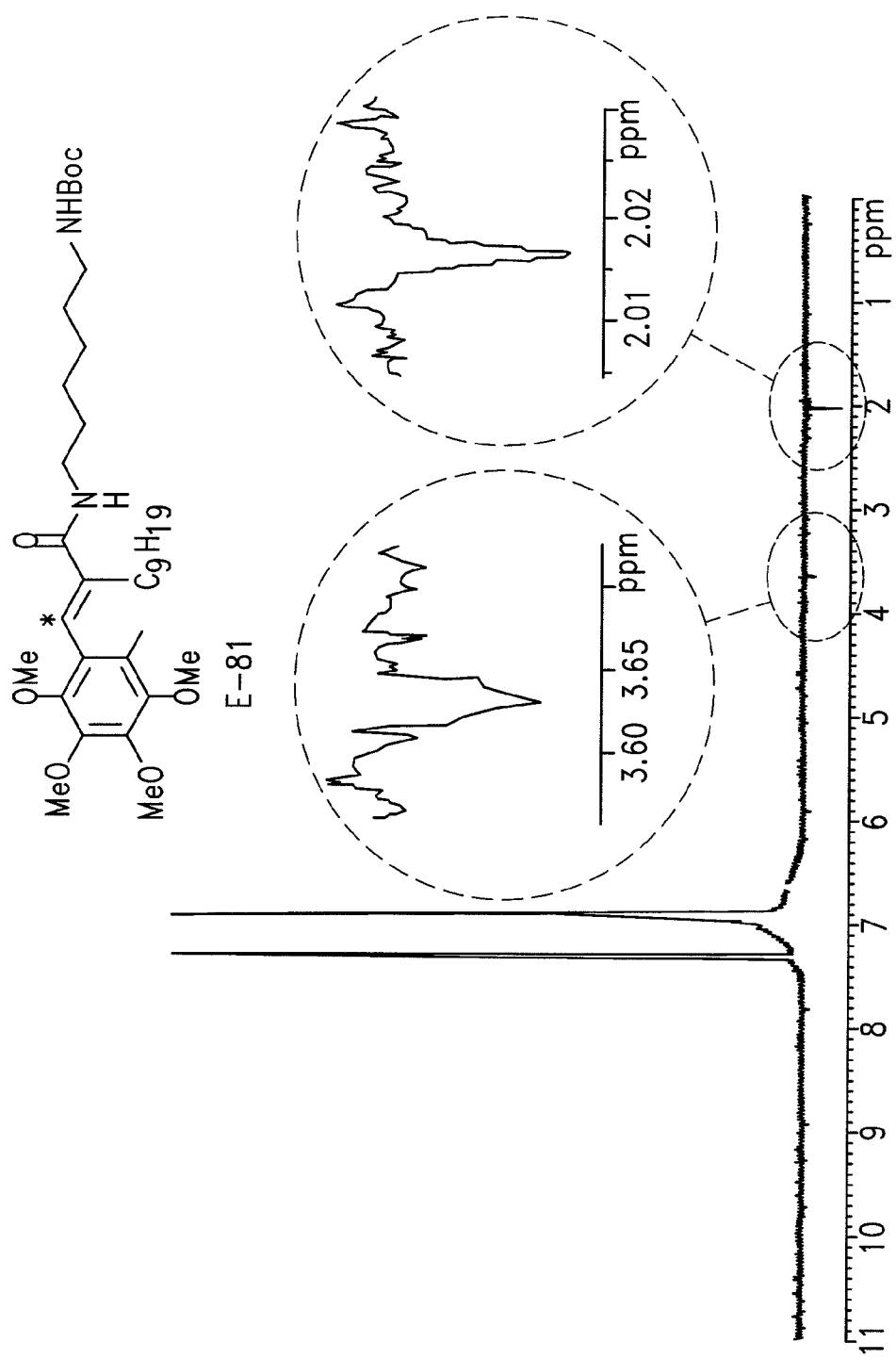
Figure 17G:
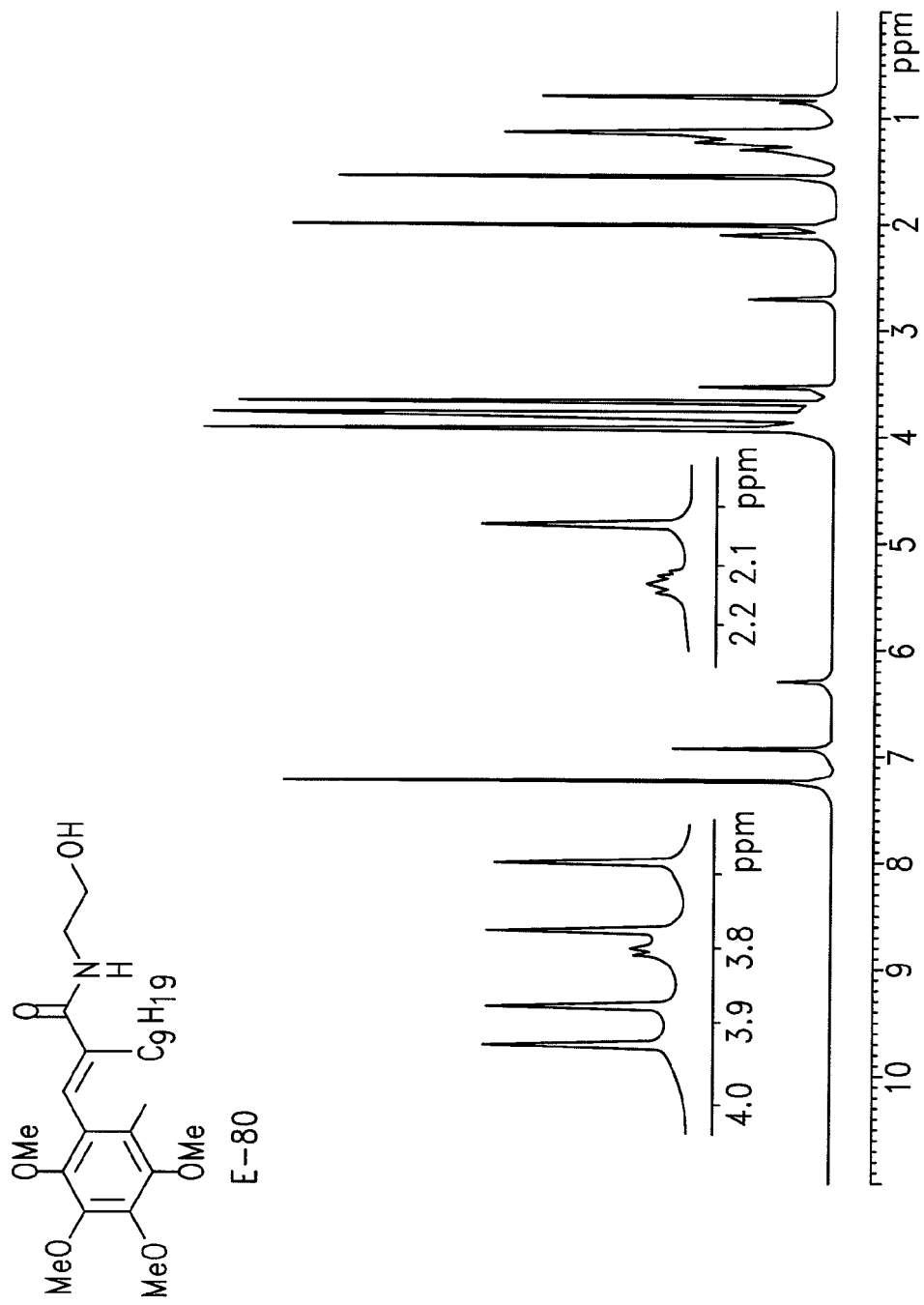
Figure 17H:
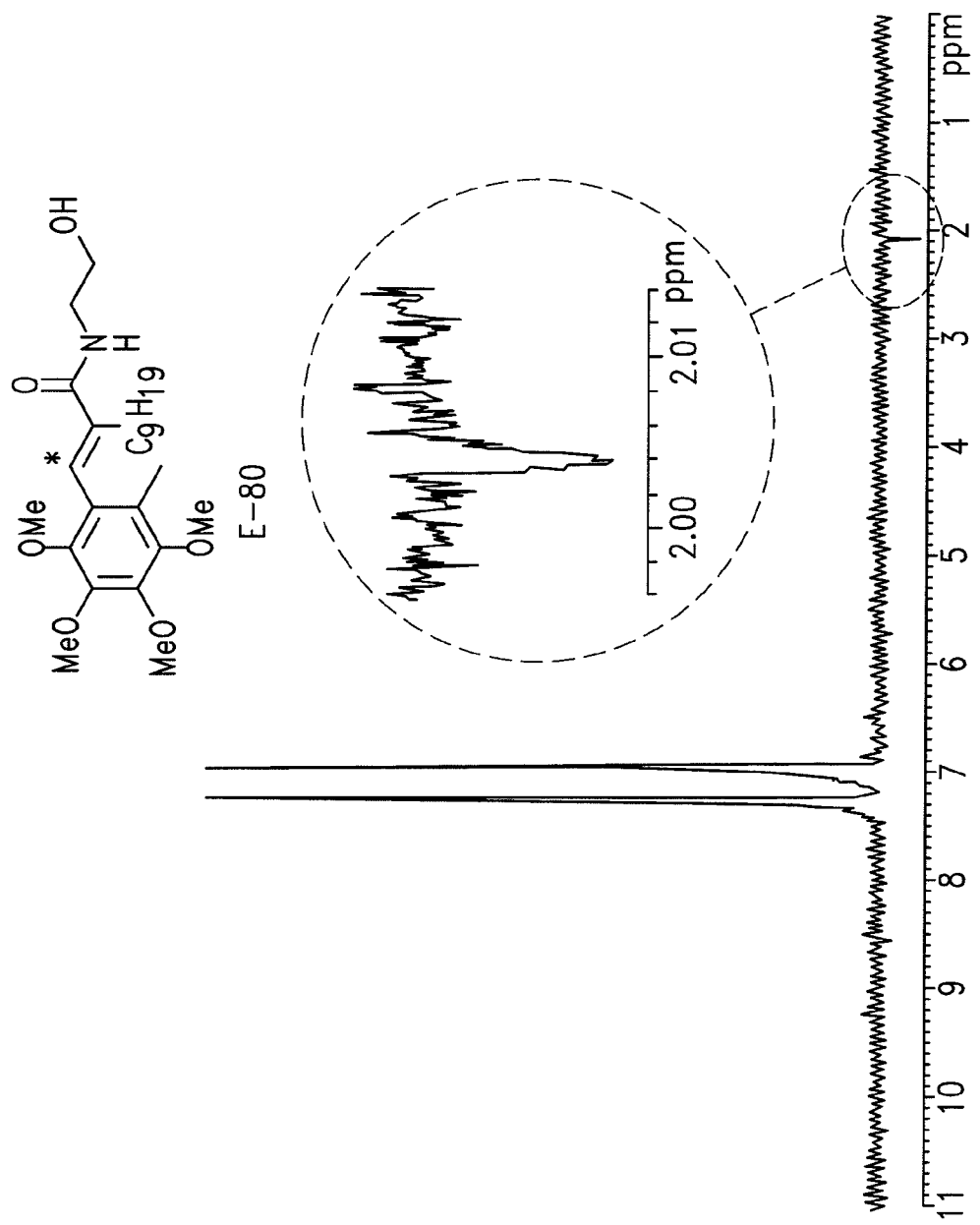

Previously identified E and Z isomers E-42a and Z-42a were again used in both type of advanced NMR experiments. First, HMQC spectra of E-42a and Z-42a were collected to identify the beta carbon, and it was determined that the E isomer had a downfield shift of 3.5 ppm (134.6 and 131.1 ppm respectively). (FIGS. 14A and 14B) Second, the same samples were run in nOe experiments where the allylic methyl protons were irradiated (1.90 ppm for E and 2.20 ppm for Z). For the E isomer no enhancements were observed to the vinyl proton; the Z isomer did experience enhancement of the vinyl proton upon irradiation of the allylic protons. (FIG. 15A and FIG. 15B) A third known entity was incorporated into the "training" data set, and this was 9f (Scheme 1), the unsaturated acid precursor to E3330. In this instance the beta carbon was again identified via the HMQC spectra (136.4 ppm, FIG. 14C); however the nOe irradiation was performed on the vinyl proton rather than the allylic protons because the alpha substituent has now changed from a simple methyl to a nonyl group. Irradiation did not show enhancement of the methylene protons of the nonyl group, but did show enhancement of the ring methyl, as expected. (FIG. 15C) Finally, the first simple amide generated (79) was examined to compare the effects of converting an unsaturated acid to the unsaturated amide. (FIG. 14D and FIG. 15D) The nOe enhancement followed the experimental data of the other E isomers where no enhancement of the vinyl proton was observed upon irradiation of the allylic protons. Without having the Z isomer, comparisons could not be made regarding the chemical shifts of the beta carbons from the HMQC data; however, assignment of the beta carbon (128.12 ppm) was still possible. Later the E isomer of 79 was synthesized from pure E acid using methyl chloroformate, confirming the geometry of the previous NMR sample.

FIG. 14: HMQC spectra of A. E-42a; B. Z-42a; C. 9f; and D. 79. Peaks corresponding to the vinyl proton/beta carbon have been circled in black.

FIG. 15: nOe spectra of A. E-42a; B. Z-42a; C. 9f; and D. 79. Site of proton irradiated in experiment is denoted on structure by an asterix. Diagnostic regions positive for enhancement are represented by a closed circle, a broken circle denotes diagnostic areas negative for enhancement. A. No enhancement of the vinyl proton is observed by the irradiation of the allylic protons of E-42a at 1.95 ppm. These are expected results for a confirmed E olefin. B. Enhancement of the vinyl proton at 6.98 ppm is observed after irradiation of the allylic protons of Z-42a at 2.28 ppm. Enhancement was expected for the confirmed Z olefin. C. Irradiation of the vinyl proton at 7.62 ppm does not show enhancement of the methylene protons of 9f; however, enhancement is observed in the ring methyl peak at 2.12 ppm. This is keeping with the lack of enhancement observed in the E olefins. D. Irradiation of the allylic protons of 79 does not show enhancement of the vinyl protons, suggesting an E olefin.

FIG. 16: Analysis of Z and E isomers (Z)-77 and (E)-77, respectively, by direct comparison of $^1$H NMR spectra (A/B), HMQC spectra (C/D), nOe enhancement from irradiation of allylic protons (E/F), and nOe enhancement from irradiation of vinyl protons (G/H). A/B. The vinyl proton of the Z isomer (6.64 ppm, FIG. 16A) is significantly further upfield than that of the corresponding E isomer (7.36 ppm, FIG. 16B). C/D. The HMQC data for the Z and E isomers correlate to the same pattern observed in authentic E and Z isomers, where the Z beta carbon is further upfield (122.4 ppm, FIG. 16C) than the E beta carbon (127.3 ppm, FIG. 16D). nOe spectra of the Z isomer shows irradiation at the allylic position (FIG. 16E) has little effect on the remainder of the molecule, but irradiation at the vinyl proton (FIG. 16G) shows enhancement to a ring methoxy group. Irradiation of both the allylic (FIG. 16F) and vinyl (FIG. 16H) protons of the E isomer has no transference to other parts of the molecule.

FIG. 17: Direct comparison of Z and E isomers (Z)-81 and (E)-81, respectively, by their corresponding $^1$H NMR spectra (NB), HMQC spectra (C/D), and nOe enhancement from irradiation of vinyl protons (E/F). Comparison to the $^1$H spectrum (G) and nOe enhancement by irradiation of the vinyl proton (H) of another compound ((E)-80) helps identify conserved phenomena. A/B. As before the Z isomer displays an upfield shift of the vinyl protons. C/D. The chemical shift for the beta carbon in the Z isomer is further upfield (123.6 ppm vs. 126.7 ppm), consistent with the training set of known compounds. E. Interestingly, the irradiation of the vinyl proton from the Z isomer does not generate a nOe effect to the methylene protons. F. Further strange phenomena are observed upon irradiation of the vinyl protons of the E isomer. Transference is observed to a methoxy peak (3.69 ppm) and a peak at 2.02 ppm. Closer examination indicates the enhanced peak at 2.02 ppm is the ring methyl and not the allylic methylene protons, thus the E assignment for the spectra on the right stands. G. The proton spectrum is provided for (E)-80, which shows similar peak patterns to the E isomers. Furthermore the beta carbon is shifter to 127.8 ppm, corresponding to the E isomers. H. Irradiation of the vinyl proton of (E)-80 results in a nOe enhancement of a peak at 2.03 ppm, corresponding to the ring methyl and not the allylic methylene protons.

Derivatives of E3330 have been synthesized where five aspects of the inhibitor were systematically examined, including: 1) benzoquinone core; 2) ring methyl; 3) alpha n-nonyl substituent; 4) exocyclic double bond; and 5) carboxylic acid moiety. Without structural insight into the binding pocket of Ape1, derivatives were designed in a SAR approach to develop a lead inhibitor that could later be further elaborated with structural information.

Data collected from the limited benzoquinone series showed the nonyl sidechain of E3330 to be similar in activity to the methyl and butyl derivatives; furthermore, the data showed that a sidechain of at least a methyl group was desirable to retain an activity level near that of E3330. Knowledge of the alpha substituent on the double bond was then transferred to the more easily modified naphthoquinone series where further explorations into the 3-substituent on the ring could commence. Naphthoquinone derivatives were first developed with modifications to the 3-position including unsubstituted, methyl, fluoro, chloro, bromo, methoxy, and methylthio derivatives. All derivatives with an electronegative atom attached to the 3-position showed 3 to 30 times greater activity than the methyl substituted derivative.

The final derivatives in the naphthoquinone series defined the significance of the unsaturated acid moiety. Methyl ester and hydroxyethylamide derivatives both showed complete retention of activity compared to the parent carboxylic acids. Furthermore, diversification of the double bond through epoxidation and saturation provided compounds with similar activities to the unsaturated derivatives. The most interesting discovery came from the Z isomer of the potent naphthoquinone 43a; activity was retained while reversing the orientation of the acid and alpha substituent on the double bond. This data was the most compelling suggesting the lack of significance of the exocyclic unsaturated acid in binding.

The data collected from the derivatives prepared begin to show preferences for the redox active site of Ape1. Biotin-conjugated inhibitors have been synthesized to provide samples for SPR studies to determine dissociation constants for 43a. This molecular tool may also be used in affinity chromatography to determine selectivity among proteins from a cell lysate.

Reagents were used as received from commercial sources, as were anhydrous solvents including ethyl acetate, toluene, benzene, methanol, DMF, diethyl ether, and 1,2-dimethoxyethane. THF, $CH_2Cl_2$, and acetonitrile were distilled prior to use, and acetone was dried over activated MS for 2 hours under argon. Flash chromatographic separations were performed using 32-63 μm silica gel; thin layer chromatography was performed with Analtech 250 μm GHLF plates with 254 nm fluorescent indicator. All $^1$H NMR were run on a Bruker 300 MHz NMR equipped with a multinuclear ($^1$H, $^{13}$C, $^{19}$F, and $^{31}$P) 5 mm probe. $^1$H spectra were calibrated either CHCl$_3$ at 7.24 ppm, (CH$_3$)$_2$SO at 2.49, or (CH$_3$)CO at 2.04 ppm. $^{13}$C NMR were calibrated to CHCl$_3$ at 77.0 ppm. 2D NMR and nOe experiments were performed on a Bruker 500 MHz NMR equipped with a multinuclear ($^1$H, $^{13}$C, $^{19}$F, and $^{31}$P) 5 mm probe. Melting points were measured using a Mel-Temp II and 300° C. mercury thermometer. All MP are reported unadjusted. Elemental analyses were performed at the Purdue University Microanalysis Lab. Small molecule crystallography was performed at the Purdue University Chemistry Crystallography Center. Mass Spectrum data were collected at the Purdue University Mass Spectrum lab. Ape1 redox inhibition assays were performed at Indiana University School of Medicine. Data were then analyzed by EMSA in the same lab. Cell killing data were collected on compounds of interest. Initial toxicology was performed in the toxicology lab at IUSoM.

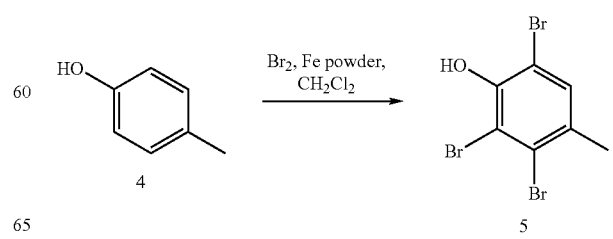

4-Methyl-2,3,6-tribromophenol (5)

According to the modified procedures of Shinkawa et al. and Keinan et al.,[14,16] p-cresol (4, 5.2 mL, 50 mmol) was dissolved in $CH_2Cl_2$ (300 mL) at room temperature in a 2-neck 500 mL round bottom flask attached to an addition funnel and a KOH trap. Fe (0.050 g, 0.90 mmol) was added at room temperature, and then bromine (7.8 mL, 150 mmol) in $CH_2Cl_2$ (50.0 mL) was added dropwise to the reaction. Following the addition the reaction was stirred for an additional 8 hrs at room temperature. The reaction was then added to a separation funnel and shaken with water until the red color disappeared. The organic layer was then separated, dried over $MgSO_4$, filtered, and condensed to provide a white solid. The crude product was separated from 2,6-dibromo p-cresol via recrystallization from hexanes. (15.39 g, 44.74 mmol, 89%) was obtained as fine white needles.

$R_f$=0.20 (1:9 EtOAc:hexanes)

mp=90-91° C. (Literature 95-106° C.){#930}{#920}

$^1$H NMR (CDCl$_3$): δ 2.38 (s, 3H); 5.85 (s, 1H, OH); 7.36 (s, 1H)

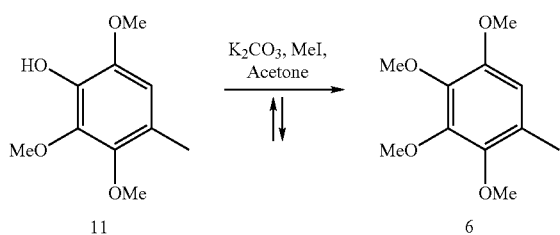

2,3,4,5-tetramethoxytoluene (6)

According to a modification of the procedure by Brimble et al.,[36] 11 (0.660 g, 3.33 mmol) and $K_2CO_3$ (4.08 g, 29.5 mmol) were added to a flame-dried 250 mL round bottom flask followed by dry acetone (120.0 mL) and MeI (2.0 mL, 32 mmol) at room temperature. A water-jacketed reflux condenser was attached and the reaction was heated under reflux for 12 hours. The reaction was then cooled, filtered, and the solvent was removed under reduced pressure. The brown residue was then resuspended in $CH_2Cl_2$, dried over $MgSO_4$, filtered, and condensed. The resulting colorless oil was then purified by flash chromatography (1:9 EtOAc:hexanes) to provide 6 (0.690 g, 3.25 mmol, 99%) as a colorless oil.

$R_f$=0.57 (7:13 EtOAc:hexanes)

$^1$H NMR (CDCl$_3$): δ 2.20 (s, 3H); 3.76 (s, 3H); 3.79 (s, 3H); 3.84 (s, 3H); 3.91 (s, 3H); 6.42 (s, 1H)

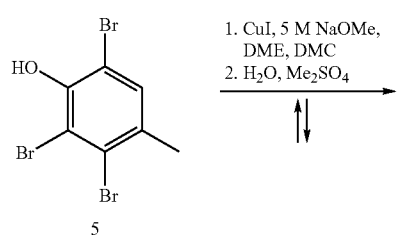

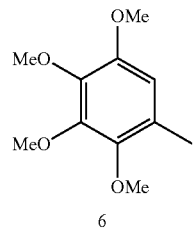

2,3,4,5-tetramethoxytoluene (6)

Following a modified procedure by Keinan et al.,[14] NaOMe (25%, 4.37 M, 60.0 mL, 262 mmol) was added to a 3 neck flame-dried 250 mL round bottom flask attached to a dean stark trap. DME (60.0 mL) and DMC (5.0 mL) were added and the reaction was distilled until 38.0 mL of MeOH was removed (54%, 11.9 M NaOMe). Alternatively Na (6.03 g, 262 mmol) can be dissolved in MeOH (70.0 mL), DME (60.0 mL) and DMC (5.0 mL) are then added, and MeOH (44.0 mL) was distilled to provide 54% NaOMe. The reaction was cooled to room temperature and CuI (6.32 g, 33.2 mmol) was added, and the thick white reaction becomes a thick dark purple solution. The reaction was heated to boiling and the dean stark trap was replaced with a water-jacketed reflux condenser. 5 (7.97 g, 23.2 mmol) was dissolved in DME (10.0 mL) and then added at reflux slow enough to prevent bumping. Eventually the solution becomes too thick to stir and boils violently. The solution was allowed to boil under reflux for 24 hrs and progress was monitored by NMR.

Upon reaching completion the reaction was cooled to ~50° C. and water (155.0 mL) was added. Then $Me_2SO_4$ (20.0 mL, 211 mmol) was added slowly and the reaction was allowed to cool to room temperature while stirring. The reaction stirs for a further 2 hrs and was then acidified and filtered through celite. The reaction was then extracted with ethyl acetate and washed with brine. After drying over $MgSO_4$ the reaction was filtered and condensed. The crude oil was purified by flash column chromatography (1:49 EtOAc:hexanes or 1:49 EtOAc/$CH_2Cl_2$) to provide 6 (3.21 g, 15.1 mmol, 65%) as a colorless oil that was modestly contaminated with 2,4,5-trimethoxytoluene and 3,4,5-trimethoxytoluene.

$R_f$=0.57 (7:13 EtOAc:hexanes)

$^1$H NMR (CDCl$_3$): δ 2.20 (s, 3H); 3.76 (s, 3H); 3.79 (s, 3H); 3.84 (s, 3H); 3.91 (s, 3H); 6.42 (s, 1H)

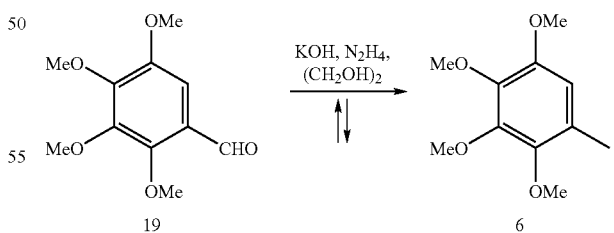

2,3,4,5-tetramethoxytoluene (6)

According to a generalized procedure by Matsubara et al.,[21] 19 (2.99 g, 13.2 mmol) was added to a flame-dried 100 mL round bottom flask, and then ethylene glycol (28.0 mL), KOH (2.36 g, 42.1 mmol), and hydrazine (6.0 ml, 190 mmol) was added at room temperature. The reaction was heated under reflux for 8 hours and then cooled. The solution was poured into brine and extracted with $CH_2Cl_2$. The organic layer was washed with dilute NaOH, brine, and then dried over $MgSO_4$. The crude product could be used without further purification, or purified using flash:chromatography (7:13 EtOAc:hexanes) to provide 6 (2.37 g, 11.2 mmol, 85%) as a colorless oil.

$R_f$=0.57 (7:13 EtOAc:hexanes)

$^1$H NMR (CDCl$_3$): δ 2.43 (s, 3H); 3.74 (s, 3H); 3.89 (s, 3H); 3.92 (s, 3H); 4.00 (s, 3H); 10.41 (s, 1H)

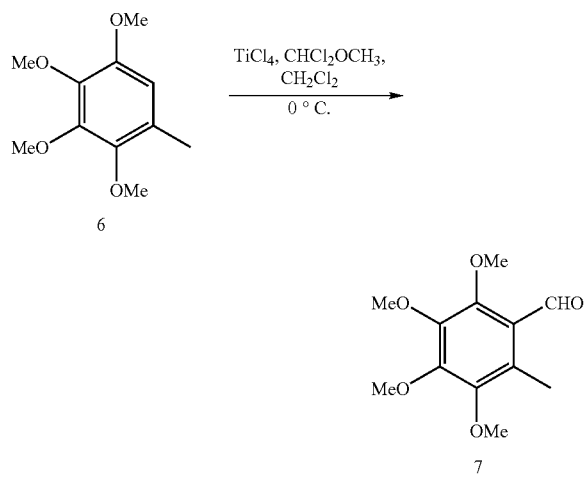

6-methyl-2,3,4,5-tetramethoxybenzaldehyde (7)

According to the procedure by Ohkawa et al.,[15] 6 (0.690 g, 3.25 mmol) was dissolved in $CH_2Cl_2$ (2.0 mL) in a flame-dried 25 mL round bottom flask and cooled to 0° C. α,α-dichloromethyl methyl ether (0.85 ml, 9.6 mmol) was then added at 0° C., followed by TiCl$_4$ (1 M in $CH_2Cl_2$, 9.0 ml, 9.0 mmol) at 0° C. The reaction was warmed slowly to room temperature and stirred for 6 hours under argon. The reaction was then poured into chilled water and stirred for 10 minutes. The reaction was diluted with EtOAc, washed with brine, dried over $MgSO_4$, filtered, and condensed. The crude oil was then purified by flash chromatography (1:49 EtOAc:hexanes if made via p-cresol; 3:17 EtOAc:hexanes if made via Wolffe-Kishner reduction) to provide 7 (0.696 g, 2.90 mmol, 89%) as a yellow oil.

$R_f$=0.26 (3:17 EtOAc:hexanes)

$^1$H NMR (CDCl$_3$): δ 2.44 (s, 3H); 3.74 (s, 3H); 3.89 (s, 3H); 3.92 (s, 3H); 4.00 (s, 3H); 10.24 (s, 1H)

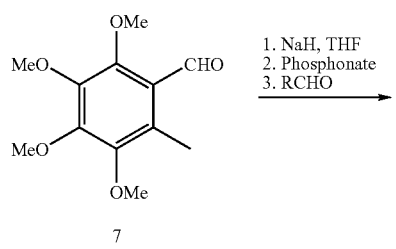

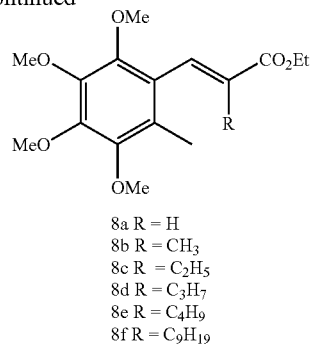

8a R = H
8b R = CH$_3$
8c R = C$_2$H$_5$
8d R = C$_3$H$_7$
8e R = C$_4$H$_9$
8f R = C$_9$H$_{19}$

Ethyl (E)-3-(6-methyl-2,3,4,5-tetramethoxyphenyl)-propenoate (8a)

According to the modified procedure of Murphy et al.,[26] NaH (0.131 g, 3.27 mmol) was added to a flame-dried 50 mL 3-neck round bottom flask connected to a water-jacketed reflux condenser. The flask was purged with Argon and a drying tube was attached to the top. THF (15.0 mL) was added to the flask followed by phosphonate (triethylphosphonoacetate, 0.36 ml, 1.8 mmol) at room temperature. The reaction was stirred at room temperature for 30 minutes, and then the aldehyde (0.323 g, 1.34 mmol) was dissolved in THF (10.0 mL) and added quickly at room temperature. The reaction was stirred for another 12 h at room temperature, then diluted with ethyl acetate and washed with brine. The organic layer was dried, filtered, and condensed. The resulting oil was purified via flash column chromatography ($CH_2Cl_2$ to 1:19 EtOAc:$CH_2Cl_2$) to provide 8a (0.343 g, 1.11 mmol, 83%) as a pale yellow oil.

$R_f$=0.17 ($CH_2Cl_2$)

E:Z=1:0 in THF at room temperature.

$^1$H NMR (CDCl$_3$): δ 1.32 (t, 3H, J=7.2 Hz); 2.26 (s, 3H); 3.76 (s, 3H); 3.78 (s, 3H); 3.88 (s, 3H); 3.94 (s, 3H); 4.24 (q, 2H, J=7.2 Hz); 6.52 (d, 1H, J=16.2 Hz); 7.77 (d, 1H; J=16.2 Hz)

Ethyl (E)-3-(6-methyl-2,3,4,5-tetramethoxyphenyl)-2-methylpropenoate (8b)

Compound 8b was prepared from 7 (0.569 g, 2.37 mmol) as described above for 8a to give 0.674 g (2.08 mmol, 88%) of the product as a yellow oil following flash chromatography (1:3 EtOAc:hexanes).

$R_f$=0.48 (1:3 EtOAc:hexanes)

$^1$H NMR (CDCl$_3$): δ 1.31 (t, 3H, J=7.2 Hz); 1.71 (d, 3H, J=1.2 Hz); 2.01 (s, 3H); 3.67 (s, 3H); 3.77 (s, 3H); 3.87 (s, 3H); 3.91 (s, 3H); 4.24 (q, 2H, J=7.2 Hz); 7.47 (d, 1H, J=0.6 Hz)

Ethyl (E)-3-(6-methyl-2,3,4,5-tetramethoxyphenyl)-2-ethylpropenoate (8c)

Compound 8c was prepared from 7 (0.437 g, 1.82 mmol) as described above for 8a to give 0.258 g (0.762 mmol, 42%) of the product as a colorless oil following flash chromatography (1:3 EtOAc:hexanes).

$R_f$=0.50 (1:3 EtOAc:hexanes)

¹H NMR (CDCl₃): δ 0.94 (t, 3H, J=7.5 Hz); 1.33 (t, 3H, J=7.2 Hz); 2.02 (s, 3H); 2.15 (q, 2H, J=7.5 Hz); 3.69 (s, 3H); 3.78 (s, 3H); 3.89 (s, 3H); 3.92 (s, 3H); 4.26 (q, 2H, J=7.2 Hz); 7.36 (s, 1H)

Ethyl (E)-3-(6-methyl-2,3,4,5-tetramethoxyphenyl)-2-propylpropenoate (8d)

Compound 8d was prepared from 7 (0.437 g, 1.82 mmol) as described above for 8a to give 0.275 g (0.780 mmol, 43%) of the product as a colorless oil following flash chromatography (1:3 EtOAc:hexanes).

$R_f$=0.52 (1:3 EtOAc:hexanes)

¹H NMR (CDCl₃): δ 0.75 (t, 3H, J=7.2 Hz); 1.33 (t, 3H, J=7.2 Hz); 1.35 (m, 2H); 2.03 (s, 3H); 2.11 (m, 2H); 3.69 (s, 3H); 3.78 (s, 3H); 3.88 (s, 3H); 3.93 (s, 3H); 4.25 (q, 2H, J=7.2 Hz); 7.38 (s, 1H)

Ethyl (E)-3-(6-methyl-2,3,4,5-tetramethoxyphenyl)-2-butylpropenoate (8e)

Compound 8e was prepared from 7 (0.650 g, 2.71 mmol) as described above for 8a to give 0.484 g (1.32 mmol, 49%) of the product as a yellow oil following flash chromatography (1:9 EtOAc:hexanes).

$R_f$=0.54 (1:3 EtOAc:hexanes)

¹H NMR (CDCl₃): δ 0.73 (t, 3H, J=7.2 Hz); 1.12 (m, 2H); 1.29 (m, 2H); 1.32 (t, 3H, J=7.2 Hz); 2.03 (s, 3H); 2.13 (m, 2H); 3.69 (s, 3H); 3.78 (s, 3H); 3.88 (s, 3H); 3.92 (s, 3H); 4.25 (q, 2H, J=7.2 Hz); 7.37 (s, 1H)

Ethyl (E)-3-(6-methyl-2,3,4,5-tetramethoxyphenyl)-2-nonylpropenoate (8f)

Compound 8f was prepared from 7 (0.581 g, 2.42 mmol) as described above for 8a to give 0.621 g (1.42 mmol, 59%) of the product as a colorless oil following flash chromatography (3:17 EtOAc:hexanes).

$R_f$=0.40 (3:17 EtOAc:hexanes)

¹H NMR (CDCl₃): δ 0.84 (t, 3H, J=7.2 Hz); 1.08-1.22 (m, 11H); 1.24-1.35 (m, 3H); 1.33 (t, 3H, J=7.2 Hz); 2.03 (s, 3H); 2.12 (m, 2H); 3.69 (s, 3H); 3.78 (s, 3H); 3.88 (s, 3H); 3.93 (s, 3H); 4.25 (q, 2H, J=7.2 Hz); 7.37 (s, 1H)

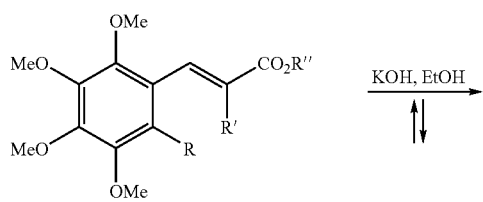

8a R = CH₃, R' = H, R" = C₂H₅
8b R = CH₃, R' = CH₃, R" = C₂H₅
8c R = CH₃, R' = C₂H₅, R" = C₂H₅
8d R = CH₃, R' = C₃H₇, R" = C₂H₅
8e R = CH₃, R' = C₄H₉, R" = C₂H₅
9S R = CH₃, R' = CH₂CH₂OCH₃, R" = CH₃
8g R = CH₃, R' = C₉H₁₉, R" = C₂H₅
21 R = Cl, R' = CH₃, R" = C₂H₅

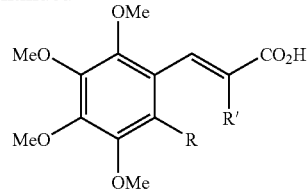

9a R = CH₃, R' = H
9b R = CH₃, R' = CH₃
9c R = CH₃, R' = C₂H₅
9d R = CH₃, R' = C₃H₇
9e R = CH₃, R' = C₄H₉
96 R = CH₃, R' = CH₂CH₂OCH₃
9f R = CH₃, R' = C₉H₁₉
22 R = Cl, R' = CH₃

(E)-3-(6-methyl-2,3,4,5-tetramethoxyphenyl)-propenoic acid (9a)

Method A: Emmons ester 8a (0.066 g, 0.21 mmol) was dissolved in EtOH (10.0 mL) and then KOH (0.095 g, 1.69 mmol) was added to the reaction. The reaction was heated to boiling and stirred at this temperature for 30 minutes. The reaction was then cooled, acidified, and extracted with ethyl acetate. The organic layer was washed with brine, dried over MgSO₄, filtered, and condensed. The resulting acid was then used as crude, or can be purified via flash chromatography (2:3 Et₂O:hexanes 0.5% AcOH) or recrystallization from Et₂O/hexanes to provide 9a (0.046 g, 0.16 mmol, 78%) as a light tan solid.

Method B: Emmons ester 8a was dissolved in DME (10.0 mL) to which NaOH (2 M, 2.0 mL, 2.0 mmol) was then added at room temperature. The reaction was heated to reflux for 3 hours or until TLC (1:4 EtOAc:hexanes) indicated that all starting material had been consumed. The reaction was then acidified, diluted with EtOAc, washed 3 times with brine, dried over MgSO₄, filtered, and condensed.

$R_f$=0.16 (2:3 Et₂O:hexanes 0.5% AcOH)

mp=96-97° C.

¹H NMR (CDCl₃): δ 3.77 (s, 3H); 3.81 (s, 3H); 3.89 (s, 3H); 3.95 (s, 3H); 6.59 (d, 1H, J=16.2 Hz); 7.90 (d, 1H, J=16.2 Hz)

(E)-3-(6-methyl-2,3,4,5-tetramethoxyphenyl)-2-methylpropenoic acid (9b)

Compound 9b was prepared from 8b (0.156 g, 0.481 mmol) as described above for 9a using Method B to give 0.121 g (0.408 mmol, 85%) of the product as a light yellow solid following flash chromatography (2:3 Et₂O:hexanes 0.5% AcOH) and recrystallization from Et₂O/hexanes.

$R_f$=0.16 (2:3 Et₂O:hexanes 0.5% AcOH)

mp=98-102° C.

¹H NMR (CDCl₃): δ 1.76 (d, 3H, J=1.2 Hz); 2.05 (s, 3H); 3.69 (s, 3H); 3.79 (s, 3H); 3.90 (s, 3H); 3.93 (s, 3H); 7.64 (d, 1H, J=1.2 Hz)

(E)-3-(6-methyl-2,3,4,5-tetramethoxyphenyl)-2-ethylpropenoic acid (9c)

Compound 9c was prepared from 8c (0.041 g, 0.12 mmol) as described above for 9a to give 0.010 g (0.033 mmol, 27%) of the product as a gold oil following flash chromatography (2:3 Et₂O:hexanes 0.5% AcOH).

$R_f$=0.16 (2:3 Et₂O:hexanes 0.5% AcOH)

$^1$H NMR (CDCl$_3$): δ 0.98 (t, 3H, J=7.2 Hz); 2.04 (s, 3H); 2.18 (q, 2H, J=7.2 Hz); 3.70 (s, 3H); 3.79 (s, 3H); 3.90 (s, 3H); 3.93 (s, 3H); 7.53 (s, 1H)

(E)-3-(6-methyl-2,3,4,5-tetramethoxyphenyl)-2-propylpropenoic acid (9d)

Compound 9d was prepared from 8d (0.034 g, 0.098 mmol) as described above for 9a to give 0.029 g (0.090 mmol, 92%) of the product as a gold oil following flash chromatography (2:3 Et$_2$O:hexanes 0.5% AcOH).

R$_f$=0.18 (2:3 Et$_2$O:hexanes 0.5% AcOH)

$^1$H NMR (CDCl$_3$): δ 0.77 (t, 3H, J=7.2 Hz); 1.41 (m, 2H); 2.04 (s, 3H); 2.13 (m, 2H); 3.70 (s, 3H); 3.79 (s, 3H); 3.89 (s, 3H); 3.93 (s, 3H); 7.55 (s, 1H)

(E)-3-(6-methyl-2,3,4,5-tetramethoxyphenyl)-2-butylpropenoic acid (9e)

Compound 9e was prepared from 8e (0.166 g, 0.453 mmol) as described above for 9a using Method B to give 0.144 g (0.426 mmol, 94%) of the product as a yellow amorphous solid following flash chromatography (2:3 Et$_2$O:hexanes 0.5% AcOH) and recrystallization from Et$_2$O/hexanes.

R$_f$=0.26 (2:3 Et$_2$O:hexanes 0.5% AcOH)

mp=70-85° C.

$^1$H NMR (CDCl$_3$): δ 0.74 (t, 3H, J=7.2 Hz); 1.19 (m, 4H); 2.04 (s, 3H); 2.15 (m, 2H); 3.70 (s, 3H); 3.79 (s, 3H); 3.89 (s, 3H); 3.93 (s, 3H); 7.53 (s, 1H)

(E)-3-(6-methyl-2,3,4,5-tetramethoxyphenyl)-2-nonylpropenoic acid (9f)

Compound 9f was prepared from 8f (0.121 g, 0.277 mmol) as described above for 9a using Method B to give 0.107 g (0.262 mmol, 93%) of the product as a colorless oil following flash chromatography (2:3 Et$_2$O:hexanes 0.5% AcOH).

R$_f$=0.36 (2:3 Et$_2$O:hexanes 0.5% AcOH)

$^1$H NMR (CDCl$_3$): δ 0.84 (t, 3H, J=6.9 Hz); 1.13 (m, 12H); 1.36 (m, 2H); 2.04 (s, 3H); 2.14 (m, 2H); 3.70 (s, 3H); 3.79 (s, 3H); 3.89 (s, 3H); 3.93 (s, 3H); 7.537 (s, 1H)

$^{13}$C NMR (CDCl$_3$): δ 12.9, 14.1, 22.7, 28.0, 28.3, 29.3, 29.5, 33.8, 31.9, 53.4, 60.7, 60.9, 61.1, 61.3, 124.7, 135.6, 136.6, 144.7, 146.5, 146.7, 147.8, 172.5

(E)-3-(2-chloro-3,4,5,6-tetramethoxyphenyl)-2-methylpropenoic acid (22)

Compound 22 was prepared from 21 (0.255 g, 0.740 mmol) as described above for 9a using Method A to give 0.222 g (0.701 mmol, 95%) of the product as a red amorphous solid following flash chromatography (2:3 Et$_2$O:hexanes 0.5% AcOH) and recrystallization from Et$_2$O/hexanes.

R$_f$=0.20 (2:3 Et$_2$O:hexanes 0.5% AcOH)

$^1$H NMR (CDCl$_3$): δ 1.81 (s, 3H); 3.71 (s, 3H); 3.86 (s, 3H); 3.91 (s, 3H); 7.57 (d, 1H, J=1.2 Hz)

(E)-3-(6-methyl-2,3,4,5-tetramethoxyphenyl)-2-methoxyethylpropenoic acid (96)

Compound 96 was prepared from 95 (0.074 g, 0.21 mmol) as described above for 9a using Method A to give 0.070 g (0.21 mmol, 100%) of the product as a tan solid following flash chromatography (2:3 Et$_2$O:hexanes 0.5% AcOH) and recrystallization from Et$_2$O/hexanes.

R$_f$=0.16 (2:3 Et$_2$O:hexanes 0.5% AcOH)

mp=97-99° C.

$^1$H NMR (CDCl$_3$): δ 2.07 (s, 3H); 2.45 (t, 2H, J=6.9 Hz); 3.20 (s, 3H); 3.68 (s, 3H); 3.69 (q, 2H, J=6.9 Hz); 3.76 (s, 3H); 3.87 (s, 3H); 3.90 (s, 3H); 7.59 (s, 1H)

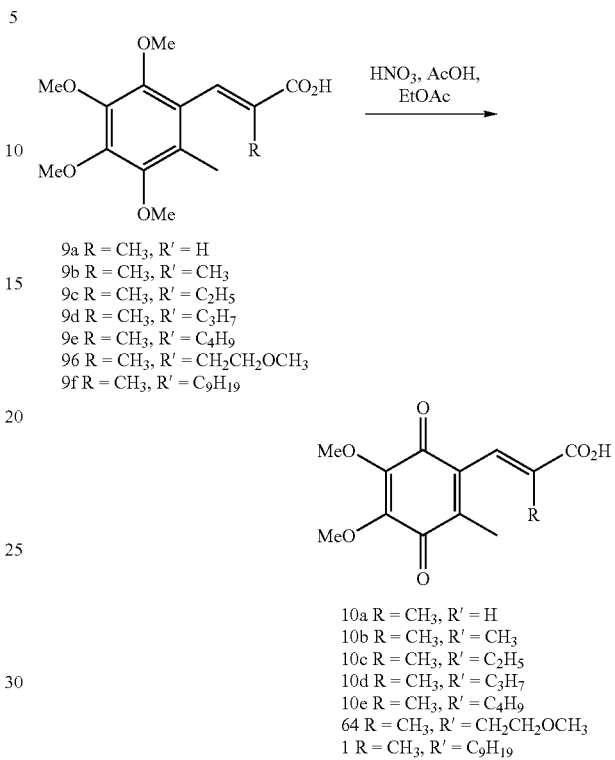

9a R = CH$_3$, R' = H
9b R = CH$_3$, R' = CH$_3$
9c R = CH$_3$, R' = C$_2$H$_5$
9d R = CH$_3$, R' = C$_3$H$_7$
9e R = CH$_3$, R' = C$_4$H$_9$
96 R = CH$_3$, R' = CH$_2$CH$_2$OCH$_3$
9f R = CH$_3$, R' = C$_9$H$_{19}$

10a R = CH$_3$, R' = H
10b R = CH$_3$, R' = CH$_3$
10c R = CH$_3$, R' = C$_2$H$_5$
10d R = CH$_3$, R' = C$_3$H$_7$
10e R = CH$_3$, R' = C$_4$H$_9$
64 R = CH$_3$, R' = CH$_2$CH$_2$OCH$_3$
1 R = CH$_3$, R' = C$_9$H$_{19}$

(E)-3-(4,5-dimethoxy-2-methyl-3,6-dioxocyclohexa-1,4-dienyl)-propenoic acid (10a)

Method A: Following modifications to the procedures by Shinkawa et al. and Flader et al.,[16,22] acid 9a (0.089 g, 0.31 mmol) was dissolved in ethyl acetate (10.0 mL) at room temperature, then HNO$_3$ (1.0 mL) and AcOH (6 drops) are added at room temperature and the reaction was stirred for 4 hours. The reaction was then diluted with EtOAc (20.0 mL) washed with brine, dried over MgSO$_4$, filtered, and condensed. The red oil was then purified by either flash column chromatography (1:1 Et$_2$O:hexanes 0.5% AcOH) or recrystallization from Et$_2$O/hexanes to afford 10a.

Method B: Following the procedure of Flader et al.,[22] 9a (0.046, 0.16 mmol) was dissolved in acetonitrile (5.0 mL) at room temperature, then ceric ammonium nitrate (0.294 g, 0.536 mmol) dissolved in water (5.0 ml) was added at room temperature. The reaction was stirred for 30 minutes and then extracted with CH$_2$Cl$_2$. The organic layer was washed with brine, dried over MgSO$_4$, filtered, and condensed. The resulting red solid was the recrystallized (Et$_2$O/hexanes) to provide 10a (0.024 g, 0.093 mmol, 57%) as a red solid.

R$_f$=0.06 (2:3 Et$_2$O:hexanes 0.5% AcOH)

mp=116-125° C.

$^1$H NMR (CDCl$_3$): δ 2.19 (s, 3H); 4.00 (s, 6H); 6.76 (d, 1H, J=16.2 Hz); 7.60 (d, 1H, J=16.2 Hz)

(E)-3-(4,5-dimethoxy-2-methyl-3,6-dioxocyclohexa-1,4-dienyl)-2-methylpropenoic acid (10b)

Compound 10b was prepared from 9b (0.057 g, 0.19 mmol) as described above for 10a using Method B to give 0.016 g (0.060 mmol, 31%) of the product as a red solid following flash chromatography (1:1 Et$_2$O:hexanes 0.5% AcOH) and recrystallization from Et$_2$O/hexanes.

R$_f$=0.06 (2:3 Et$_2$O:hexanes 0.5% AcOH)
mp=134-136° C.
$^1$H NMR (CDCl$_3$): δ 1.77 (d, 3H, J=1.2 Hz); 1.95 (d, 3H, J=1.2 Hz); 4.01 (s, 3H); 4.03 (s, 3H); 7.39 (s, 1H)

(E)-3-(4,5-dimethoxy-2-methyl-3,6-dioxocyclohexa-1,4-dienyl)-2-ethylpropenoic acid (10c)

Compound 10c was prepared from 9c (0.010 g, 0.033 mmol) as described above for 10a to give 0.003 g (0.010 mmol, 32%) of the product as a red solid following flash chromatography (1:1 Et$_2$O:hexanes 0.5% AcOH) and recrystallization from Et$_2$O/hexanes.

R$_f$=0.10 (2:3 Et$_2$O:hexanes 0.5% AcOH)
mp=124-131° C.
$^1$H NMR (CDCl$_3$): δ 1.01 (t, 3H, J=7.2 Hz); 1.94 (d, 31-1, J=1.2 Hz); 2.12 (q, 2H, J=7.2 Hz); 3.99 (s, 3H); 4.01 (s, 3H); 7.23 (d, 1H, J=1.2 Hz)

(E)-3-(4,5-dimethoxy-2-methyl-3,6-dioxocyclohexa-1,4-dienyl)-2-propylpropenoic acid (10d)

Compound 10d was prepared from 9d (0.029 g, 0.090 mmol) as described above for 10a to give 0.016 g (0.053 mmol, 59%) of the product as a red solid following flash chromatography (1:1 Et$_2$O:hexanes 0.5% AcOH) and recrystallization from Et$_2$O/hexanes.

R$_f$=0.12 (2:3 Et$_2$O:hexanes 0.5% AcOH)
mp=95-99° C.
$^1$H NMR (CDCl$_3$): δ
0.76 (t, 3H, J=7.2 Hz); 1.41 (m, 2H); 1.91 (d, 3H, J=1.5 Hz); 2.04 (m, 2H); 3.95 (s, 3H); 3.98 (s, 3H); 7.24 (s, 1H)

(E)-3-(4,5-dimethoxy-2-methyl-3,6-dioxocyclohexa-1,4-dienyl)-2-butylpropenoic acid (10e)

Compound 10e was prepared from 9e (0.015 g, 0.044 mmol) as described above for 10a to give 0.005 g (0.018 mmol, 40%) of the product as a red solid following flash chromatography (1:1 Et$_2$O:hexanes 0.5% AcOH) and recrystallization from Et$_2$O/hexanes.

R$_f$=0.12 (2:3 Et$_2$O:hexanes 0.5% AcOH)
mp=54-55° C.
$^1$H NMR (CDCl$_3$): δ 0.82 (t, 3H, J=7.2 Hz); 1.22 (m, 2H); 1.39 (m, 2H); 1.95 (d, 3H, J=1.2 Hz); 2.10 (m, 2H); 3.99 (s, 3H); 4.02 (s, 3H); 7.24 (s, 1H)

(E)-3-(4,5-dimethoxy-2-methyl-3,6-dioxocyclohexa-1,4-dienyl)-2-nonylpropenoic acid (1)

Compound 1 was prepared from 9f (1.13 g, 2.77 mmol) as described above for 10a using Method A to give 0.443 g (1.17 mmol, 42%) of the product as a red solid following flash chromatography (2:3 Et$_2$O:hexanes 0.5% AcOH) and recrystallization from Et$_2$O/hexanes.

R$_f$=0.16 (2:3 Et$_2$O:hexanes 0.5% AcOH)
mp=56-57° C. (Lit. 68° C.){#280}
elemental analysis: calculated C, (66.65%); H, (7.99%); found C, (66.32%); H, (7.89%)
$^1$H NMR (CDCl$_3$): δ 0.84 (t, 3H, J=6.6 Hz), 1.18 (bs, 14H); 1.39 (bs, 2H); 1.94 (d, 3H, J=1.5 Hz); 2.09 (t, 2H, J=7.2 Hz); 3.99 (s, 3H); 4.02 (s, 3H); 7.26 (d, 1H, J=1.5 Hz)

(E)-3-(4,5-dimethoxy-2-methyl-3,6-dioxocyclohexa-1,4-dienyl)-2-methoxyethylpropenoic acid (64)

Compound 64 was prepared from 96 (0.070 g, 0.21 mmol) as described above for 10a using Method A to give 0.012 g (0.039 mmol, 19%) of the product as a red solid following flash chromatography (2:3 Et$_2$O:hexanes 0.5% AcOH) and recrystallization from Et$_2$O/hexanes.

R$_f$=0.06 (2:3 Et$_2$O:hexanes 0.5% AcOH)
mp=104-106° C.
$^1$H NMR (CDCl$_3$): δ 1.95 (d, 3H, J=1.5 Hz); 2.40 (t, 2H, J=6.6 Hz); 3.24 (s, 3H); 3.44 (t, 2H, 6.6 Hz); 3.99 (s, 3H); 4.01 (s, 3H); 7.35 (d, 1H, J=1.5 Hz)

4-Methyl-2,3,6-trimethoxyphenol (11)

Following a modified procedure by Shinkawa et al. and Keinan et al.,[14,16] NaOMe (25%, 4.37 M, 50.0 mL, 219 mmol) was added to a 3 neck flame-dried 100 mL round bottom flask attached to a dean stark trap. It was imperative to use a sufficiently large stirbar to allow stirring of the very concentrated solution. DME (24.0 mL) and DMC (8.5 mL) were added and the reaction was distilled until 31.5 mL of MeOH was removed (11.8 M NaOMe). Alternatively, Na (5.04 g, 219 mmol) can be dissolved in MeOH (70.0 mL), DME (60.0 mL) and DMC (5.0 mL) are then added, and MeOH (45.0 mL) was distilled. The white, opaque reaction was cooled to room temperature and CuI (5.173 g, 27.1 mmol) was added, at which point the reaction becomes a thick dark purple solution. The reaction was heated to boiling and the dean stark trap was replaced with a water-jacketed reflux condenser. 5 (5.89 g, 17.1 mmol) was dissolved in DME (10.0 mL) and then added at reflux slow enough to prevent bumping. Eventually the solution becomes too thick to stir and boils violently. The solution was allowed to boil under reflux for 24 hrs and progress was monitored by NMR.

Upon reaching completion the reaction was cooled to ~50° C. and water was added (50.0 mL). The reaction was acidified slowly and then filtered through celite. The reaction was then extracted with ethyl acetate and washed with brine. After drying over MgSO$_4$ the reaction was filtered and condensed. The crude oil was purified by flash column chromatography (1:49 Et$_2$O:CH$_2$Cl$_2$) to provide 11 (1.67 g, 8.43 mmol, 49%) as a colorless oil.

R$_f$=0.26 (1:4 EtOAc:hexanes)
$^1$H NMR (CDCl$_3$): δ 2.18 (s, 3H); 3.76, (s, 3H); 3.82 (s, 3H); 3.92 (s, 3H); 5.42 (bs, 1H, OH); 6.41 (s, 1H)

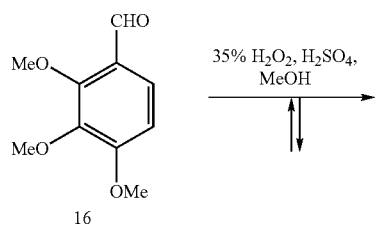

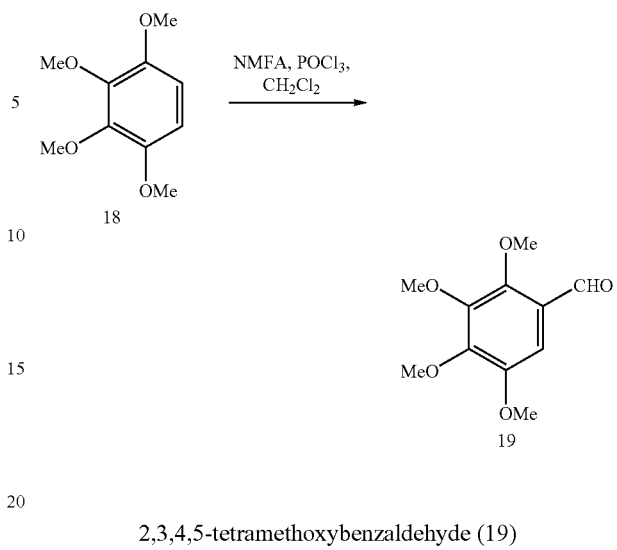

2,3,4-trimethoxyphenol (17)

2,3,4,5-tetramethoxybenzaldehyde (19)

Following a modified procedure by Tremblay et al.,[17] 2,3,4-trimethoxybenzaldehyde (16, 6.075 g, 31.0 mmol) was dissolved in MeOH (60.0 mL), and then $H_2SO_4$ (0.6 mL) and 35% aq. $H_2O_2$ (4.0 mL, ~40 mmol) was added at room temperature. The reaction was then heated to reflux for 2 hrs and monitored by TLC (1:4 EtOAc:hexanes) for completion. When the reaction was complete the solution was cooled and extracted with ethyl acetate. The layers are separated and the organic layer was washed with brine, dried over $MgSO_4$, and filtered. Flash chromatography (1:4 EtOAc:hexanes) provides 17 (5.564 g, 30.2 mmol, 98%) as a light red oil.

$R_f$=0.29 (1:4 EtOAc:hexanes)

$^1$H NMR (CDCl$_3$): δ 3.79 (s, 3H); 3.87 (s, 3H); 3.94 (s, 3H); 5.34 (broad s, 1H, OH); 6.57 (q, 2H, J=9.0, 22.8 Hz)

Following the procedure by Syper et al.,[19] N-methylformanilide (1.0 mL, 8.1 mmol) was added to a flame dried 10 mL round bottom flask under argon and a drying tube. POCl$_3$ (1.0 mL, 11 mmol) was added at room temperature and the Argon line was removed. After 5 minutes 18 (1.067 g, 5.38 mmol) was dissolved in CH$_2$Cl$_2$ (2.0 mL) and added at room temperature. The reaction was stirred at room temperature under a drying tube for 48 hrs and monitored by $^1$H NMR. When complete the reaction was diluted with EtOAc, washed with saturated brine, dried over MgSO$_4$, filtered, and condensed. The resulting product was separated from remaining N-methylformanilide using flash chromatography (1:4 Et$_2$O:hexanes) to provide 19 (1.141 g, 5.04 mmol, 94%) as a colorless oil.

$R_f$=0.17 (1:4 Et$_2$O:hexanes)

Mp=oil (Lit. 38° C. d)[38]

$^1$H NMR (CDCl$_3$): δ 3.85 (s, 3H); 3.92 (s, 3H); 3.95 (s, 3H); 3.97 (s, 3H); 7.09 (s, 1H); 10.27 (s, 1H)

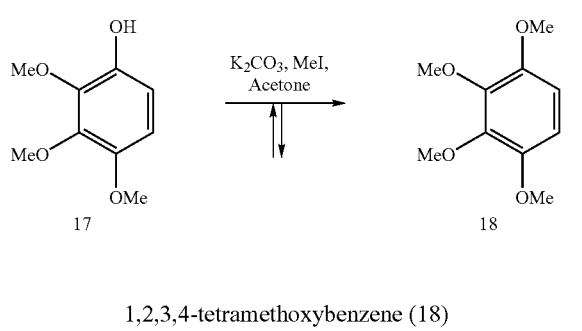

1,2,3,4-tetramethoxybenzene (18)

Following the procedure by Tremblay et al.,[17] 17 (3.851 g, 20.9 mmol) was dissolved in dry acetone (90.0 ml), and K$_2$CO$_3$ (9.36 g, 67.7 mmol) was added followed by MeI (9.0 mL, 144 mmol). The reaction was heated under reflux for 26 h and monitored by TLC (1:9 EtOAc:hexanes) for completion. When complete the reaction was cooled to room temperature and filtered. The acetone was removed under reduced pressure and the residue was taken up in CH$_2$Cl$_2$ (50 mL). The suspension was filtered, dried over MgSO$_4$, filtered again, and condensed. The crude product can be purified by flash chromatography (1:4 EtOAc:hexanes), however, recrystallization from Et$_2$O/hexanes was sufficient to provide pure 18 (3.405 g, 17.2 mmol, 82%) as white needles.

$R_f$=0.35 (1:4 EtOAc:hexanes)

mp=86-87° C. (Lit. 87-87.5° C.)[37]

$^1$H NMR (CDCl$_3$): δ 3.80 (s, 6H); 3.88 (s, 6H); 6.56 (s, 2H)

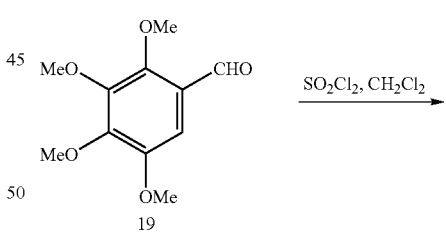

2-Chloro-3,4,5,6-tetramethoxybenzaldehyde (20)

According to a general aryl chlorination procedure by Lopez-Alvarado,[39] 19 (0.767 g, 3.39 mmol) was dissolved in CH$_2$Cl$_2$ (10.0 mL) at room temperature and then SO$_2$Cl$_2$ (neat, 0.31 mL, 3.7 mmol) was added at room temperature. The reaction was stirred for 1 hour and monitored by $^1$H NMR for completion. The reaction was then diluted with $CH_2Cl_2$, washed with brine, dried over $MgSO_4$, filtered, and condensed. The resulting oil was then purified by flash column chromatography (1:4 $Et_2O$:hexanes) to provide 20 (0.861 g, 3.30 mmol, 97%) as a colorless oil.

$R_f$=0.27 (1:4 $Et_2O$:hexanes)

$^1$H NMR (CDCl$_3$): δ 3.84 (s, 3H); 3.89 (s, 3H); 3.90 (s, 3H); 4.02 (s, 3H); 10.34 (s, 1H)

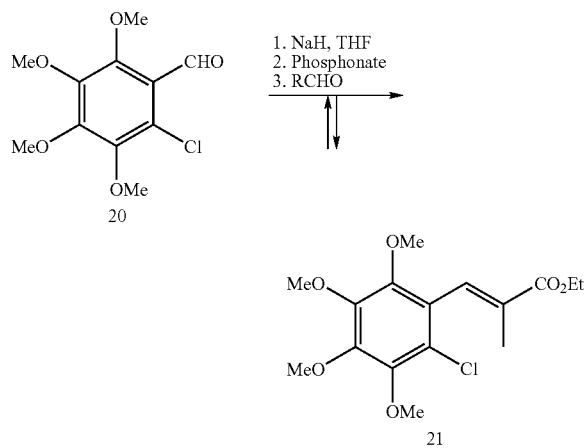

Ethyl (E)-3-(2-chloro-3,4,5,6-tetramethoxyphenyl)-2-methylpropenoate (21)

According to the modified procedure of Murphy et al.,[26] NaH (0.455 g, 11.3 mmol) was added to a flame-dried 50 mL 3-neck round bottom flask connected to a water-jacketed reflux condenser. The flask was purged with Argon and a drying tube was attached to the top. Toluene (20.0 mL) was added to the flask followed by phosphonate (1.3 ml, 6.0 mmol) at room temperature. The reaction was heated under reflux for 30 minutes, and the aldehyde (20, 0.861 g, 3.30 mmol) was dissolved in toluene (14.0 mL) and added slowly at reflux. The reaction was heated for another 8 h under reflux. The reaction was then cooled to room temperature, diluted with ethyl acetate, and washed with brine. The organic layer was dried, filtered, and condensed. The resulting oil was purified via flash column chromatography (1:9 i-Pr$_2$O:hexanes) to provide 21 (0.559 g, 1.62 mmol, 49%) as a colorless oil.

$R_f$=0.29 (1:4 $Et_2O$:hexanes)

E:Z=1:0 in refluxing toluene $^1$H NMR (CDCl$_3$): δ 1.34 (t, 3H, J=7.2 Hz); 1.78 (d, 3H, J=1.5 Hz); 3.69 (s, 3H); 3.86 (s, 3H); 3.90 (s, 3H); 3.94 (s, 3H); 4.26 (q, 2H, J=7.2 Hz); 7.42 (q, 1H, J=1.5 Hz)

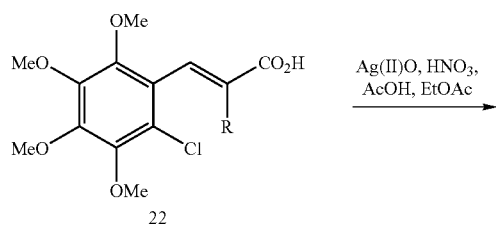

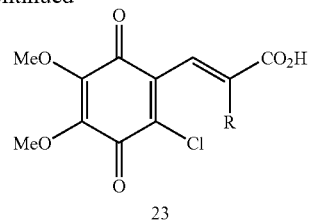

(E)-3-(2-chloro-4,5-dimethoxy-3,6-dioxocyclohexa-1,4-dienyl)-2-methylpropenoic acid (23)

Following a modified procedure of Flader et al.,[22] 22 (0.124 g, 0.391 mmol) was dissolved in acetonitrile (10.0 mL) at room temperature, then ceric ammonium nitrate (0.970 g, 1.77 mmol) dissolved in water (8.0 ml) was added at room temperature. The reaction was stirred for 30 minutes and then extracted with $CH_2Cl_2$. The organic layer was washed with brine, dried over $MgSO_4$, filtered, and condensed. The red oil was then purified by either flash column chromatography (1:1 $Et_2O$:hexanes 0.5% AcOH) or recrystallization from $Et_2O$/hexanes to afford 23 (0.026 g, 0.091 mmol, 22%) as a red solid.

$R_f$=0.32 (1:1 $Et_2O$:hexanes 0.5% AcOH)

mp=183-185° C.

$^1$H NMR (CDCl$_3$): δ 1.83 (d, 3H, J=1.2 Hz); 4.03 (s, 3H); 4.05 (s, 3H); 7.28 (d, 1H, J=1.2 Hz)

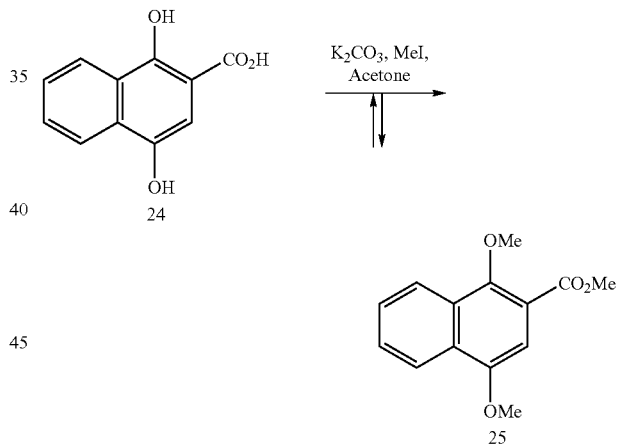

Methyl 1,4-dimethoxy-2-naphthoate (25)

According to a modification of the procedure by Brimble et al.,[36] 1,4-dihydroxy-2-naphthoic acid (24, 2.77 g, 13.6 mmol) and $K_2CO_3$ (14.01 g, 101.4 mmol) were added to a flame-dried 250 mL round bottom flask followed by dry acetone (120.0 mL) and MeI (13.0 mL, 209 mmol) at room temperature. A water-jacketed reflux condenser was attached and the reaction was heated under reflux for 12 hours. The reaction was then cooled, filtered, and the solvent was removed under reduced pressure. The brown residue was then resuspended in $CH_2Cl_2$, dried over $MgSO_4$, filtered, and condensed. The resulting brown oil/solid was then purified by either flash chromatography (7:13 EtOAc:hexanes) or recrystallized from $Et_2O$/hexanes to afford 25 (3.19 g, 13.0 mmol, 96%) as brown granular crystals.

$R_f$=0.44 (3:17 EtOAc:hexanes)

mp=50-52° C. (Lit. 48-50° C.)[22]

$^1$H NMR (CDCl$_3$): δ 3.98 (s, 3H); 3.99 (s, 3H); 4.00 (s, 3H); 7.14 (s, 1H); 7.57 (m, 2H); 8.22 (m, 2H)

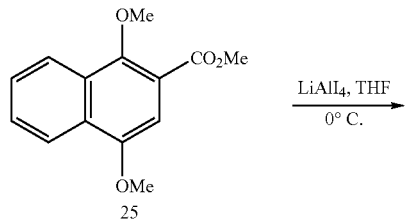

1,4-dimethoxy-2-hydroxymethylnaphthalene (26)

According to the procedure by Flader et al.,[22] lithium aluminum hydride (0.855 g, 21.4 mmol) was added to a flame-dried 250 mL round bottom flask under argon to which dry THF (150.0 mL) was added at room temperature. Ester 25 (5.05 g, 20.5 mmol) was then dissolved in THF (50.0 mL) and added slowly at room temperature under argon, and the reaction was stirred at room temperature for 8 hours. The reaction was then quenched by adding H$_2$O (1.0 mL) dropwise at 0° C., followed by 2 M NaOH (2.0 mL), and then H$_2$O (3.0 mL). The resulting suspension was then filtered and the filtrated was acidified with dilute HCl, washed with saturated brine, dried over MgSO$_4$, and filtered. The condensed filtrate resulted in a crude solid that could be purified by flash column chromatography (7:13 EtOAc:hexanes) or recrystallization from Et$_2$O/hexanes to afford 26 (4.34 g, 19.9 mmol, 97%) as long white needles.

$R_f$=0.30 (7:13 EtOAc:hexanes)

mp=66-68° C. (Lit. 69-70° C.)[22]

$^1$H NMR (CDCl$_3$): δ 2.29 (broad s, 1H); 3.89 (s, 3H); 3.96 (s, 3H); 4.86 (s, 2H); 6.79 (s, 1H); 7.49 (m, 2H); 8.01 (dd, 1H, J=1.2, 7.5 Hz); 8.21 (dd, 1H, J=1.2, 7.5 Hz)

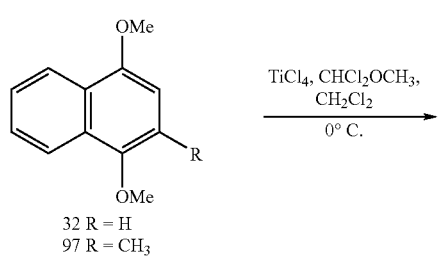

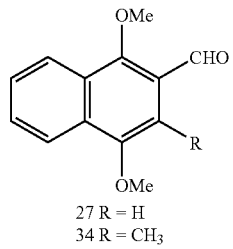

1,4-dimethoxy-2-naphthaldehyde (27)

Method A:

Following a modified procedure of Ito et al.,[24] to a flame-dried 50 mL round bottom flask was added 32 (1.34 g, 7.12 mmol) dissolved in CH$_2$Cl$_2$ (10.0 mL) and then cooled to 0° C. under Argon. Then TiCl$_4$ (1 M in CH$_2$Cl$_2$, 8.0 mL, 8.0 mmol) was added slowly at 0° C. followed by α,α-dichloromethyl methyl ether (0.71 mL, 8.0 mmol) at 0° C. The reaction was stirred at 0° C. for 3 hours and the poured into water and stirred for 10 minutes at room temperature. The reaction was then extracted with EtOAc, washed with saturated brine, dried over MgSO$_4$, filtered, and condensed. The resulting oil was purified using flash chromatography (CH$_2$Cl$_2$) to provide 27 (1.43 g, 6.62 mmol, 93%) as a white solid that was recrystallized from Et$_2$O:hexanes to provide white needles.

Alternatively, α,α-dichloromethyl methyl ether was added to CH$_2$Cl$_2$ in a flame-dried round bottom flask 0° C. TiCl$_4$ was added at 0° C. and stirred for 5 minutes. Then 32 was added at 0° C. dissolved in CH$_2$Cl$_2$ and the reaction was stirred at 0° C. for 4 hrs. The reaction was then poured into water and stirred for 10 minutes at room temperature. The reaction was extracted with EtOAc, washed with saturated brine, dried over MgSO$_4$, filtered, and condensed.

Method B:

To a flame dried 50 mL round bottom flask was added phosphorousoxychloride (5.0 mL, 55 mmol) and then N-methylformanilide (4.9 mL, 54 mmol) at room temperature. The colorless clear solution became a pale yellow solution over 10 minutes at room temperature, and then solid 32 (4.99 g, 40.5 mmol) was added to the reaction at room temperature, and the residual 32 was added dissolved in CH$_2$Cl$_2$ (2.0 mL). The reaction quickly became orange and too thick to stir. After 12 h at room temperature CH$_2$Cl$_2$ was added (5×5.0 mL) in portions over a 4 hour period to resume stirring while keeping the reaction concentrated. After 30 hours a sample was removed, treated with water, dried, and analyzed by TLC (1:3 EtOAc:hexanes) and $^1$H NMR to determine no remaining starting material. The orange suspension was then diluted with CH$_2$Cl$_2$ to a final volume of 150 mL, and the red solution was treated with ice and stirred for 2 hours. The organic layer was then separated, washed with brine, dried over MgSO$_4$, filtered, and condensed. The resulting tan solid was then suspended in acetone (75.0 mL) and brought to a boil at which point the solution was clear/brown. Boiling hexane was added to a total volume of 125 mL and the solution was cooled to room temperature and then to 20° C. Tan needles were collected and 27 (4.77 g, 22.1 mmol, 83%) was determined pure by NMR.

$R_f$=0.62 (CH$_2$Cl$_2$)

mp=108-109° C. (Lit. 120-121° C.)[23]

¹H NMR (CDCl₃): δ 4.01 (s, 3H); 4.08 (s, 3H); 7.11 (s, 1H); 7.62 (m, 2H); 8.23 (m, 2H); 10.56 (s, 1H)

1,4-dimethoxy-3-methyl-2-naphthaldehyde (34)

Compound 34 was prepared from 97 (1.90 g, 9.39 mmol) as described above for 27 following method A to give 1.490 g (6.47 mmol, 69%) of the product as a white solid that was recrystallized from Et₂O/hexanes to provide white needles.
$R_f$=0.57 (3:7 EtOAc:hexanes)
mp=78-80° C. (Lit. 83.5-93.7° C.)²⁴
¹H NMR (CDCl₃): δ 2.63 (s, 3H); 3.85 (s, 3H); 4.05 (s, 3H); 7.59 (dt, 2H, J=7.2, 33.3 Hz); 8.14 (dd, 2H, J=8.4, 26.1 Hz)

$R_f$=0.29 (1:9 EtOAc:hexanes)
mp=99-100° C. (Lit. 110° C.)³⁸
¹H NMR (CDCl₃): δ 3.98 (s, 3H); 4.05 (s, 3H); 7.65 (m, 2H); 8.18 (dd, 2H, J=8.1, 33 Hz); 10.53 (s, 1H)

1,4-Dimethoxy-3-methylsulfanyl-2-naphthaldehyde (57)

Compound 57 was prepared from 56 (0.514 g, 1.94 mmol) as described above for 27 to give 0.308 g (1.17 mmol, 62%) of the product as a yellow oil/solid following flash chromatography (1:9 EtOAc:hexanes).
$R_f$=0.26 (1:9 EtOAc:hexanes)
¹H NMR (CDCl₃): δ 2.47 (s, 3H); 4.01 (s, 3H); 4.04 (s, 3H); 7.62 (m, 2H); 8.13 (d, 1H, J=8.1 Hz); 8.21 (d, 1H, J=8.1 Hz); 10.70 (s, 1H)

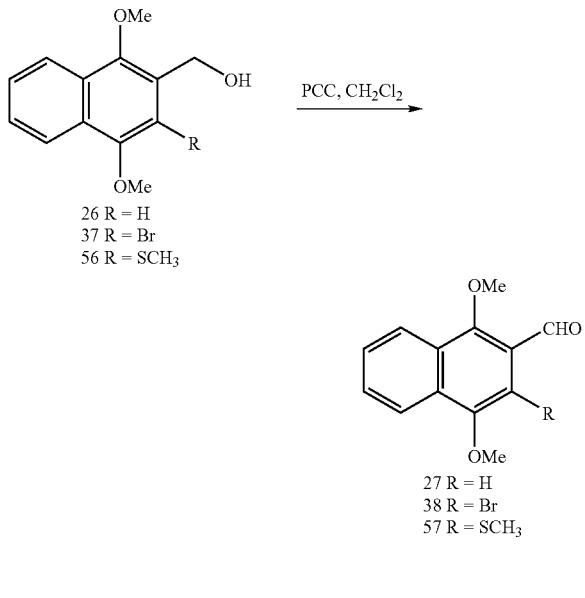

26 R = H
37 R = Br
56 R = SCH₃

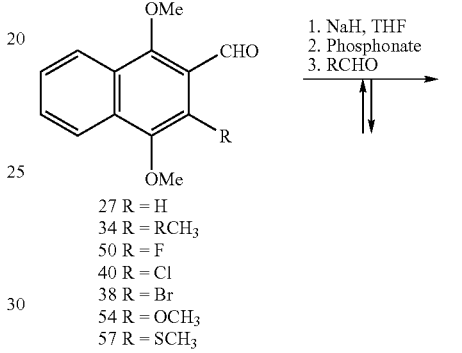

27 R = H
34 R = RCH₃
50 R = F
40 R = Cl
38 R = Br
54 R = OCH₃
57 R = SCH₃

27 R = H
38 R = Br
57 R = SCH₃

1,4-dimethoxy-2-naphthaldehyde (27)

Pyridinium chlorochromate (PCC, 1.04 g, 4.8 mmol) was added to a flame-dried 100 mL round bottom flask followed by dry CH₂Cl₂ (25.0 mL) at room temperature under Argon. Alcohol 26 (0.607 g, 2.78 mmol) was dissolved in CH₂Cl₂ (5.0 mL) and added slowly at room temperature. The reaction was stirred for a further 12 h at room temperature before being poured into a slurry of fluoricil, MgSO₄, and CH₂Cl₂. After stirring the suspension was filtered through celite and condensed. The resulting solid was purified by flash column chromatography (CH₂Cl₂) to provide 27 (0.510 g, 2.36 mmol, 85%) as white needles. The product was also purified by recrystallization in Et₂O:hexanes if no starting material was present.
$R_f$=0.62 (CH₂Cl₂)
mp=108-109° C. (Lit. 120-121° C.)²³
¹H NMR (CDCl₃): δ 4.01 (s, 3H); 4.08 (s, 3H); 7.11 (s, 1H); 7.62 (m, 2H); 8.23 (m, 2H); 10.56 (s, 1H)

3-bromo-1,4-dimethoxy-2-naphthaldehyde (38)

Compound 38 was prepared from 37 (1.85 g, 6.24 mmol) as described above for 27 to give 1.61 g (5.47 mmol, 88%) of the product as a white needles following flash chromatography (3:17 EtOAc:hexanes). The product was also purified by recrystallization in Et₂O/hexanes if no starting material was present.

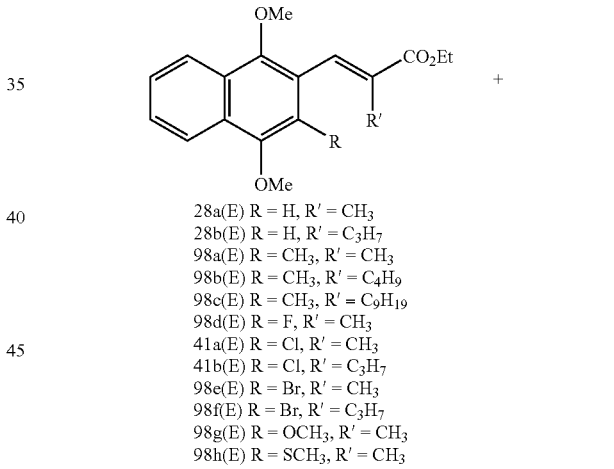

28a(E) R = H, R' = CH₃
28b(E) R = H, R' = C₃H₇
98a(E) R = CH₃, R' = CH₃
98b(E) R = CH₃, R' = C₄H₉
98c(E) R = CH₃, R' = C₉H₁₉
98d(E) R = F, R' = CH₃
41a(E) R = Cl, R' = CH₃
41b(E) R = Cl, R' = C₃H₇
98e(E) R = Br, R' = CH₃
98f(E) R = Br, R' = C₃H₇
98g(E) R = OCH₃, R' = CH₃
98h(E) R = SCH₃, R' = CH₃

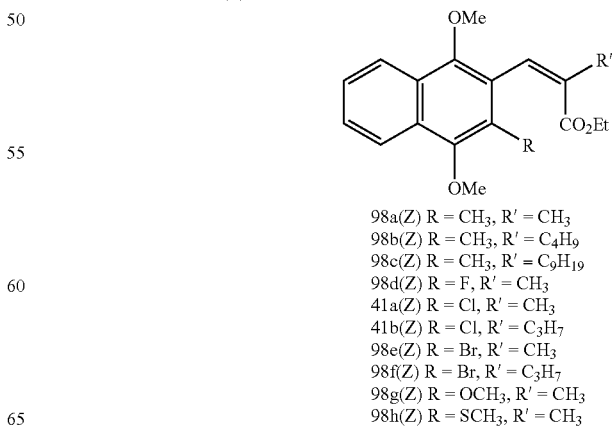

98a(Z) R = CH₃, R' = CH₃
98b(Z) R = CH₃, R' = C₄H₉
98c(Z) R = CH₃, R' = C₉H₁₉
98d(Z) R = F, R' = CH₃
41a(Z) R = Cl, R' = CH₃
41b(Z) R = Cl, R' = C₃H₇
98e(Z) R = Br, R' = CH₃
98f(Z) R = Br, R' = C₃H₇
98g(Z) R = OCH₃, R' = CH₃
98h(Z) R = SCH₃, R' = CH₃

Ethyl (E)-3-(1,4-dimethoxynaphthalen-2-yl)-2-methylpropenoate (28a)

According to the modified procedure of Murphy et al., 26 NaH (0.303 g, 7.59 mmol) was added to a flame-dried 50 mL round bottom flask connected to a water-jacketed reflux condenser. The flask was purged with Argon and a drying tube was attached to the top. Toluene (20.0 mL) was added to the flask followed by phosphonate (1.0 ml, 4.6 mmol) at room temperature. The reaction was heated under reflux for 30 minutes, and aldehyde 27 (0.542 g, 2.51 mmol) was dissolved in toluene (5.0 mL) and added slowly at reflux. The reaction was heated for another 8 h under reflux. The reaction was then cooled to room temperature, diluted with ethyl acetate, and washed with brine. The organic layer was dried, filtered, and condensed. The resulting oil was purified via flash column chromatography (<1:19 iPr2O:hexanes) and recrystallized from $Et_2O$/hexanes to provide pure 28a (0.554 g, 1.84 mmol, 73%) as a colorless oil.

Rf=0.30 (1:19 iPr2O:hexanes, 4 developments)
E:Z=20:1 in refluxing toluene
$^1$H NMR (CDCl$_3$): □ 1.36 (t, 3H, J=7.2 Hz); 2.10 (d, 3H, J=1.2 Hz); 3.91 (s, 3H); 3.96 (s, 3H); 4.29 (q, 2H, J=7.2 Hz); 6.70 (s, 1H); 7.51 (m, 2H); 7.96 (d, 1H, J=1.2 Hz); 8.152 (m, 2H)

Ethyl (E)-3-(1,4-dimethoxynaphthalen-2-yl)-2-propylpropenoate (28b)

Compound 28b was prepared from 27 (0.495 g, 2.29 mmol) as described above for 28a to give 0.443 g (1.35 mmol, 59%) of the product as a white solid following flash chromatography (1:19 $Et_2O$:hexanes) and recrystallization from $Et_2O$/hexanes.

$R_f$=0.35 (1:19 i-Pr$_2$O:hexanes, 4 developments)
E:Z=20:1 at −78° C.
mp=36-38° C.
$^1$H NMR (CDCl$_3$): δ 0.94 (t, 3H, J=7.2 Hz); 1.36 (t, 3H, J=7.2 Hz); 1.60 (m, 2H); 2.53 (m, 2H); 3.84 (s, 3H); 3.96 (s, 3H); 4.29 (q, 2H, J=7.2 Hz); 6.71 (s, 1H); 7.51 (m, 2H); 7.96 (s, 1H); 8.09 (dd, 1H, J=1.2, 7.5 Hz); 8.21 (dd, 1H, J=1.8, 7.5 Hz)

Ethyl (E)-3-(3-chloro-1,4-dimethoxynaphthalen-2-yl)-2-methylpropenoate (41a)

Compound 41a was prepared from 40 (2.93 g, 11.7 mmol) as described above for 28a to give 2.56 g (7.65 mmol, 65%) of the product as a yellow solid following flash chromatography (1:19 $Et_2O$:hexanes) and recrystallization from $Et_2O$/hexanes. (1.50 g E, yellow solid; 0.960 g E/Z, gold oil; 0.101 g Z, gold solid)

Rf=E=0.32; Z=0.24 (1:19 iPr2O:hexanes, 4 developments)
E:Z=15:5 in refluxing toluene
mp=108-109° C.
1H NMR (CDCl$_3$): □ 1.37 (t, 3H, J=7.2 Hz); 1.83 (s, 3H); 3.75 (s, 3H); 3.98 (s, 3H); 4.30 (q, 2H, J=7.2); 7.55 (m, 2H); 7.68 (s, 1H); 8.11 (m, 2H)

Ethyl (E)-3-(3-chloro-1,4-dimethoxynaphthalen-2-yl)-2-propylpropenoate (41b)

Compound 41b was prepared from 40 (0.261 g, 1.04 mmol) as described above for 28a to give 0.115 g (0.32 mmol, 32%) of the product as a yellow solid following flash chromatography (1:19 $Et_2O$:hexanes) and recrystallization from $Et_2O$/hexanes. (0.057 g E; 0.098 g E/Z)

$R_f$=E=0.31; Z=0.23 (1:19 i-Pr$_2$O:hexanes, 4 developments)
E:Z=15:5 in refluxing toluene
$^1$H NMR (CDCl$_3$): δ 0.72 (t, 3H, J=7.5); 1.36 (t, 3H, J=7.2); 1.41 (m, 2H); 2.22 (m, 2H); 3.77 (s, 3H); 3.98 (s, 3H); 4.30 (q, 2H, J=7.2); 7.55 (m, 2H); 7.57 (s, 1H); 8.11 (m, 2H)

Ethyl (E)-3-(1,4-dimethoxy-3-methylnaphthalen-2-yl)-2-methylpropenoate (98a)

Compound 98a was prepared from 34 (0.506 g, 2.20 mmol) as described above for 28a to give 0.541 g (1.42 mmol, 65%) of the product as a colorless oil following flash chromatography (1:19 i-Pr$_2$O:hexanes).

$R_f$=E=0.22; Z=0.15 (1:19 i-Pr$_2$O:hexanes, 4 developments)
E:Z=20:1 in refluxing toluene.
$^1$H NMR (CDCl$_3$): δ 1.36 (t, 3H, J=7.2 Hz); 1.79 (s, 3H); 2.28 (s, 3H); 3.73 (s, 3H); 3.87 (s, 3H); 4.30 (q, 2H, J=7.2 Hz); 7.49 (m, 2H); 7.70 (s, 1H); 8.07 (m, 2H)

Ethyl (E)-3-(1,4-dimethoxy-3-methylnaphthalen-2-yl)-2-butylpropenoate (98b)

Compound 98b was prepared from 34 (0.383 g, 1.67 mmol) as described above for 28a to give 0.209 g (0.58 mmol, 34%) of the product as a colorless oil following flash chromatography (1:9 EtOAc:hexanes) and recrystallization from $Et_2O$/hexanes.

$R_f$=E=0.37; Z=0.27 (1:19 i-Pr$_2$O:hexanes, 4 developments)
E:Z=20:1 in refluxing toluene
$^1$H NMR (CDCl$_3$): δ 0.70 (t, 3H, J=7.2 Hz); 1.11 (m, 2H); 1.31 (m, 2H); 1.36 (t, 3H, J=7.2 Hz); 2.21 (m, 2H); 2.28 (s, 3H); 3.75 (s, 3H); 3.86 (s, 3H); 4.29 (q, 2H, J=7.2 Hz); 7.49 (m, 2H); 7.59 (s, 1H); 8.08 (m, 2H)

Ethyl (E)-3-(1,4-dimethoxy-3-methylnaphthalen-2-yl)-2-nonylpropenoate (98c)

Compound 98c was prepared from 34 (0.479 g, 2.08 mmol) as described above for 28a to give 0.373 g (0.874 mmol, 41%) of the product as a yellow oil following flash chromatography (1:9 EtOAc:hexanes).

$R_f$=0.29 (1:19 i-Pr$_2$O:hexanes, 4 developments)
E:Z=20:1 in refluxing toluene
$^1$H NMR (CDCl$_3$): δ 0.81 (t, 3H, J=6.9 Hz); 1.07 (m, 10H); 1.29 (m, 4H); 1.36 (t, 3H, J=7.2 Hz); 2.20 (t, 2 hexanes, J=7.2 Hz); 2.28 (s, 3H); 3.75 (s, 3H); 3.87 (s, 3H); 4.30 (q, 2H, J=7.2 Hz); 7.48 (m, 2H); 7.59 (s, 1H); 8.08 (m, 2H)

Ethyl (E)-3-(1,4-dimethoxy-3-fluoronaphthalen-2-yl)-2-methylpropeonoate (98d)

Compound 98d was prepared from 50 (0.216 g, 0.922 mmol) as described above for 28a to give 0.226 g (0.710 mmol, 77%) of the product as a yellow oil following flash chromatography (1:19 $Et_2O$:hexanes). (0.093 g pure E; 0.128 g E/Z; 0.005 g Z)

$R_f$=E=0.25; Z=0.17 (1:19 $Et_2O$:hexanes, 3 developments)
E:Z=5:1 in refluxing toluene
$^1$H NMR (CDCl$_3$): δ 1.36 (t, 3H, J=7.2 Hz); 1.91 (t, 3H, J=1.8 Hz); 3.80 (s, 3H); 4.05 (d, 3H, J=1.2 Hz); 4.30 (q, 2H, J=7.2 Hz); 7.51 (m, 2H); 7.67 (s, 1H); 8.09 (dd, 1H, J=1.2, 7.5 Hz); 8.14 (dd, 1H, J=1.2, 7.5 Hz)
$^{19}$F NMR (CDCl$_3$): 8-137.41 (s, 1F)

Ethyl (E)-3-(3-bromo-1,4-dimethoxynaphthalen-2-yl)-2-methylpropenoate (98e)

Compound 98e was prepared from 38 (0.515 g, 1.75 mmol) as described above for 28a to give 0.373 g (0.984 mmol, 56%) of the product as a white solid following flash chromatography (1:19 i-Pr₂O:hexanes) and recrystallization from Et₂O/hexanes. (0.314 g E; 0.059 g Z)

R$_f$=E=0.26; Z=0.19 (1:19 i-Pr₂O:hexanes, 4 developments)

E:Z=17:3 in refluxing toluene mp=102-103° C.

¹H NMR (CDCl₃): δ 1.37 (t, 3H, 7.2 Hz); 1.81 (d, 3H, J=1.2 Hz); 3.74 (s, 3H); 3.97 (s, 3H); 4.31 (q, 2H, J=7.2 Hz); 7.56 (m, 2H); 7.65 (d, 1H, J=1.2 Hz); 8.11 (m, 2H)

Ethyl (E)-3-(3-bromo-1,4-dimethoxynaphthalen-2-yl)-2-propylpropenoate (98f)

Compound 98f was prepared from 38 (0.514 g, 1.75 mmol) as described above for 28a to give 0.346 g (0.849 mmol, 49%) of the product as a yellow solid following flash chromatography (1:19 Et₂O:hexanes) and recrystallization from Et₂O/hexanes. (0.291 g E; 0.055 g Z)

R$_f$=E=0.33; Z=0.23 (1:19 i-Pr₂O:hexanes, 4 developments)

E:Z=17:3 in refluxing toluene mp=89-90° C.

¹H NMR (CDCl₃): δ 0.72 (t, 3H, J=7.2 Hz); 1.36 (t, 3H, J=6.9 Hz); 1.40 (m, 2H); 2.21 (m, 2H); 3.76 (s, 3H); 3.97 (s, 3H); 4.30 (q, 2H, J=7.2 Hz); 7.54 (s, 1H); 7.56 (m, 2H); 8.11 (m, 2H)

Ethyl (E)-3-(1,3,4-trimethoxynaphthalen-2-yl)-2-methylpropenoate (98g)

Compound 98g was prepared from 54 (0.330 g, 1.33 mmol) as described above for 28a to give 0.119 g (0.360 mmol, 27%) of the product as a yellow oil following flash chromatography (1:9 Et₂O:hexanes) and recrystallization from Et₂O/hexanes. (E/Z fractions discarded)

R$_f$=E=0.17; Z=0.11 (1:19 i-Pr₂O:hexanes, 4 developments)

E:Z=11:9 in refluxing toluene

¹H NMR (CDCl₃): δ 1.36 (t, 3H, J=7.2 Hz); 1.87 (d, 3H, J=1.5 Hz); 3.75 (s, 3H); 3.87 (s, 3H); 3.98 (s, 3H); 4.29 (q, 2H, J=7.2 Hz); 7.47 (m, 2H); 7.73 (d, 1H, J=1.5 Hz); 8.09 (m, 2H)

Ethyl (E)-3-(1,4-dimethoxy-3-methylsulfanylnaphthalen-2-yl)-2-methylpropenoate (98h)

Compound 98h was prepared from 57 (0.308 g, 1.17 mmol) as described above for 28a to give 0.231 g (0.667 mmol, 55%) of the product as an amorphous yellow solid following flash chromatography (1:9 EtOAc:hexanes) and recrystallization from Et2O/hexanes. (0.165 g E; 0.065 g E/Z)

Rf=0.26 (1:9 EtOAc:hexanes)

E:Z=7:3 in refluxing toluene

1H NMR (CDCl₃): □ 1.37 (t, 3H, J=7.2 Hz); 1.82 (s, 3H); 2.37 (s, 3H); 3.72 (s, 3H); 4.00 (s, 3H); 4.30 (q, 2H, J=7.2 Hz); 7.54 (m, 2H); 7.86 (s, 1H); 8.10 (m, 2H)

Z Isomers:

Ethyl (3Z)-3-(3-chloro-1,4-dimethoxynaphthalen-2-yl)-2-methylpropenoate ((Z)-41a)

Compound (Z)-41a was prepared from 40 (2.93 g, 11.7 mmol) as described above for 28a to give 2.56 g (7.65 mmol, 65%) of the product as a yellow solid following flash chromatography (1:19 Et₂O:hexanes) and recrystallization from Et₂O/hexanes. (1.50 g E, yellow solid; 0.959 g E/Z, gold oil; 0.101 g Z, gold solid)

R$_f$=0.24 (1:19 i-Pr₂O:hexanes, 4 developments)

E:Z=15:5 in refluxing toluene mp=122-128° C.

¹H NMR (CDCl₃): δ 0.81 (t, 3H, J=7.2 Hz); 2.20 (d, 3H, J=1.8 Hz); 3.77 (s, 3H); 3.96 (q, 2H, J=7.2 Hz); 3.96 (s, 3H); 6.83 (d, 1H, J=1.5 Hz); 7.50 (m, 2H); 8.06 (m, 2H)

Ethyl (3Z)-3-(1,4-dimethoxy-3-fluoronaphthalen-2-yl)-2-methylpropenoate ((Z)-98d)

Compound (Z)-98d was prepared from 50 (0.216 g, 0.922 mmol) as described above for 28a to give 0.226 g (0.710 mmol, 77%) of the product as a yellow solid following flash chromatography (1:19 Et₂O:hexanes). (0.093 g pure E; 0.128 g E/Z; 0.0047 g Z)

R$_f$=0.17 (1:19 iPr₂O:hexanes)

mp=37-39° C.

E:Z=17:3 in refluxing toluene

¹H NMR (CDCl₃): δ 0.97 (t, 3H, J=7.2 Hz); 2.20 (d, 3H, J=1.5 Hz); 3.83 (s, 3H); 4.01 (d, 3H, J=1.2 Hz); 4.05 (, 2H, J=7.2 Hz); 6.79 (d, 1H, J=1.5 Hz); 7.47 (m, 2H); 8.08 (m, 2H)

¹⁹F NMR (CDCl₃): δ-138.93 (s, 1F)

Ethyl (3Z)-3-(1,4-dimethoxy-3-methylsulfanylnaphthalen-2-yl)-2-methylpropenoate ((Z)-98h, NO REFERENCE)

Compound (Z)-98h was prepared from 57 (0.308 g, 1.17 mmol) as described above for 28a to give 0.2306 g (0.667 mmol, 55%) of the product as an amorphous yellow solid following flash chromatography (1:9 EtOAc:hexanes). (0.165 g E; 0.065 g E/Z)

R$_f$=0.26 (1:9 EtOAc:hexanes)

E:Z=7:3 in refluxing toluene

¹H NMR (CDCl₃): δ 0.78 (t, 3H, J=7.2 Hz); 2.20 (d, 3H, J=1.8 Hz); 2.38 (s, 3H); 3.72 (s, 3H); 3.93 (q, 2H, J=7.2 Hz); 3.99 (s, 3H); 6.99 (d, 1H, J=1.5 Hz); 7.48 (m, 2H); 8.05 (m, 2H)

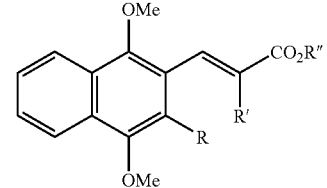

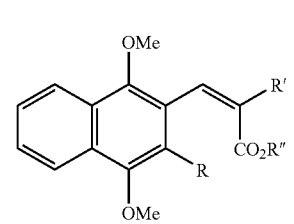

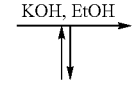

28a(E/Z) R = H, R' = CH₃, R" = C₂H₅
28b(E/Z) R = H, R' = C₃H₇, R" = C₂H₅
98(E/Z) R = CH₃, R' = CH₃, R" = C₂H₅
98b(E/Z) R = CH₃, R' = C₄H₉, R" = C₂H₅
59a(E/Z) R = CH₃, R' = CH₂CH₂OCH₃, R" = CH₃
98c(E/Z) R = CH₃, R' = C₉H₁₉, R" = C₂H₅
98d(E/Z) R = F, R' = CH₃, R" = C₂H₅
41a(E/Z) R = Cl, R' = CH₃, R" = C₂H₅
41b(E/Z) R = Cl, R' = C₃H₇, R" = C₂H₅
59c(E/Z) R = Cl, R' = CH₂CH₂OCH₃, R" = CH₃
98e(E/Z) R = Br, R' = CH₃, R" = C₂H₅
98f(E/Z) R = Br, R' = C₃H₇, R" = C₂H₅
59b(E/Z) R = Br, R' = CH₂CH₂OCH₃, R" = CH₃
98g(E/Z) R = OCH₃, R' = CH₃, R" = C₂H₅
98h(E/Z) R = SCH₃, R' = CH₃, R" = C₂H₅

-continued

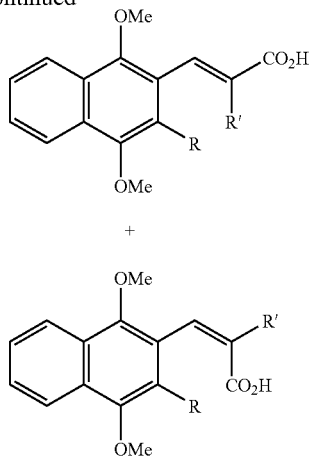

29a(E/Z) R = H, R' = CH$_3$
29b(E/Z) R = H, R' = C$_3$H$_7$
99a(E/Z) R = CH$_3$, R' = CH$_3$
98b(E/Z) R = CH$_3$, R' = C$_4$H$_9$
60a(E/Z) R = CH$_3$, R' = CH$_2$CH$_2$OCH$_3$
99c(E/Z) R = CH$_3$, R' = C$_9$H$_{19}$
99d(E/Z) R = F, R' = CH$_3$
42a(E/Z) R = Cl, R' = CH$_3$
42b(E/Z) R = Cl, R' = C$_3$H$_7$
60c(E/Z) R = Cl, R' = CH$_2$CH$_2$OCH$_3$
99e(E/Z) R = Br, R' = CH$_3$
99f(E/Z) R = Br, R' = C$_3$H$_7$
60b(E/Z) R = Br, R' = CH$_2$CH$_2$OCH$_3$
99g(E/Z) R = OCH$_3$, R' = CH$_3$
99h(E/Z) R = SCH$_3$, R' = CH$_3$ (E)-3-(1,4-dimethoxynaphthalen-2-yl)-2-methylpropenoic acid (29a)

Emmons ester 28a (0.231 g, 0.769 mmol) was dissolved in EtOH (10.0 mL) and then KOH (0.400 g, 7.13 mmol) was added to the reaction. The reaction was heated to boiling and stirred at this temperature for 30 minutes. The reaction was then cooled, acidified, and extracted with ethyl acetate. The organic layer was washed with brine, dried over MgSO$_4$, filtered, and condensed. The resulting acid was then used as crude, or can be purified via flash chromatography (1:3 EtOAc:hexanes 0.5% AcOH) or recrystallization from Et$_2$O/hexanes to provide 29a (0.175 g, 0.643 mmol, 83%) as a white solid.

R$_f$=0.24 (1:3 EtOAc:hexanes 0.5% AcOH)
mp=149-155° C.
$^1$H NMR (CDCl$_3$): δ 2.16 (d, 3H, J=1.2); 3.86 (s, 3H); 3.99 (s, 3H); 6.75 (s, 1H); 7.53 (m, 2H); 8.15 (d, 1H, J=1.2 Hz); 8.17 (m, 2H)

(E)-3-(1,4-dimethoxynaphthalen-2-yl)-2-propylpropenoic acid (29b)

Compound 29b was prepared from 28b (0.215 g, 0.656 mmol) as described above for 29a to give 0.193 g (0.642 mmol, 99%) of the product as a white solid following flash chromatography (1:3 EtOAc:hexanes 0.5% AcOH) and recrystallization from Et$_2$O/hexanes.

R$_f$=0.24 (1:3 EtOAc:hexanes 0.5% AcOH)
mp=139-141.5° C.
$^1$H NMR (CDCl$_3$): δ 0.98 (t, 3H, J=7.2 Hz); 1.67 (m, 2H); 2.58 (m, 2h); 3.87 (s, 3H); 3.99 (s, 3H); 6.76 (s, 1H); 7.53 (m, 2H); 8.11 (m, 1H); 8.16 (s, 1H); 8.22 (m, 2H)

(E)-3-(3-chloro-1,4-dimethoxynaphthalen-2-yl)-2-methylpropenoic acid (42a)

Compound 42a was prepared from 41a (0.959 g, 2.90 mmol) as described above for 29a to give 0.872 g (2.84 mmol, 98%) of the product as a tan solid following flash chromatography (3:17 acetone:hexanes 0.5% AcOH) and recrystallization from Et$_2$O/hexanes.

R$_f$=0.08 (3:17 acetone:hexanes 0.5% AcOH)
mp=155-157° C.
$^1$H NMR (CDCl$_3$): δ 1.88 (s, 3H); 3.77 (s, 3H); 3.99 (s, 3H); 7.58 (m, 2H); 7.85 (s, 1H); 8.123 (m, 2H)
$^{13}$C NMR (CDCl$_3$): δ 14.7, 61.4, 62.0, 122.2, 123.0, 124.2, 126.8, 127.5, 127.7, 129.0, 132.1, 135.0, 148.7, 150.7, 172.3

(E)-3-(3-chloro-1,4-dimethoxynaphthalen-2-yl)-2-propylpropenoic acid (42b)

Compound 42b was prepared from 41b (0.028 g, 0.077 mmol) as described above for 29a to give 0.026 g (0.077 mmol, 100%) of the product as a red solid following flash chromatography (1:3 EtOAc:hexanes 0.5% AcOH) and recrystallization from Et$_2$O/hexanes.

R$_f$=0.19 (1:3 EtOAc:hexanes 0.5% AcOH)
mp=188-190° C.
$^1$H NMR (CDCl$_3$): δ 0.74 (t, 3H, J=7.2 Hz); 1.44 (m, 2H); 2.26 (m, 3H); 3.79 (s, 3H); 3.989 (s, 3H); 7.56 (m, 2H); 7.75 (s, 1H); 8.13 (m, 2H)

(E)-3-(1,4-dimethoxy-3-methylnaphthalen-2-yl)-2-methoxyethylpropenoic acid (60a)

Compound 60a was prepared from 59a (0.104 g, 0.302 mmol) as described above for 29a to give 0.076 g (0.23 mmol, 77%) of the product as a tan solid following flash chromatography (1:3 EtOAc:hexanes 0.5% AcOH) and recrystallization from Et$_2$O/hexanes.

R$_f$=0.10 (1:3 EtOAc:hexanes 0.5% AcOH)
mp=145-148° C.
$^1$H NMR (CDCl$_3$): δ 2.30 (s, 3H); 2.57 (t, 2H, J=6.6 Hz); 3.17 (s, 3H); 3.44 (t, 2H, J=6.6 Hz); 3.77 (s, 3H); 3.88 (s, 3H); 7.50 (m, 2H); 7.86 (s, 1H); 8.08 (dt, 2H, J=8.4, 1.2 Hz)

(E)-3-(3-bromo-1,4-dimethoxynaphthalen-2-yl)-2-methoxyethylpropenoic acid (60b)

Compound 60b was prepared from 59b (0.179 g, 0.437 mmol) as described above for 29a to give 0.060 g (0.15 mmol, 35%) of the product as a tan solid following flash chromatography (1:3 EtOAc:hexanes 0.5% AcOH) and recrystallization from Et$_2$O/hexanes.

R$_f$=0.12 (1:3 EtOAc:hexanes 0.5% AcOH)
mp=158-160° C.
$^1$H NMR (CDCl$_3$): δ 2.57 (t, 3H, J=6.3 Hz); 3.27 (s, 3H); 3.45 (t, 3H, J=6.3 Hz); 3.79 (s, 3H); 3.98 (s, 3H); 7.57 (m, 2H); 7.72 (s, 1H); 8.12 (m, 2H)

(E)-3-(3-chloro-1,4-dimethoxynaphthalen-2-yl)-2-methoxyethylpropenoic acid (60c)

Compound 60c was prepared from 59c (0.064 g, 0.17 mmol) as described above for 29a to give 0.067 g (0.19 mmol, 112%) of the product as a tan solid following flash chromatography (1:3 EtOAc:hexanes 0.5% AcOH) and recrystallization from Et$_2$O/hexanes.

R$_f$=0.12 (1:3 EtOAc:hexanes 0.5% AcOH)
mp=145-146° C.
$^1$H NMR (CDCl$_3$): δ 2.60 (t, 2H, J=6.6 Hz); 3.21 (s, 3H); 3.45 (t, 2H, J=6.6 Hz); 3.80 (s, 3H); 3.98 (s, 3H); 7.56 (m, 2H); 7.80 (s, 1H); 8.11 (m, 2H)

(E)-3-(1,4-dimethoxy-3-methylnaphthalen-2-yl)-2-methylpropenoic acid (99a)

Compound 99a was prepared from 98a (0.176 g, 0.560 mmol) as described above for 29a to give 0.134 g (0.468 mmol, 83%) of the product as a light yellow solid following flash chromatography (3:17 acetone:hexanes 0.5% AcOH) and recrystallization from Et$_2$O/hexanes.
$R_f$=0.20 (1:3 EtOAc:hexanes 0.5% AcOH)
mp=153-155° C.
$^1$H NMR (CDCl$_3$): δ 1.80 (s, 3H); 3.75 (s, 3H); 3.89 (s, 3H); 7.51 (m, 2H); 7.72 (s, 1H); 8.09 (m, 2H)

(E)-3-(1,4-dimethoxy-3-methylnaphthalen-2-yl)-2-butylpropenoic acid (99b)

Compound 99b was prepared from 98b (0.148 g, 0.415 mmol) as described above for 29a to give 0.154 g (0.469 mmol, 113%) of the product as a white solid following flash chromatography (1:3 EtOAc:hexanes 0.5% AcOH) and recrystallization from Et$_2$O/hexanes.
$R_f$=0.24 (1:3 EtOAc:hexanes 0.5% AcOH)
mp=133-134° C.
$^1$H NMR (CDCl$_3$): δ 0.70 (t, 3H, J=7.2 Hz); 1.13 (m, 2H); 1.38 (m, 2H); 2.26 (m, 2H); 2.31 (s, 3H); 3.77 (s, 3H); 3.88 (s, 3H); 7.51 (m, 2H); 7.78 (s, 1H); 8.10 (m, 2H)

(E)-3-(1,4-dimethoxy-3-methylnaphthalen-2-yl)-2-nonylpropenoic acid (99c)

Compound 99c was prepared from 98c (0.164 g, 0.384 mmol) as described above for 29a to give 0.152 g (0.381 mmol, 96%) of the product as a colorless oil following flash chromatography (1:3 EtOAc:hexanes 0.5% AcOH).
$R_f$=0.33 (1:3 EtOAc:hexanes 0.5% AcOH)
$^1$H NMR (CDCl$_3$): δ 0.81 (t, 3H, J=7.2 Hz); 1.07 (m, 10H); 1.18 (m, 2H); 1.37 (m, 2H); 2.24 (m, 2H); 2.30 (s, 3H); 3.77 (s, 3H); 3.88 (s, 3H); 7.50 (m, 2H); 7.77 (s, 1H); 8.09 (m, 2H)

(E)-3-(1,4-dimethoxy-3-fluoronaphthalen-2-yl)-2-methylpropenoic acid (99d)

Compound 99d was prepared from 98d (0.128 g, 0.402 mmol) as described above for 29a to give 0.097 g (0.33 mmol, 83%) of the product as a white solid following flash chromatography (1:4 acetone:hexanes 0.5% AcOH) and recrystallization from Et$_2$O/hexanes.
$R_f$=0.13 (1:4 acetone:hexanes 0.5% AcOH)
mp=157-158.5° C.
$^1$H NMR. (CDCl$_3$): δ 1.93 (d, 3H, J=1.5 Hz); 3.82 (s, 3H); 4.06 (d, 3H, J=1.5 Hz); 7.52 (m, 2H); 7.83 (d, 1H, J=1.2 Hz); 8.10 (d, 1H, J=8.4 Hz); 8.15 (d, 1H, J=8.4 Hz)
$^{19}$F NMR (CDCl$_3$): δ-137.38 (s, 1F)

(E)-3-(3-bromo-1,4-dimethoxynaphthalen-2-yl)-2-methylpropenoic acid (99e)

Compound 99e was prepared from 98e (0.314 g, 0.828 mmol) as described above for 29a to give 0.291 g (0.829 mmol, 100%) of the product as a white solid following recrystallization from Et$_2$O/hexanes.
$R_f$=0.32 (1:1 Et$_2$O:hexanes 0.5% AcOH)
mp=143-145° C.
$^1$H NMR (CDCl$_3$): δ 1.86 (d, 3H, J=1.2 Hz); 3.77 (s, 3H); 3.99 (s, 3H); 7.57 (m, 2H); 7.82 (d, 1H, J=1.2 Hz); 8.13 (m, 2H)

(E)-3-(3-bromo-1,4-dimethoxynaphthalen-2-yl)-2-propylpropenoic acid (99f)

Compound 99f was prepared from 98f (0.177 g, 0.435 mmol) as described above for 29a to give 0.078 g (0.21 mmol, 47%) of the product as a white solid following flash chromatography (1:3 EtOAc:hexanes 0.5% AcOH) and recrystallization from Et$_2$O/hexanes.
$R_f$=0.19 (1:3 EtOAc:hexanes 0.5% AcOH)
mp=187-194° C.
$^1$H NMR (CDCl$_3$): δ 0.74 (t, 3H, J=7.2 Hz); 1.45 (m, 2H); 2.25 (m, 2H); 3.79 (s, 3H); 3.98 (s, 3H); 7.57 (m, 2H); 7.71 (s, 1H); 8.13 (m, 2H)

(E)-3-(1,3,4-trimethoxynaphthalen-2-yl)-2-methylpropenoic acid (99g)

Compound 99g was prepared from 98g (0.073 g, 0.22 mmol) as described above for 29a to give 0.068 g (0.22 mmol, 100%) of the product as a tan solid following flash chromatography (1:3 EtOAc:hexanes 0.5% AcOH) and recrystallization from Et$_2$O/hexanes.
$R_f$=0.13 (1:3 EtOAc:hexanes 0.5% AcOH)
mp=119-123° C.
$^1$H NMR (CDCl$_3$): δ 1.91 (s, 3H); 3.77 (s, 3H); 3.89 (s, 3H); 3.99 (s, 3H); 7.49 (m, 2H); 7.91 (s, 1H); 8.10 (t, 2H, J=6.6 Hz)

(E)-3-(1,4-dimethoxy-3-methylsulfanylnaphthalen-2-yl)-2-methylpropenoic acid (99h)

Compound 99h was prepared from 98h (0.165 g, 0.476 mmol) as described above for 29a to give 0.181 g (0.568 mmol, 118%) of the product as a orange solid following flash chromatography (1:3 EtOAc:hexanes 0.5% AcOH) and recrystallization from Et$_2$O/hexanes.
$R_f$=0.18 (1:3 EtOAc:hexanes 0.5% AcOH)
mp=XX-XX ° C.
$^1$H NMR (CDCl$_3$): δ 1.82 (d, 3H, J=1.2 Hz); 2.37 (s, 3H); 3.72 (s, 3H); 4.00 (s, 3H); 7.51 (m, 2H); 7.99 (d, 1H, J=1.2 Hz); 8.07 (m, 2H)

Z Isomers:

(3Z)-3-(3-chloro-1,4-dimethoxynaphthalen-2-yl)-2-methylpropenoic acid ((Z)-42a)

Compound (Z)-42a was prepared from (Z)-41a (0.959 g, 2.90 mmol) as described above for 29a to give 0.872 g (2.84 mmol, 99%) of the product as a yellow solid following flash chromatography (3:17 acetone:hexanes 0.5% AcOH) and recrystallization from Et$_2$O/hexanes.
$R_f$=0.08 (3:17 acetone:hexanes 0.5% AcOH)
mp=145-155° C.
$^1$H NMR (CDCl$_3$): δ 2.20 (d, 3H, J=1.5 Hz); 3.77 (s, 3H); 3.90 (s, 3H); 6.89 (q, 1H, J=1.5 Hz); 7.50 (m, 2H); 8.04 (m, 2H)
$^{13}$C NMR (CDCl$_3$): δ 20.8, 61.3, 61.7, 122.2, 122.8, 125.9, 126.5, 127.1, 127.3, 128.6, 131.1, 132.6, 148.6, 149.9, 171.0

(3Z)-3-(1,4-dimethoxy-3-fluoronaphthalen-2-yl)-2-methylpropenoic acid ((Z) 99d)

Compound (Z)-99d was prepared from (Z)-98e (0.128 g, 0.402 mmol) as described above for 29a to give 0.097 g (0.33 mmol, 83%) of the product as a white solid following flash chromatography (1:4 acetone:hexanes 0.5% AcOH) and recrystallization from Et$_2$O/hexanes.
$R_f$=0.13 (1:4 acetone:hexanes 0.5% AcOH)
mp=XX-XX ° C.
$^1$H NMR (CDCl$_3$): 2.23 (d, 3H, J=1.5 Hz); 3.86 (s, 3H); 4.00 (d, 3H, J=1.2 Hz); 6.92 (d, 1H, J=1.5 Hz); 7.49 (m, 2H); 8.11 (two d, 2 H, buried under E isomer)
$^{19}$F NMR (CDCl$_3$): δ-138.26 (s, 1F)

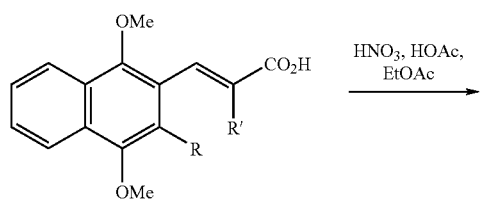

29a(E) R = H, R' = CH₃
29b(E) R = H, R' = C₃H₇
99a(E) R = CH₃, R' = CH₃
99b(E) R = CH₃, R' = C₄H₉
61(E) R = CH₃, R' = CH₂CH₂OCH₃
99c(E) R = CH₃, R' = C₉H₁₉
98g(E) R = OCH₃, R' = CH₃
98h(E) R = SCH₃, R' = CH₃

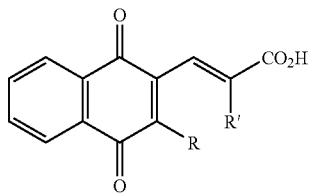

30a(E) R = H, R' = CH₃
30b(E) R = H, R' = C₃H₇
35a(E) R = CH₃, R' = CH₃
35b(E) R = CH₃, R' = C₄H₉
62a(E) R = CH₃, R' = CH₂CH₂OCH₃
35c(E) R = CH₃, R' = C₉H₁₉
55(E) R = OCH₃, R' = CH₃
58(E) R = SCH₃, R' = CH₃

(E)-3-(1,4-naphthoquinon-2-yl)-2-methylpropenoic acid (30a)

Following modified procedures of Shinkawa et al. and Flader et al.[16,22] the acid 29a (0.114 g, 0.419 mmol) was dissolved in ethyl acetate (10 mL) at room temperature, then $HNO_3$ (1.0 mL) and AcOH (3 drops) were added at room temperature. The reaction was stirred at room temperature for 4 hours before being diluted with ethyl acetate and washed with brine. The organic layer was dried over $MgSO_4$, filtered, and condensed. The yellow oil was then purified by either flash column chromatography (2:3 $Et_2O$:hexanes 0.5% AcOH) or recrystallization from $Et_2O$/hexanes to afford 30a (0.059 g, 0.24 mmol, 58%) as a yellow solid.

Alternatively the reaction can be run as a mixture of E and Z isomers under the same conditions. Following workup the mixture will be the E acid and the Z methyl ester from an intramolecular esterification event taking place with the oxonium intermediate. Separation via flash chromatography (2:3 $Et_2O$:hexanes 0.5% AcOH) was necessary to separate the ester and acid components.

$R_f$=0.43 (2:3 $Et_2O$:hexanes 0.5% AcOH)
mp=205° C. d
$^1$H NMR ($CDCl_3$): δ 2.13 (d, 3H, J=1.2 Hz); 6.99 (s, 1H); 7.79 (m, 3H); 8.11 (m, 2H)
$^1$H NMR (acetone-$D_6$): δ 2.15 (d, 3H, J=1.5 Hz); 7.06 (s, 1H); 7.72 (m, 1H); 7.89 (m, 2H); 8.09 (m, 2H)
$^1$H NMR (DMSO-$D_6$): δ 2.04 (s, 3H); 7.06 (s, 1H); 7.52 (d, 1H, J=1.5 Hz); 7.90 (m, 2H); 8.04 (m, 2H)

(E)-3-(1,4-naphthoquinon-2-yl)-2-propylpropenoic acid (30b)

Compound 30b was prepared from 29b (0.193 g, 0.643 mmol) as described above for 30a to give 0.064 g (0.24 mmol, 37%) of the product as a yellow solid following flash chromatography (2:3 $Et_2O$:hexanes 0.5% AcOH) and recrystallization from $Et_2O$/hexanes. (0.064 g E; 0.006 g Z methyl ester)
$R_f$=0.60 (2:3 $Et_2O$:hexanes 0.5% AcOH)
mp=156-160° C.
$^1$H NMR ($CDCl_3$): δ 0.97 (t, 3H, J=7.5 Hz); 1.58 (m, 2H); 2.46 (m, 2H); 6.94 (d, 1H, J=1.2 Hz); 7.77 (m, 3H); 8.12 (m, 2H)

(E)-3-(3-methyl-1,4-naphthoquinon-2-yl)-2-methylpropenoic acid (35a)

Compound 35a was prepared from 99a (0.083 g, 0.29 mmol) as described above for 30a to give 0.048 g (0.19 mmol, 65%) of the product as a yellow solid following flash chromatography (3:17 acetone:hexanes 0.5% AcOH) and recrystallization from $Et_2O$/hexanes.
$R_f$=0.30 (2:3 $Et_2O$:hexanes)
mp=195-196° C.
elemental analysis: calculated C, (70.31%); H, (4.72%); found C, (69.93%); H, (4.79%)
$^1$H NMR ($CDCl_3$): δ 1.81 (bs, 3H, J=1.2 Hz); 2.11 (bs, 3H, J=1.2 Hz); 7.58 (m, 1H, J=1.2, 1.2 Hz); 7.73 (m, 2H); 8.09 (m, 2H)

(E)-3-(3-methyl-1,4-naphthoquinon-2-yl)-2-butylpropenoic acid (35b)

Compound 35b was prepared from 99b (0.148 g, 0.45 mmol) as described above for 30a to give 0.050 g (0.17 mmol, 37%) of the product as a yellow solid following flash chromatography (2:3 $Et_2O$:hexanes 0.5% AcOH) and recrystallization from $Et_2O$/hexanes.
$R_f$=0.47 (2:3 $Et_2O$:hexanes 0.5% AcOH)
mp=119-121° C.
$^1$H NMR ($CDCl_3$): δ 0.78 (t, 3H, J=7.2 Hz); 1.20 (m, 2H); 1.41 (m, 2H); 2.12 (d, 3H, J=1.5 Hz); 2.16 (m, 2H); 7.46 (d, 1H, J=1.5 Hz); 7.73 (m, 2H); 8.10 (m, 2H)

(E)-3-(3-methyl-1,4-naphthoquinon-2-yl)-2-nonylpropenoic acid (35c)

Compound 35c was prepared from 99c (0.152 g, 0.381 mmol) as described above for 30a to give 0.050 g (0.14 mmol, 36%) of the product as a yellow solid following flash chromatography (2:3 $Et_2O$:hexanes 0.5% AcOH) and recrystallization from $Et_2O$/hexanes.
$R_f$=0.60 (2:3 $Et_2O$:hexanes 0.5% AcOH)
mp=64-66° C.
$^1$H NMR ($CDCl_3$): δ 0.81 (t, 3H, J=6.9 Hz); 1.18 (m, 15H); 1.42 (m, 2H); 2.12 (d, 3H, J=1.5 Hz); 2.14 (m, 2H); 7.46 (d, 1H, J=1.5 Hz); 7.73 (m, 2H); 8.10 (m, 2H)

(E)-3-(3-methoxy-1,4-naphthoquinon-2-yl)-2-methylpropenoic acid (55)

Compound 58 was prepared from 99g (0.060 g, 0.20 mmol) as described above for 30a to give 0.015 g (0.05 mmol, 27%) of the product as a yellow solid following flash chromatography (2:3 $Et_2O$:hexanes 0.5% AcOH) and recrystallization from $Et_2O$/hexanes.
$R_f$=0.43 (2:3 $Et_2O$:hexanes 0.5% AcOH)
mp=205° C. d
$^1$H NMR ($CDCl_3$): δ 1.83 (d, 31-1, J=1.5 Hz); 4.15 (s, 3H); 7.53 (d, 1H, J=1.5 Hz); 7.73 (m (5), 2H); 8.08 (m, 2H)

(E)-3-(3-methylsulfanyl-1,4-naphthoquinon-2-yl)-2-methylpropenoic acid (58)

Compound 55 was prepared from 99h (0.180 g, 0.565 mmol) as described above for 30a to give 0.063 g (0.22 mmol, 38%) of the product as a red fluffy solid following flash chromatography (2:3 Et$_2$O:hexanes 0.5% AcOH) and recrystallization from Et$_2$O/hexanes.

R$_f$=0.45 (2:3 Et$_2$O:hexanes 0.5% AcOH)

mp=195-196° C.

$^1$H NMR (CDCl$_3$): δ 1.81 (d, 3H, J=1.2 Hz); 2.58 (s, 3H); 7.56 (d, 1H, J=1.2 Hz); 7.72 (m, 2H); 8.09 (m, 2H)

(E)-3-(3-methyl-1,4-naphthoquinon-2-yl)-2-methoxyethylpropenoic acid (62a)

Compound 62a was prepared from 61a (0.076 g, 0.23 mmol) as described above for 30a to give 0.049 g (0.16 mmol, 70%) of the product as a yellow solid following flash chromatography (2:3 Et$_2$O:hexanes 0.5% AcOH) and recrystallization from Et$_2$O/hexanes.

R$_f$=0.45 (2:3 Et$_2$O:hexanes 0.5% AcOH)

mp=147-148° C.

elemental analysis: calculated C, (67.99%); H, (5.37%); found C, (68.10%); H, (5.51%)

$^1$H NMR (CDCl$_3$): δ 2.12 (d, 3H, J=1.2 Hz); 2.45 (t, 2H, J=6.6 Hz); 3.20 (s, 3H); 3.44 (t, 2H, J=6.6 Hz); 7.53 (d, 1H, J=1.2 Hz); 7.73 (m, 2H); 8.09 (m, 2H)

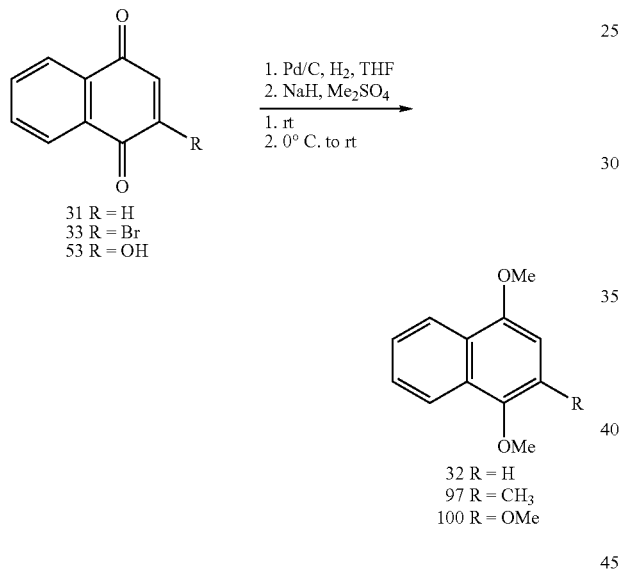

1,4-dimethoxynaphthalene (32)

Following the procedure of Evans et al.,[23] 1,4-naphthoquinone (31, 10.00 g, 63.20 mmol) and Pd/C (10 wt %, 0.994 g) were added to a flame-dried 500 mL round bottom flask at room temperature under Argon. THF (250.0 mL) was then added at room temperature, the reaction vessel was covered in foil, and then purged with H$_2$ for 10 minutes. A balloon filled with H$_2$ was attached and the reaction stirred for 4 hrs at room temperature. The reaction was then purged with Argon before adding NaH (5.66 g, 142 mmol) slowly at 0° C. After 10 minutes Me$_2$SO$_4$ (13.0 mL, 137 mmol) was added slowly at 0° C. The reaction became too thick to stir after adding Me$_2$SO$_4$, and 50 mL of THF were added to facilitate stirring. The dark green mixture was allowed to stir at room temperature for 4 hrs. The reaction was then filtered through celite, washed with brine, dried over MgSO$_4$, and condensed. The resulting solid was then purified by flash chromatography (EtOAc:hexanes) or recrystallized from Et$_2$O:hexanes to provide 32 (11.74 g, 62.42 mmol, 99%) as pink needles.

R$_f$=0.76 (CH$_2$Cl$_2$)

mp=74-78° C. (Lit. 84-86° C.)[23]

$^1$H NMR (CDCl$_3$): δ 3.95 (s, 6H); 6.69 (s, 2H), 7.50 (m, 2H); 8.20 (m, 2H)

1,4-dimethoxy-2-methylnaphthalene (97)

Compound 97 was prepared from 33 (3.54 g, 20.6 mmol) as described above for 32 to give 4.02 g (19.9 mmol, 97%) of the product as a low melting white solid following flash chromatography (1:19 EtOAc:hexanes).

R$_f$=0.60 (3:7 EtOAc:hexanes)

mp=29-31° C. (Literature 35.9-36.3)[24]

$^1$H NMR (CDCl$_3$): δ 2.43 (s, 3H); 3.85 (s, 3H); 3.95 (s, 3H); 7.45 (dt, 2H, J=7.2, 27.3 Hz); 8.09 (dd, 2H, J=8.4, 50.1 Hz)

1,2,4-trimethoxynaphthalene (100)

Compound 100 was prepared from 53 (5.23 g, 33.3 mmol) as described above for 32 to give 5.19 g (23.8 mmol, 71%) of the product as a red oil that solidified in the freezer.

R$_f$=0.17 (1:9 EtOAc:hexanes); 0.50 (CH$_2$Cl$_2$)

Mp=oil (Lit. 38-40° C.)[38]

$^1$H NMR (CDCl$_3$): δ 3.91 (s, 3H); 3.98 (s, 3H); 3.99 (s, 3H); 6.63 (s, 1H); 7.40 (m, 2H); 8.09 (dd, 2H, J=8.4, 30.9 Hz)

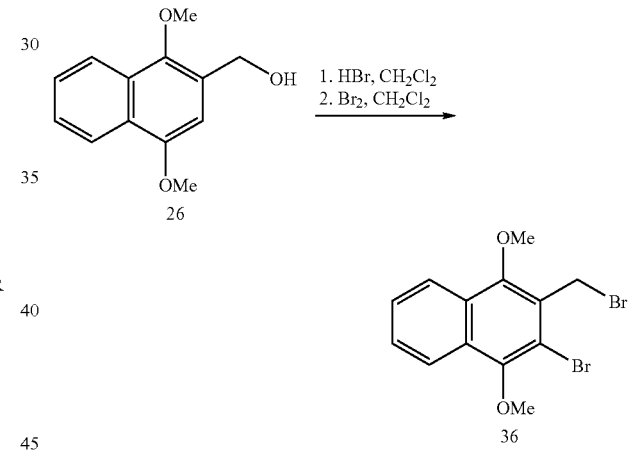

2-bromo-3-bromomethyl-1,4-dimethoxynaphthalene (36)

Alcohol 26 (9.80 g, 45.0 mmol) was dissolved in CH$_2$Cl$_2$ (150.0 mL) in a flame-dried 500 mL round bottom flask. Concentrated HBr (22.0 mL) was added to displace the alcohol, the solution was stirred for 2 h at room temperature. The reaction was then diluted with CH$_2$Cl$_2$ (300.0 mL) and Br$_2$ (2.40 mL, 47.7 mmol) was added dropwise dissolved in CH$_2$Cl$_2$ (50.0 mL) at room temperature. The reaction was stirred for 6 hours further before being washed with brine, dried over MgSO$_4$, and filtered. The resulting solid was purified using flash column chromatography (1:19 EtOAc:hexanes) to provide 36 (9.02 g, 25.1 mmol, 56%) as a yellow powder.

R$_f$=0.46 (3:17 EtOAc:hexanes)

mp=81-83° C. (Lit. 85° C.)[40]

$^1$H NMR (CDCl$_3$): δ 3.98 (s, 3H); 4.08 (s, 3H); 4.92 (s, 2H); 7.56 (m, 2H); 8.08 (m, 2H)

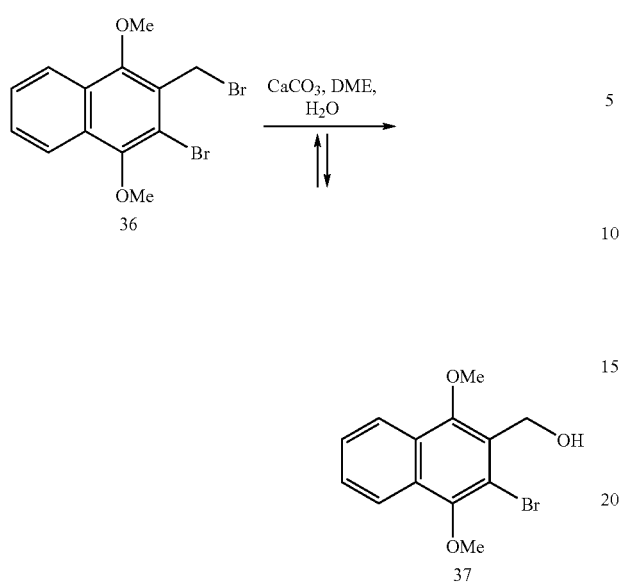

36

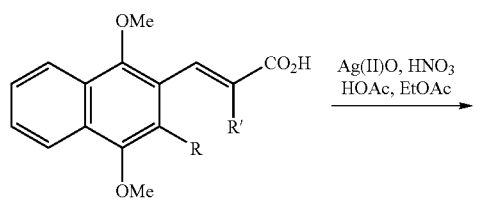

2-bromo-1,4-dimethoxy-3-hydroxymethylnapthalene (37)

Following a modified procedure of Smith et al.,[25] dibromide 36 (1.73 g, 4.80 mmol) was dissolved in 1,2-dimethoxyethane (50.0 mL), and then added to CaCO$_3$ (2.50 g, 25.0 mmol) in H$_2$O (50.0 mL) at room temperature. The reaction was heated under reflux for TIME and then cooled to room temperature. The reaction was extracted with EtOAc (75.0 mL), and the organic layers are washed with brine. The organic layer was dried over MgSO$_4$ and filtered. The resulting pink solid was then purified by flash column chromatography (1:3 EtOAc:hexanes) to provide 37 (1.49 g, 5.01 mmol, 105%) as a pink solid.

R$_f$=0.26 (1:3 EtOAc:hexanes)

mp=93-96° C. (Lit. 116-117° C.)[22]

$^1$H NMR (CDCl$_3$): δ 3.97 (s, 3H); 4.00 (s, 3H); 5.01 (s, 2H); 7.55 (m, 2H); 8.09 (m, 2H)

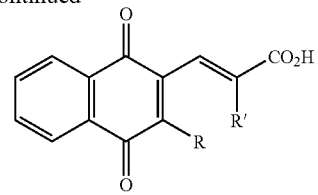

99e(E) R = Br, R' = CH$_3$
99f(E) R = Br, R' = C$_3$H$_7$
99d(E) R = F, R' = CH$_3$
42a(E) R = Cl, R' = CH$_3$
42b(E) R = Cl, R' = C$_3$H$_7$
61c(E) R = Cl, R' = CH$_2$CH$_2$OCH$_3$
61b(E)R = Br, R' = CH$_2$CH$_2$OCH$_3$

-continued

39a(E) R = Br, R' = CH$_3$
39b(E) R = Br, R' = C$_3$H$_7$
52(E) R = F, R' = CH$_3$
43a(E) R = Cl, R' = CH$_3$
43b(E) R = Cl, R' = C$_3$H$_7$
62c(E) R = Cl, R' = CH$_2$CH$_2$OCH$_3$
62b(E)R = Br, R' = CH$_2$CH$_2$OCH$_3$ (E)-3-(3-bromo-1,4-naphthoquinon-2-yl)-2-methyl-propenoic acid (39a)

Following a modified procedure of Shinkawa et al. and Flader et al.,[16,22] the acid 99e (0.291 g, 0.829 mmol) was dissolved in ethyl acetate (10.0 mL) at room temperature, then HNO$_3$ (1.0 mL) and AcOH (6 drops) are added at room temperature. Silver (II) oxide (0.379 g, 3.05 mmol) was then added and the reaction was stirred vigorously at room temperature for 1 hour before being filtered through a pasture pipette and cotton plug, washing the solid with ethyl acetate, and then washing the organic layer with brine. The organic layer was dried over MgSO$_4$, filtered, and condensed. The yellow oil was then purified by either flash column:chromatography (1:1 Et$_2$O:hexanes 0.5% AcOH) or recrystallization from Et$_2$O/hexanes to afford 39a (0.122 g 0.380 mmol, 46%) as a yellow solid.

Alternatively the reaction can be run as a mixture of E and Z isomers under the same conditions. Following workup the mixture will be the E acid and the Z methyl ester from an intramolecular esterification event taking place with the oxonium intermediate. Separation via flash chromatography (1:1 Et$_2$O:hexanes 0.5% AcOH) was necessary to separate the ester and acid components.

R$_f$=0.32 (1:1 Et$_2$O:hexanes 0.5% AcOH)

mp=186-189° C.

elemental analysis: calculated C, (52.36%); H, (2.28%); found C, (52.50%); H, (4.01%)

$^1$H NMR (CDCl$_3$): δ 1.85 (d, 3H, J=1.2 Hz); 7.33 (m, 1H); 7.91 (m, 2H); 8.14 (m, 2H)

(E)-3-(3-bromo-1,4-naphthoquinon-2-yl)-2-propyl-propenoic acid (39b)

Compound 39b was prepared from 99f (0.078 g, 0.21 mmol) as described above for 39a to give 0.033 g (0.10 mmol, 46%) of the product as a yellow solid following flash chromatography (3:7 acetone:hexanes 0.5% AcOH) and recrystallization from Et$_2$O/hexanes.

R$_f$=0.22 (3:7 acetone:hexanes 0.5% AcOH)

mp=145° C. d $^1$H NMR (CDCl$_3$): δ 0.81 (t, 3H, J=7.2 Hz); 1.48 (m, 2H); 2.18 (dd, 1H, J=7.5, 9.3 Hz); 7.29 (s, 1H); 7.79 (m, 2H); 8.13 (m, 1H); 8.20 (m, 1H)

(E)-3-(3-chloro-1,4-naphthoquinon-2-yl)-2-methyl-propenoic acid (43a)

Compound 43a was prepared from 42a (0.872 g, 2.84 mmol) as described above for 39a to give 0.121 g (0.437 mmol, 16%) of the product as a yellow solid following flash chromatography (2:3 acetone:hexanes 0.5% AcOH) and recrystallization from Et$_2$O/hexanes. (0.121 g E; 0.115 g Z methyl ester)

R$_f$=0.44 (2:3 acetone:hexanes 0.5% AcOH)

mp=229-230° C.

elemental analysis: calculated C, (60.78%); H, (3.28%); found C, (60.48%); H, (3.40%)

$^1$H NMR (CDCl$_3$): δ 1.87 (d, 3H, J=1.5 Hz); 7.45 (d, 1H, J=1.5 Hz); 7.79 (m, 2H); 8.13 (m, 1H); 8.19 (m, 1H)

(E)-3-(3-chloro-1,4-naphthoquinon-2-yl)-2-propyl-propenoic acid (43b)

Compound 43b was prepared from 42b (0.053 g, 0.16 mmol) as described above for 39a to give 0.016 g (0.05 mmol, 33%) of the product as a yellow solid following flash chromatography (2:3 acetone:hexanes 0.5% AcOH) and recrystallization from Et$_2$O/hexanes.

R$_f$=0.47 (2:3 acetone:hexanes 0.5% AcOH)

mp=164° C. d $^1$H NMR (CDCl$_3$): δ 0.81 (t, 3H, J=7.5 Hz); 1.50 (m, 2H); 2.19 (t, 2H, J=7.5 Hz); 7.36 (s, 1H); 7.79 (m, 2H); 8.14 (m, 1H); 8.20 (m, 1H)

(E)-3-(3-fluoro-1,4-naphthoquinon-2-yl)-2-methyl-propenoic acid (52)

Compound 52 was prepared from 99d (0.097 g, 0.33 mmol) as described above for 39a to give 0.020 g (0.08 mmol, 23%) of the product as a yellow solid following flash chromatography (3:17 acetone:hexanes 0.5% AcOH) and recrystallization from Et$_2$O/hexanes. (0.020 g E; 0.015 g E starting material; 0.023 g Z methyl ester)

R$_f$=0.08 (1:4 EtOAc:hexanes 0.5% AcOH)

mp=185-190° C. d $^1$H NMR (CDCl$_3$): δ 1.94 (d, 3H, J=3.9 Hz); 7.45 (s, 1H); 7.80 (m, 2H); 8.15 (m, 2H)

$^1$H NMR (DMSO): δ 1.83 (d, 3H, J=3.9 Hz); 7.15 (s, 1H); 7.91 (m, 2H); 8.06 (m, 2H)

$^{19}$F NMR (CDCl$_3$): δ-109.67 (s, 1F)

(E)-3-(3-bromo-1,4-naphthoquinon-2-yl)-2-methoxyethylpropenoic acid (62b)

Compound 62b was prepared from 61b (0.060 g, 0.15 mmol) as described above for 39a to give 0.029 g (0.08 mmol, 53%) of the product as a yellow solid following flash chromatography (2:3 acetone:hexanes 0.5% AcOH) and recrystallization from Et$_2$O/hexanes.

R$_f$=0.45 (2:3 acetone:hexanes 0.5% AcOH)

mp=168-172° C.

elemental analysis: calculated C, (52.62%); H, (3.59%); found C, (53.57%); H, (3.59%)

$^1$H NMR (CDCl$_3$): δ 2.52 (t, 2H, J=6.6 Hz); 3.18 (s, 3H); 3.46 (t, 2H, J=6.6 Hz); 7.41 (s, 1H); 7.78 (m, 2H); 8.12 (m, 1H); 8.19 (m, 1H)

(E)-3-(3-chloro-1,4-naphthoquinon-2-yl)-2-methoxyethylpropenoic acid (62c)

Compound 62c was prepared from 61c (0.067 g, 0.19 mmol) as described above for 39a to give 0.032 g (0.10 mmol, 53%) of the product as a yellow solid following flash chromatography (2:3 acetone:hexanes 0.5% AcOH) and recrystallization from Et$_2$O/hexanes.

R$_f$=0.48 (2:3 acetone:hexanes 0.5% AcOH)

mp=160° C. d $^1$H NMR (CDCl$_3$): δ 2.52 (t, 2H, J=6.3 Hz); 3.17 (s, 3H); 3.45 (t, 2H, J=6.3 Hz); 7.47 (s, 1H); 7.78 (m, 2H); 8.12 (m, 1H); 8.18 (m, 1H)

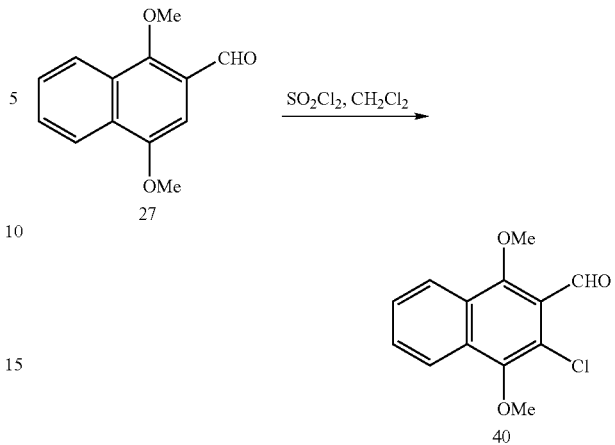

3-Chloro-1,4-dimethoxy-2-naphthaledehyde (40)

Following a general aromatic chlorination procedure by Lopez-Alvarado[39], aldehyde 27 (2.12 g, 9.81 mmol) was dissolved in CH$_2$Cl$_2$ (15.0 mL) at room temperature in a flame-dried 50 mL round bottom flask under argon and a drying tube. Neat SO$_2$Cl$_2$ (0.92 mL, 11 mmol) was added at room temperature and the Argon line was removed. After 20 h the reaction was complete by NMR, and the reaction was diluted with CH$_2$Cl$_2$ (50.0 mL), washed with brine, dried over MgSO$_4$, and filtered. The resulting solid was purified by flash chromatography (1:1 CH$_2$Cl$_2$:hexanes) to provide 40 (1.63 g, 6.52 mmol, 66%) as white needles.

R$_f$=0.21 (1:1 CH$_2$Cl$_2$:hexanes)

mp=94-96° C.

$^1$H NMR (CDCl$_3$): δ 3.99 (s, 3H); 4.05 (s, 3H); 7.64 (m, 2H); 8.17 (dd, 2H, J=8.4, 33 Hz); 10.61 (s, 1H)

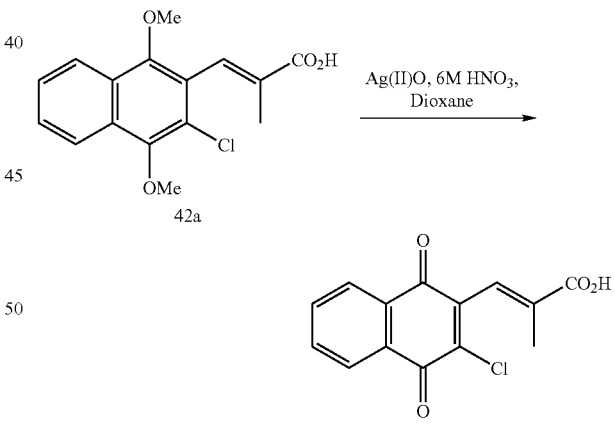

(E)-3-(3-chloro-1,4-naphthoquinon-2-yl)-2-methyl-propenoic acid (43a)

Following a modified procedure by Snyder et al.,[33] dimethoxynaphthalene 42a (0.146 g, 0.476 mmol) and Ag(II)O (0.434 g, 3.51 mmol) were combined in a 5 mL round bottom flask and suspended in dioxane (1.5 mL). To the black suspension was added 6 M HNO$_3$ (1.0 mL, 6.0 mmol) at room temperature. The black Ag(II)O quickly dissolved with gas evolution resulting in a yellow solute with yellow precipitate. The reaction was stirred for 10 minutes at room temperature and TLC showed no starting material present. The suspension was first filtered and the filter cake was suspended in CH$_2$Cl$_2$, treated with water, separated, washed with brine, dried, filtered, and condensed. The yellow reaction filtrate was likewise diluted with CH$_2$Cl$_2$, treated with water, separated, washed with brine, dried over MgSO$_4$, filtered, and condensed. The filter cake provided pure 43a that was then purified by recrystallization from acetone/hexane (0.0601 g, 0.22 mmol, 47%). The filtrate provided a less pure 43a that was first purified by flash chromatography (1:4 EtOAc:hexanes 0.5% AcOH) and then recrystallized from acetone/hexane (0.027 g, 0.099 mmol, 21%).

$R_f$=0.44 (2:3 acetone:hexanes 0.5% AcOH)

mp=229-230° C.

$^1$H NMR (CDCl$_3$): δ 1.87 (d, 3H, J=1.5 Hz); 7.45 (d, 1H, J=1.5 Hz); 7.79 (m, 2H); 8.13 (m, 1H); 8.19 (m, 1H)

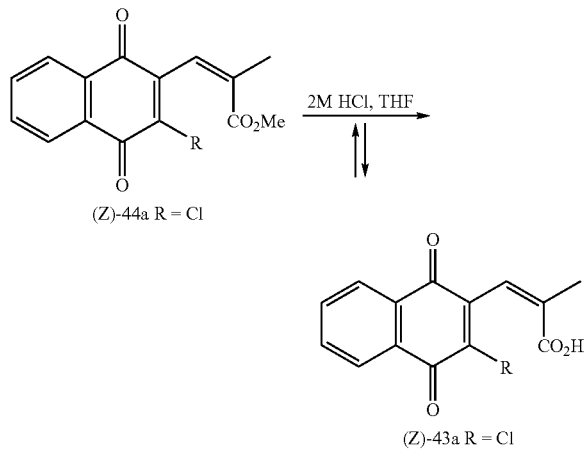

(2Z)-3-(3-chloro-1,4-naphthoquinon-2-yl)-2-methylpropenoic acid ((Z)-43a):

Methyl ester 44a (0.100 g, 0.344 mmol) was suspended in EtOH (3.0 mL), then 2 M HCl (10.0 mL) was added and the reaction was heated under reflux for 24 h. After TLC suggested all starting material was consumed the reaction was cooled to room temperature, diluted with brine, and extracted twice with CH$_2$Cl$_2$. The organic fractions were washed with brine, dried over MgSO$_4$, filtered and condensed. The resulting acid was then separated from remaining starting material via flash column chromatography (1:9 EtOAc:hexanes 0 to 0.5% AcOH) to provide (Z)-43a (0.046 g, 0.16 mmol, 49%) as a fluffy yellow solid that was recrystallized from acetone:hexanes.

$R_f$=0.20 (1:3 EtOAc:hexanes 0.5% AcOH)

mp=166-169° C.

$^1$H NMR (CDCl$_3$): δ 2.19 (d, 3H, J=1.5 Hz); 6.58 (d, 1H, J=1.5 Hz); 7.73 (m, 2H); 8.06 (m, 1H); 8.14 (m, 1H)

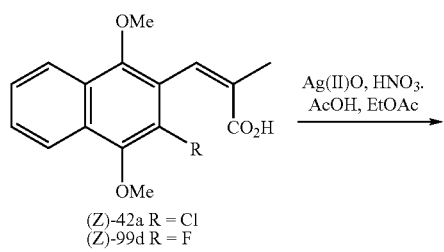

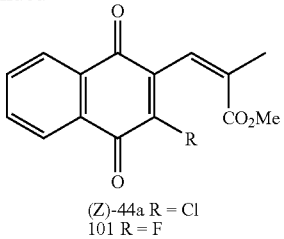

Methyl (2Z)-3-(3-chloro-1,4-naphthoquinon-2-yl)-2-methylpropenoate ((Z)-44a)

Following a modified procedure of Shinkawa et al. and Flader et al.,[16,22] the acid (Z)-42a (0.872 g, 2.84 mmol) was dissolved in ethyl acetate (10 mL) at room temperature, then HNO$_3$ (1.0 mL) and AcOH (6 drops) are added at room temperature. Silver (II) oxide (2.63 g, 21.2 mmol) was then added in portions and the reaction was stirred vigorously at room temperature for 1 hour before being filtered through a pipette plugged with cotton, diluted with ethyl acetate, and washed with brine. The organic layer was dried over MgSO$_4$, filtered, and condensed. The yellow oil was then purified by either flash column chromatography (3:17 acetone:hexanes 0.5% AcOH) or recrystallization from Et$_2$O/hexanes to afford (Z)-44a (0.115 g, 0.396 mmol, 14%) as a dark gold solid. (0.115 g Z methyl ester; 0.121 g E acid)

Alternatively the reaction can be run as a mixture of E and Z isomers under the same conditions. Following workup the mixture will be the E acid and the Z methyl ester from an intramolecular esterification event taking place with the oxonium intermediate. Separation via flash chromatography (3:17 acetone:hexanes 0.5% AcOH) was necessary to separate the ester and acid components.

$R_f$=0.24 (3:17 acetone:hexanes 0.5% AcOH)

mp=227° C. d $^1$H NMR (CDCl$_3$): δ 2.21 (d, 3H, J=1.5 Hz); 3.06 (s, 3H); 7.43 (d, 1H, J=1.5 Hz); 7.58 (dt, 1H, J=7.5, 0.6 Hz); 7.77 (dt, 1H, J=7.5, 1.5 Hz); 7.95 (d, 1H, J=7.8 Hz); 8.15 (d, 1H, J=7.5 Hz)

Methyl (2Z)-3-(3-fluoro-1,4-naphthoquinon-2-yl)-2-methylpropenoate (101)

Compound 101 was prepared from (Z)-99d (0.097 g, 0.33 mmol) as described above for (Z)-43a using silver (II) oxide (0.309 g, 2.49 mmol) to give 0.023 g (0.082 mmol, 25%) of the product as a dark gold solid following flash:chromatography (3:17 acetone:hexanes 0.5% AcOH) and recrystallization from Et$_2$O/hexanes. (0.0225 g Z; 0.0201 g E acid; 0.0151 g E starting material)

$R_f$=0.32 (1:4 EtOAc:hexanes 0.5% AcOH)

mp=118-120° C.

$^1$H NMR (CDCl$_3$): δ 2.18 (s, 3H); 3.07 (s, 3H); 7.32 (s, 1H); 7.60 (dt, 1H, J=7.8, 1.5 Hz); 7.73 (dt, 1H, J=7.8, 1.5 Hz); 7.94 (dd, 1H, J=7.8, 1.5 Hz); 8.14 (dd, 1H, J=7.8, 1.5 Hz)

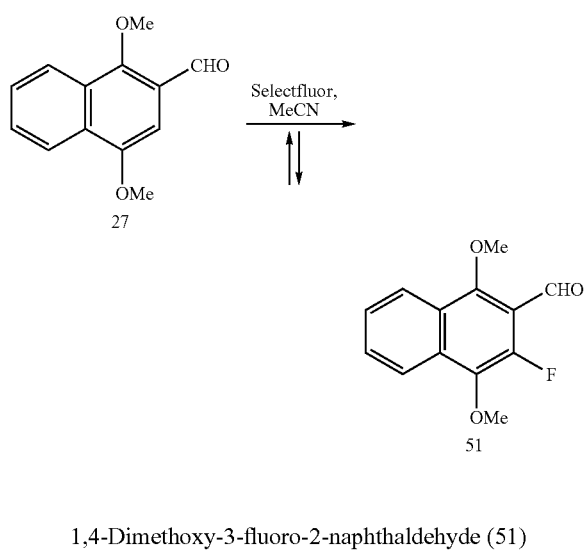

27

1,4-Dimethoxy-3-fluoro-2-naphthaldehyde (51)

Aldehyde 27 (0.517 g, 2.39 mmol) was added to a flame-dried 50 mL round bottom flask under Argon, followed by Selectfluor (1.25 g, 3.37 mmol) and MeCN (20.0 mL). The reaction was then heated to reflux for 8 hours before being cooled and extracted with EtOAc. The organic layer was washed 3 times with brine, dried over $MgSO_4$, filtered, and condensed to provide the crude aldehyde as a yellow solid. Following flash chromatography (3:1 $CH_2Cl_2$:hexanes) aldehyde 51 (0.254 g, 1.08 mmol, 45%) was obtained as a yellow solid.

$R_f$=0.36 (3:1 $CH_2Cl_2$:hexanes)
mp=69-71° C.
$^1$H NMR (CDCl$_3$): δ 4.07 (s, 3H); 4.09 (d, 3H, J=1.5 Hz); 7.54 (t, 1H, J=7.8 Hz); 7.66 (t, 1H, J=7.8 Hz); 8.18 (m, 2H); 10.54 (s, 1H)
$^{19}$F NMR (CDCl$_3$): δ-146.26 (s, 1F)

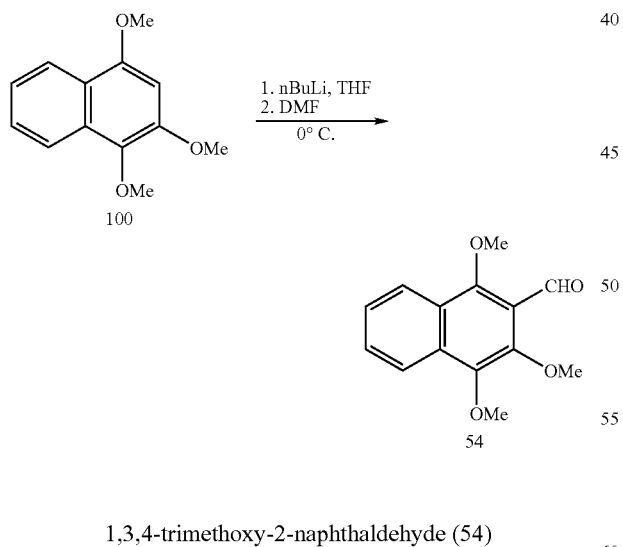

1,3,4-trimethoxy-2-naphthaldehyde (54)

According to the procedure by Syper et al.,[38] 100 (1.07 g, 4.90 mmol) was dissolved in THF (20.0 mL) at 0° C. under Argon, and then nBuLi (1.6 M in hexanes, 4.0 mL, 10.0 mmol) was added at 0° C. The reaction was stirred at 0° C. for 5 hours before DMF (0.850 mL, 11.0 mmol) was added at 0° C. The reaction was stirred for another 30 minutes at room temperature before quenching with water. The reaction was diluted with ethyl ether and washed with saturated brine. The organic layer was dried over $MgSO_4$, filtered, and condensed. Crude product was used as a 5:1 mixture of product:starting material, affording 54 (1.07 g, 4.35 mmol, 89%) as a yellow oil. Following purification via column chromatography ($CH_2Cl_2$ to 1:9 EtOAc:$CH_2Cl_2$) pure aldehyde 54 was obtained as a yellow solid.

$R_f$=0.25 (1:9 EtOAc:hexanes); 0.20 ($CH_2Cl_2$)
mp=43-45° C. (Lit. 53° C. d)[38]
$^1$H NMR (CDCl$_3$): δ 3.99 (s, 3H); 4.00 (s, 3H); 4.03 (s, 3H); 7.55 (m, 2H); 8.15 (dd, 2H, J=8.4, 21 Hz); 10.57 (s, 1H)

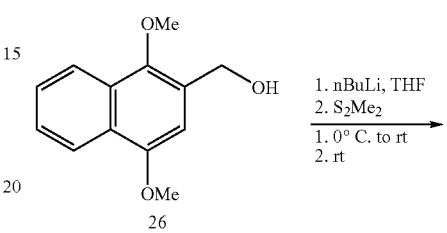

26

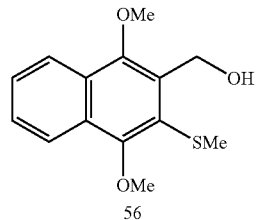

56

1,4-dimethoxy-2-hydroxymethyl-3-methylsulfanyl-naphthalene (56)

Following the procedure of Flader et al.,[22] alcohol 26 (0.521 g, 2.39 mmol) was dissolved in THF (9.0 ml) in a flame-dried 25 mL round bottom flask under Argon, and then cooled to 0° C. At 0° C. nBuLi (2.5 M in hexanes, 2.4 ml, 6.0 mmol) was added slowly, then the ice bath was removed and the reaction was stirred at room temperature for 1 hour. Dimethyldisulfide (0.50 mL, 5.6 mmol) was added slowly at room temperature and the reaction was stirred for another 30 minutes at room temperature before being poured into water, acidified with 2 M HCl, and extracted with ethyl acetate. The organic fractions were combined and washed with brine, dried over $MgSO_4$, and filtered. The resulting solid was purified via flash column chromatography (1:4 EtOAc:hexanes) to afford 56 (0.446 g, 1.69 mmol, 71%) as a green solid.

$R_f$=0.48 (7:13 EtOAc:hexanes)
mp=60-62° C. (Lit. Oil)[22]
$^1$H NMR (CDCl$_3$): δ 2.51 (s, 3H); 3.97 (s, 3H); 4.01 (s, 3H); 5.05 (s, 2H); 7.53 (m, 2H); 8.09 (m, 2H)

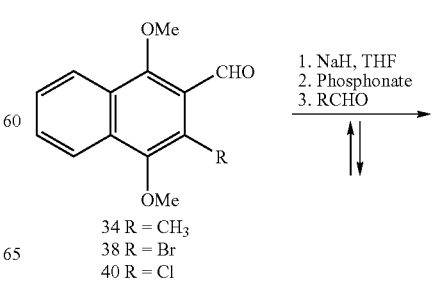

34 R = CH$_3$
38 R = Br
40 R = Cl

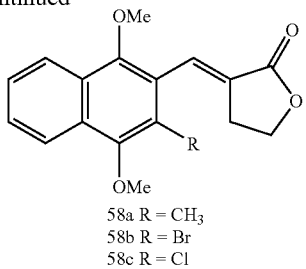

58a R = CH₃
58b R = Br
58c R = Cl

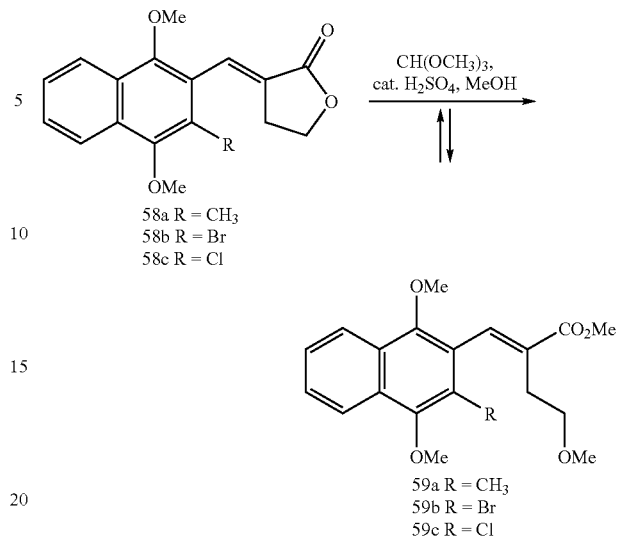

58a R = CH₃
58b R = Br
58c R = Cl

59a R = CH₃
59b R = Br
59c R = Cl

(E)-4'-(1,4-dimethoxy-2-methylnaphthalen-2-yl)-3-ethylidenetetrahydrofuran-2-one (58a)

According to the modified procedure of Murphy et al.,[26] NaH (0.269 g, 6.72 mmol) was added to a flame-dried 100 mL 3-neck round bottom flask connected to a water-jacketed reflux condenser. The flask was purged with Argon and a drying tube was attached to the top. Toluene (10.0 mL) was added to the flask followed by phosphonate (1.54 g, 6.95 mmol) dissolved in toluene (10.0 mL) at room temperature. The reaction was heated under reflux for 30 minutes, and the aldehyde (34, 0.486 g, 2.11 mmol) was dissolved in toluene (10.0 mL) and added slowly at reflux. The reaction was heated for another 8 h under reflux before being cooled to room temperature, diluted with ethyl acetate, and washed with brine. The organic layer was dried, filtered, and condensed. The resulting oil was purified via flash column chromatography (1:4 EtOAc:hexanes) and recrystallized from Et₂O/hexanes to provide 58a (0.674 g, 2.26 mmol, 107%) as a white solid.

$R_f$=0.32 (1:3 EtOAc:hexanes)
E:Z=100:0 in refluxing toluene
mp=105-107° C.
¹H NMR (CDCl₃): δ 2.37 (s, 3H); 2.92 (dt, 2H, J=7.2, 3 Hz); 3.70 (s, 3H); 3.87 (s, 3H); 4.40 (t, 2H, J=7.2 Hz); 7.52 (m, 2H); 7.69 (t, 1H, J=3 Hz); 8.09 (m, 2H)

(E)-4'-(3-bromo-1,4-dimethoxynaphthalen-2-yl)-3-ethylidenetetrahydrofuran-2-one (58b)

Compound 58b was prepared from 38 (0.588 g, 1.99 mmol) as described above for 58a to give 0.307 g (0.845 mmol, 42%) of the product as a colorless oil following flash chromatography (3:17 EtOAc:hexanes) and recrystallization from Et₂O/hexanes.

$R_f$=0.09 (1:9 EtOAc:hexanes)
E:Z=3:1 in refluxing toluene
¹H NMR (CDCl₃): δ 2.92 (dt, 2H, J=3, 7.2 Hz); 3.73 (s, 3H); 3.98 (s, 3H); 4.41 (t, 2H, J=7.2 Hz); 7.59 (m, 2H); 7.74 (t, 1H, J=3 Hz); 8.12 (m, 2H)

(E)-4'-(3-chloro-1,4-dimethoxynaphthalen-2-yl)-3-ethylidenetetrahydrofuran-2-one (58c)

Compound 58c was prepared from 40 (0.484 g, 1.94 mmol) as described above for 58a to give 0.311 g (0.974 mmol, 51%) of the product as a colorless oil following flash chromatography (1:9 EtOAc:hexanes). (0.137 g E; 0.174 g E/Z)

$R_f$-E=0.13; Z=0.07 (3:37 EtOAc:hexanes, developed 4×)
E:Z=9:1 in refluxing toluene.
¹H NMR (CDCl₃): δ 2.94 (dt, 2H, J=7.2, 3 Hz); 3.73 (s, 3H); 3.99 (s, 3H); 4.41 (t, 2H, J=7.2 Hz); 7.58 (m, 2H); 7.77 (t, 1H, 3 Hz); 8.12 (m, 2H)

Methyl (E)-3-(1,4-dimethoxy-3-methylnaphthalen-2-yl)-2-methoxyethylpropenoate (59a)

According to a modified procedure by King et al.,[27] 58a (0.243 g, 0.815 mmol) was added to a flame-dried 10 mL round bottom flask under argon and a water-jacketed reflux condenser was attached. Anhydrous MeOH (3.0 mL) was then added, followed by H₂SO₄ (10 drops) and trimethyl orthoformate (0.65 mL, 8.5 mmol) at room temperature. The reaction was then heated under reflux for 12 hours, cooled to room temperature, and the solvent was removed under reduced pressure. The residue was dissolved in EtOAc, washed with saturated brine, dried over MgSO₄, filtered, and condensed. The resulting crude product was the chromatographed (1:3 EtOAc:hexanes) and recrystallized from Et₂O/hexanes to provide 59a (0.249 g, 0.723 mmol, 59%) as tan crystals.

$R_f$=0.43 (1:3 EtOAc:hexanes)
mp=64-65° C.
¹H NMR (CDCl₃): δ 2.28 (s, 3H); 2.55 (t, 2H, J=7.2 Hz); 3.07 (s, 3H); 3.37 (t, 2H, J=7.2 Hz); 3.75 (s, 3H); 3.85 (s, 3H); 3.86 (s, 3H); 7.48 (m, 2H); 7.71 (s, 3H); 8.07 (m, 2H)

Methyl (E)-3-(3-bromo-1,4-dimethoxynaphthalen-2-yl)-2-methoxyethylpropenoate (59b)

Compound 59b was prepared from 58b (0.257 g, 0.708 mmol) as described above for 59c to give 0.291 g (0.711 mmol, 100%) of the product as tan crystals following flash chromatography (1:3 EtOAc:hexanes) and recrystallization from Et₂O/hexanes.

$R_f$=0.42 (1:3 EtOAc:hexanes)
mp=66-67° C.
¹H NMR (CDCl₃): δ 2.57 (t, 2H, J=7.2 Hz); 3.12 (s, 3H); 3.39 (t, 2H, J=7.2 Hz); 3.77 (s, 3H); 3.86 (s, 3H); 3.97 (s, 3H); 7.42 (m, 2H); 7.65 (s, 1H); 8.10 (m, 2H)

Methyl(E)-3-(3-chloro-1,4-dimethoxynaphthalen-2-yl)-2-methoxyethylpropenoate (59c)

Compound 59c was prepared from 58c (0.098 g, 0.30 mmol) as described above for 59a to give 0.064 g (0.17 mmol, 58%) of the product as tan crystals following flash chromatography (1:3 EtOAc:hexanes) and recrystallization from Et₂O/hexanes.

R$_f$=0.44 (1:3 EtOAc:hexanes)
mp=61-62° C.
$^1$H NMR (CDCl$_3$): δ 2.59 (t, 2H, J=7.2 Hz); 3.12 (s, 3H); 3.39 (t, 2H, J=7.2 Hz); 3.78 (s, 3H); 3.39 (s, 3H); 3.98 (s, 3H); 7.55 (m, 2H); 7.68 (s, 1H); 8.10 (m, 2H)

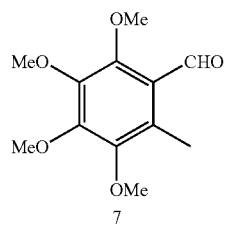

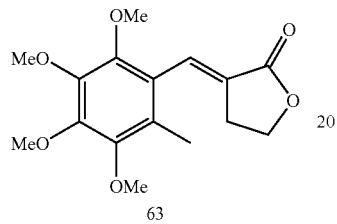

(E)-4'-(6-methyl-2,3,4,5-tetramethoxyphenyl)-3-ethylidenetetrahydrofuran-2-one (63)

According to the modified procedure of Murphy et al.,[26] NaH (0.210 g, 5.25 mmol) was added to a flame-dried 100 mL 3-neck round bottom flask connected to a water-jacketed reflux condenser. The flask was purged with Argon and a drying tube was attached to the top. Toluene (30.0 mL) was added to the flask followed by phosphonate (1.83 g, 8.2 mmol) dissolved in toluene (10.0 mL) at room temperature. The reaction was heated under reflux for 30 minutes, and the aldehyde (7, 0.501 g, 2.09 mmol) was dissolved in toluene (5.0 mL) and added slowly at reflux. The reaction was heated for another 8 h under reflux before being cooled to room temperature, diluted with ethyl acetate, and washed with brine. The organic layer was dried, filtered, and condensed. The resulting oil was purified via flash column:chromatography (1:3 EtOAc:hexanes) to provide 63 (0.429 g, 1.39 mmol, 66%) as a white solid.
R$_f$=0.18 (1:3 EtOAc:hexanes)
E:Z=20:1 in refluxing toluene.
mp=78-79° C.
$^1$H NMR (CDCl$_3$): δ 2.12 (s, 3H); 2.85 (dt, 2H, J=7.2, 3 Hz); 3.65 (s, 3H); 3.78 (s, 3H); 3.90 (s, 3H); 3.93 (s, 3H); 4.35 (t, 2H, J=7.2 Hz); 7.48 (t, 1H, J=3 Hz)

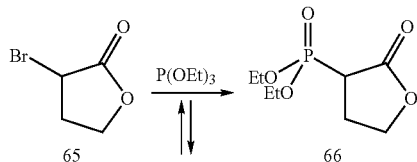

Diethyl 3-phosphonotetrahydrofuran-2-one (66)

Following the procedure by Murphy et al.[26] α-bromo-γ-butyro lactone (65, 3.0 mL, 32.2 mmol) was added to a flame-dried 25 mL round bottom flask followed by triethylphosphite (6.0 mL, 35 mmol). The mixture was refluxed for 4 hours and then ethyl bromide was removed under reduced pressure. The resulting oil was then purified by fractional distillation at reduced pressure to afford 66 (5.16 g, 23.2 mmol, 72%) as a colorless oil.
R$_f$=0.26 (1:1 EtOAc:hexanes)
$^1$H NMR (CDCl$_3$): δ 1.31 (dt, 6H, J=3, 7.2 Hz); 2.54 (m, 2H); 3.02 (ddd, 1H, J=9.3, 6.3, 23.4 Hz); 4.15 (m, 4H); 4.28 (m, 1H); 4.39 (m, 1H)
$^{31}$P NMR (CDCl$_3$): δ 24.90 (s)

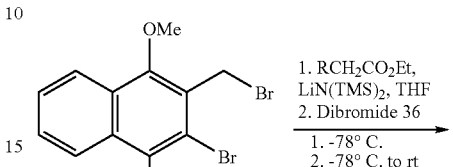

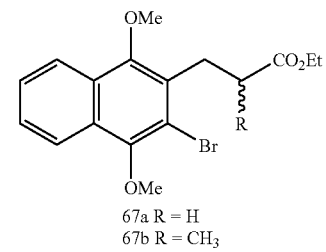

Ethyl 3-(3-bromo-1,4-dimethoxynaphthalen-2-yl)-propionate (67a)

Following a modified procedure of Clegg et al.,[28] lithium hexamethyldisilizade (LiHMDS, 1 M in THF, 1.5 ml, 1.5 mmol) was added to a flame-dried round bottom flask containing THF (20.0 mL) at 78° C. Ethyl acetate (0.15 ml, 1.5 mmol) was then added slowly at 78° C. and stirred at 78° C. for 30 minutes. 36 (0.415 g, 1.15 mmol) was then dissolved in THF (10.0 mL) and added at 78° C., at which point the reaction was allowed to warm to room temperature, and was stirred at room temperature for 4 h. The reaction was monitored by TLC (CH$_2$Cl$_2$) for disappearance of the less polar starting material. More LiHMDS (2.0 mL, 2.0 mmol) and EtOAc (0.70 mL, 0.70 mmol) were added and the reaction was monitored for the disappearance of starting material. When no starting material was present, 10 hours, the reaction was then poured into water, extracted with ethyl acetate, washed with brine, dried over MgSO$_4$, filtered, and condensed. The product was the purified by column chromatography (CH$_2$Cl$_2$ to 1:19 EtOAc:CH$_2$Cl$_2$) to provide 67a (0.361 g, 0.983 mmol, 86%) as a yellow oil.
R$_f$=0.43 (CH$_2$Cl$_2$)
$^1$H NMR (CDCl$_3$): δ 1.26 (t, 3H, J=7.2 Hz); 2.62 (m, 2H); 3.29 (m, 2H); 3.91 (s, 3H); 3.95 (s, 3H); 4.17 (q, 2H, J=7.2 Hz); 7.51 (m, 2H); 8.02 (m, 1H); 8.07 (m, 1H)

Ethyl (2R/S)-3-(3-bromo-1,4-dimethoxynaphthalen-2-yl)-2-methylpropionate (67b)

Compound 67b was prepared from 36 (0.244 g, 0.678 mmol) as described above for 67a to give 0.258 g (0.678 mmol, 100%) of the product as a EtOAc following flash chromatography (1:1 to 3:1 CH$_2$Cl$_2$:hexanes).
R$_f$=0.39 (3:1 CH$_2$Cl$_2$:hexanes)
$^1$H NMR (CDCl$_3$): δ 1.15 (d, 3H, J=7.2 Hz); 1.14 (t, 3H, J=7.2 Hz); 2.92 (m, 1H); 3.12 (dd, 1H, J=8.7, 13.2 Hz); 3.32 (dd, 1H, J=6.3, 13.2 Hz); 3.87 (s, 3H); 3.95 (s, 3H); 4.09 (q, 2H, J=7.2 Hz); 7.51 (m, 2H); 8.02 (m, 1H); 8.07 (m, 1H)

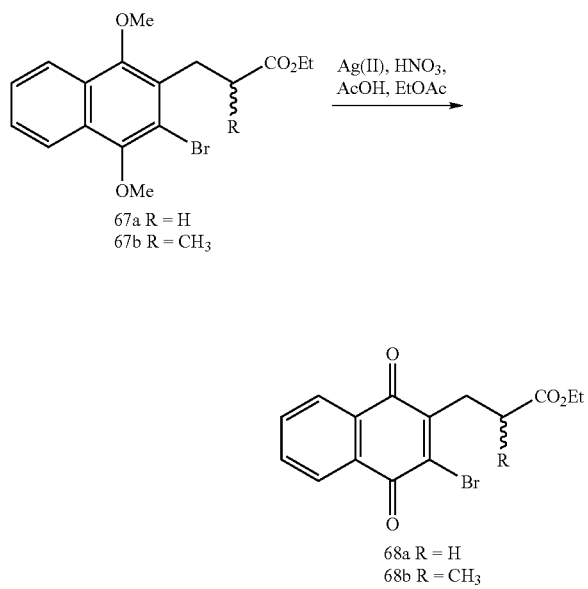

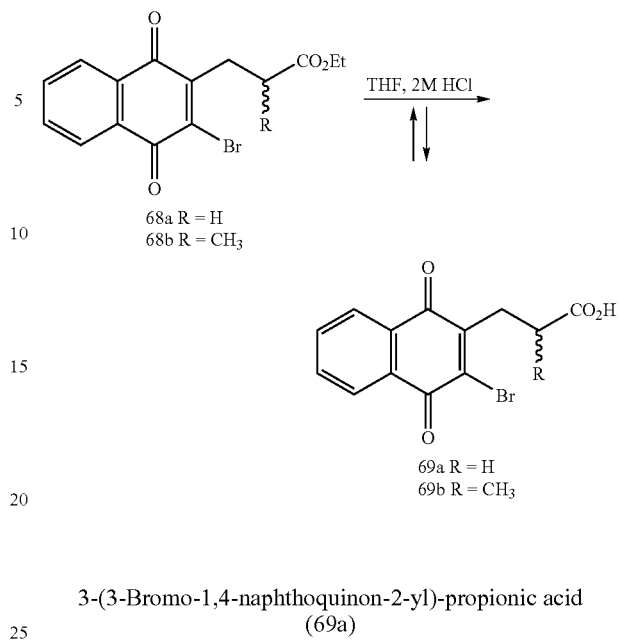

Ethyl (3-bromo-1,4-naphthoquinon-2-yl)-propionate (68a)

Following the general procedures by Shinkawa et al. and Flader et al.,[16,22] 67a (0.361 g, 0.983 mmol) was dissolved in EtOAc (10.0 mL) and then AcOH (6 drops) and HNO$_3$ (1.0 mL) were added at room temperature. Then Ag(II)O (0.473 g, 3.82 mmol) was added in one portion at room temperature and stirred for 30 minutes at room temperature, the reaction was monitored by TLC (1:4 acetone:hexanes). After 30 minutes another addition of Ag(II)O (0.147 g, 1.19 mmol) was required, and the reaction stirred at room temperature for another 30 minutes. TLC showed the reaction to be complete, and the solvent was then separated from the silver solid by passing the reaction through a pipette with cotton plug, the solid was rinsed with EtOAc (4×5.0 mL), and then the solution was diluted with EtOAc (50.0 mL). The solution was then washed 2 times with saturated brine, dried over MgSO$_4$, filtered, and condensed. The crude yellow solid was recrystallized from acetone/hexane to provide 68a (0.135 g, 0.400 mmol, 41%) as a yellow solid.

R$_f$=0.44 (1:4 acetone:hexanes)

mp=78-79° C.

$^1$H NMR (CDCl$_3$): δ 1.23 (t, 3H, J=7.2 Hz); 2.59 (t, 2H, J=7.8 Hz); 3.16 (t, 2H, J=7.8 Hz); 4.12 (q, 2H, J=7.2 Hz); 7.74 (m, 2H); 8.13 (m, 2H)

Ethyl (2R/S)-3-(3-bromo-1,4-naphthoquinon-2-yl)-2-methylpropionate (68b)

Compound 68b was prepared from 67b (0.258 g, 0.678 mmol) as described above for 68a to give 0.064 g (0.18 mmol, 27%) of the product as a yellow solid following flash chromatography (3:1 CH$_2$Cl$_2$:hexane).

R$_f$=0.26 (3:1 CH$_2$Cl$_2$:hexanes)

$^1$H NMR (CDCl$_3$): δ 1.12 (t, 3H, J=7.2 Hz); 1.24 (d, 3H, J=6.9 Hz); 2.94 (m, 2H); 3.23 (dd, 1H, J=12.0, 7.5); 4.05 (m, 2H); 7.74 (m, 2H); 8.10 (m, 1H); 8.15 (m, 1H)

3-(3-Bromo-1,4-naphthoquinon-2-yl)-propionic acid (69a)

Ester 68a (0.108, 0.320 mmol) was dissolved in THF (5.0 mL) at room temperature and then 2 M HCl (4.0 mL) was added at room temperature. The homogeneous solution was then stirred vigorously and heated under reflux for 24 h, or until no starting material was observed by TLC (1:4 EtOAc:hexanes). The reaction was then cooled and diluted with EtOAc (30.0 mL), then washed 2 times with saturated brine, dried over MgSO$_4$, filtered, and condensed. If any starting material ester was still present the resulting yellow oil was first purified via flash column:chromatography (1:4 acetone:hexanes 0 to 0.5% AcOH) followed by recrystallization from Et$_2$O/hexanes to provide 69a (0.077 g, 0.25 mmol, 78%) as fine yellow needles.

R$_f$=0.14 (1:3 EtOAc:hexanes 0.5% AcOH)

Mp=156-157° C.

$^1$H NMR (CDCl$_3$): δ 2.65 (t, 2H, J=7.5 Hz); 3.15 (m, 2H); 7.74 (m, 2H); 8.13 (m, 2H)

(2R/S)-3-(3-bromo-1,4-naphthoquinon-2-yl)-2-methylpropionic acid (69b)

Compound 69b was prepared from racemic 68b (0.027 g, 0.08 mmol) as described above for 69a to give 0.016 g (0.05 mmol, 63%) of the product as a yellow solid following flash chromatography (1:4 acetone:hexanes 0 to 0.5% AcOH) and recrystallization from Et$_2$O/hexanes.

R$_f$=0.10 (1:4 acetone:hexanes 0.5% AcOH)

$^1$H NMR (CDCl$_3$): δ 1.26 (d, 3H, J=6.3 Hz); 3.00 (m, 2H); 3.25 (m, 1H); 7.74 (m, 2H); 8.10 (m, 1H); 8.14 (m, 1H)

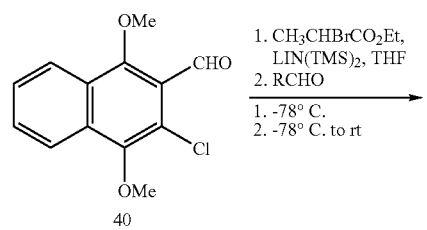

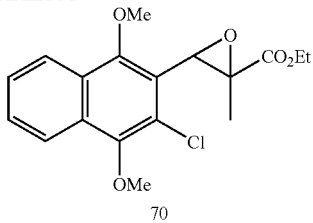

Ethyl 3-(3-chloro-1,4-dimethoxynaphthalen-2-yl)-2-epoxy-2-methylpropionate (70)

Following a modified procedure of Clegg et al.,[28] lithium hexamethyldisilizade (LiHMDS, 1 M in THF, 3.1 ml, 3.1 mmol) was added to a flame-dried round bottom flask containing THF (2.0 mL) at 78° C. Ethyl 2-bromopropionate (0.28 ml, 2.1 mmol) was then added slowly at 78° C. and stirred at −78° C. for 30 minutes. 40 (0.518 g, 2.07 mmol) was then dissolved in THF (1.0 mL) and added at 78° C., at which point the reaction was allowed to warm to room temperature, and was stirred at room temperature for 4 h. The reaction was then poured into water, extracted with ethyl acetate, washed with brine, dried over $MgSO_4$, filtered, and condensed. The product was the purified by column chromatography (1:9 EtOAc:hexanes) to provide a racemic mixture of 4 diastereomers of 70 (0.646 g, 1.84 mmol, 89%) as a yellow oil.

$R_f$=0.12 (1:9 EtOAc:hexanes)

$^1$H NMR (CDCl$_3$): δ

Enanteomer pair 1: 1.27 (t, 3H, J=7.2 Hz); 1.83 (s, 3H); 3.94 (s, 3H); 4.04 (s, 3H); 4.14 (s, 1H); 4.19 (q, 2H, J=7.2 Hz); 7.56 (m, 2H); 8.11 (m, 2H)

Enanteomer pair 2: 1.35 (t, 3H, J=7.2 Hz); 1.93 (s, 3H); 3.98 (s, 3H); 4.00 (s, 3H); 4.32 (q, 2H, J=7.2 Hz); 4.43 (s, 1H); 7.56 (m, 2H); 8.11 (m, 2H)

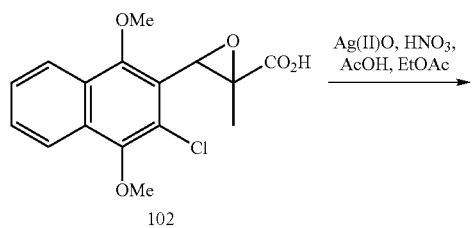

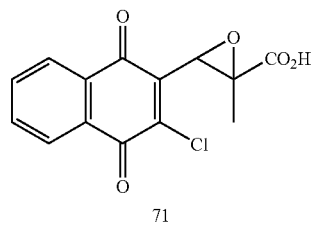

3-(3-chloro-1,4-naphthoquinon-2-yl)-2-epoxy-2-methylpropionic acid (71)

Following a modified procedure of Shinkawa et al. and Flader et al.,[16,22] the racemic acid mixture 102 (0.180 g, 0.558 mmol) was dissolved in ethyl acetate (10.0 mL) at room temperature, then HNO$_3$ (1.0 mL) and AcOH (5 drops) are added at room temperature. Silver (II) oxide (0.883 g, 7.13 mmol) was then added and the reaction was stirred vigorously at room temperature for 1 hour before being filtered through a cotton-plugged pipette, washing the solid with ethyl acetate, and then washing the organic layer with brine. The organic layer was dried over MgSO$_4$, filtered, and condensed. The yellow oil was then purified by either flash column chromatography (1:1 EtOAc:hexanes 0.5% AcOH) or recrystallization from Et$_2$O/hexanes to afford 71 (0.033 g, 0.11 mmol, 20%) as a yellow solid.

Alternatively the reaction can be run as a mixture of E and Z isomers under the same conditions. Separation of the E and Z isomers can be achieved by flash chromatography (<1:1 Et$_2$O:hexanes 0.5% AcOH).

$R_f$=0.14 (1:1 Et$_2$O:hexanes 0.5% AcOH)

$^1$H NMR (CDCl$_3$): δ

Enanteomer Pair 1: 2.15 (s, 3H); 4.28 (s, 1H); 7.80 (m, 2H); 8.12 (m, 1H); 8.18 (m, 1H)

Enanteomer Pair 2: 1.82 (s, 3H); 3.96 (s, 1H); 7.76 (m, 2H); 8.08 (m, 1H); 8.14 (m, 1H)

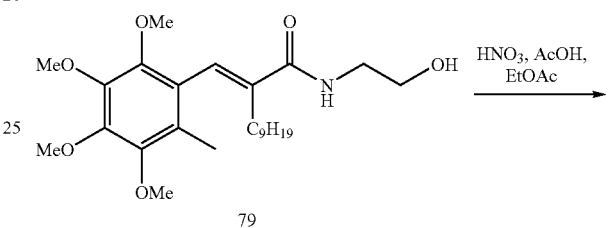

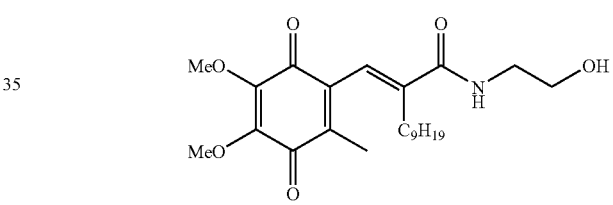

(E)-N-(2-hydroxyethyl)-3-(3,4-dimethoxy-2-methyl-3,6-dioxocyclohexa-1,4-dienyl)-2-nonylpropenamide (72)

Following a modified procedure of Shinkawa et al., 16 amide 79 (0.088 g, 0.20 mmol) was added to a flame-dried round bottom flask and dissolved in EtOAc (7.0 mL). Then AcOH (5 drops) and HNO$_3$ (0.5 mL) were added at rt and the reaction was stirred for 3 hours at room temperature. The colorless oil easily dissolved in EtOAc and the reaction turned orange upon addition of HNO$_3$. The reaction was then diluted with EtOAc (40.0 mL), washed 3 times with brine, dried over MgSO$_4$, filtered, and condensed to provide an orange oil. The oil was then purified using flash chromatography (1:2-1:1 EtOAc:hexanes) and recrystallized from acetone/hexane to provide 72 (0.037 g, 0.09 mmol, 45%) as a red oil.

$R_f$=0.24 (2:3 EtOAc:hexanes)

$^1$H NMR (CDCl$_3$): δ 0.84 (t, 3H, J=6.6 Hz); 1.17 (m, 12H); 1.33 (m, 2H); 1.93 (d, 3H, J=1.2 Hz); 2.09 (t, 2H, J=7.5 Hz); 2.51 (t, 1H, J=5.1 Hz); 3.52 (q, 2H, J=4.8 Hz); 3.79 (dd, 2H, J=4.8 Hz); 3.98 (s, 3H); 4.02 (s, 3H); 6.48 (bs, 1H); 6.53 (s, 1H)

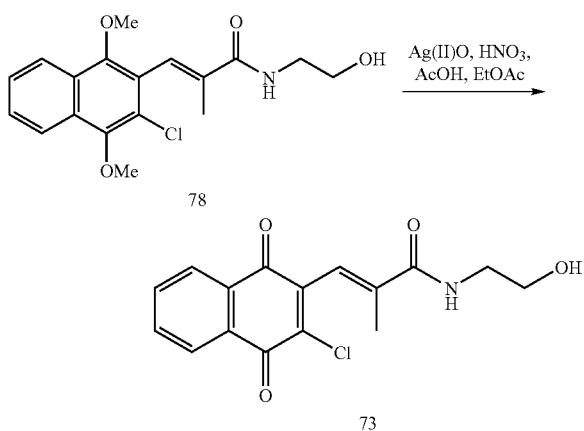

(E)-N-(2-hydroxyethyl)-3-(3-chloro-1,4-dioxonaph-thoquinon-2-yl)-2-methylpropenamide (73)

Following a modified procedure of Shinkawa et al. and Flader et al.,[16,22] amide 78 (0.050 g, 0.14 mmol) was added to a flame-dried round bottom flask and dissolved in EtOAc (15.0 mL). Then AcOH (6 drops) and HNO$_3$ (1.0 mL) were added at rt, followed by Ag(II)O (0.123 g, 0.993 mmol), and the reaction was stirred for 30 minutes at room temperature. The white solid did not dissolve until the addition of HNO$_3$, and the colorless solution immediately became a yellow/green suspension after adding Ag(II)O. The reaction was monitored by TLC (1:1 EtOAc:hexanes), after 30 minutes the reaction was not complete and more Ag(II)O (0.145 g, 1.17 mmol) was added, and the reaction was stirred for an additional 30 minutes at rt. The suspension was then filtered through a pasture pipette with a cotton plug, and the silver solid was rinsed with EtOAc. The filtrate was then diluted with EtOAc, washed 3 times with brine, dried over MgSO$_4$, filtered, and condensed to provide a yellow oil. The oil was then purified using flash chromatography (2:3 EtOAc:hexanes) and recrystallized from acetone/hexane to provide 73 (0.027 g, 0.084 mmol, 60%) as a yellow solid. A mixture of 5.2 mg of starting material and product also coeluted.

R$_f$=0.25 (1:1 acetone:hexanes)
mp=120° C. d
$^1$H NMR (CDCl$_3$): δ 1.87 (s, 3H); 2.51 (bs, 1H, OH); 3.56 (q, 2H, J=5.1 Hz); 3.81 (m, 2H); 6.46 (bs, 1H, NH); 7.03 (s, 1H); 7.77 (m, 2H); 8.10 (m, 1H); 8.17 (m, 1H)

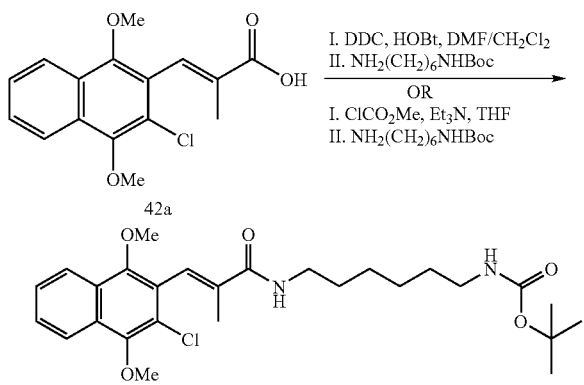

(E)-N—(N'-tert-butoxycarbonyl-6-aminohexyl)-3-(3-chloro-1,4-dimethoxynaphthalen-2-yl)-2-methyl-propenamide (77)

Method A: DCC (0.070 g, 0.34 mmol) was added to a flame dried 10 mL round bottom flask under argon, and then CH$_2$Cl$_2$ (2.0 mL) was added at rt. In a second flame-dried flask under argon a solution of acid 42a (0.050 g, 0.16 mmol) and HOBt (0.006 g, 0.04 mmol) was prepared using DMF (3.0 mL) and CH$_2$Cl$_2$ (1.0 mL) at rt. The acid/HOBt solution was then added to the DCC solution at rt and stirred for 2 h before the amine (0.060 mL, 0.27 mmol) was added quickly at rt. The reaction was stirred for an additional 12 hours before being diluted with EtOAc, washed with brine, dried over MgSO$_4$, filtered, and condensed. The resulting white solid, a combination of dicyclohexylurea, DCC, and product, was first suspended in approximately 5 mL CH$_2$Cl$_2$. The suspension was then filtered through a pipette with cotton plug to remove the insoluble DCU, and the pipette was washed 2 times with 2 mL CH$_2$Cl$_2$. The combined fractions were then purified via flash chromatography (2:3 EtOAc:hexanes) to provide 77 (E: 0.045 g, 0.089 mmol, 55%; Z: 0.020 g, 0.040 mmol, 25%) as a faint yellow oil.

Method B: Using a modified mixed anhydride procedure by Rajesh et al.,[41] starting material (42a, 0.020 g, 0.064 mmol) was dissolved in THF (2.0 ml) at rt in a 10 mL round bottom flask to produce a yellow solution. Triethylamine (0.022 mL, 0.16 mmol) was added at rt and the reaction retained the same appearance, then methyl chloroformate (0.007 mL, 0.09 mmol) was added quickly at rt. The reaction immediately became cloudy and proceeded to change into a cloudy pink suspension within 15 seconds. After stirring for 2 minutes at room temperature N-Boc-1,6-diaminohexane (0.030 mL, 0.13 mmol) was added quickly. The reaction immediately lost the pink color and became an orange suspension. TLC (2:3 EtOAc:hexanes) indicated the reaction was complete in less than 30 minutes, resulting in minimal sideproduct formation. The reaction was then diluted with EtOAc, washed with bring, dried over MgSO$_4$, filtered, and condensed. 0.025 g (0.050 mmol, 78%) of pure E 77 was obtained from chromatography.

Method C: Acid 42a (0.478 g, 0.156 mmol) and PyBOP (0.119 g, 0.229 mmol) were added to a flame-dried 10 mL round bottom flask and purged with Argon. CH$_2$Cl$_2$ (4.0 mL) was then added at room temperature followed by triethylamine (0.060 mL, 0.43 mmol). The clear/colorless solution was stirred at room temperature for 1 hour before N-Boc-1,6-diaminohexane (0.050 mL, 0.22 mmol) was added at room temperature. The faint yellow/clear solution was stirred for an additional 4 hours at room temperature before being diluted with CH$_2$Cl$_2$ (70.0 mL), washed 3 times with dilute (0.25 M) NaOH, one time with brine, dried over MgSO$_4$, filtered, and condensed. The resulting yellow oil was then purified by flash:chromatography (1:4 EtOAc:hexanes) to provide 77 (0.079 g, 0.16 mmol, 100%) as a faint yellow oil that began to solidify in the freezer.

R$_f$=0.50 (2:3 EtOAc:hexanes)
$^1$H NMR (CDCl$_3$): δ 1.42 (s/m, 13H); 1.56 (s/m, 3H); 1.84 (d, 3H, J=1.2 Hz); 3.11 (q, 2H, J=6.0 Hz); 3.39 (q, 2H, J=6.9 Hz); 3.75 (s, 3H); 3.98 (s, 3H); 4.54 (bs, 1H); 6.06 (bs, 1H); 7.36 (s, 1H); 7.54 (m, 2H); 8.11 (m, 2H)
$^{13}$C NMR (CDCl$_3$): δ 15.1, 26.2, 26.3, 28.4, 29.5, 30.0, 34.0, 39.7, 61.4, 61.8, 85.5, 122.2, 122.9, 123.4, 124.8, 126.7, 127.3, 127.5, 127.7, 128.7, 136.0, 148.6, 150.5, 156.1, 168.3

(Z)—N—(N'-tert-butoxycarbonyl-6-aminohexyl)-3-(3-chloro-1,4-dimethoxynaphthalen-2-yl)-2-methyl-propenamide (Z-77)

R$_f$=0.67 (2:3 EtOAc:hexanes)
$^1$H NMR (CDCl$_3$): δ 1.24 (m, 10H); 1.55 (s/m, 2H); 1.69 (m, 3H); 1.80 (m, 1H); 1.85 (d, 3H, J=1.5 Hz); 1.98 (m, 3H);

2.40 (q, 2H, J=10.8 Hz); 3.69 (m, 1H); 3.84 (s, 3H); 3.99 (s, 3H); 4.05 (m, 1H); 6.64 (bs, 1H); 7.55 (m, 2H); 8.12 (m, 2H); 8.29 (d, 1H, J=6.6 Hz);
$^{13}$C NMR (CDCl$_3$): δ 16.5, 24.8, 25.2, 25.6, 26.5, 30.7, 28.5, 49.4, 53.4, 60.0, 61.4, 62.0, 122.1, 122.4, 122.9, 123.3, 123.6, 126.7, 127.4, 127.7, 138.7, 139.0, 148.5, 150.9, 153.9, 175.6 plug to remove the insoluble DCU, and the pipette was washed 2 times with 2 mL CH$_2$Cl$_2$. The combined fractions were then purified via flash chromatography (2:3 EtOAc: hexanes) to provide 79 (0.110 g, 0.314 mmol, 83%) as a white solid.

R$_f$=0.28 (1:1 EtOAc:hexanes)
mp=165-167° C.

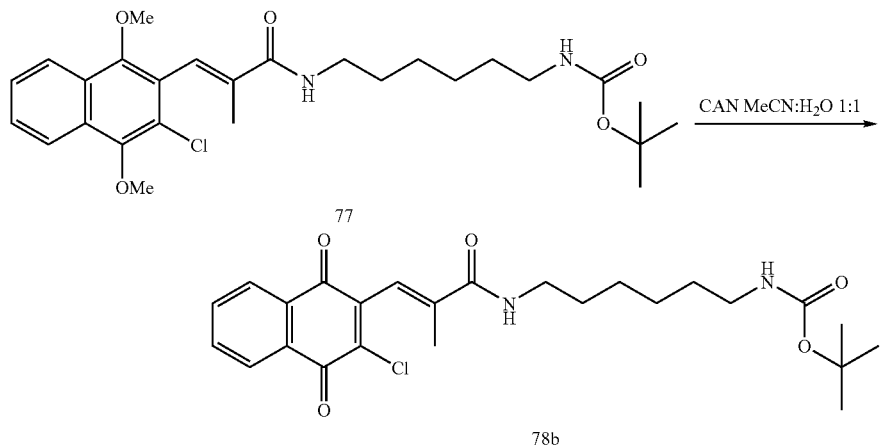

(E)-N—(N'-tert-butoxycarbonyl-6-aminohexyl)-3-(3-chloro-1,4-naphthoquinon-2-yl)-2-methylpropenamide (78b)

$^1$H NMR (CDCl$_3$): δ 1.86 (d, 3H, J=1.2 Hz); 2.68 (bs, 1H, OH); 3.60 (q, 2H, J=5.4 Hz); 3.75 (s, 3H); 3.84 (t, 2H, J=4.8 Hz); 3.98 (s, 3H); 6.42 (bs, 1H, NH); 7.43 (s, 1H); 7.55 (m, 2H); 8.10 (m, 2H)
$^{13}$C NMR (CDCl$_3$): δ 14.1, 15.0, 29.7, 43.0, 61.4, 61.9, 62.7, 122.2, 122.9, 124.6, 126.7, 127.4, 128.5, 134.3, 135.3, 148.7, 150.5, 169.6

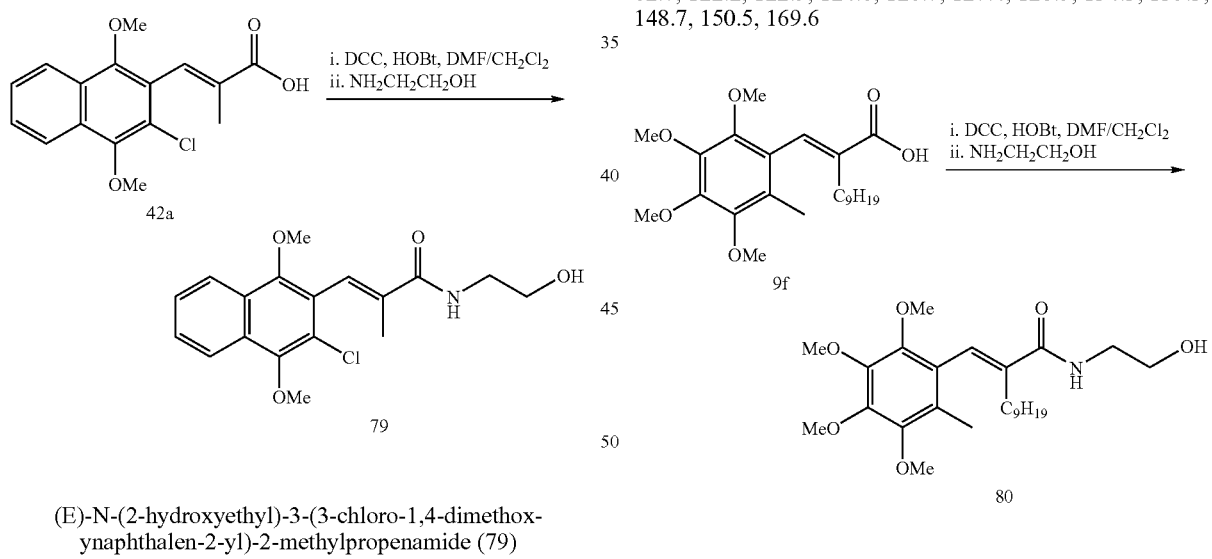

(E)-N-(2-hydroxyethyl)-3-(3-chloro-1,4-dimethoxynaphthalen-2-yl)-2-methylpropenamide (79)

DCC (0.135 g, 0.654 mmol) was added to a flame dried 10 mL round bottom flask under argon, and then CH$_2$Cl$_2$ (2.0 mL) was added at rt. In a second flame-dried flask under argon a solution of acid 42a (0.117 g, 0.381 mmol) and HOBt (0.025 g, 0.19 mmol) was prepared using DMF (3.0 mL) and CH$_2$Cl$_2$ (1.0 mL) at rt. The acid/HOBt solution was then added at rt and stirred for 2 h before amine (0.024 mL, 0.40 mmol) was added quickly at rt. The reaction was stirred for an additional 12 hours before being diluted with EtOAc, washed with brine, dried over MgSO$_4$, filtered, and condensed. The resulting white solid, a combination of dicyclohexylurea, DCC, and product, was first suspended in approximately 5 mL CH$_2$Cl$_2$. The suspension was then filtered through a pipette with cotton (E)-N-(2-hydroxyethyl)-3-(6-methyl-2,3,4,5-tetramethoxyphenyl)-2-nonylpropenamide (80)

DCC (0.106 g, 0.514 mmol) was added to a flame dried 10 mL round bottom flask under argon, and then CH$_2$Cl$_2$ (2.0 mL) was added at rt. In a second flame-dried flask under argon a solution of acid 9f (0.167 g, 0.409 mmol) and HOBt (0.008 g, 0.06 mmol) was prepared using DMF (3.0 mL) and CH$_2$Cl$_2$ (1.0 mL) at rt. The acid/HOBt solution was then added at rt and stirred for 2 h before amine (0.040 mL, 0.66 mmol) was added quickly at rt. The reaction was stirred for an additional 12 hours before being diluted with EtOAc, washed with brine, dried over MgSO$_4$, filtered, and condensed. The resulting white solid, a combination of dicyclohexylurea, DCC, and product, was first suspended in approximately 5 mL CH$_2$Cl$_2$. The suspension was then filtered through a pipette with cotton plug to remove the insoluble DCU, and the pipette was washed 2 times with 2 mL CH$_2$Cl$_2$. The combined fractions were then purified via flash chromatography (1:4 EtOAc: hexanes) to provide two compounds that appeared to be isomers: (E)-80 (0.088 g, 0.20 mmol, 48%, 2:3 EtOAc:hexanes R$_f$=0.36) and (Z)-80 (0.063 g, 0.14 mmol, 33%, 2:3 EtOAc: hexanes R$_f$=0.71, coleluted with DCC), both as a colorless oils.

R$_f$=0.36 (2:3 EtOAc:hexanes)
$^1$H NMR (CDCl$_3$): δ 0.83 (t, 3H, J=6.9 Hz); 1.13 (m, 12H); 1.32 (m, 2H); 2.03 (s, 3H); 2.13 (m, 2H); 2.70 (t, 1H, J=5.1 Hz); 3.55 (m, 2H); 3.69 (s, 3H); 3.78 (s, 3H); 3.80 (m, 2H); 3.88 (s, 3H); 3.92 (s, 3H); 6.31 (bs, 1H); 6.92 (s, 1H)
$^{13}$C NMR (CDCl$_3$): δ 13.0, 14.1, 22.6, 27.8, 28.8, 29.3, 29.5, 29.6, 31.8, 42.8, 60.6, 60.9, 61.1, 61.2, 62.8, 124.9, 125.0, 128.0, 140.3, 144.6, 146.3, 146.8, 147.8, 170.4

(Z)—N-(2-hydroxyethyl)-3-(6-methyl-2,3,4,5-tetramethoxyphenyl)-2-nonylpropenamide (Z-80)

R$_f$=0.71 (2:3 EtOAc:hexanes)
$^1$H NMR (CDCl$_3$): δ LOWER REGION OBSCURED BY DCC 3.19 (s, 3H); 2.14 (m, 2H); 2.42 (m, 2H); 3.68 (m, 1H); 3.75 (s, 3H); 3.78 (s, 3H); 3.88 (s, 3H); 3.92 (s, 3H); 4.07 (m, 1H); 6.64 (s, 1H); 8.53 (d, 1H, J=7.2 Hz)

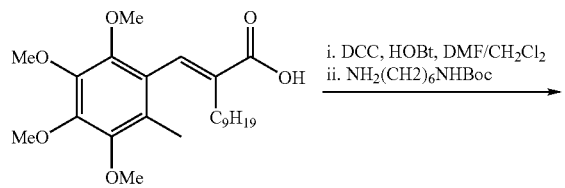

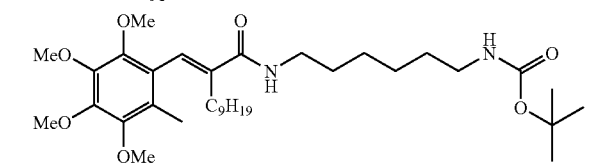

(E)-N—(N'-tert-butoxycarbonyl-6-aminohexyl)-3-(6-methyl-2,3,4,5-tetramethoxyphenyl)-2-methylpropenamide (81)

81 was prepared from 9f (0.439 g, 1.07 mmol) following method A for 88. E and Z isomers were separated using flash chromatography (1:4 acetone:hexanes). E isomer (0.360 g, 0.059 mmol, 55%); Z isomer (0.379 g, contaminated with DCC).

R$_f$=0.61 (2:3 EtOAc:hexanes)
$^1$H NMR (CDCl$_3$): δ 0.82 (t, 3H, J=6.6 Hz); 1.12 (m, 12H); 1.22 (m, 3H); 1.35 (m, 7H); 1.41 (s, 9H); 1.46 (m, 2H); 1.56 (m, 3H); 2.02 (s, 3H); 2.11 (m, 2H); 3.08 (q, 2H, J=6.0 Hz); 3.33 (q, 2H, J=6.6 Hz); 3.68 (s, 3H); 3.76 (s, 3H); 3.87 (s, 3H); 3.91 (s, 3H); 4.54 (bs, 1H); 5.92 (bs, 1H); 6.83 (s, 1H)
$^{13}$C NMR (CDCl$_3$): δ 13.0; 13.5; 22.6; 26.2; 26.4; 27.8; 28.4; 28.9; 29.3; 29.5; 29.6; 30.0; 31.8; 39.4; 40.3; 53.4; 60.6; 60.8; 61.1; 61.2; 125.1; 126.9; 141.1; 144.6; 146.2; 146.9; 147.8; 156.0; 169.2

(Z)—N—(N'-tert-butoxycarbonyl-6-aminohexyl)-3-(6-methyl-2,3,4,5-tetramethoxyphenyl)-2-methylpropenamide (Z-81)

R$_f$=0.75 (2:3 EtOAc:hexanes)
$^1$H NMR (CDCl$_3$): δ 0.84 (t, 3H, J=6.9 Hz); 1.38-1.17 (m, 28H); 1.42 (m, 1H); 1.57 (m, 2H); 1.72 (m, 7H); 1.93 (m, 3H); 2.08 (s, 3H); 2.14 (m, 2H); 2.42 (q, 2H, J=11.7 Hz); 3.68 (m, 1H); 3.75 (s, 3H); 3.79 (s, 3H); 3.89 (s, 3H); 3.92 (s, 3H); 4.07 (m, 1H); 6.37 (s, 1H); 8.54 (d, 1H, J=7.5 Hz);
$^{13}$C NMR (CDCl$_3$): δ 13.0; 14.1; 22.6; 24.8; 25.2; 25.7; 26.5; 27.3; 29.3; 29.4; 29.7; 30.4; 30.8; 31.8; 32.9; 49.4; 60.7; 60.9; 61.1; 61.2; 65.0; 123.6; 124.1; 125.2; 142.1; 144.6; 146.4; 147.2; 147.7; 154.1; 176.0

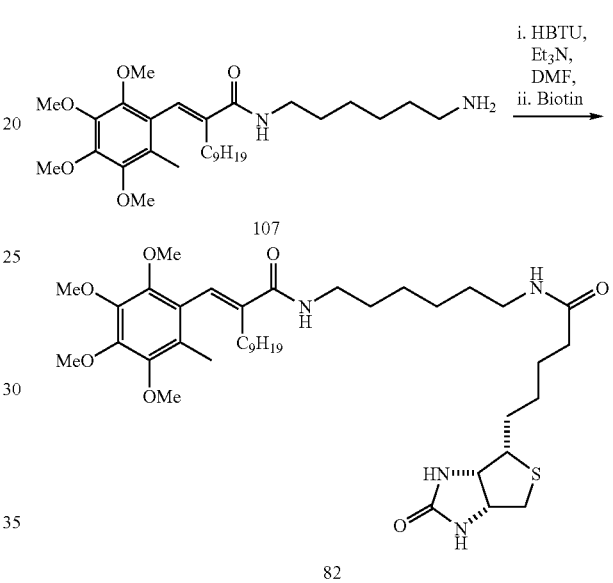

(E)-N-[5-((1R,5S,6S)-3-oxo-7-thia-2,4-diazabicyclo[3.3.0]oct-6-yl)pentanoylamino]hexyl-3-(6-methyl-2,3,4,5-tetramethoxyphenyl)-2-methylpropenamide (82)

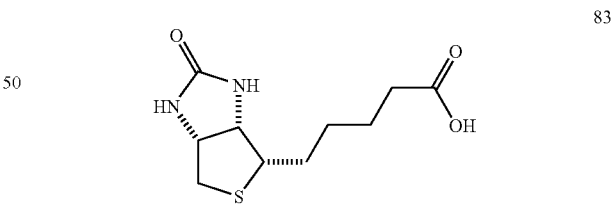

5-((1R,5S,6S)-3-oxo-7-thia-2,4-diazabicyclo[3.3.0]oct-6-yl)pentanoic acid D-(+)-Biotin (83, Aldrich)

$^1$H NMR (DMSO): δ 1.32 (m, 2H); 1.49 (m, 2H)); 1.60 (m, 2H); 2.19 (t, 2H, J=7.2 Hz); 2.56 (d, 1H, J=12.6 Hz); 2.81 (dd, 1H, J=12.6, 5.1 Hz); 3.09 (m, 1H); 4.12 (ddd, 1H; J=7.5, 4.2, 1.5 Hz); 4.29 (dd, 1H, J=7.5, 5.1 Hz); 6.35 (s, 1H); 6.42 (s, 1H); 11.93 (bs, 1H)
$^{13}$C NMR (DMSO): δ 24.5, 28.0, 28.1, 33.48, 40.3, 55.4, 59.2, 61.0, 162.7, 174.4

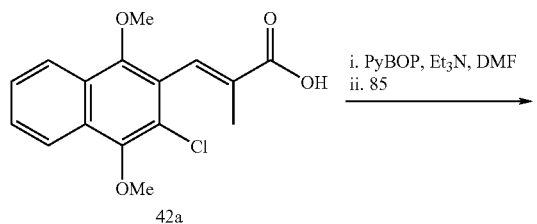

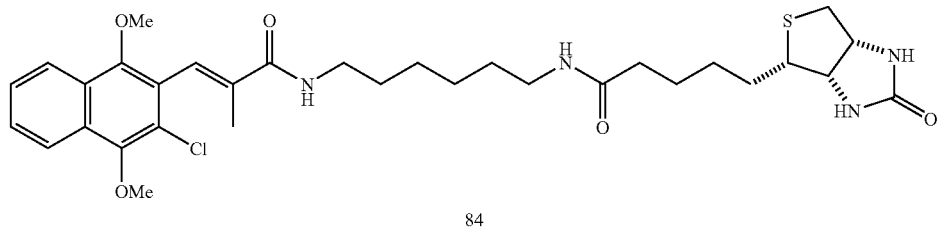

(E)-N-[5-((1R,5S,6S)-3-oxo-7-thia-2,4-bicyclo[3.3.0]oct-6-yl)pentanoylamino]hexyl-3-(3-chloro-1,4-dimethoxynaphthalen-2-yl)-2-methylpropenamide (84)

To a flame dried 10 mL round bottom flask was added 42a (0.015 g, 0.049 mmol) and PyBOP (0.031 g, 0.060 mmol), and then DMF (2.0 mL) was added to produce a yellow solution. Et$_3$N (0.020 mL, 0.14 mmol) was added at room temperature and the solution remained yellow/clear. After stirring at room temperature for 45 minutes amine 85 (0.1 M in DMF, 0.60 mL, 0.060 mmol) was added and the solution became a darker gold color but remained clear. After 20 minutes TLC (1:9 MeOH:CH$_2$Cl$_2$) indicated the starting material was no longer present and a new spot (R$_f$ 0.29) appeared. The reaction stirred for 12 hours more before the solvent was stripped off under reduced pressure. The resultant gold oil was immediately chromatographed (1:9 MeOH:CH$_2$Cl$_2$) to provide two yellow bands corresponding to two spots on TLC(R$_f$ 0.39 and 0.29). NMR of the higher spot indicated it was potentially the HOBt ester of the starting material. The lower spot was confirmed by NMR to be the coupled product, 84. The product was collected as a yellow oil that solidified in the freezer (0.031 g, 0.048 mmol, 99%).

R$_f$=0.29 (1:9 MeOH:CH$_2$Cl$_2$)

$^1$H NMR (CDCl$_3$): δ 1.05 (m, 2H); 1.33 (obscured by MeOH); 1.49 (m, 3H); 1.61 (m, 6H); 1.82 (s, 6H); 2.20 (m, 2H); 2.72 (bd, 1H, J=13.2 Hz); 2.86 (bd, 1H, J=9.3 Hz); 3.36 (m, 2H); 3.73 (s, 3H); 3.96 (s, 3H); 4.33 (bs, 1H); 4.51 (bs, 1H); 5.28 (m, 0.5H); 5.72 (bs, 0.5H); 6.33 (m, 0.5H); 6.41 (bs, 0.5H); 7.35 (s, 1H); 7.53 (m, 2H); 8.08 (m, 2H); 8.70 (bs, 0.5H)

$^1$H NMR (CD$_3$CN:D$_2$O 1:1): δ 1.70 (s, 3H); 2.10 (t, 3H, J=7.2 Hz); 2.62 (d, 2H, J=11.1 Hz); 3.23 (t, 3H, J=7.8 Hz); 3.69 (s, 3H); 3.90 (s, 3H); 4.42 (m, 3H); 7.20 (s, 1H); 7.59 (m, 2H); 8.07 (m, 2H)

$^{13}$C NMR (CDCl$_3$): δ 8.7, 15.0, 25.7, 26.0, 26.2, 27.7, 27.9, 29.1, 29.3, 35.7, 39.1, 39.7, 40.4, 55.4, 60.4, 61.4, 61.9, 62.0, 62.3, 122.1, 122.9, 123.2, 124.7, 126.7, 127.3, 127.6, 127.8, 128.7, 135.8, 148.5, 150.6, 168.6, 173.7, 192.8

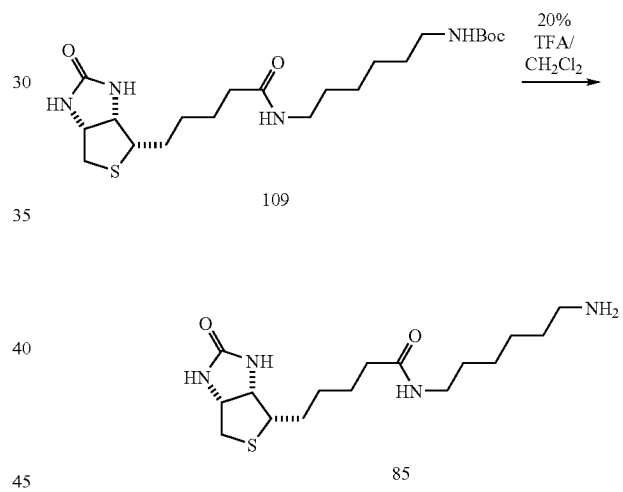

N-(6-aminohexyl)-5-(1R,5S,6S)-3-oxo-7-thia-2,4-diazabicyclo[3.3.0]oct-6-yl)pentanamide (85)

Boc protected amine 109 (0.034 g, 0.08 mmol) was dissolved in CH$_2$Cl$_2$ (2.0 mL) and TFA (0.4 mL, 5.2 mmol) was added at room temperature. The reaction stirred at room temperature for 20 minutes and then monitored by TLC (1:9 MeOH:CH$_2$Cl$_2$). When starting material was no longer observed by TLC the TFA/CH$_2$Cl$_2$ was removed under reduced pressure and the vial was placed under high vacuum for 2 hours. The tan residue was then taken up in DMF and used without purification. 85 was obtained quantitatively.

R$_f$=0.00 (1:9 MeOH:CH$_2$Cl$_2$)

$^1$H NMR (DMSO): δ 1.18-1.65 (m, 14H); 2.03 (t, 2H, J=7.2 Hz); 2.56 (d, 1H, J=12.3 Hz); 2.76 (m, 2H); 2.81 (dd, 1H, J=5.1, 12.6 Hz); 3.00 (q, 2H, J=6.3 Hz); 3.08 (m, 1H); 4.11 (dd, 1H, J=4.5, 7.5 Hz); 4.30 (dd, 1H, J=4.8, 7.5 Hz); 6.42 (bs, 2H); 7.67 (bs, 1H); 7.75 (t, 1H, J=5.1 Hz)

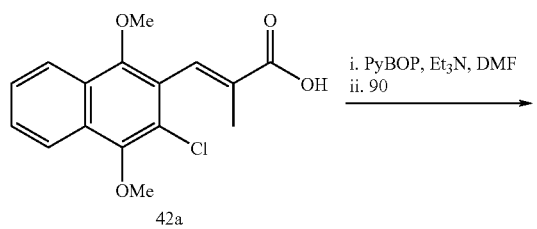

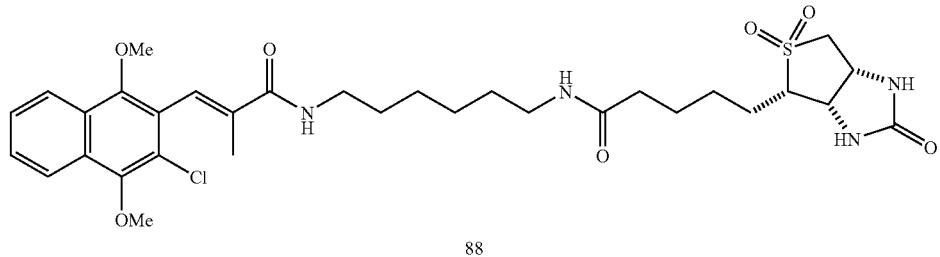

(E)-N—(N'-[5-(((1R,5S,6S)-3,7,7,-trioxo-7-thia-2,4-bicyclo[3.3.0]oct-6-yl)propanoylamino]hexyl-3-(3-chloro-1,4-dimethoxynaphthalen-2-yl)-2-methylpropenamide (88)

$^1$H NMR (DMSO): δ 1.41 (m, 2H); 1.53 (m, 2H); 1.63 (m, 2H); 2.20 (t, 2H, J=7.2 Hz); 3.01 (d, 1H, J=13.8 Hz); 3.16 (q, 1H, J=6.3 Hz); 3.30 (m, 3H); 4.38 (m, 2H); 6.59 (s, 1H); 6.69 (s, 1H)
$^{13}$C NMR (DMSO): δ 21.1, 24.4, 25.5, 33.4, 49.0, 53.5, 54.2, 60.2, 161.6, 174.4

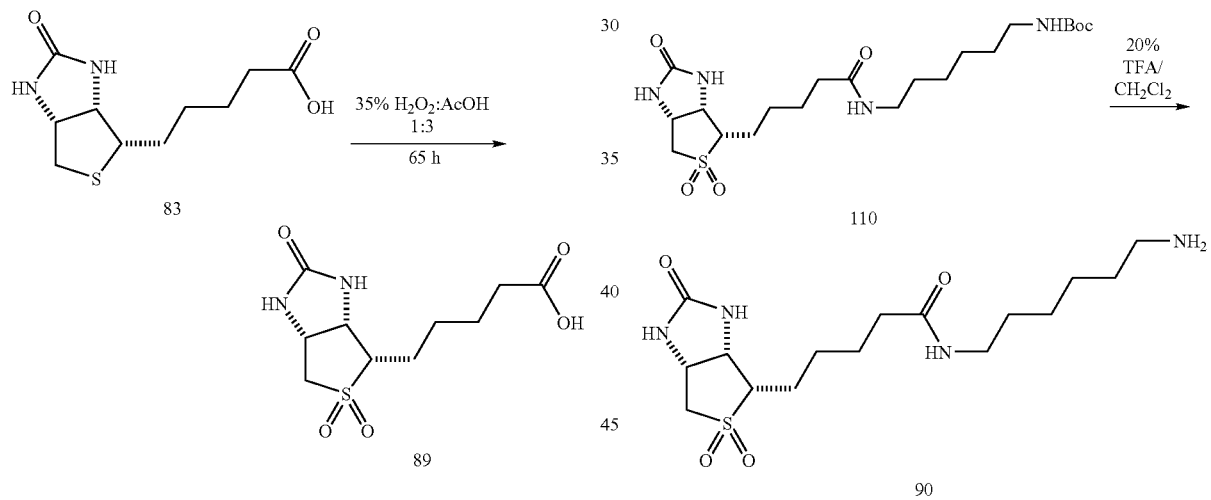

5-((1R,5S,6S)-3,7,7-trioxo-7-thia-2,4-diazabicyclo[3.3.0]oct-6-yl)pentanoic acid (89)

Following the procedure of Sachon et al.,[42] D-biotin (83, 0.304 g, 1.24 mmol) was suspended in AcOH (3.0 mL) and then H$_2$O$_2$ (35% in H$_2$O, 1.0 mL) was added at room temperature. The suspension became a colorless, clear solution after 10 min at room temperature, and biotin sulfoxide began to precipitate after 5 hours. The reaction was stirred at room temperature for 65 hours, then filtered. The white filter cake was then washed with 20 mL of ether and dried under reduced pressure to provide 89 as a white solid (0.298 g, 1.08 mmol, 87%).

Insoluble in CH$_2$Cl$_2$, acetone, MeOH, water.
Soluble in DMSO and NaOH aq.
R$_f$=
Mp=255° C. d (Lit.>260° C.)[42]

N-(6-aminohexyl)-5-((1R,5S,6S)-3,7,7-trioxo-7-thia-2,4-diazabicyclo[3.3.0]oct-6-yl)pentanamide (90)

N-Boc protected sulfonobiotin 110 (0.014 g, 0.03 mmol) was added to a flame-dried 5 ml round bottom flask and purged with argon. The white solid was suspended in CH$_2$Cl$_2$ (1.0 mL) and stirred at room temperature. TFA (0.2 mL) was added at room temperature and the white solid immediately dissolved to produce a clear, peach solution. The solution was stirred at room temperature for an additional 45 minutes before the solvents were removed under reduced pressure to provide the product as a tan residue. The residue was insoluble in CH$_2$Cl$_2$, but soluble in DMF. Amine 90 was synthesized quantitatively.

R$_f$=0.00 (1:9 MeOH:CH$_2$Cl$_2$)
$^1$H NMR (DMSO): δ 1.26 (m, 4H); 1.37 (m, 6H); 1.50 (m, 2H); 1.63 (m, 2H); 2.05 (t, 2H, J=7.2 Hz); 2.75 (m, 2H); 2.99 (m, 1H); 3.03 (m, 1H); 3.15 (m, 1H); 3.30 (dd, 1H, J=6.3, 13.8 Hz); 4.38 (m, 2H); 6.60 (s, 1H); 6.68 (s, 1H); 7.66 (bs, 2H); 7.76 (t, 1H, J=5.4 Hz)

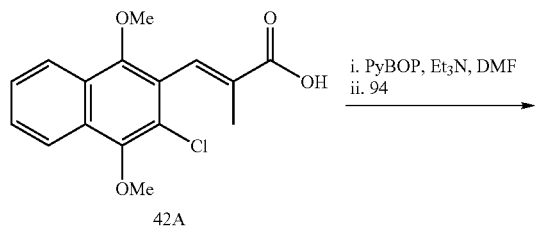

42A

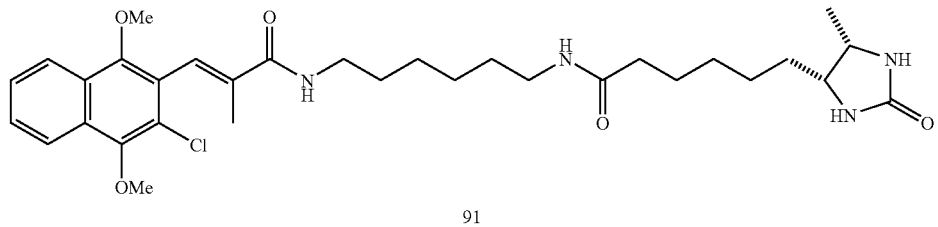

91

(E)-N—(N'-[6-((4R,5S)-5-methyl-imidazolidin-2-on-6-yl)hexanoylamino]hexyl-3-(3-chloro-1,4-dimethoxynaphthalen-2-yl)-2-methylpropenamide (91)

Unsaturated acid 42a (0.033 g, 0.11 mmol) and PyBOP (0.690 g, 0.133 mmol) were added to a flame-dried 10 mL round bottom flask and purged with argon. $CH_2Cl_2$ (2.0 mL) was then added resulting in a yellow solution, and then triethylamine (0.040 mL, 0.29 mmol) was added at room temperature and the yellow solution was stirred at room temperature for 40 minutes. Amine 94 (0.133 M in DMF/$CH_2Cl_2$ 1:5, 1.1 mL, 0.147 mmol) was added quickly at room temperature and the reaction turned orange. The reaction was stirred for an additional 17 h before the solvents were removed under reduced pressure resulting in a red oil that was purified by flash chromatography (7:93 MeOH:$CH_2Cl_2$) to provide a yellow oil that was contaminated with triethylammonium-hexafluorophosphate. To remove the contaminating salt the oil was dissolved in $Et_2O$/$CH_2Cl_2$ and washed 4 times with dilute NaOH, then one time with brine, and dried over $Na_2SO_4$. The resultant white foam 91 (0.044 g, 0.073 mmol, 68%) was free of ammonium salts.

Alternatively, upon completion the reaction is diluted with $Et_2O$ and washed 3 times with dilute NaOH (0.1 M), one time with saturated brine, dried over $MgSO_4$, filtered, and condensed under reduced pressure. The resulting gold oil was then purified by flash chromatography (7:93 MeOH: $CH_2Cl_2$).

$R_f$=0.35 (1:9 MeOH:$CH_2Cl_2$)
HRMS (ESI) calc. 623.2976 M+Na found 623.2978 M+Na
HPLC (econosphere C8, 40:60 MeCN:H2O) rt=28.2 min
Elemental analysis: calculated C, (63.93%); H, (7.54%); N, (9.32%); found C, (63.55%); H, (7.32%); N, (9.06%)

$^1$H NMR (CDCl$_3$): δ 1.09 (d, 3H, J=6.6 Hz); 1.23 (m, 2H); 1.38 (m, 9H); 1.50 (m, 3H); 1.63 (m, 4H); 1.73 (m, 2H); 1.83 (d, 3H, J=1.2 Hz); 2.16 (t, 2H, J=7.5 Hz); 3.23 (q, 2H, J=6.6 Hz); 3.39 (m, 2H); 3.67 (m, 1H); 3.75 (s, 3H); 3.80 (m, 1H); 3.97 (s, 3H); 4.50 (s, 1H); 5.12 (s, 1H); 5.93 (t, 1H, J=5.4 Hz)); 6.21 (t, 1H, J=5.4 Hz); 7.36 (d, 1H, J=1.2 Hz); 7.54 (m, 2H); 8.09 (m, 2H)

$^{13}$C NMR (CDCl$_3$): δ 15.0, 15.8, 25.4, 26.0, 28.8, 29.5, 30.9, 36.23, 38.9, 39.5, 51.4, 55.9, 61.4, 61.8, 122.2, 122.8, 123.3, 124.7, 126.7, 127.3, 127.5, 127.6, 128.7, 136.0, 148.6, 150.5, 163.3, 168.5, 172.9

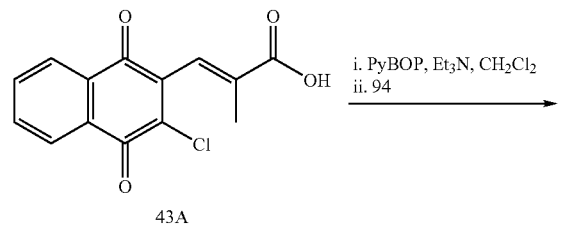

43A

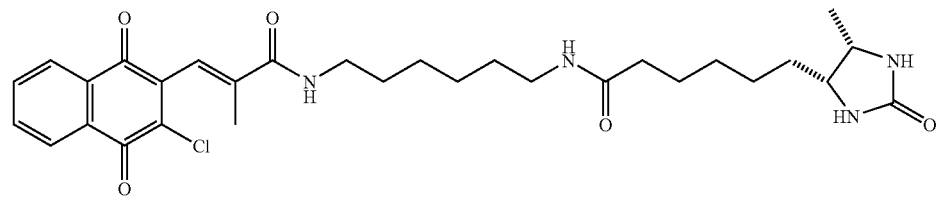

92

(E)-N—(N'-[6-((4R,5S)-5-methyl-imidazolidin-2-on-6-3H)hexanoylamino]hexyl-3-(3-chloro-1,4-naphthoquinon-2-yl)-2-methylpropenamide (92)

Method A: Quinone 43a (0.032 g, 0.11 mmol) and PyBOP (0.084 g, 0.16 mmol) were added to a 10 mL flame-dried round bottom flask and purged with Argon. $CH_2Cl_2$ (1.5 mL) was added at room temperature resulting in a yellow suspension. The suspension clarified to a yellow solution (sometimes a dark green solution) upon the addition of $Et_3N$ (0.035 mL, 0.25 mmol) at room temperature. The acid was allowed to activate for 10 minutes at room temperature before amine 94 (0.24 M in DMF, 0.50 mL, 0.12 mmol) was added at room temperature. The reaction was allowed to stir at room temperature for 30 minutes before being added to a column and purified ($CH_2Cl_2$ to 1:9 MeOH:$CH_2Cl_2$). 92 (0.052 g, 0.091 mmol, 80%) was collected as a dark gold oil and determined pure by NMR.

Method B: To a flame-dried 10 mL round bottom flask was added quinone 43a (9.921 mg, 0.0359 mmol), PyBOP (22.299 mg, 0.0428 mmol), and NaH (4.092 mg, 0.1705 mmol) and the flask was purged with argon for 10 minutes. The solid reagents were suspended in $CH_2Cl_2$ (2.0 mL) and then DMF was added slowly until the yellow suspension had become completely clear (0.4 mL). The reaction changed from golden/clear to light red/clear in 1 minute at room temperature, and after 10 minutes a solution of 94 (0.05 M in DMF, 0.68 mL, 0.034 mmol) was added to the reaction immediately changing the reaction to a yellow/clear solution. The reaction was allowed to stir at room temperature for 20 minutes before the clear yellow solution was stripped of $CH_2Cl_2$ under reduced pressure and then added directly to a column for purification ($CH_2Cl_2$ to 3:40 MeOH:$CH_2Cl_2$)

$R_f$=0.34 (1:9 MeOH:$CH_2Cl_2$)

HRMS (MALDI) $C_{30}H_{39}{}^{37}ClN_4O_5$ Calc. 573.2657 Found 573.2684

HPLC (econosphere C8, 40:60 MeCN:H2O) rt=12.9 min room temperature for 10 minutes before being added to a column and purified (0 to 1:9 MeOH:$CH_2Cl_2$). The fractions containing product and unhydrolyzed intermediate were combined in a separatory funnel and washed once with brine. The organic layer was separated, dried over $MgSO_4$, filtered, and condensed. The product was collected as a yellow residue (0.073 g, 0.13 mmol, 74%).

$R_f$=0.34 (1:9 MeOH:$CH_2Cl_2$)

HRMS (MALDI) $C_{30}H_{39}{}^{37}ClN_4O_5$ Calc. 573.2657 Found 573.2684

HPLC (econosphere C8, 40:60 MeCN:H2O) rt=12.9 min $^1$H NMR (CDCl$_3$): δ 1.11 (d, 3H, J=6.3 Hz); 1.24 (m, 4H); 1.37 (m, 9H); 1.48 (m, 5H); 1.61 (m, 11H); 1.86 (d, 3H, J=1.2 Hz); 2.16 (t, 2H, J=7.2 Hz); 3.24 (m, 2H); 3.35 (m, 2H); 3.68 (m, 1H); 3.83 (m, 1H); 4.45 (bs, 1H); 4.87 (bs, 1H); 5.74 (bs, 1H); 6.29 (bs, 1H); 6.99 (d, 1H, J=1.2 Hz); 7.78 (m, 2H); 8.11 (m, 1H); 8.18 (m, 1H)

$^{13}$C NMR (CDCl$_3$): δ 16.4, 25.4, 24.8, 26.0, 28.8, 29.3, 36.3, 39.0, 39.6, 51.4, 55.9, 57.8, 124.0, 127.2, 127.4, 131.3, 131.7, 134.3, 134.5, 140.0, 141.9, 142.6, 143.5, 146.3, 163.3, 167.1, 172.9, 177.5, 181.6, 185.4

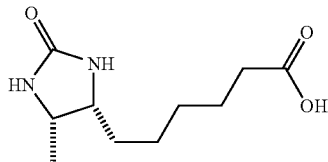

93

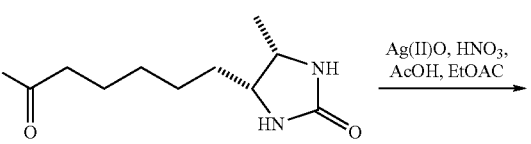

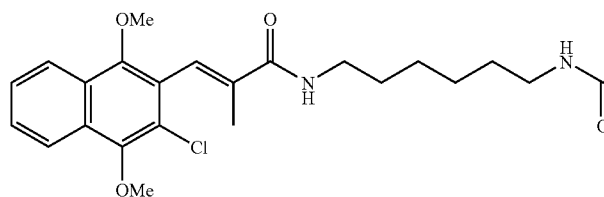

92

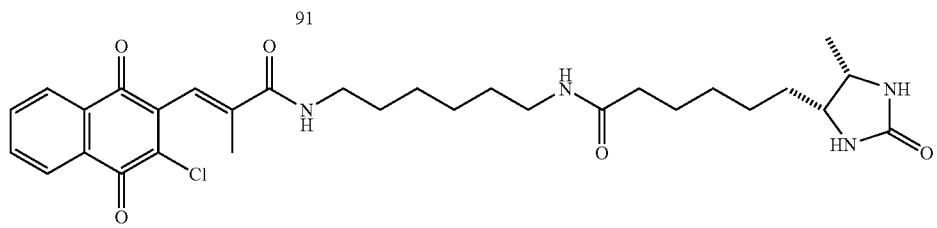

(E)-N—(N'-[6-((4R,5S)-5-methyl-imidazolidin-2-on-6-yl)hexanoylamino]hexyl-3-(3-chloro-1,4-naphthoquinon-2-yl)-2-methylpropenamide (92)

Dimethoxynaphthalene 91 (0.104 g, 0.172 mmol) was combined with Ag(II)O (1.58 g, 1.28 mmol) in a 4 mL vial and suspended in dioxane (2.0 mL). The suspension was sonicated until the starting material was completely dispersed (2 minutes). Nitric acid (6.0 M, 0.50 mL, 3.0 mmol) was added to the black suspension dropwise at room temperature and the suspension changed to a yellow solvent with yellow precipitate in less than one minute. The reaction was stirred at

6-[(4R,5S)-5-methyl-imidazolidin-2-on-4-yl]hexanoic acid (93, Aldrich)

Insoluble: $CH_2Cl_2$, $H_2O$, acetone

Soluble: NaOH aq.

$^1$H NMR (DMSO): δ 0.94 (d, 3H, J=6.3 Hz); 1.26 (m, 6H); 1.47 (m, 2H); 2.18 (t, 2H, J=7.2 Hz); 3.47 (m, 1H); 3.59 (m, 1H); 6.10 (s, 1H); 6.30 (s, 1H)

$^{13}$C NMR (DMSO): δ 15.5, 24.4, 25.5, 28.6, 29.5, 33.6, 50.2, 54.9, 162.8, 174.5

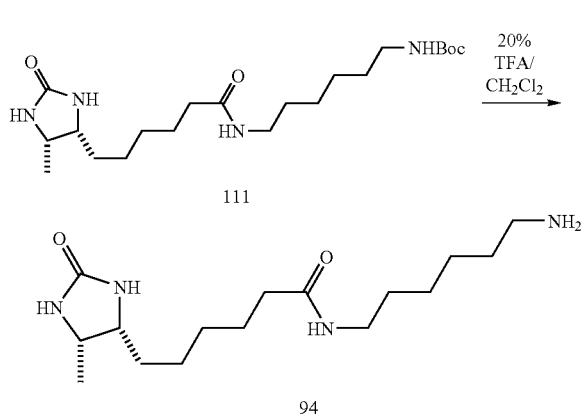

N-(6-aminohexyl)-6-[(4R,5S)-5-methyl-imidazolidin-2-on-4-yl]hexanamide (94)

N-Boc protected desthiobiotinylating reagent 111 (0.082 g, 0.20 mmol) was added to a flame-dried 5 mL conical vial and purged with Argon before CH$_2$Cl$_2$ (1.0 mL) was added. The starting material dissolved in approximately 2 minutes at room temperature to provide a colorless, clear solution. TFA (0.2 mL) was added at room temperature and the reaction became opaque, pale yellow. The reaction was stirred at room temperature for an additional 45 minutes before the solvent was removed under reduced pressure to provide the product as a tan oil. The product was used without further purification. 94 was synthesized quantitatively. 1.0 mL of CH$_2$Cl$_2$ were added to the oil resulting in two layers, and then 0.2 mL of DMF were added and the oil dissolved to make a pale tan solution.

$^1$H NMR (CDCl$_3$): δ 0.94 (d, 3H, J=6.6 Hz); 1.29 (m, 12H); 1.48 (m, 5H); 2.02 (t, 2H, J=7.2 Hz); 2.53 (t, 1H, J=5.4 Hz); 2.74 (m, 2H); 3.00 (m, 2H); 3.46 (m, 1H); 3.60 (m, 1H); 7.76 (m, 4H)

$^{13}$C NMR (CDCl$_3$): δ 15.5, 25.3, 25.5, 25.9, 27.0, 28.7, 29.0, 29.5, 34.3, 35.4, 38.3, 50.3, 55.1, 158.2, 158.67, 163.0, 172.0

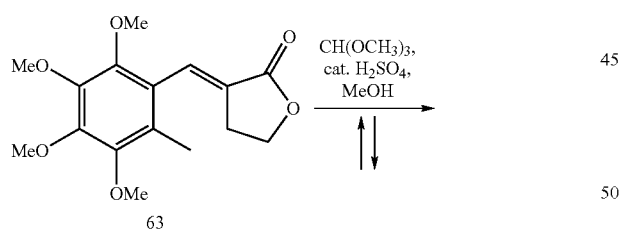

Methyl (E)-3-(6-methyl-2,3,4,5-tetramethoxyphenyl)-2-methoxyethylpropenoate (95)

According to a modified procedure by King et al.,[27] 63 (0.084 g, 0.27 mmol) was added to a flame-dried 10 mL round bottom flask under argon and a water-jacketed reflux condenser was attached. Anhydrous MeOH (2.0 mL) was then added, followed by H$_2$SO$_4$ (4 drops) and trimethyl orthoformate (0.31 mL, 4.0 mmol) at room temperature. The reaction was then heated under reflux for 12 hours, cooled to room temperature, and the solvent was removed under reduced pressure. The residue was dissolved in EtOAc, washed with saturated brine, dried over MgSO$_4$, filtered, and condensed. The resulting crude product was the purified via flash column chromatography (1:3 EtOAc:hexanes) to provide 95 (0.073 g, 0.20 mmol, 76%) as a faint yellow solid.

R$_f$=0.25 (1:3 EtOAc:hexanes)

mp=35-37° C.

$^1$H NMR (CDCl$_3$): δ 2.02 (s, 3H); 2.47 (t, 2H, J=7.2 Hz); 3.17 (s, 3H); 3.37 (t, 2H, J=7.2 Hz); 3.69 (s, 3H); 3.78 (s, 3H); 3.81 (s, 3H); 3.88 (s, 3H); 3.92 (s, 3H); 7.49 (s, 1H)

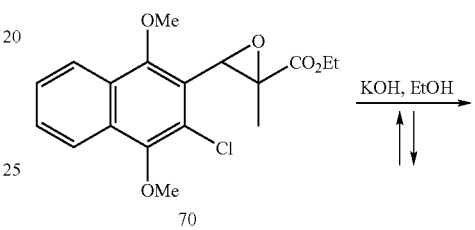

3-(3-chloro-1,4-dimethoxynaphthalen-2-yl)-2-epoxy-2-methylpropionic acid (102)

Darzens esters 70 (0.193 g, 0.550 mmol) were dissolved in EtOH (10.0 mL) and then KOH (0.200 g, 3.56 mmol) was added to the reaction. The reaction was heated to boiling and stirred at this temperature for 30 minutes. The reaction was then cooled, acidified, and extracted with ethyl acetate. The organic layer was washed with brine, dried over MgSO$_4$, filtered, and condensed. The resulting acid was then used as crude, or can be purified via flash chromatography (1:3 EtOAc:hexanes 0.5% AcOH) or recrystallization from Et$_2$O/hexanes to provide 102 (0.179 g, 0.555 mmol, 101%) as a yellow oil made up of 4 diastereomers.

R$_f$=0.07 (1:3 EtOAc:hexanes 0.5% AcOH)

$^1$H NMR (CDCl$_3$): δ

Enanteomer pair 1: 1.87 (s, 3H); 3.98 (s, 3H); 4.00 (s, 3H); 4.47 (s, 1H); 7.57 (m, 2H); 8.11 (m, 2H)

Enanteomer pair 2: 2.03 (s, 3H); 3.96 (s, 3H); 4.04 (s, 3H); 4.35 (s, 1H); 7.57 (m, 2H); 8.11 (m, 2H)

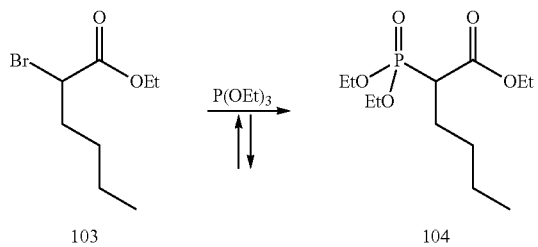 [SMILES: CCCCC(Br)C(=O)OCC ; CCCCC(C(=O)OCC)P(=O)(OCC)OCC ; "P(OEt)3"]

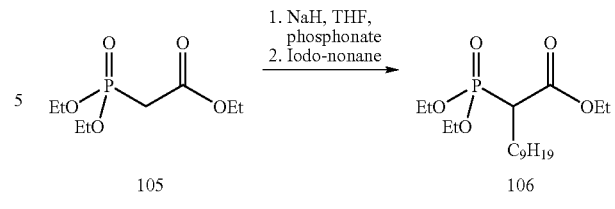

Triethyl 2-phosphonoundecanoate (106)

Following a slightly modified procedure by Kirschleger et al.,[43] NaH (1.00 g, 25.1 mmol) was added to a flame-dried 250 mL round bottom flask under argon and a drying tube. THF (100.0 mL) was then added at room temperature followed by triethyl phosphonoacetate (4.0 mL, 20.0 mmol) added dropwise at room temperature. After 30 minutes at room temperature iodononane (4.25 mL, 20.5 mmol) was added quickly and the reaction was stirred for 7 days at room temperature. The reaction was then washed with brine, dried over MgSO$_4$, filtered, and condensed. The resulting oil was then purified by either flash column chromatography (1:3 acetone:hexanes) or fractional distillation at reduced pressure to provide 106 (4.73 g, 13.5 mmol, 67%) as a colorless oil.

$R_f$=0.30 (1:3 acetone:hexanes)

$^1$H NMR (CDCl$_3$): δ 0.85 (t, 3H, J=6.6 Hz); 1.26 (m, 23H); 1.81 (bs, 1H); 1.94 (bs, 1H); 2.90 (dddd, 1H, J=33.6, 22.5, 11.1, 3.3 Hz); 4.15 (m, 6H)

$^{31}$P NMR (CDCl$_3$): δ 26.87 (s)

Triethyl 2-phosphonohexanoate (104)

Method A: Following a modified procedure by Kirschleger et al.,[43] NaH (0.762 g, 19.0 mmol) was added to a flame-dried 250 mL round bottom flask under argon and a drying tube. THF (75.0 mL) was then added at room temperature followed by triethyl phosphonoacetate (4.20 mL, 21.0 mmol) added dropwise at room temperature. After 30 minutes at room temperature iodobutane (2.10 mL, 18.4 mmol) was added quickly and the reaction was stirred for 7 days at room temperature. The reaction was then washed with brine, dried over MgSO$_4$, filtered, and condensed. The resulting oil was then purified by either flash column chromatography (1:3 acetone:hexanes) or fractional distillation at reduced pressure to provide 104 (4.29 g, 15.3 mmol, 83%) as a colorless oil.

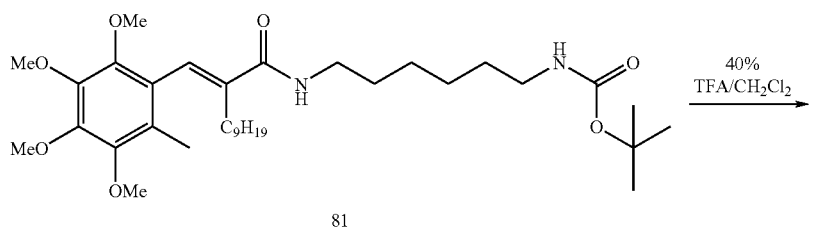

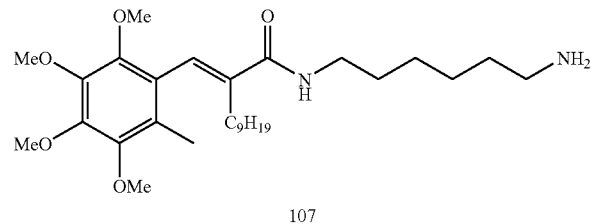

Method B: Following a modified procedure by Murphy et al.,[26] ethyl α-bromohexanoate (103, 1 eq) was added to a flame-dried round bottom flask followed by triethylphosphite (1 eq). The mixture was refluxed for 4 hours and then ethyl bromide was removed under reduced pressure. The resulting oil was then purified by fractional distillation at reduced pressure to afford 104 as a colorless oil.

$R_f$=0.34 (1:3 EtOAc:hexanes)

$^1$H NMR (CDCl$_3$): δ 0.86 (t, 3H, J=7.2 Hz); 1.23 (t, 3H, J=7.2 Hz); 1.28 (m, 12H); 2.89 (dddd, 1H, J=33.6, 22.5, 11.1, 3.9 Hz); 4.09 (q, 2H, J=7.2 Hz); 4.14 (m, 4H)

$^{31}$P NMR (CDCl$_3$): δ 26.98 (s)

(E)-N-(6-aminohexyl)-3-(6-methyl-2,3,4,5-tetramethoxyphenyl)-2-methylpropenamide (107)

Boc protected amine 81 (0.097 g, 0.16 mmol) was dissolved in CH$_2$Cl$_2$ (1.0 mL) and TFA (0.43 mL, 5.5 mmol) was added at rt. The reaction stirred at room temperature for 1 hour and the TFA/CH$_2$Cl$_2$ was then removed under reduced pressure. The residue was then taken up in DMF and used without purification. 107 was synthesized quantitatively.

$R_f$=0.00 (1:9 MeOH:CH$_2$Cl$_2$)

$^1$H NMR (CDCl$_3$): δ 0.82 (t, 3H, J=6.9 Hz); 1.11 (m, 12H); 1.23 (m, 3H); 1.39 (m, 4H); 1.56 (m, 2H); 1.68 (m, 3H); 2.01 (s, 3H); 2.09 (m, 2H); 2.96 (m, 2H); 3.30 (q, 2H, J=6.9 Hz); 3.67 (s, 3H); 3.77 (s, 3H); 3.87 (s, 3H); 3.91 (s, 3H); 6.04 (bs, 1H); 6.84 (s, 1H); 8.11 (bs, 2H)

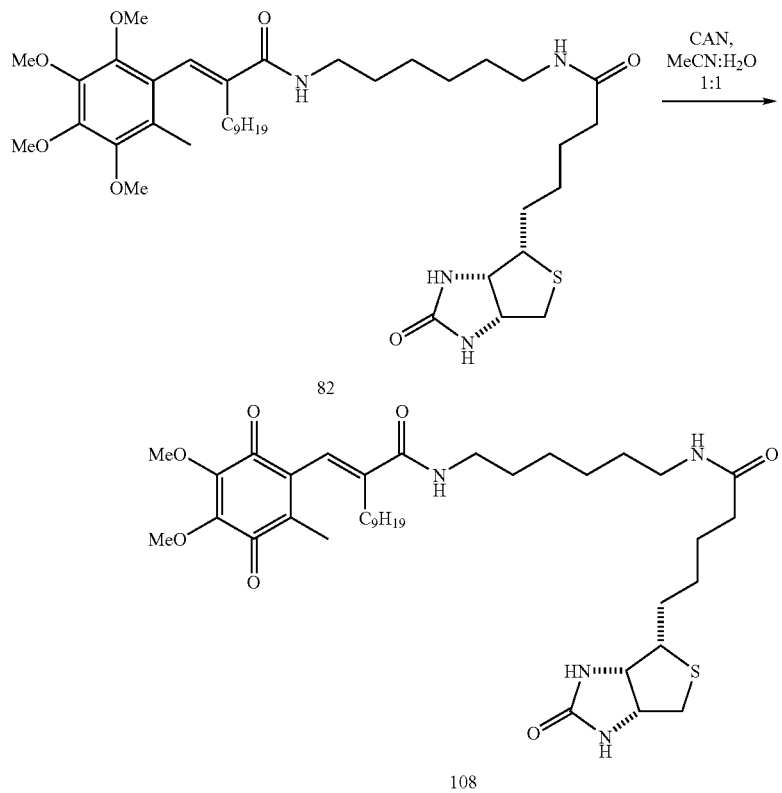

(E)-N-[5-((1R,5S,6S)-3-oxo-7-thia-2,4-diazabicyclo [3.3.0]oct-6-yl)pentanoylamino]hexyl-3-(3,4-dimethoxy-2-methyl-3,6-dioxocyclohexa-1,4-dienyl)-2-methylpropenamide (108)

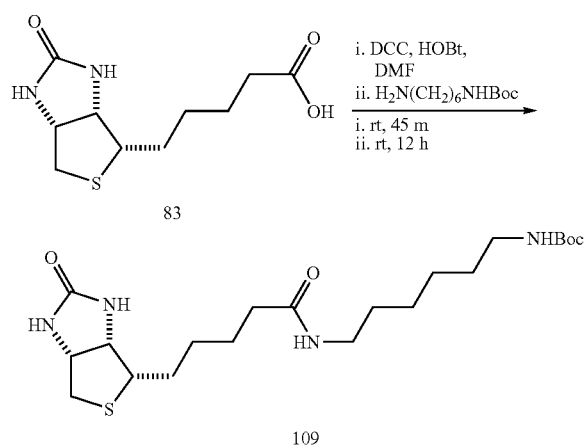

N—(N'-tert-butoxycarbonyl-6-aminohexyl)-511R, 5S,6S)-3-oxo-7-thia-2,4-diazabicyclo[3.3.0]oct-6-yl) pentanamide (109)

Following a significantly modified procedure by Sabatino et al.,[44] Biotin (83, 0.527 g, 2.16 mmol) and PyBOP (1.24 g, 2.39 mmol) were added to a flame-dried 50 mL round bottom flask, to which DMF (10.0 mL) was added at rt. To the white suspension was added $Et_3N$ (0.70 ml, 5.0 mmol) at rt and the suspension cleared to a light yellow, clear solution. The reaction was stirred at rt for 45 minutes before the amine (0.55 mL, 2.5 mmol) was added at rt. The yellow clear reaction was stirred at rt for 10 hours and then the solvent was removed under reduced pressure. The resulting yellow oil was then suspended in water (30.0 mL) and sonicated for 10 minutes. The white suspension was then filtered to produce a light tan filter cake. The filter cake was taken up in boiling acetone (200.0 mL) and recrystallized using acetone. The resulting white powder was collected by filtration, NMR showed pure 109 (0.655 g, 1.48 mmol, 69%).

$R_f$=0.24 (1:9 MeOH:$CH_2Cl_2$, Hanessian stain)
MP=163-164° C. (Literature 174-176° C.)[44]
$^1$H NMR (DMSO): δ 1.10-1.40 (m, 19H); 1.47 (m, 2H); 1.58 (m, 2H); 2.03 (t, 2H, J=7.5 Hz); 2.79 (d, 1H, J=5.4 Hz); 2.86 (m, 2H); 2.99 (q, 2H, J=6.3 Hz); 3.08 (m, 1H); 4.11 (m, 1H); 4.29 (m, 1H); 6.35 (s, 1H); 6.41 (s, 1H); 6.76 (t, 1H, J=5.1 Hz); 7.71 (t, 1H, J=5.4 Hz)
$^1$H NMR ($CDCl_3$/$CD_3OD$): δ 1.14 (m, 4H); 1.25 (s, 9H); 1.28 (m, 5H); 1.47 (m, 4H); 2.00 (dt, 2H, J=7.5 and 1.5 Hz); 2.55 (d, 11-1, J=12.9 Hz); 2.74 (dd, 1H, J=5.1 and 12.9 Hz); 2.88 (q, 2H, J=6.6 Hz); 2.99 (q, 3H, J=5.7 Hz); 4.12 (dd, 1H, J=8.1, 4.5 Hz); 4.32 (dd, 11-1, J=7.8, 4.8 Hz); 5.20 (bs, 1H); 6.99 (bs, 1H) (2 protons exchange)
$^1$H NMR ($CD_3CN$:$D_2O$ 1:1): δ 1.21 (m, 4H); 1.26-1.43 (m, 15H); 1.53 (m, 4H); 2.09 (t, 2H, J=7.2 Hz); 2.64 (d, 1H, J=12.9 Hz); 2.85 (dd, 1H, J=4.8, 12.9 Hz); 2.92 (m, 2H); 3.04 (t, 2H, 6.6 Hz); 3.14 (m, 1H); 4.34 (d, 1H, J=19.6 ppm); 4.44 (dd, 1H, J=5.1, 6.6 Hz); 5.90 (bs, 1H); 7.382 (bs, 1H)
$^{13}$C NMR ($CDCl_3$/$CD_3OD$): δ 25.3, 25.9, 26.0, 27.8, 28.0, 28.1, 28.8, 29.4, 35.5, 38.9, 40.0, 55.3, 59.9, 61.7, 79.0, 156.6, 163.9, 173.9
$^{13}$C NMR (DMSO): δ 25.3, 26.0, 26.1, 28.0, 28.3, 29.2, 29.5, 30.7, 35.2, 38.3, 55.4, 59.2, 61.0, 77.3, 155.6, 162.7, 171.78

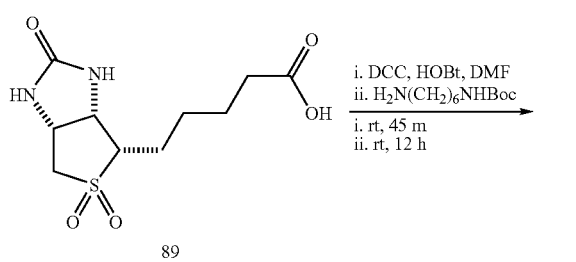

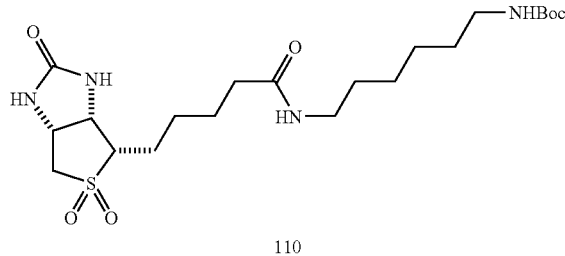

N—(N'-tert-butoxycarbonyl-6-aminohexyl)-5-((1R, 5S,6S)-3,7,7-trioxo-7-thia-2,4-diazabicyclo[3.3.0] oct-6-yl)pentanamide (110)

Biotinsulfone (89, 0.165 g, 0.597 mmol) was added to a flame-dried 10 mL round bottom flask followed by PyBOP (0.395 g, 0.759 mmol). The flask was purged with argon and then DMF (2.5 mL) was added resulting in a white suspension. Triethylamine (0.200 mL, 1.42 mmol) was then added at room temperature and the solution became clear and colorless. The reaction was stirred for 15 minutes at room temperature before a white precipitate began to form. N-Boc-1,6-diaminohexane (0.78 M in DMF, 0.90 mL, 0.70 mmol) was added quickly at room temperature resulting in an opaque white suspension. The reaction was stirred for an additional 4 hours at room temperature before the suspension was diluted with water (80.0 mL) and stirred for 10 minutes before the white precipitate was collected by filtration. The white precipitate was washed with dilute NaOH to remove biotinsulfone and then washed with $CH_2Cl_2$ to remove PyBOP, HOBt, and Et3NHCl. Compound 110 (0.236 g, 0.497 mmol, 83%) was collected as a white solid and determined to be pure by NMR.

Insoluble: $CH_2Cl_2$, acetone, NaOH aq.
Mildly Soluble MeOH, EtOH
Soluble: DMSO
$R_f$=0.15 (1:9 MeOH:$CH_2Cl_2$)
MP=213-215° C.

$^1$H NMR (DMSO): δ 1.21 (m, 4H); 1.36 (s, 15H); 1.51 (m, 2H); 1.63 (m, 2H); 2.05 (t, 2H, J=7.5 Hz); 2.73 (m, 2H); 2.99 (m, 3H); 3.15 (m, 1H); 3.30 (m, 1H); 4.38 (m, 2H); 6.59 (s, 1H); 6.68 (s, 1H); 6.75 (t, 1H, J=5.4 Hz); 7.73 (t, 1H, J=5.4 Hz)

$^{13}$C NMR (DMSO): δ 21.1, 25.2, 25.6, 26.0, 26.1, 28.3, 29.1, 29.4, 35.0, 38.3, 48.9, 53.4, 54.2, 60.3, 77.3, 85.1, 155.6, 161.6, 171.7

N—(N'-tert-butoxycarbonyl-6-aminohexyl)-6-[(4R, 5S)-5-methyl-imidazolidin-2-on-4-yl]hexanamide (1H)

Desthiobiotin (93, 0.288 g, 1.34 mmol) and PyBOP (0.792 g, 1.52 mmol) were added to a flame-dried 10 mL round bottom flask and purged with Argon. DMF (2.5 mL) was then added at room temperature producing a clear, colorless solution, to which was added triethylamine (0.420 mL, 2.99 mmol). The reaction was stirred at room temperature for 15 min before N-Boc-1,6-diaminohexane (0.78 M in DMF, 2.0 mL, 1.6 mmol) was added at room temperature. The reaction became a clear yellow solution and was stirred at room temperature for 14 hours before having the solvents removed under reduced pressure. The resulting yellow oil was taken up in $CH_2Cl_2$ and washed with brine 4 times, dried over $MgSO_4$, filtered, and condensed. The yellow oil was then purified by flash chromatography (7:93 MeOH:$CH_2Cl_2$) to yield 111 (0.405 g, 0.982 mmol, 73%) as a white solid/foam. Recrystallization was performed in acetone/hexane to further purify the product.

Insoluble: EtOAc, $Et_2O$, $H_2O$, NaOH aq.
Soluble: acetone, $CH_2Cl_2$
$R_f$=0.29 (1:9 MeOH:$CH_2Cl_2$)
MP=85-87° C.

$^1$H NMR (CDCl$_3$): δ 1.11 (d, 3H, J=6.6 Hz); 1.31 (m, 8H); 1.42 (s, 9H); 1.46 (m, 6H); 1.63 (m, 2H); 2.15 (t, 2H, J=7.2 Hz); 3.09 (m, 2H); 3.21 (m, 2H); 3.68 (m, 1H); 3.83 (m, 1H); 4.31 (bs, 1H); 4.55 (bs, 1H); 4.65 (bs, 1H); 5.65 (bs, 1H)

$^1$H NMR (DMSO): δ 0.94 (d, 3H, J=6.3 Hz); 1.20 (m, 8H); 1.32 (m, 6H); 1.36 (s, 9H); 1.46 (m, 2H); 2.02 (t, 2H, J=7.2 Hz); 2.87 (m, 2H); 2.99 (m, 2H); 3.46 (m, 1H); 3.59 (m, 1H); 6.10 (s, 1H); 6.28 (s, 1H); 6.75 (bs, 1H); 7.69 (bs, 1H)

$^{13}$C NMR (CDCl$_3$): δ 15.8, 25.4, 26.1, 28.4, 28.9, 29.5, 30.0, 36.4, 39.1, 40.2, 51.4, 53.4, 56.0, 79.1, 156.1, 163.2, 172.8

$^{13}$C NMR (DMSO): δ 15.5, 25.2, 25.5, 26.0, 26.1, 28.3, 28.7, 29.1, 29.4, 29.5, 35.2, 38.3, 45.7, 50.2, 54.9, 77.3, 155.6, 162.7, 171.8

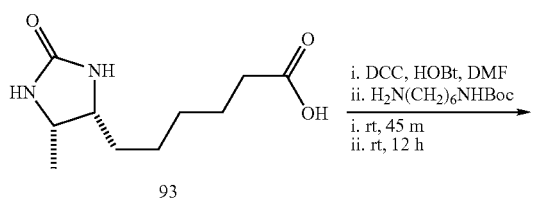

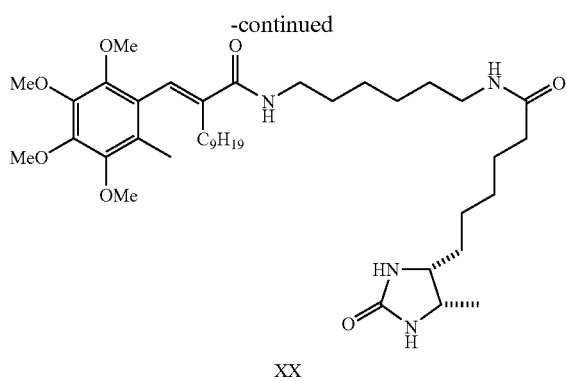

XX (E)-N—(N'-[6-((4R,5S)-5-methyl-imidazolidin-2-on-6-yl)hexanoylamino]hexyl-3-(6-methyl-2,3,4,5-tetramethoxyphenyl)-2-methylpropenamide (XX)

Desthiobiotin (93, 0.066 g, 0.306 mmol) was added to a flame-dried 10 mL round bottom flask followed by PyBOP (0.164 g, 0.314 mmol) and the flask was purged with Argon. $CH_2Cl_2$ (3.0 mL) was added to the flask making a white suspension, and then triethylamine (0.10 mL, 0.71 mmol) was added and the suspension quickly clarified to a clear, colorless solution. After stirring for 25 minutes at room temperature a solution of 107 (0.47 M in DMF:$CH_2Cl_2$ 1:1, 0.60 mL, 0.28 mmol) was added at room temperature, the flask containing 107 was rinsed with $CH_2Cl_2$ (0.5 mL) and added to the reaction. The reaction stirred at room temperature for 3 hours before being diluted with $CH_2Cl_2$ (20 mL), washed twice with dilute NaOH, washed once with brine, dried over $MgSO_4$, filtered, and condensed. The colorless oil was then purified by flash chromatography ($CH_2Cl_2$ to 3:40 MeOH:$CH_2Cl_2$) to provide XX (0.115 g, 0.16 mmol, 58%) as a colorless oil.

$R_f$=0.43 (1:9 MeOH:$CH_2Cl_2$)

$^1$H NMR (CDCl$_3$): δ 0.82 (t, 3H, J=6.9 Hz); 1.09 (d, 3H, J=6.3 Hz); 1.12 (m, 12 H); 1.20 (m, 2H); 1.34 (m, 10H); 1.46 (m, 2H); 1.55 (m, 2H); 1.65 (m, 2H); 2.01 (s, 3H); 2.10 (m, 2H); 2.16 (t, 2H, J=7.2 Hz); 3.20 (m, 2H); 3.33 (m, 2H); 3.65 (m, 1H); 3.68 (s, 3H); 3.76 (s, 3H); 3.81 (m, 1H); 3.86 (s, 3H); 3.90 (s, 3H); 4.81 (s, 1H); 5.49 (s, 1H); 6.14 (bs, 2H); 6.83 (s, 1H)

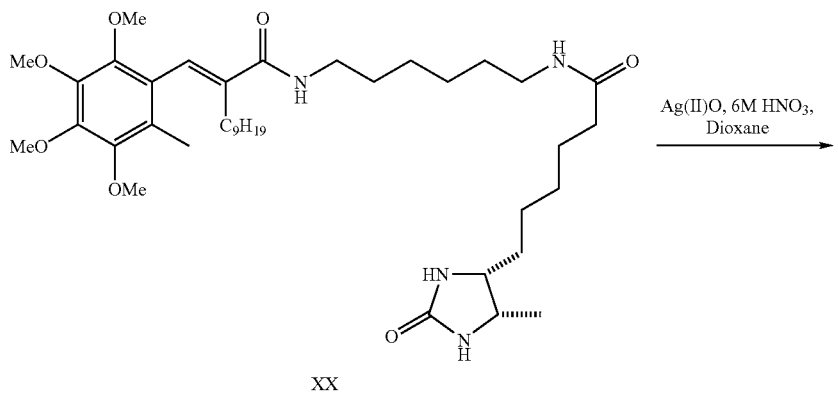

XX

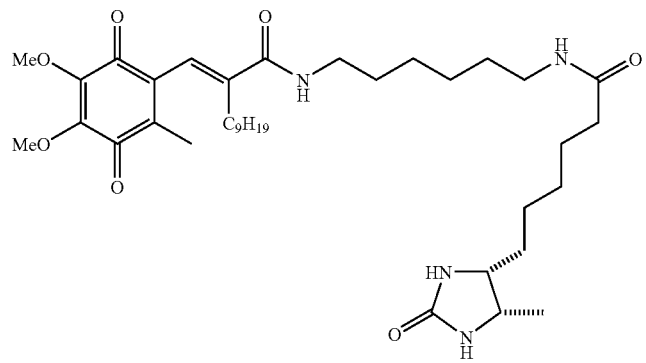

XX + 1

(E)-N—(N'-[6-((4R,5S)-5-methyl-imidazolidin-2-on-6-yl)hexanoylamino]hexyl-3-(3,4-dimethoxy-2-methyl-3,6-dioxocyclohexa-1,4-dienyl)-2-methylpropenamide (XX+1)

Tetramethoxybenzene XX (0.018 g, 0.026 mmol) was dissolved in dioxane (0.5 mL) in a 4 mL vial at room temperature, and then Ag(II)O (0.021 g, 0.16 mmol) was added to make a black suspension. At room temperature 6 M $HNO_3$ (0.12 mL, 0.72 mmol) was added slowly until the reaction became a clear orange solution. The reaction was stirred for ten minutes at room temperature, and then water (1.0 mL) was added to hydrolyze the formed intermediate. After stirring for 5 minutes at room temperature the reaction was extracted three times with $CH_2Cl_2$ (0.4 mL each) and the resulting orange organic layers were added to a column and purified ($CH_2Cl_2$ to 3:40 MeOH:$CH_2Cl_2$). XX was collected as a gold oil and determined pure by NMR (0.007 g, 0.010 mmol, 37%).

$R_f$=0.43 (1:9 MeOH:$CH_2Cl_2$)

$^1H$ NMR ($CDCl_3$): δ 0.84 (t, 3H, J=7.2 Hz); 1.16 (m, 15H); 1.34 (m, 12H); 1.48 (m, 2H); 1.55 (m, 4H); 1.92 (s, 3H); 2.08 (m, 2H); 2.15 (m, 2H); 3.21 (m, 2H); 3.30 (m, 2H); 3.72 (m, 1H); 3.841 (m, 1H); 3.97 (s, 3H); 4.01 (s, 3H); 4.66 (bs, 1H); 5.75 (bs, 1H); 6.25 (bs, 2H); 6.48 (s, 1H)

$^{13}C$ NMR ($CDCl_3$): δ 13.7; 14.1; 22.6; 25.5; 26.1; 27.7; 29.3; 29.4; 31.8; 36.3; 39.0; 39.5; 52.8; 54.0; 56.0; 61.2; 122.5; 137.5; 140.3; 144.2; 144.8; 168.7; 172.9; 183.3; 184.0 XX

The term $C_1$-$C_9$ alkyl refers to substituted or unsubstituted, straight and branched aliphatic hydrocarbon chains, containing from 1 to 9 carbon atoms, including 1 to 6 carbon atoms. For example, methyl, ethyl, propyl, isopropyl, butyl, i-butyl and t-butyl are encompassed by the term alkyl. Specifically included within the definition of alkyl are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. The term alkoxy as used herein, refers to the group —OR wherein R is an alkyl group as defined above. Halo is defined to include fluoro, chloro and bromo.

The present invention is also directed to the use of the compounds described herein for inhibiting the redox of Ape1/Ref1, by administering to a subject in need thereof such a quinone derivative, as well as inhibiting a physiological disorder associated with altered angiogenesis or cancer by administering to a subject in need thereof an effective amount of a quinone derivative of the invention.

Selective inhibition includes specific inhibition, or, in other words, where there is no or no appreciable effect on the BER function of APE1/Ref-1, as well as where the predominant effect is on the redox function, vis-à-vis the BER function. Also encompassed by the invention is the use of the quninone derivatives of the invention in combination with additional chemotherapeutic/therapeutic agents. It is preferable that the other agents work on a subject in a different way to that of the quinone derivatives. Such other therapeutic agents include, but are not limited to, Avastin, melphalan, gemcitabine, cisplatin, methoxyamine, thalidomide and its derivatives, and retinoic acid, as well as other therapies including radiation.

Physiological disorders associated with altered angiogenesis encompass those disorders associated with inappropriate angiogenesis, which are directly or indirectly deleterious to the subject. Altered angiogenesis contributes to pathological conditions related to, among others, cancer (including growth, survival, migration, metastasis, and microenvironment effects), cardiovascular disease, chronic inflammatory disease, rheumatoid arthritis, diabetic retinopathy, degenerative maculopathy, retrolental fibroplasias, idiopathic pulmonary fibrosis, acute adult respiratory distress syndrome, asthma, endometriosis, psoriasis, keloids, and systemic sclerosis.

Examples of types of cancers in the methods of the invention include, among others, breast, prostate, pancreas, colon, cervical, germ cell tumors, adult and pediatric gliomas, osteosarcomas, rhabdomyosarcomas, non-small cell lung cancer, leukemias, and multiple myeloma.

The term subject includes vertebrate animals, and preferably is a human subject. The term inhibit, and derivates thereof, includes its generally accepted meaning, which includes prohibiting, preventing, restraining, and slowing, stopping, or reversing progression or severity. Thus, the present methods include both medical therapeutic and prophylactic administration, as appropriate. As such, a subject in need thereof, as it relates to the therapeutic uses herein, is one identified to require or desire medical intervention. An effective amount is that amount of an agent necessary to inhibit the pathological diseases and disorders herein described. When at least one additional therapeutic agent is administered to a subject, such agents may be administered sequentially, concurrently, or simultaneously, in order to obtain the benefits of the agents.

An important aspect of the invention is the ability to protect "normal" cells, while still providing therapeutic value. By administering the compounds of the invention, it is possible to administer lower amounts of other therapeutics to the subject, while retaining the same outcomes. Also, by enhancing the apoptosis of cancer cells without a concomitant apoptosis in normal cells, a more targeted therapeutic approach may be taken.

The compounds used in the methods of this invention may form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, B-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethane-sulfonate, methanesulfonate, naphthalene-1-sulfonate, naphthalene-2-sulfonate, p-toluenesulfonate, xylene-sulfonate, tartarate, and the like.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and primary, secondary and tertiary amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Where subject applications, particularly human clinical use, are contemplated, it will be necessary to prepare pharmaceutical compositions in a form appropriate for the intended application. Generally, this will entail preparing compositions that are essentially free of impurities that could be harmful to a subject.

The agents can be administered orally, intravenously, intramuscularly, intrapleurally or intraperitoneally at doses based on the body weight and degree of disease progression of the subject, and may be given in one, two or even four daily administrations.

For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

One will generally desire to employ appropriate salts and buffers to render agents stable and allow for uptake by target cells. Aqueous compositions of the present invention comprise an effective amount of the agent, dissolved or dispersed in a pharmaceutically acceptable carrier or aqueous medium. Such compositions also are referred to as innocuously. The phrase pharmaceutically or pharmacologically acceptable refers to molecular entities and compositions that do not produce adverse, allergic, or other untoward reactions when administered to a subject. As used herein, pharmaceutically acceptable carrier includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

Compositions for use in the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration agents of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

The compositions for use in the present invention may be formulated in a neutral or salt form, as described above.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, general safety and purity standards as required by FDA and foreign counterpart agencies.

Enzymatic Redox Assays

Following a modified procedure of Gius et al., EMSA assays were performed on all compounds to determine redox 1050 values.[34] Briefly, purified Ape1 protein (10 mg/mL) was reduced with DTT (1.0 mM) at 37° C. for 10 min and then diluted with PBS buffer to final concentrations of Ape1 and DTT of 2 mg/mL and 0.2 mM respectively. A final volume of 18 mL was prepared from EMSA buffer (10 mM Tris [pH 7.5], 50 mM NaCl, 1 mM $MgCl_2$, 1 mM EDTA, 5% [vol/vol] glycerol) to which was added two mL of reduced Ape1 protein and 6 mg of oxidized nuclear extracts (Hey-C2 cells, treated with 0.01 mM diamide for 10 min); and the reaction was incubated at room temperature for 30 mM.

One mL of poly(dI-dC)•poly(dI-dC) (1 mg/1 µL, Amersham Biosciences, Piscataway, N.J.) was added for 5 min followed by one mL of the 5′ hexachloro-fluorescein phosphoramidite (HEX)-labeled double-stranded oligonucleotide DNA (0.1 µmol, The Midland Certified Reagent Company, Midland, Tex.) containing the AP-1 consensus sequence (5′CGCTTGATGACTCAGCCGGAA-3′), and the mixture was further incubated for 30 min. at room temperature. The final concentration of DTT in the redox reactions was 0.02 mM.

Samples were loaded on a 5% nondenaturing polyacrylamide gel and subjected to electrophoresis in 0.5×TBE buffer (200 V for 1 h at 4° C.) and detected using the Hitachi FMBio II Fluorescence Imaging System (Hitachi Genetic Systems, South San Francisco, Calif.). The HEX fluorophore is excited by a solid-state laser at 532 nm (Perkin-Elmer) and emits a fluorescent light signal at 560 nm, which is then measured using a 585 nm filter.

If the compound does not affect the redox function of Ape1, oxidized AP1 will become reduced by Ape1 and bind DNA, thus retarding the migration of DNA. (FIG. 10, lane 3) If the drug blocks the ability of Ape1 to reduce AP1, then AP1 will remain oxidized, no binding will take place between AP1 and DNA, and DNA migration will not be retarded. (FIG. 10, lane 1) A later experiment used Ape1 and purified, oxidized AP1 rather than a cell lysate to confirm a direct relationship between the inhibitors and the interaction between Ape1 and AP1.

Growth Inhibition Assays

Growth inhibitory data was also collected for all the compounds tested in the redox assay. Following the procedure of Fishel et al, cells were aliquoted into 96 well plates at a concentration of 2-4,000 cells/well in triplicate and allowed to adhere overnight. Cells were then treated with compound for either 24 or 72 h. 3-(4-5-Dimethylthiazol-2-yl)-5-(3-carboxymethoxyphenyl)-2-(4-sulfophenyl)-2H-tetrazolium salt (MTS) was added to the cells following compound treatment and the cells were incubated for an additional 4 hours at 37° C. After incubation with MTS the plates were measured for absorbance at 490 nm. The values were standardized to wells containing media alone.

The benzoquinone series results are found in Table 1. The benzoquinone series included derivatives that varied either in the olefin sidechain adjacent to the carbonyl or the 2-substituent of the ring. Sidechain variants including methyl (10b), butyl (10e), and nonyl (1) showed redox $IC_{50}$ values in the range of 3-15 µM, with the methyl derivative having the lowest $IC_{50}$. The $GI_{50}$ values for the same three compounds showed an inverse relationship to the $IC_{50}$ values. The range for $GI_{50}$ was 35-130 µM, where the nonyl derivative had the greatest activity. A rationale for the inverse relationship between redox and growth inhibition data rests on transportation of the drug molecules across the cell and nuclear membranes to interact with Ape1. The longer aliphatic chain may mediate transport through the lipophilic membranes resulting in greater activity in cell-based assays.

Figure 11:
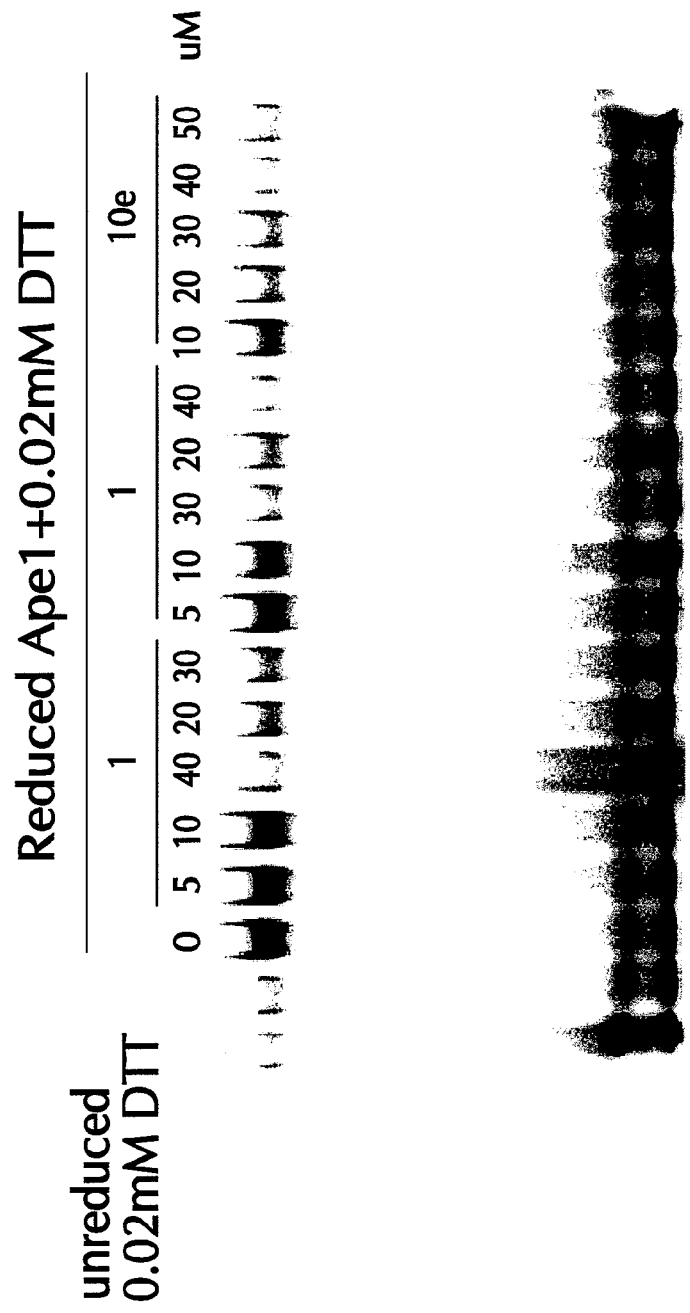
FIG. 11: EMSA data for E3330 (1) and derivative 10e (nbutyl substituted olefin).

The hydrocarbon sidechain was also studied by replacing the butyl sidechain with a methoxyethyl group (67). In redox assays the compounds showed similar activity, 15 µM for the hydrocarbon and 10 µM for ether 67. Cell-based growth inhibition data again was in opposition to the enzymatic redox assay, where the ether derivative 67 has a $GI_{50}$ of 200 µM and the butyl derivative 10e has a $GI_{50}$ of 85 µM. Further exploration of the sidechain was undertaken utilizing unsubstituted derivative 10a, where the sidechain is completely removed. Both redox and cell-based growth inhibition activities decreased upon removal of the sidechain. The redox $IC_{50}$ for the unsubstituted derivative was 40 µM compared to 3 µM for the methyl substituted derivative 10b. Growth inhibition was similarly affected, where the $GI_{50}$ for the methyl sidechain was 130 µM the unsubstituted derivative had a $GI_{50}$ of 250 µM. The unsubstituted derivative shows the significance of the sidechain for retaining activity in the benzoquinone series. Representative EMSA data are shown in FIG. 10 and FIG. 11. In FIG. 10 the nonyl derivative 1 (E3330) is compared to the unsubstituted derivative 10a and the methoxyethyl derivative 67. FIG. 11 shows two different samples of E3330 (1) compared to the n-butyl derivative 10e.

The 2-position methyl group of the benzoquinone ring in E3330 was explored by synthesizing the 2-chloro derivative 23. The chloro derivative with a methyl sidechain had equal activity to the 2-methyl derivative 10b in enzymatic redox assays (2.5 and 3.0 µM respectively). In cell-based assays, the 2-chloro derivative was superior to the methyl derivative by a factor of 3, where the alkyl substituted 10b has a $GI_{50}$ of 130 µM and the halogenated derivative 23 had a $GI_{50}$ of 45 µM.

One significant advance from the benzoquinone series was the realization that truncating the n-nonyl sidechain to a methyl substituent did not affect redox inhibition, but completely removing the sidechain had negative effects. (Table 1).

TABLE 1

Benzoquinone derivatives: Side chain variation and 3-position substitution

| Structure | Name | 3-Substituent | Side chain | Redox/ µM | Cell Killing/ µM |
|---|---|---|---|---|---|
| (structure shown) | 10a | Methyl | Unsubstituted | 40 | 250 |

TABLE 1-continued

Benzoquinone derivatives: Side chain variation and 3-position substitution

| Structure | Name | 3-Substituent | Side chain | Redox/ μM | Cell Killing/ μM |
|---|---|---|---|---|---|
| (structure) | 10b | Methyl | Methyl | 3 | 130 |
| (structure) | 23 | Chloro | Methyl | 2.5 | 45 |
| (structure) | 10e | Methyl | nButyl | 15 | 85 |
| (structure) | 64 | Methyl | Methoxyethyl | 10 | 200 |
| (structure) | 1 | Methyl | nNonyl | 10 | 35 |

FIG. 10: EMSA data for E3330 (1) and derivatives 10a (unsubstituted double bond) and 64 (methoxyethyl substituted double bond). Lanes: 1) oxidized Ape1, oxidized AP1, DNA probe; 2) 0.02 mM DTT, oxidized AP1, DNA probe; 3-15) Inhibitor (μM), reduced Ape1, oxidized AP1, DNA probe.

FIG. 11: EMSA data for E3330 (1) and derivative 10e (nbutyl substituted olefin). Lanes: 1) oxidized Ape1, oxidized AP1, DNA probe; 2) 0.02 mM DTT, oxidized AP1, DNA probe; 3-18) Inhibitor (μM), reduced Ape1, oxidized AP1, DNA probe.

The naphthoquinone derivatives showed little variation in activity when the substituent on the double bond was changed from a methyl to a n-butyl or even a methoxyethyl substituent. The more significant activity changes came from modifying the 3-position substituent. The 3-methyl derivatives, which are structurally most similar to E3330, showed the worst redox inhibition of the naphthoquinone derivatives at 10-25 μM (Tables 2 and 3). The 3-unsubstituted derivative possessed the potential to have an alternative mechanism of action from the substituted derivatives, where addition to the quinone can be imagined.

The other 3-position derivatives all had redox $IC_{50}$ values below 5 μM, and discerning among them based on structure was difficult. One conclusion from the data is that having an electronegative substituent at the 3 position greatly enhances the redox inhibition of the compound. The chloro, bromo, methoxy, and methylthio derivatives all inhibited redox function between 7.5 and 30 times more than the 3-methyl derivative (Table 2). The 3-fluoro derivative still inhibited redox function at 4 μM; however, with such an electronegative atom it was expected to significantly enhance the effects observed in the other 3-halo derivatives. Size of the substituent at the 3-position did not seem to have an effect either, where the small chloro and bulky methoxy and methylthio derivatives were nearly identical in activity.

TABLE 2

Naphthoquinone Derivatives: 3-position substitution

| Structure | Name | 3-Substituent | Redox/ μM | Cell Killing/ μM |
|---|---|---|---|---|
| 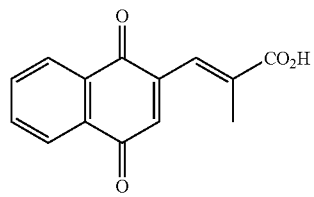 [SMILES: C/C(=C\C1=CC(=O)c2ccccc2C1=O)C(=O)O] | 30a | Unsubstituted | 2.5 | 20 |
| 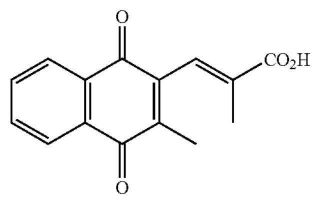 [SMILES: CC1=C(/C=C(\C)C(=O)O)C(=O)c2ccccc2C1=O] | 35a | Methyl | 15 | 45 |
| 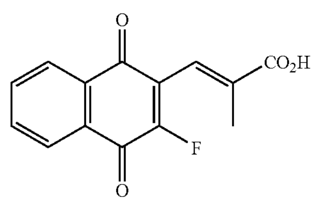 [SMILES: C/C(=C\C1=C(F)C(=O)c2ccccc2C1=O)C(=O)O] | 52 | Fluoro | 4 | 50 |
| 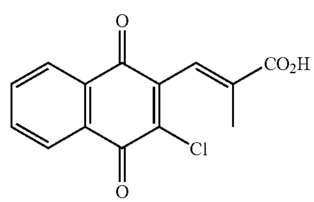 [SMILES: C/C(=C\C1=C(Cl)C(=O)c2ccccc2C1=O)C(=O)O] | 43a | Chloro | 1.0 | 15 |
| 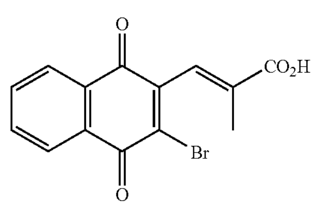 [SMILES: C/C(=C\C1=C(Br)C(=O)c2ccccc2C1=O)C(=O)O] | 39a | Bromo | 2.0 | 12.5 |
| 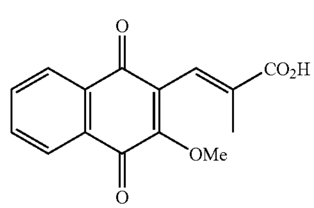 [SMILES: COC1=C(/C=C(\C)C(=O)O)C(=O)c2ccccc2C1=O] | 55 | Methoxy | 0.5 | 40 |

TABLE 2-continued

Naphthoquinone Derivatives: 3-position substitution

| Structure | Name | 3-Substituent | Redox/ μM | Cell Killing/ μM |
|---|---|---|---|---|
| (naphthoquinone with CO₂H vinyl and SMe) | 58 | Thiomethyl | 1.0 | 30 |

TABLE 3

Naphthoquinone Derivatives: Sidechain variation

| Structure | Name | 3-position | Side chain | Redox/ μM | Cell Killing/ μM |
|---|---|---|---|---|---|
| (structure) | 35a | Methyl | Methyl | 15 | 45 |
| (structure) | 35b | Methyl | nButyl | 25 | 40 |
| (structure) | 62a | Methyl | Methoxy Ethyl | 10 | 30 |
| (structure) | 43a | Chloro | Methyl | 1.0 | 15 |
| (structure) | 62c | Chloro | Methoxy Ethyl | 3.0 | 30 |

TABLE 3-continued

Naphthoquinone Derivatives: Sidechain variation

| Structure | Name | 3-position | Side chain | Redox/ µM | Cell Killing/ µM |
|---|---|---|---|---|---|
| [structure: naphthoquinone with Br at 3-position and propenoic acid sidechain] | 39a | Bromo | Methyl | 2.0 | 12.5 |
| [structure: naphthoquinone with Br at 3-position and methoxyethyl-substituted acrylate sidechain] | 62b | Bromo | Methoxy Ethyl | 0.5 | 25 |

Further derivatives considered all have a degree of modification to the unsaturated acid moiety (Table 4). The double bond was modified first by saturating the olefin to modify the 3-dimensional orientation of the acid and alpha substituent. Two saturated derivatives of 3-bromo 39a were tested, with either unsubstituted (69a) or methyl substitution (69b) alpha to the carbonyl. The methyl substituted derivatives 69b (R/S) were tested as a racemic mixture and were equal in activity to the unsubstituted derivative. With an $IC_{50}$ of 5 µM and a $GI_{50}$ of 15 µM, the saturated derivatives were not much different in activity than the parent unsaturated derivative 39a ($IC_{50}$=2.0 µM, $GI_{50}$=12.5 µM). The olefin was also epoxidized to keep a rigid structure that possessed a new polar contact and different 3-dimensional shape. A mixture of four diastereomers (71a,b) was tested in enzymatic and cell-based assays. The mixture had an $IC_{50}$ of 4.0 µM in the redox assay and a $GI_{50}$ of 10 µM in the cell-based assay. The related unsaturated derivative 43a has an $IC_{50}$ of 1.0 µM and a $GI_{50}$ of 15 µM.

Because the mixtures of methyl-substituted saturated derivatives (69b R/S) were so similar in activity to the unsubstituted single compound (69a) and the related unsaturated derivative (39a) it was hypothesized there was no need to test the enantiomers separately. The epoxide mixture (71a/b) was also not separated because the activity of the four component mixture was equivalent to that of the unsaturated derivative 43a.

Derivatives of inhibitors with modifications to the carboxyl moiety including esters and amides were synthesized. 3-Chloro acid 43a showed equal activity to the methyl ester (E-44a, $IC_{50}$=µM, $GI_{50}$=µM) and the hydroxyethylamide (76b, $IC_{50}$=$GI_{50}$=µM). Ester derivatives could possibly be hydrolyzed in cellular experiments; however, the stabile amides provided further evidence that the carboxylic acid functional group may not play a role in binding. The most dramatic derivative examined was the Z isomer Z-43a, where the double bond geometry is reversed. Enzymatic and growth inhibition experiments showed little difference in activity between the E ($IC_{50}$=1.0 µM, $GI_{50}$=15 µM) and Z ($IC_{50}$=1.5 µM, $GI_{50}$=30 µM) isomers (Table 4).

TABLE 4

Naphthoquinone Derivatives: Miscellaneous modifications

| Structure | Name | 3-Substituent | Double Bond | Carbonyl | Redox/ µM | Cell Killing/ µM |
|---|---|---|---|---|---|---|
| [structure: naphthoquinone with Cl at 3-position, E-configured acrylate] | E-43a | Chloro | E | Acid | 1.0 | 15 |
| [structure: naphthoquinone with Cl at 3-position, Z-configured acrylate] | Z-43a | Chloro | Z | Acid | 1.5 | 30 |

TABLE 4-continued

Naphthoquinone Derivatives: Miscellaneous modifications

| Structure | Name | 3-Substituent | Double Bond | Carbonyl | Redox/ μM | Cell Killing/ μM |
|---|---|---|---|---|---|---|
| 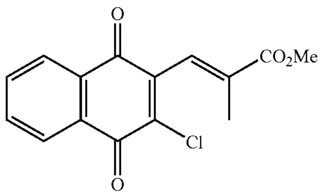 [SMILES: COC(=O)/C(C)=C/C1=C(Cl)C(=O)c2ccccc2C1=O] | E-44a | Chloro | E | Methyl ester | 1.0 | 17.5 |
| 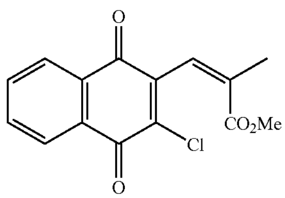 [SMILES: COC(=O)/C(C)=C\C1=C(Cl)C(=O)c2ccccc2C1=O] | Z-44a | Chloro | Z | Methyl Ester | 2.0 | 20 |
| 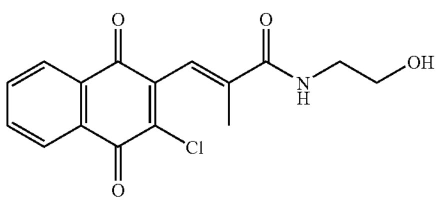 [SMILES: C/C(=C\C1=C(Cl)C(=O)c2ccccc2C1=O)C(=O)NCCO] | 73 | Chloro | E | Amide | 1.0 | 7.5 |
| 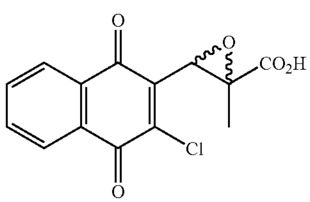 | 71 | Chloro | Epoxide | Acid | 4.0 | 10 |
| 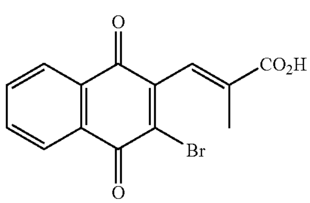 [SMILES: C/C(=C\C1=C(Br)C(=O)c2ccccc2C1=O)C(=O)O] | 39a | Bromo | E | Acid | 2.0 | 12.5 |
| 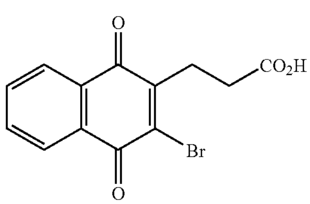 [SMILES: O=C(O)CCC1=C(Br)C(=O)c2ccccc2C1=O] | 69a | Bromo | Saturated | Acid | 5 | 15 |
| 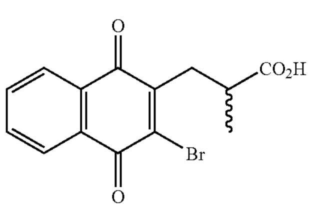 [SMILES: CC(CC1=C(Br)C(=O)c2ccccc2C1=O)C(=O)O] | 69b | Bromo | Saturated | Acid | 5 | 15 |

TABLE 4-continued

Naphthoquinone Derivatives: Miscellaneous modifications

| Structure | Name | 3-Substituent | Double Bond | Carbonyl | Redox/ μM | Cell Killing/ μM |
|---|---|---|---|---|---|---|
| 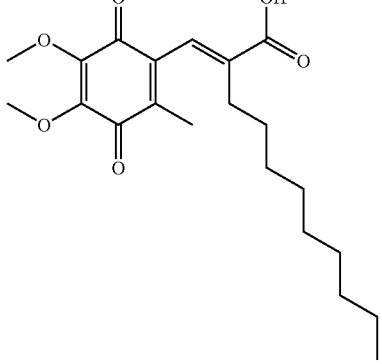 | 1 | Methyl | Unsaturated | Acid | 10 | 35 |
| 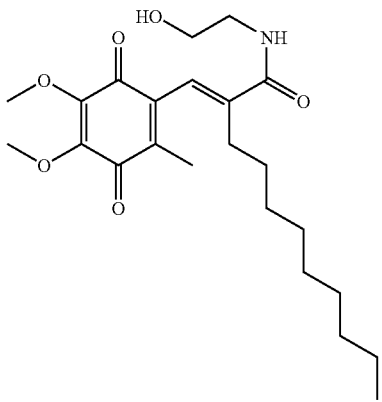 [SMILES: CCCCCCCCC/C(=C\C1=C(C)C(=O)C(OC)=C(OC)C1=O)C(=O)NCCO] | 72 | Methyl | Unsaturated | Amide | 10 | 35 |

The biological analyses of the benzoquinone and naphthoquinone derivatives provide a glimpse into the preferences of the redox active site on Ape1. First, the naphthoquinone derivatives show an increase in activity of an order of magnitude over the benzoquinone derivatives. Second, the nonyl sidechain of E3330 can be reduced to a methyl substituent without a significant loss of activity. In the benzoquinone series a preferred requirement for retention of activity was at least a methyl substituent on the double bond. Third, in both the benzoquinone and naphthoquinone series an electronegative ring-substituent ortho to the double bond showed increased activity compared to the methyl derivatives. Fourth, the saturation, epoxidation, and geometry reversal of the double bond in the naphthoquinone series showed no decrease in activity. Finally, amidation of the carboxylate in both the benzoquinone and naphthoquinone series showed activity retention.

LIST OF REFERENCES REFERRED TO IN THE PRECEDING PAGES

1 Tupler, R.; Perini, G.; Green, M. R. *Nature* 2001, 409 (6822), 832-3.
2 Evans, A. R.; Limp-Foster, M.; Kelley, M. R. *Mutat Res* 2000, 461(2), 83-108.
3 Wilson, D. M. 3rd *J Mol Biol* 2003, 330(5), 1027-37.
4 Xanthoudakis, S.; Curran, T. *EMBO J.* 1992, 11(2), 653-65.
5 Walker, L. J.; Robson, C. N.; Black, E.; Gillespie, D.; Hickson, I. D. *Mol Cell Biol* 1993, 13(9), 5370-6.
6 Kelley, M. R.; Luo, M.
7 Ordway, J. M.; Eberhart, D.; Curran, T. *Mol Cell Biol* 2003, 23(12), 4257-66.
8 Izumi, T.; Brown, D. B.; Naidu, C. V.; Bhakat, K. K.; Macinnes, M. A.; Saito, H.; Chen, D. J.; Mitra, S. *Proc Natl Acad Sci USA* 2005, 102(16), 5739-43.
9 Mol, C. D.; Izumi, T.; Mitra, S.; Tainer, J. A. *Nature* 2000, 403(6768), 451-6.
10 Luo, M.; Kelley, M. R. *Anticancer Res* 2004, 24(4), 2127-34.
11 Fishel, M. L.; He, Y.; Smith, M. L.; Kelley, M. R. *Clin Cancer Res* 2007, 13(1), 260-267.
12 Shimizu, N.; Sugimoto, K.; Tang, J.; Nishi, T.; Sato, I.; Hiramoto, M.; Aizawa, S.; Hatakeyama, M.; Ohba, R.; Hatori, H.; Yoshikawa, T.; Suzuki, F.; Oomori, A.; Tanaka, H.; Kawaguchi, H.; Watanabe, H.; Handa, H. *Nat Biotechnol* 2000, 18(8), 877-81.
13 Shinkawa, N.; Ichino, T.; Tsuruki, T.; Kuroda, H. Japan Patent JP 05148183, Jun. 15, 1993.
14 Keinan, E.; Doron, E. *J. Org. Chem.* 1987, 52(17), 3872-3875.
15 Ohkawa, S.; Terao, S.; Terashita, Z.; Shibouta, Y.; Nishikawa, K. *J. Med. Chem.* 1991, 34, 267-276.
16 Shinkawa, N.; Ichino, T.; Tsuruki, T.; Kuroda, H. Japan Patent 05-148183, Jun. 15, 1993.
17 Tremblay, M. S.; Sames, D. *Org. Lett.* 2005, 7, 2417-20.
18 Matsumoto, M.; Kobayashi, H.; Hotta, Y. *J. Org. Chem.* 1984, 49, 4740-4741.
19 Syper, L.; Kloc, K.; Mlochowski, J. *Tetrahedron* 1980, 36, 123-129.

20 Benington, F.; Morin, R. D.; Clark J R, L. C. *J. Org. Chem.* 1955, 20, 102-108.

21 Matsubara, H.; Yasuda, S.; Sugiyama, H.; Ryu, I.; Fujii, Y.; Kita, K. *Tetrahedron* 2002, 58, 4071-4076.

22 Flader, C.; Liu, J.; Borch, R. F. *J. Med. Chem.* 2000, 43(16), 3157-67.

23 Evans, P. A.; Brandt, T. A. *J. Org. Chem.* 1997, 62, 5321-5326.

24 Ito, T.; Ikemoto, T.; Yamano, T.; Mizuno, Y.; Tomimatsu, K. *Tetrahedron: Asymmetry* 2003, 14, 3525-3531.

25 Smith, J. G.; Dibble, P. W.; Sandborn, R. E. *J. Org. Chem.* 1986, 51, 3762-3768.

26 Murphy, J. A.; Rasheed, F.; Roome, S. J.; Scott, K. A.; Lewis, N. *J. Chem. Soc., Perkin Trans.* 1 1998, 2331-2339.

27 King, S. A. *J. Org. Chem.* 1994, 59, 2253-2256.

28 Clegg, N. J.; Paruthiyil, S.; Leitman, D. C.; Scanlan, T. S. *J. Med. Chem.* 2005, 48, 5989-6003.

29 Nakamura, M.; Kakuda, T.; Oba, Y.; Ojika, M.; Nakamura, H. *Bioorg Med Chem* 2003, 11(14), 3077-82.

30 Zempleni, J.; McCormick, D. B.; Stratton, S. L.; Mock, D. M. *The Journal of Nutritional Biochemistry* 1996, 7(9), 518-523.

31 Gregory, K. J.; Bachas, L. G. *Anal Biochem* 2001, 289(1), 82-8.

32 Yoon, H. C.; Hong, M.-Y.; Kim, H.-S. *Langmuir* 2001, 17(4), 1234-1239.

33 Snyder, C. D.; Rapoport, H. *J. Am. Chem. Soc.* 1972, 94(1), 227-231.

34 Gius, D.; Cao, X. M.; Rauscher, F. J. 3rd; Cohen, D. R.; Curran, T.; Sukhatme, V. P. *Mol Cell Biol* 1990, 10(8), 4243-55.

35 Fischer, A. H. G. N. *Can. J. Chem.* 1983, 61(6), 1045-1052.

36 Brimble, M. A.; McEwan, J. F.; Turner, P. *Tetrahedron: Asymmetry* 1998, 9, 1239-1255.

37 Yang, J.; Weng, L.; Zheng, H. *Synth. Commun.* 2006, 36(16), 2401-2405.

38 Syper, L.; Mlochowski, J.; Kloc, K. *Tetrahedron* 1983, 39(5), 781-792.

39 Lopez-Alvarado, P.; Avendano, C.; Menendez, J. C. *Synth. Commun.* 2002, 32, 3233-3239.

40 Bauer, H.; Fritz-Wolf, K.; Winzer, A.; Kuhner, S.; Little, S.; Yardley, V.; Vezin, H.; Palfey, B.; Schirmer, R. H.; Davioud-Charvet, E. *J. Am. Chem. Soc.* 2006, 128(33), 10784-10794.

41 Rajesh, S.; Banerji, B.; Iqbal, J. *J. Org. Chem.* 2002, 67(22), 7852-7857.

42 Sachon, E.; Tasseau, O.; Lavielle, S.; Sagan, S.; Bolbach, G. *Anal Chem* 2003, 75(23), 6536-43.

43 Kirschleger, B. Q. R. *Synthesis* 1986, 926.

44 Sabatino, G.; Chinol, M.; Paganelli, G.; Papi, S.; Chelli, M.; Leone, G.; Papini, A. M.; DeLuca, A.; Ginanneschi, M. *J. Med. Chem.* 2003, 46(14), 3170-3173.

We claim:

1. A compound of the formula (e)

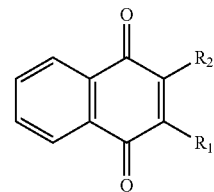

wherein
$R_1$ is $C_1$-$C_6$ alkyl:
$R_2$ is

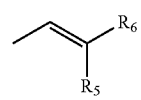

where
$R_5$ is hydrogen or optionally substituted $C_1$-$C_9$ alkyl; and
$R_6$ is

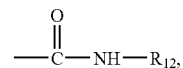

where $R_{12}$ is optionally substituted $C_1$-$C_6$ alkyl or

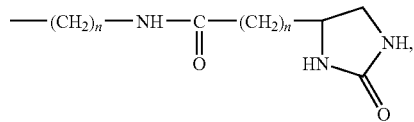

where n is 1-6;
or a pharmaceutically acceptable salt thereof.

2. A pharmaceutical composition comprising a compound of claim 1, or a pharmaceutically acceptable salt thereof, in combination with a pharmaceutically acceptable carrier, diluent, or excipient.

* * * * *

UNITED STATES PATENT AND TRADEMARK OFFICE
CERTIFICATE OF CORRECTION

PATENT NO. : 9,089,605 B2
APPLICATION NO. : 12/679828
DATED : July 28, 2015
INVENTOR(S) : Mark R. Kelley et al.

Page 1 of 1

It is certified that error appears in the above-identified patent and that said Letters Patent is hereby corrected as shown below:

Claims

In Claim 1, col. 130, line 15, please delete "alkyl:" and insert --alkyl;-- therefor.

Signed and Sealed this
Sixteenth Day of February, 2016

Michelle K. Lee
*Director of the United States Patent and Trademark Office*